US008394828B2

(12) United States Patent
Codd et al.

(10) Patent No.: US 8,394,828 B2
(45) Date of Patent: Mar. 12, 2013

(54) QUINOLINE-DERIVED AMIDE MODULATORS OF VANILLOID VR1 RECEPTOR

(75) Inventors: Ellen Codd, Blue Bell, PA (US); Scott L. Dax, Landenberg, PA (US); Michele Jetter, Norristown, PA (US); Mark McDonnell, Lansdale, PA (US); James J. McNally, Souderton, PA (US); Mark Youngman, Warminster, PA (US)

(73) Assignee: Janssen Pharmaceutica, NV (BE)

( * ) Notice: Subject to any disclaimer, the term of this patent is extended or adjusted under 35 U.S.C. 154(b) by 697 days.

(21) Appl. No.: 12/174,017

(22) Filed: Jul. 16, 2008

(65) Prior Publication Data

US 2008/0300236 A1 Dec. 4, 2008

Related U.S. Application Data

(63) Continuation of application No. 10/770,204, filed on Feb. 2, 2004, now abandoned.

(60) Provisional application No. 60/444,442, filed on Feb. 3, 2003.

(51) Int. Cl.
*A61K 31/04* (2006.01)
*C07D 215/38* (2006.01)

(52) U.S. Cl. ........................................ 514/312; 546/159

(58) Field of Classification Search .................. 546/159; 514/312
See application file for complete search history.

(56) References Cited

U.S. PATENT DOCUMENTS

| 4,786,644 | A | 11/1988 | Glamkowski et al. |
| 5,399,564 | A | 3/1995 | Hackler et al. |
| 5,410,024 | A | 4/1995 | Pettit et al. |
| 7,122,547 | B1 * | 10/2006 | Huth et al. ..................... 514/241 |

FOREIGN PATENT DOCUMENTS

| EP | 0223420 | | 5/1987 |
| EP | 335381 A1 | | 3/1989 |
| WO | WO 91/17162 | | 11/1991 |
| WO | WO 93/04580 | | 3/1993 |
| WO | WO 96/01825 | | 1/1996 |
| WO | WO 97/15308 | | 5/1997 |
| WO | WO 97/48694 | | 12/1997 |
| WO | 00/27819 | * | 5/2000 |
| WO | WO 00/27819 | | 5/2000 |
| WO | WO 01/74771 A1 | | 10/2001 |
| WO | WO 02/088086 | | 11/2002 |
| WO | WO 03/049702 | | 6/2003 |
| WO | WO 2004/005261 | | 1/2004 |

OTHER PUBLICATIONS

Schultz, H.W. & Wiese, G.A. "The synthesis of some derivatives of cinnamic acid and their antifungal action". J.Am. Pharm. Assoc., vol. 48, No. 12, 1959, pp. 750-752.
Takada, S. et al. "Synthesis and Structure-Activity relationships of fused imidazopyridines: a new series of benzodiazepine receptor ligands". J. Med. Chem. vol. 39, No. 14, 1996, pp. 2844-2851. XP002289506.
Database Chemcats, Chemical Abstracts Service, Columbus, Ohio, US; Jan. 1, 2004. XP002289507.
Order No. 0435-5625 & "Ambinter Screening Library Catalogue" Jan. 1, 2004, Ambinter, Paris.
Database Chemcats, Chemical Abstracts Service, Columbus, Ohio, US, Jul. 9, 2002. XP002289508.
Order Nos. BAS0631860, 0160-0736, 0160-0737, 0938-8056, 0938-8098 & "Interchim Intermediates Catalogue" Julu 9, 2002, Interchim, Montllucon.
Caplus English Abstract DN 65:51494, Ts'ao Tan-P'u, et al., Studies of Insect Chemosterilants, 1966, vol. 15, Issue 1, pp. 13-27.
Modena et al., Caplus English abstract DN 119:197690, 1993, vol. 48, Issue 4, pp. 567-572.
Atwell et al., Caplus English abstract, Caplus English abstract DN 120:216381, 1994, vol. 37, Issue 3.
English abstract DN 122:214532, Pettit, George et al., US 5410024, Apr. 1995.
Side Reaction chapter 1, pp. 8 and 9, Zaragoza Dorwald, 2005.
PCT International Search Report dated Jun. 8, 2004 for PCT App. No. PCT/IB2004/000785, which relates to U.S. Appl. No. 10/770,204.
Gould P.L., "Salt Selection for Basic Drugs.", Ref. International J. Pharm., 1986, pp. 201-217, vol. 33.
Berge et al., "Pharmaceutical Salts.", J. Pharm. Sci., 1977, pp. 1-19, vol. 66(1).
Comins et al., "Regioselective Addition of Grignard Reagents to the 1-Phenoxycarbonyl Salts of Alkyl Nicotinates.", Heterocyles, 1984, pp. 151-157, vol. 22(1).
Denney et al., "Preparation and Reactions of Some Phosphates1.", Journal of Organic Chemistry, Oct. 1962, pp. 3404-3408, vol. 27.
Farrar et al., "Condensations Effected by Boron Fluoaride Complexes. III. The Acylation of Certain Substituted Thiophenes and Furan.", JACS, Aug. 1950, pp. 3695-3698, vol. 72.
Still et al., "Rapid Chromatographic Technique for Preparative Separations with Moderate Resolution.", J. Org. Chem., 1978, pp. 2923-2925, vol. 43(14).

* cited by examiner

*Primary Examiner* — D M Seaman

(57) ABSTRACT

This invention is directed to vanilloid receptor VR1 ligands. More particularly, this invention relates to quinoline-derived amides that are potent antagonists or agonists of VR1 which are useful for the treatment and prevention of inflammatory and other pain conditions in mammals.

142 Claims, 4 Drawing Sheets

QUINOLINE-DERIVED AMIDE MODULATORS OF VANILLOID VR1 RECEPTOR

CROSS-REFERENCE TO RELATED APPLICATIONS

This is a continuation of U.S. patent application Ser. No. 10/770,204 filed on Feb. 2, 2004 now abandoned, which claims priority under 35 U.S.C. §119(e) of U.S. Provisional Patent Application No. 60/444,442 filed on Feb. 3, 2003.

STATEMENT REGARDING FEDERALLY SPONSORED RESEARCH OR DEVELOPMENT

The research and development of the invention described below was not federally sponsored.

BACKGROUND OF THE INVENTION

This invention is directed to novel vanilloid receptor VR1 ligands. More particularly, this invention relates to novel quinoline-derived amides that are potent antagonists or agonists of VR1 and exhibit activity in animal models of hyperalgesia and colitis, and are useful for the treatment and prevention of pain conditions in humans including arthritis, and for the treatment of irritable-bowel syndrome and associated conditions.

Noxious chemical, thermal and mechanical stimuli excite peripheral nerve endings of small diameter sensory neurons (nociceptors) in sensory ganglia (e.g., dorsal root, nodose and trigeminal ganglia) and initiate signals that are perceived as pain. These neurons are crucial for the detection of harmful or potentially harmful stimuli (heat) and tissue damage (local tissue acidosis and/or stretch) that arise from changes in the extracellular space during inflammatory or ischaemic conditions (Wall, P. D., and Melzack, R., *Textbook of Pain,* 1994, New York: Churchill Livingstone). Nociceptors transduce noxious stimuli into membrane depolarization that triggers action potential, conducts the action potential from the sensory sites to the synapses in the CNS, and conversion of action potentials invokes a perception of pain, discomfort, and appropriate mechanical/physical protective reflexes. At the molecular level, nociception is carried out by ion channels or receptors. Plant derived vanilloid compounds (capsaicin and its ultrapotent analog, resiniferatoxin, etc.) are known to selectively depolarize nociceptors and elicit sensations of burning pain—the sensation that is typically obtained by hot chili peppers. Therefore, capsaicin mimics the action of physiological/endogenous stimuli that activates the "nociceptive pathway". Recent advances in pain biology have identified receptors for vanilloids, protons (i.e., acidic solutions), and for heat. Because nociceptors are involved with unwanted pain and inflammatory conditions in human beings and animals, modulation of their nociceptive pathway is important in palliative and other therapies.

U.S. Pat. No. 4,786,644 discloses 1-aryl-3-quinoline carboxamides as analgesics and antiinflammatory agents. This patent, however, does not disclose or suggest the compounds, compositions or methods of the present invention.

Thus, there is a need for potent modulators of VR, and in particular, for novel quinoline-derived amides that exhibit potent binding affinity for the human and rat VR1 ion channel. There is also a need for novel quinoline-derived amides that act as potent functional antagonists and/or agonists of the human and rat VR1 ion channel. Finally, there is a need for novel quinoline-derived amides that bind with high affinity to VR1 and also act as potent functional antagonists of the human and rat VR1 ion channel.

SUMMARY OF THE INVENTION

The present invention is directed to a compound of Formula (I):

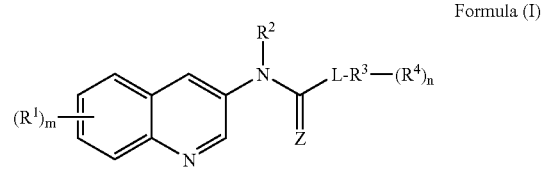

Formula (I)

wherein:
$R^1$ is a substituent independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; $diC_{1-7}$alkanylaminocarbonyl; and formyl; wherein the heteroatom contained in the quinoline ring of Formula (I) is optionally substituted with an oxo substituent;
m is 0, 1 or 2;
$R^2$ is hydrogen or $C_{1-8}$alkanyl;
L is a direct bond or $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;
$R^3$ is selected from the group consisting of pyrrolyl, pyridyl, furyl, thienyl, phenyl and cyclohexyl;
$R^4$ is independently selected from the group consisting of $C_{1-12}$alkanyl, $C_{4-8}$alkanyloxy, $C_{3-8}$cycloalkanyloxy, $C_{1-8}$alkanylamino, $C_{3-8}$cycloalkanylamino, $C_{3-14}$ cyclic heteroalkanyl, $C_{1-6}$fluorinated alkanyl, and —N($R^5$)($R^6$); or when n is 2 or 3, optionally two $R^4$ substituents taken together form a $C_{3-14}$ cyclic heteroalkyl or $C_{3-14}$ cyclic alkanyl;
$R^5$ is hydrogen, $C_{1-16}$alkyl, alkanylcarbonyl or arylcarbonyl;
$R_6$ is $C_{4-16}$ alkyl, alkanylcarbonyl, $C_{1-3}$alkyl substituted with a substituent selected from the group consisting of pyrrolyl, pyridyl, furyl, thienyl, phenyl, and furyl, or arylcarbonyl; or optionally $R^6$ and one of $R^4$ taken together form a saturated or partially unsaturated cyclic heteroalkyl or a heteroaryl; or $R^5$ and $R^6$ optionally taken together form a bridged or non-bridged cyclic heteroalkanyl, wherein said heteroalkanyl is optionally substituted with $C_{1-6}$alkanylcarbonyl;
wherein the alkanyls in any of the foregoing alkanyl-containing substituents of $R^4$, $R^5$ or $R^6$ are optionally and independently substituted with pyrrolyl, pyridyl, furyl, thienyl, phenyl, furyl, $C_{1-4}$alkylpyrrolyl, $C_{1-4}$alkylpyridyl, $C_{1-4}$alkylthienyl, $C_{1-4}$alkylphenyl, or $C_{1-4}$alkylfuryl;

n is 1, 2 or 3;

Z is O or S; and enantiomers, diastereomers, tautomers, solvates, and pharmaceutically acceptable salts thereof.

In another embodiment, the present invention is directed to a compound of Formula (I) wherein:

$R^1$ is a substituent independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; $diC_{1-7}$alkanylaminocarbonyl; and formyl; wherein the heteroatom contained in the quinoline ring of Formula (I) is optionally substituted with an oxo substituent;

m is 0, 1 or 2;

$R^2$ is hydrogen or $C_{1-8}$alkanyl;

L is a $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, $di(C_{1-3})$alkanylamino, and $C_{1-3}$alkanylamino;

$R^3$ is selected from the group consisting of pyrrolyl, pyridyl, furyl, thienyl, phenyl and cyclohexyl;

$R^4$ is independently selected from the group consisting of $C_{1-12}$alkanyl, $C_{4-8}$alkanyloxy, $C_{3-8}$cycloalkanyloxy, $C_{1-8}$alkanylamino, $C_{3-8}$cycloalkanylamino, $C_{3-14}$ cyclic heteroalkanyl, $C_{1-6}$fluorinated alkanyl, and $-N(R^5)(R^6)$; or when n is 2 or 3, optionally two $R^4$ substituents taken together form a $C_{3-14}$ cyclic heteroalkyl or $C_{3-14}$ cyclic alkanyl;

$R^5$ is hydrogen, $C_{1-16}$alkyl, alkanylcarbonyl or arylcarbonyl;

$R_6$ is $C_{4-16}$ alkyl, alkanylcarbonyl, $C_{1-3}$alkyl substituted with a substituent selected from the group consisting of pyrrolyl, pyridyl, furyl, thienyl, phenyl, and furyl, or arylcarbonyl; or optionally $R^6$ and one of $R^4$ taken together form a saturated or partially unsaturated cyclic heteroalkyl or a heteroaryl; or $R^5$ and $R^6$ optionally taken together form a bridged or non-bridged cyclic heteroalkanyl, wherein said heteroalkanyl is optionally substituted with $C_{1-6}$alkanylcarbonyl;

wherein the alkanyls in any of the foregoing alkanyl-containing substituents of $R^4$, $R^5$ or $R^6$ are optionally and independently substituted with pyrrolyl, pyridyl, furyl, thienyl, phenyl, furyl, $C_{1-4}$alkylpyrrolyl, $C_{1-4}$alkylpyridyl, $C_{1-4}$alkylthienyl, $C_{1-4}$alkylphenyl, or $C_{1-4}$alkylfuryl;

n is 1, 2 or 3;

Z is O or S; and enantiomers, diastereomers, tautomers, solvates, and pharmaceutically acceptable salts thereof.

In another embodiment, the present invention is directed to a compound of Formula (I) wherein:

$R^1$ is a substituent independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; $diC_{1-7}$alkanylaminocarbonyl; and formyl; wherein the heteroatom contained in the quinoline ring of Formula (I) is optionally substituted with an oxo substituent;

m is 0, 1 or 2;

$R^2$ is hydrogen or $C_{1-8}$alkanyl;

L is a direct bond or $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, $di(C_{1-3})$alkanylamino, and $C_{1-3}$alkanylamino;

$R^3$ is selected from the group consisting of pyrrolyl, pyridyl, furyl, thienyl, phenyl and cyclohexyl;

$R^4$ is independently selected from the group consisting of $C_{1-12}$alkanyl, $C_{1-8}$alkanyloxy, $C_{3-8}$cycloalkanyloxy, $C_{1-8}$alkanylamino, $C_{3-8}$cycloalkanylamino, $C_{3-14}$ cyclic heteroalkanyl, $C_{1-6}$fluorinated alkanyl and $-N(R^5)(R^6)$; or when n is 2 or 3, optionally two $R^4$ substituents taken together form a $C_{3-14}$ cyclic heteroalkyl or $C_{3-14}$ cyclic alkanyl;

$R^5$ is hydrogen, $C_{1-16}$alkyl, alkanylcarbonyl or arylcarbonyl;

$R_6$ is $C_{4-16}$ alkyl, alkanylcarbonyl, $C_{1-3}$alkyl substituted with a substituent selected from the group consisting of pyrrolyl, pyridyl, furyl, thienyl, phenyl, and furyl, or arylcarbonyl; or optionally $R^6$ and one of $R^4$ taken together form a saturated or partially unsaturated cyclic heteroalkyl or a heteroaryl; or $R^5$ and $R^6$ optionally taken together form a bridged or non-bridged cyclic heteroalkanyl, wherein said heteroalkanyl is optionally substituted with $C_{1-6}$alkanylcarbonyl;

wherein the alkanyls in any of the foregoing alkanyl-containing substituents of $R^4$, $R^5$ or $R^6$ are optionally and independently substituted with pyrrolyl, pyridyl, furyl, thienyl, phenyl, furyl, $C_{1-4}$alkylpyrrolyl, $C_{1-4}$alkylpyridyl, $C_{1-4}$alkylthienyl, $C_{1-4}$alkylphenyl, or $C_{1-4}$alkylfuryl;

n is 2 or 3;

Z is O or S; and enantiomers, diastereomers, tautomers, solvates, and pharmaceutically acceptable salts thereof.

In another embodiment, the present invention is directed to a compound of Formula (I) wherein:

$R^1$ is a substituent independently selected from the group consisting of hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl; wherein the heteroatom contained in the quinoline ring of Formula (I) is optionally substituted with an oxo substituent;

m is 1 or 2;

$R^2$ is hydrogen or $C_{1-8}$alkanyl;

L is a direct bond or $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R^3$ is selected from the group consisting of pyrrolyl, pyridyl, furyl, thienyl, phenyl and cyclohexyl;

$R^4$ is independently selected from the group consisting of $C_{1-8}$alkanyl, $C_{1-8}$alkanyloxy, $C_{3-8}$cycloalkanyloxy, $C_{1-8}$alkanylamino, $C_{3-8}$cycloalkanylamino, $C_{3-14}$ cyclic heteroalkanyl, $C_{1-6}$ fluorinated alkyl, and —N($R^5$)($R^6$); or when n is 2 or 3, optionally two $R^4$ substituents taken together form a $C_{3-14}$ cyclic heteroalkyl or $C_{3-14}$ cyclic alkanyl;

$R^5$ is hydrogen, $C_{1-16}$alkyl, alkanylcarbonyl or arylcarbonyl;

$R_6$ is $C_{4-16}$ alkyl, alkanylcarbonyl, $C_{1-3}$alkyl substituted with a substituent selected from the group consisting of pyrrolyl, pyridyl, furyl, thienyl, phenyl, and furyl, or arylcarbonyl; or optionally $R^6$ and one of $R^4$ taken together form a saturated or partially unsaturated cyclic heteroalkyl or a heteroaryl; or $R^5$ and $R^6$ optionally taken together form a bridged or non-bridged cyclic heteroalkanyl, wherein said heteroalkanyl is optionally substituted with $C_{1-6}$alkanylcarbonyl;

wherein the alkanyls in any of the foregoing alkanyl-containing substituents of $R^4$, $R^5$ or $R^6$ are optionally and independently substituted with pyrrolyl, pyridyl, furyl, thienyl, phenyl, furyl, $C_{1-4}$alkylpyrrolyl, $C_{1-4}$alkylpyridyl, $C_{1-4}$alkylthienyl, $C_{1-4}$alkylphenyl, or $C_{1-4}$alkylfuryl;

n is 1, 2 or 3;

Z is O or S; and enantiomers, diastereomers, tautomers, solvates, and pharmaceutically acceptable salts thereof.

In another embodiment, the present invention is directed to a compound of Formula (I) wherein:

$R^1$ is a substituent independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl; wherein the heteroatom contained in the quinoline ring of Formula (I) is optionally substituted with an oxo substituent;

m is 0, 1 or 2;

$R^2$ is hydrogen or $C_{1-8}$alkanyl;

L is ethen-1,2-diyl;

$R^3$ is selected from the group consisting of pyrrolyl, pyridyl, furyl, thienyl, phenyl and cyclohexyl;

$R^4$ is independently selected from the group consisting of $C_{1-12}$alkanyl, $C_{4-8}$alkanyloxy, $C_{3-8}$cycloalkanyloxy, $C_{1-8}$alkanylamino, $C_{3-8}$cycloalkanylamino, $C_{3-14}$ cyclic heteroalkanyl, $C_{1-6}$fluorinated alkanyl, halogen, and —N($R^5$)($R^6$); or when n is 2 or 3, optionally two $R^4$ substituents taken together form a $C_{3-14}$ cyclic heteroalkyl or $C_{3-14}$ cyclic alkanyl;

$R^5$ is hydrogen, $C_{1-16}$alkyl, alkanylcarbonyl or arylcarbonyl;

$R_6$ is $C_{4-16}$ alkyl, alkanylcarbonyl, $C_{1-3}$alkyl substituted with a substituent selected from the group consisting of pyrrolyl, pyridyl, furyl, thienyl, phenyl, and furyl, or arylcarbonyl; or optionally $R^6$ and one of $R^4$ taken together form a saturated or partially unsaturated cyclic heteroalkyl or a heteroaryl; or $R^5$ and $R^6$ optionally taken together form a bridged or non-bridged cyclic heteroalkanyl, wherein said heteroalkanyl is optionally substituted with $C_{1-6}$alkanylcarbonyl;

wherein the alkanyls in any of the foregoing alkanyl-containing substituents of $R^4$, $R^5$ or $R^6$ are optionally and independently substituted with pyrrolyl, pyridyl, furyl, thienyl, phenyl, furyl, $C_{1-4}$alkylpyrrolyl, $C_{1-4}$alkylpyridyl, $C_{1-4}$alkylthienyl, $C_{1-4}$alkylphenyl, or $C_{1-4}$alkylfuryl;

n is 1, 2 or 3;

Z is O or S; and enantiomers, diastereomers, tautomers, solvates, and pharmaceutically acceptable salts thereof.

The present invention is also directed to a compound of Formula (I) wherein:

$R^1$ is a substituent independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl; wherein the heteroatom contained in the quinoline ring of Formula (I) is optionally substituted with an oxo substituent;

m is 0, 1 or 2;

$R^2$ is hydrogen or $C_{1-8}$alkanyl;

L is a direct bond;

$R^3$ is selected from the group consisting of pyrrolyl, pyridyl, furyl, thienyl, and cyclohexyl;

$R^4$ is selected from the group consisting of $C_{1-12}$alkanyl, $C_{4-8}$alkanyloxy, $C_{3-8}$cycloalkanyloxy, $C_{1-8}$alkanylamino, $C_{3-8}$cycloalkanylamino, $C_{3-14}$ cyclic heteroalkanyl, $C_{1-6}$fluorinated alkanyl and —N($R^5$)($R^6$), wherein the alkanyls in any of the foregoing alkanyl-containing substituents of $R^4$ is optionally substituted with thienyl or phenyl; or when n is 2 or 3, optionally two $R^4$ substituents taken together form a $C_{3-14}$ cyclic heteroalkyl or $C_{3-14}$ cyclic alkanyl;

$R^5$ is hydrogen, $C_{1-16}$alkyl, alkanylcarbonyl or arylcarbonyl;

$R_6$ is $C_{4-16}$ alkyl, alkanylcarbonyl, $C_{1-3}$alkyl substituted with a substituent selected from the group consisting of pyrrolyl, pyridyl, furyl, thienyl, phenyl, and furyl, or arylcarbonyl; or optionally $R^6$ and one of $R^4$ taken together form a saturated or partially unsaturated cyclic heteroalkyl or a heteroaryl; or $R^5$ and $R^6$ optionally taken together form a bridged or non-bridged cyclic heteroalkanyl, wherein said heteroalkanyl is optionally substituted with $C_{1-6}$alkanyl-carbonyl;

wherein the alkanyls in any of the foregoing alkanyl-containing substituents of $R^4$, $R^5$ or $R^6$ are optionally and independently substituted with pyrrolyl, pyridyl, furyl, thienyl, phenyl, furyl, $C_{1-4}$alkylpyrrolyl, $C_{1-4}$alkylpyridyl, $C_{1-4}$alkylthienyl, $C_{1-4}$alkylphenyl, or $C_{1-4}$alkylfuryl;

n is 1, 2 or 3;

Z is O or S; and enantiomers, diastereomers, tautomers, solvates, and pharmaceutically acceptable salts thereof.

Finally, the present invention is directed to pharmaceutical compositions containing compounds of Formula (I), as well as to methods of treatment of diseases and conditions by administration of these compositions, and also to pharmaceutical kits containing them.

DETAILED DESCRIPTION OF THE INVENTION

Figure 1:
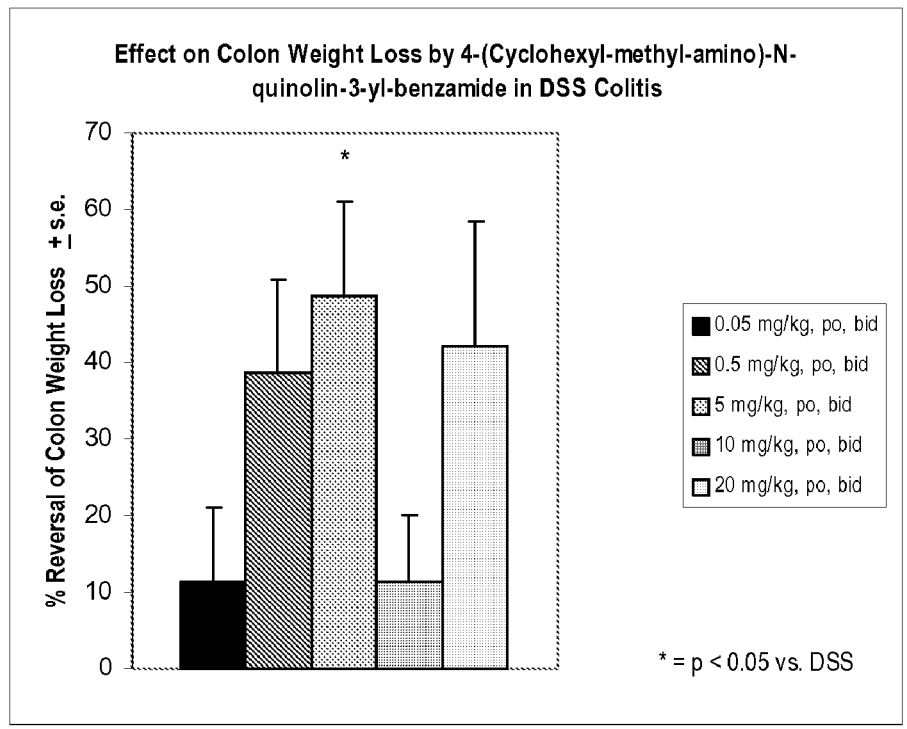
FIG. 1. Effect of a compound of the invention on Colon Weight Loss. Data presented are mean % inhibition±s.e. of colon weight loss from 3 experiments following twice daily oral administration of the compound at the doses indicated.

As used herein, the following underlined terms are intended to have the following meanings:

"$C_{a-b}$" (where a and b are integers) refers to a radical containing from a to b carbon atoms inclusive. For example, $C_{1-3}$ denotes a radical containing 1, 2 or 3 carbon atoms.

"Fluorinated alkyl" refers to a saturated branched or straight chain hydrocarbon radical derived by removal of 1 hydrogen atom from the parent alkane; the parent alkane contains from 1 to 6 carbon atoms with 1 or more hydrogen atoms substituted with fluorine atoms up to and including substitution of all hydrogen atoms with fluorine. Preferred fluorinated alkyls include trifluoromethyl substituted alkyls and perfluorinated alkyls; more preferred fluorinated alkyls include trifluoromethyl, perfluoroethyl, 2,2,2-trifluoroethyl, perfluoropropyl, 3,3,3-trifluoroprop-1-yl, 3,3,3-trifluoroprop-2-yl, 1,1,1,3,3,3-hexafluoroprop-2-yl; a particularly preferred fluorinated alkyl, is trifluoromethyl.

"Fluorinated alkanyloxy" refers to a radical derived from a fluorinated alkyl, radical attached to an oxygen atom with the oxygen atom having one open valence for attachment to a parent structure.

"Alkyl:" refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl", "alkenyl" and/or "alkynyl" is used, as defined below. In preferred embodiments, the alkyl groups are ($C_{1-8}$) alkyl, with ($C_{1-3}$) being particularly preferred.]

"Alkanyl:" refers to a saturated branched, straight-chain or cyclic monovalent hydrocarbon radical derived by the removal of one hydrogen atom from a single carbon atom of a parent alkane. Typical alkanyl groups include, but are not limited to, methanyl; ethanyl; propanyls such as propan-1-yl, propan-2-yl, cyclopropan-1-yl, etc.; butyanyls such as butan-1-yl, butan-2-yl, 2-methyl-propan-1-yl, 2-methyl-propan-2-yl, cyclobutan-1-yl, etc.; and the like. In preferred embodiments, the alkanyl groups are ($C_{1-8}$) alkanyl, with ($C_{1-3}$) being particularly preferred.

"Alkenyl:" refers to an unsaturated branched, straight-chain or cyclic monovalent hydrocarbon radical having at least one carbon-carbon double bond derived by the removal of one hydrogen atom from a single carbon atom of a parent alkene. The radical may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. In preferred embodiments, the alkenyl group is ($C_{2-8}$) alkenyl, with ($C_{2-3}$) being particularly preferred.

"Alkynyl:" refers to an unsaturated branched, straight-chain or cyclic monovalent hydrocarbon radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn- 1-yl, etc.; and the like. In preferred embodiments, the alkynyl group is $(C_{2-8})$ alkynyl, with $(C_{2-3})$ being particularly preferred.

"Alkyldiyl:" refers to a saturated or unsaturated, branched, straight-chain or cyclic divalent hydrocarbon radical derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers can form bonds with the same or different atoms. Typical alkyldiyls include, but are not limited to methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methylprop-2-en-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkandiyl, alkendiyl and/or alkyndiyl is used. In preferred embodiments, the alkyldiyl group is $(C_{1-8})$ alkyldiyl, with $(C_{1-8})$ being particularly preferred. Also preferred are saturated acyclic alkandiyl radicals in which the radical centers are at the terminal carbons, e.g., methandiyl; ethan-1,2-diyl; propan-1,3-diyl; butan-1,4-diyl; and the like (also referred to as alkylenos, as defined infra).

"Vic Alkyldiyl:" refers to a saturated or unsaturated, branched, straight-chain or cyclic hydrocarbon radical having two adjacent monovalent radical centers derived by the removal of one hydrogen atom from each of two adjacent carbon atoms of a parent alkane, alkene or alkyne. The two monovalent radical centers can form bonds with the same or different atom(s). Typical vic alkyldiyls include, but are not limited to vic ethyldiyls such as ethan-1,2-diyl, ethen-1,2-diyl; vic propyldiyls such as propan-1,2-diyl, cyclopropan-1,2-diyl, prop-1-en-1,2-diyl, prop-2-en-1,2-diyl, cycloprop-1-en-1,2-diyl, etc.; vic butyldiyls such as butan-1,2-diyl, 2-methyl-propan-1,2-diyl, cyclobutan-1,2-diyl, but-1-en-1,2-diyl, cyclobut-1-en-1,2-diyl, buta-1,3-dien-1,2-diyl, cyclobuta-1,3-dien-1,2-diyl, but-3-yn-1,2-diyl, etc.; and the like. Where specific levels of saturation are intended, the nomenclature vic alkandiyl, vic alkendiyl and/or vic alkyndiyl is used. In preferred embodiments, the vic alkyldiyl group is $(C_{2-8})$ vic alkyldiyl, with $(C_{2-3})$ being particularly preferred.

"Gem Alkyldiyl:" refers to a saturated or unsaturated, branched, straight-chain or cyclic hydrocarbon radical having one divalent radical center derived by the removal of two hydrogen atoms from a single carbon atom of a parent alkane, alkene or alkyne. The divalent radical center forms bonds with two different atoms. Typical gem alkyldiyls include, but are not limited to gem methanyldiyl; gem ethyldiyls such as ethan-1,1-diyl,ethen-1,1-diyl; gem propyldiyls such as propan-1,1-diyl, propan-2,2-diyl, cyclopropan-1,1-diyl, prop-1-en-1,1-diyl, cycloprop-2-en-1,1-diyl, prop-2-yn-1,1-diyl, etc.; butyldiyls such as butan-1,1-diyl, butan-2,2-diyl, 2-methyl-propan-1,2-diyl, cyclobutan-1,1-diyl, but-1-en-1,1-diyl, 2-methyl-prop-1-en-1,1-diyl, 2-methyl-prop-2-en-1,1-diyl, cyclobut-2-en-1,1-diyl, buta-1,3-dien-1,1-diyl, etc.; and the like. Where specific levels of saturation are intended, the nomenclature gem alkandiyl, gem alkendiyl and/or gem alkyndiyl is used. In preferred embodiments, the gem alkyldiyl group is $(C_{1-6})$ gem alkyldiyl, with $(C_{1-3})$ being particularly preferred.

"Alkyleno:" refers to a saturated or unsaturated, straight-chain or branched acyclic bivalent hydrocarbon bridge radical derived by the removal of one hydrogen atom from each of the two terminal carbon atoms of an acyclic parent alkane, alkene or alkyne. Typical alkyleno groups include, but are not limited to, methano; ethylenos such as ethano, etheno, ethyno; propylenos such as propano, propeno, prop-1,2-dieno, propyno, etc.; butylenos such as butano, 2-methyl-propano, but-1-eno, but-2-eno, 2-methyl-prop-1-eno, 2-methanylidene-propano, but-1,3-dieno, but-1-yno, but-2-yno, but-1,3-diyno, etc.; and the like. Where specific levels of saturation are intended, the nomenclature alkano, alkeno and/or alkyno is used. In preferred embodiments, the alkyleno group is $(C_{1-8})$ alkyleno, with $(C_{1-3})$ being particularly preferred. Also preferred are straight-chain saturated alkano radicals, e.g., methano, ethano, propano, butano, and the like.

"Alkylidene:" refers to a saturated or unsaturated, branched, straight-chain or cyclic divalent hydrocarbon radical derived by removal of two hydrogen atoms from the same carbon atom of a parent alkane, alkene or alkyne. The divalent radical center forms a double bond with a single atom. Typical alkylidene radicals include, but are not limited to, methanylidene, ethylidenes such as ethanylidene, ethenylidene; propylidenes such as propan-1-ylidene, propan-2-ylidene, cyclopropan-1-ylidene, prop-1-en-1-ylidene, prop-2-en-1-ylidene, cycloprop-2-en-1-ylidene, etc.; butylidenes such as butan-1-ylidene, butan-2-ylidene, 2-methyl-propan-1-ylidene, cyclobutan-1-ylidene, but-1-en-1-ylidene, but-2-en-1-ylidene, but-3-en-1-ylidene, buta-1,3-dien-1-ylidene; cyclobut-2-en-1-ylidene, etc.; and the like. Where specific levels of saturation are intended, the nomenclature alkanylidene, alkenylidene and/or alkynylidene is used. In preferred embodiments, the alkylidene group is $(C_{1-8})$ alkylidene, with $(C_{1-3})$ being particularly preferred. Also preferred are acyclic saturated alkanylidene radicals in which the divalent radical is at a terminal carbon, e.g., methanylidene, ethan-1-ylidene, propan-1-ylidene, butan-1-ylidene, 2-methyl-propan-1-ylidene, and the like.

"Alkylidyne:" refers to a saturated or unsaturated, branched or straight-chain trivalent hydrocarbon radical derived by removal of three hydrogen atoms from the same carbon atom of a parent alkane, alkene or alkyne. The trivalent radical center forms a triple bond with a single atom. Typical alkylidyne radicals include, but are not limited to, methanylidyne; ethanylidyne; propylidynes such as propan-1-ylidyne, prop-2-en-1-ylidyne, prop-2-yn-1-ylidyne; butylidynes such as butan-1-ylidyne, 2-methyl-propan-1-ylidyne, but-2-en-1-ylidyne, but-3-en-1-ylidyne, buta-2,3-dien-1-ylidyne, but-2-yn-1-ylidyne, but-3-yn-1-ylidyne, etc.; and the like. Where specific levels of saturation are intended, the nomenclature alkanylidyne, alkenylidyne and/or alkynylidyne is used. In preferred embodiments, the alkylidyne group is $(C_{1-8})$ alkylidyne, with $(C_{1-3})$ being particularly preferred. Also preferred are saturated alkanylidyne radicals, e.g., methanylidyne, ethanylidyne, propan-1-ylidyne, butan-1-ylidyne, 2-methyl-propan-1-ylidyne, and the like.

"Heteroalkyl, Heteroalkanyl, Heteroalkenyl, Heteroalkynyl Heteroalkylidene, Heteroalkylidyne, Heteroalkyldiyl, Vic Heteralkyldiyl, Gem Heteroalkyldiyl, Heteroalkyleno and Heteroalkyldiylidene:" refer to alkyl, alkanyl, alkenyl, alkynyl, alkylidene, alkylidyne, alkyldiyl, vic alkyldiyl, gem alkyldiyl, alkyleno and alkyldiylidene radicals, respectively, in which one or more carbon atoms (and any necessary associated hydrogen atoms) are independently replaced with the same or different heteroatoms (including any necessary hydrogen or other atoms). Typical heteroatoms to replace the carbon atom(s) include, but are not limited to, N, P, O, S, Si, etc. Preferred heteroatoms are O, N and S. Thus, heteroalkyl, heteroalkanyl, heteroalkenyl, heteroalkynyl, heteroalkylidene, heteroalkylidyne, heteroalkyldiyl, vic heteroalkyldiyl, gem heteroalkyldiyl, heteroalkyleno and heteroalkyldiylidene radicals can contain one or more of the same or different heteroatomic groups, including, by way of example and not limitation, epoxy (—O—), epidioxy (—O—O—), thioether (—S—), epidithio (—SS—), epoxythio (—O—S—), epoxyimino (—O—NR'-), imino (—NR'-), biimmino (—NR'-NR'-), azino (=N—N=), azo (—N=N—), azoxy (—N—O—N—), azimino (—NR'-N=N—), phosphano (—PH—), $\lambda^4$-sulfano (—SH$_2$—), sulfonyl (—S(O)$_2$—), and the like, where each R' is independently hydrogen or (C$_1$-C$_6$) alkyl.

"Parent Aromatic Ring System:" refers to an unsaturated cyclic or polycyclic ring system having a conjugated π electron system. Specifically included within the definition of "parent aromatic ring system" are fused ring systems in which one or more rings are aromatic and one or more rings are saturated or unsaturated, such as, for example, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like "Aryl:" refers to a monovalent aromatic hydrocarbon radical derived by the removal of one hydrogen atom from a single carbon atom of a parent aromatic ring system. Typical aryl groups include, but are not limited to, radicals derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In preferred embodiments, the aryl group is (C$_{5-20}$) aryl, with (C$_{5-10}$) being particularly preferred. Particularly preferred aryl groups are phenyl and naphthyl groups.

"Arylalkyl:" refers to an acyclic alkyl group in which one of the hydrogen atoms bonded to a carbon atom, typically a terminal carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylakenyl and/or arylalkynyl is used. [In preferred embodiments, the arylalkyl group is (C$_{6-26}$) arylalkyl, e.g., the alkanyl, alkenyl or alkynyl moiety of the arylalkyl group is (C$_{1-6}$) and the aryl moiety is (C$_{5-20}$). In particularly preferred embodiments the arylalkyl group is (C$_{6-13}$), e.g., the alkanyl, alkenyl or alkynyl moiety of the arylalkyl group is (C$_{1-3}$) and the aryl moiety is (C$_{5-10}$). Even more preferred arylalkyl groups are phenylalkanyls.

"Alkanyloxy:" refers to a saturated branched, straight-chain or cyclic monovalent hydrocarbon alcohol radical derived by the removal of the hydrogen atom from the hydroxide oxygen of the alcohol. Typical alkanyloxy groups include, but are not limited to, methanyl; ethanyloxy; propanyloxy groups such as propan-1-yloxy (CH$_3$CH$_2$CH$_2$O—), propan-2-yloxy ((CH$_3$)$_2$CHO—), cyclopropan-1-yloxy, etc.; butyanyloxy groups such as butan-1-yloxy, butan-2-yloxy, 2-methyl-propan-1-yloxy, 2-methyl-propan-2-yloxy, cyclobutan-1-yloxy, etc.; and the like. In preferred embodiments, the alkanyloxy groups are (C$_{1-8}$) alkanyloxy groups, with (C$_{1-3}$) being particularly preferred.

"Parent Heteroaromatic Ring System:" refers to a parent aromatic ring system in which one or more carbon atoms are each independently replaced with a heteroatom. Typical heteratoms to replace the carbon atoms include, but are not limited to, N, P, O, S, Si etc. Specifically included within the definition of "parent heteroaromatic ring systems" are fused ring systems in which one or more rings are aromatic and one or more rings are saturated or unsaturated, such as, for example, arsindole, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Heteroaryl:" refers to a monovalent heteroaromatic radical derived by the removal of one hydrogen atom from a single atom of a parent heteroaromatic ring system. Typical heteroaryl groups include, but are not limited to, radicals derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In preferred embodiments, the heteroaryl group is a 5-20 membered heteroaryl, with 5-10 membered heteroaryl being particularly preferred. Specific preferred heteroaryls for the present invention are quinoline, isoquinoline, pyridine, pyrimidine, furan, thiophene and imidazole.

"Substituted:" refers to a radical in which one or more hydrogen atoms are each independently replaced with the same or different substituent(s). Typical substituents include, but are not limited to, —X, —R, —O$^-$, =O, —OR, —O—OR, —SR, —S$^-$, =S, —NRR, =NR, —CX$_3$, —CN, —OCN, —SCN, —NCO, —NCS, —NO, —NO$_2$, =N$_2$, —N$_3$, —NHOH, —S(O)$_2$O$^-$, —S(O)$_2$OH, —S(O)$_2$R, —P(O)(O$^-$)$_2$, —P(O)(OH)$_2$, —C(O)R, —C(O)X, —C(S)R, —C(S)X, —C(O)OR, —C(O)O$^-$, —C(S)OR, —C(O)SR, —C(S)SR, —C(O)NRR, —C(S)NRR and —C(NR)NRR, where each X is independently a halogen (preferably —F, —Cl or —Br) and each R is independently —H, alkyl, alkanyl, alkenyl, alkynyl, alkylidene, alkylidyne, aryl, arylalkyl, arylheteroalkyl, heteroaryl, heteroarylalkyl or heteroaryl-heteroalkyl, as defined herein. Preferred substituents include hydroxy, halogen, $C_{1-8}$alkyl, $C_{1-8}$alkanyloxy, fluorinated alkanyloxy, fluorinated alkyl, $C_{1-8}$alkylthio, $C_{3-8}$cycloalkyl, $C_{3-8}$cycloalkanyloxy, nitro, amino, $C_{1-8}$alkylamino, $C_{1-8}$dialkylamino, $C_{3-8}$cycloalkylamino, cyano, carboxy, $C_{1-7}$alkanyloxycarbonyl, $C_{1-7}$alkylcarbonyloxy, formyl, carbamoyl, phenyl, aroyl, carbamoyl, amidino, $(C_{1-8}$alkylamino)carbonyl, (arylamino)carbonyl and aryl($C_{1-8}$alkyl)carbonyl.

"Aroyl" refers to arylacyl substituents.

"Acyl" refers to alkylcarbonyl substituents.

With reference to substituents, the term "independently" means that when more than one of such substituent is possible, such substituents may be the same or different from each other.

Throughout this disclosure, the terminal portion of the designated side chain is described first, followed by the adjacent functionality toward the point of attachment. Thus, for example, a "phenyl$C_{1-6}$alkanylaminocarbonyl$C_{1-6}$alkyl" substituent refers to a group of the formula

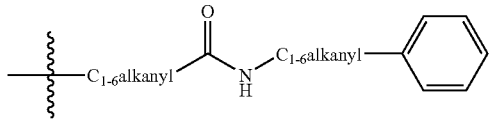

The present invention is directed to a compound of Formula (I):

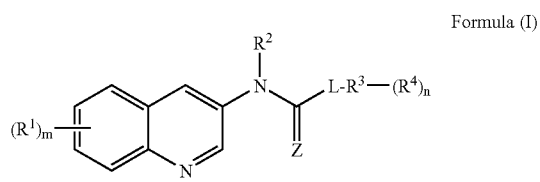

wherein:

$R^1$ is a substituent independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl; wherein the heteroatom contained in the quinoline ring of Formula (I) is optionally substituted with an oxo substituent;

m is 0, 1 or 2;

$R^2$ is hydrogen or $C_{1-8}$alkanyl;

L is a direct bond or $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R^3$ is selected from the group consisting of pyrrolyl, pyridyl, furyl, thienyl, phenyl and cyclohexyl;

$R^4$ is independently selected from the group consisting of $C_{4-8}$alkanyloxy, $C_{3-8}$cycloalkanyloxy, $C_{1-8}$alkanylamino, $C_{3-8}$cycloalkanylamino, $C_{3-14}$ cyclic heteroalkanyl and —N($R^5$)($R^6$); or when n is 2 or 3, optionally two $R^4$ substituents taken together form a $C_{3-14}$ cyclic heteroalkyl or $C_{3-14}$ cyclic alkanyl;

$R^5$ is hydrogen, $C_{1-16}$alkyl, alkanylcarbonyl or arylcarbonyl;

$R_6$ is $C_{4-16}$ alkyl, alkanylcarbonyl, $C_{1-3}$alkyl substituted with a substituent selected from the group consisting of pyrrolyl, pyridyl, furyl, thienyl, phenyl, and furyl, or arylcarbonyl; or optionally $R^6$ and one of $R^4$ taken together form a saturated or partially unsaturated cyclic heteroalkyl or a heteroaryl; or optionally $R^5$ and $R^6$ taken together form a bridged or non-bridged cyclic heteroalkanyl, wherein said heteroalkanyl is optionally substituted with $C_{1-6}$alkanylcarbonyl;

wherein the alkanyls in any of the foregoing alkanyl-containing substituents of $R^4$, $R^5$ or $R^6$ are optionally and independently substituted with pyrrolyl, pyridyl, furyl, thienyl, phenyl, furyl, $C_{1-4}$alkylpyrrolyl, $C_{1-4}$alkylpyridyl, $C_{1-4}$alkylthienyl, $C_{1-4}$alkylphenyl, or $C_{1-4}$alkylfuryl;

n is 1, 2 or 3;

Z is O or S; and enantiomers, diastereomers, tautomers, solvates, and pharmaceutically acceptable salts thereof.

In another embodiment, the present invention is directed to a compound of Formula (I) wherein:

$R^1$ is a substituent independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl; wherein the heteroatom contained in the quinoline ring of Formula (I) is optionally substituted with an oxo substituent;

m is 0, 1 or 2;

$R^2$ is hydrogen or $C_{1-8}$alkanyl;

L is a $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R^3$ is selected from the group consisting of pyrrolyl, pyridyl, furyl, thienyl, phenyl and cyclohexyl;

$R^4$ is independently selected from the group consisting of $C_{1-8}$alkanyl, $C_{4-8}$alkanyloxy, $C_{3-8}$cycloalkanyloxy, $C_{1-8}$alkanylamino, $C_{3-8}$cycloalkanylamino, $C_{3-14}$ cyclic heteroalkanyl and —N($R^5$)($R^6$); or when n is 2 or 3, optionally two $R^4$ substituents taken together form a $C_{3-14}$ cyclic heteroalkyl or $C_{3-14}$ cyclic alkanyl;

$R^5$ is hydrogen, $C_{1-16}$alkyl, alkanylcarbonyl or arylcarbonyl;

$R_6$ is $C_{4-16}$ alkyl, alkanylcarbonyl, $C_{1-3}$alkyl substituted with a substituent selected from the group consisting of pyrrolyl, pyridyl, furyl, thienyl, phenyl, and furyl, or arylcarbonyl; or optionally $R^6$ and one of $R^4$ taken together form a saturated or partially unsaturated cyclic heteroalkyl or a heteroaryl; or $R^5$ and $R^6$ optionally taken together form a bridged or non-bridged cyclic heteroalkanyl, wherein said heteroalkanyl is optionally substituted with $C_{1-6}$alkanylcarbonyl;

wherein the alkanyls in any of the foregoing alkanyl-containing substituents of $R^4$, $R^5$ or $R^6$ are optionally and independently substituted with pyrrolyl, pyridyl, furyl, thienyl, phenyl, furyl, $C_{1-4}$alkylpyrrolyl, $C_{1-4}$alkylpyridyl, $C_{1-4}$alkylthienyl, $C_{1-4}$alkylphenyl, or $C_{1-4}$alkylfuryl;

n is 1, 2 or 3;

Z is O or S; and enantiomers, diastereomers, tautomers, solvates, and pharmaceutically acceptable salts thereof.

In another embodiment, the present invention is directed to a compound of Formula (I) wherein:

$R^1$ is a substituent independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl; wherein the heteroatom contained in the quinoline ring of Formula (I) is optionally substituted with an oxo substituent;

m is 0, 1 or 2;

$R^2$ is hydrogen or $C_{1-8}$alkanyl;

L is a direct bond or $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R^3$ is selected from the group consisting of pyrrolyl, pyridyl, furyl, thienyl, phenyl and cyclohexyl;

$R^4$ is independently selected from the group consisting of $C_{1-8}$alkanyl, $C_{1-8}$alkanyloxy, $C_{3-8}$cycloalkanyloxy, $C_{1-8}$alkanylamino, $C_{3-8}$cycloalkanylamino, $C_{3-14}$ cyclic heteroalkanyl, $C_{1-6}$ fluorinated alkyl, and —N($R^5$)($R^6$); or when n is 2 or 3, optionally two $R^4$ substituents taken together form a $C_{3-14}$ cyclic heteroalkyl or $C_{3-14}$ cyclic alkanyl;

$R^5$ is hydrogen, $C_{1-16}$alkyl, alkanylcarbonyl or arylcarbonyl;

$R_6$ is $C_{4-16}$ alkyl, alkanylcarbonyl, $C_{1-3}$alkyl substituted with a substituent selected from the group consisting of pyrrolyl, pyridyl, furyl, thienyl, phenyl, and furyl, or arylcarbonyl; or optionally $R^6$ and one of $R^4$ taken together form a saturated or partially unsaturated cyclic heteroalkyl or a heteroaryl; or $R^5$ and $R^6$ optionally taken together form a bridged or non-bridged cyclic heteroalkanyl, wherein said heteroalkanyl is optionally substituted with $C_{1-6}$alkanylcarbonyl;

wherein the alkanyls in any of the foregoing alkanyl-containing substituents of $R^4$, $R^5$ or $R^6$ are optionally and independently substituted with pyrrolyl, pyridyl, furyl, thienyl, phenyl, furyl, $C_{1-4}$alkylpyrrolyl, $C_{1-4}$alkylpyridyl, $C_{1-4}$alkylthienyl, $C_{1-4}$alkylphenyl, or $C_{1-4}$alkylfuryl;

n is 2 or 3;

Z is O or S; and enantiomers, diastereomers, tautomers, solvates, and pharmaceutically acceptable salts thereof.

In another embodiment, the present invention is directed to a compound of Formula (I) wherein:

$R^1$ is a substituent independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl; wherein the heteroatom contained in the quinoline ring of Formula (I) is optionally substituted with an oxo substituent;

m is 0, 1 or 2;

$R^2$ is hydrogen or $C_{1-8}$alkanyl;

L is ethen-1,2-diyl;

$R^3$ is selected from the group consisting of pyrrolyl, pyridyl, furyl, thienyl, phenyl and cyclohexyl;

$R^4$ is independently selected from the group consisting of $C_{1-12}$alkanyl, $C_{4-8}$alkanyloxy, $C_{3-8}$cycloalkanyloxy, $C_{1-8}$alkanylamino, $C_{3-8}$cycloalkanylamino, $C_{3-14}$ cyclic heteroalkanyl, $C_{1-6}$ fluorinated alkyl, halogen, and —N($R^5$)($R^6$); or when n is 2 or 3, optionally two $R^4$ substituents taken together form a $C_{3-14}$ cyclic heteroalkyl or $C_{3-14}$ cyclic alkanyl;

$R^5$ is hydrogen, $C_{1-16}$alkyl, alkanylcarbonyl or arylcarbonyl;

$R_6$ is $C_{4-16}$ alkyl, alkanylcarbonyl, $C_{1-3}$alkyl substituted with a substituent selected from the group consisting of pyrrolyl, pyridyl, furyl, thienyl, phenyl, and furyl, or arylcarbonyl; or optionally $R^6$ and one of $R^4$ taken together form a saturated or partially unsaturated cyclic heteroalkyl or a heteroaryl; or $R^5$ and $R^6$ optionally taken together form a bridged or non-bridged cyclic heteroalkanyl, wherein said heteroalkanyl is optionally substituted with $C_{1-6}$alkanylcarbonyl;

wherein the alkanyls in any of the foregoing alkanyl-containing substituents of $R^4$, $R^5$ or $R^6$ are optionally and independently substituted with pyrrolyl, pyridyl, furyl, thienyl, phenyl, furyl, $C_{1-4}$alkylpyrrolyl, $C_{1-4}$alkylpyridyl, $C_{1-4}$alkylthienyl, $C_{1-4}$alkylphenyl, or $C_{1-4}$alkylfuryl;

n is 1, 2 or 3;

Z is O or S; and enantiomers, diastereomers, tautomers, solvates, and pharmaceutically acceptable salts thereof.

In another embodiment, the present invention is directed to a compound of Formula (I) wherein:

$R^1$ is a substituent independently selected from the group consisting of hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl; wherein the heteroatom contained in the quinoline ring of Formula (I) is optionally substituted with an oxo substituent;

m is 1 or 2;

$R^2$ is hydrogen or $C_{1-8}$alkanyl;

L is a direct bond or $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R^3$ is selected from the group consisting of pyrrolyl, pyridyl, furyl, thienyl, phenyl and cyclohexyl;

$R^4$ is independently selected from the group consisting of $C_{1-8}$alkanyl, $C_{1-8}$alkanyloxy, $C_{3-8}$cycloalkanyloxy, $C_{1-8}$alkanylamino, $C_{3-8}$cycloalkanylamino, $C_{3-14}$ cyclic heteroalkanyl, $C_{1-6}$ fluorinated alkyl, and —N($R^5$)($R^6$); or when n is 2 or 3, optionally two $R^4$ substituents taken together form a $C_{3-14}$ cyclic heteroalkyl or $C_{3-14}$ cyclic alkanyl;

$R^5$ is hydrogen, $C_{1-16}$alkyl, alkanylcarbonyl or arylcarbonyl;

$R_6$ is $C_{4-16}$ alkyl, alkanylcarbonyl, $C_{1-3}$alkyl substituted with a substituent selected from the group consisting of pyrrolyl, pyridyl, furyl, thienyl, phenyl, and furyl, or arylcarbonyl; or optionally $R^6$ and one of $R^4$ taken together form a saturated or partially unsaturated cyclic heteroalkyl or a heteroaryl; or $R^5$ and $R^6$ optionally taken together form a bridged or non-bridged cyclic heteroalkanyl, wherein said heteroalkanyl is optionally substituted with $C_{1-6}$alkanylcarbonyl;

wherein the alkanyls in any of the foregoing alkanyl-containing substituents of $R^4$, $R^5$ or $R^6$ are optionally and independently substituted with pyrrolyl, pyridyl, furyl, thienyl, phenyl, furyl, $C_{1-4}$alkylpyrrolyl, $C_{1-4}$alkylpyridyl, $C_{1-4}$alkylthienyl, $C_{1-4}$alkylphenyl, or $C_{1-4}$alkylfuryl;

n is 1, 2 or 3;

Z is O or S; and enantiomers, diastereomers, tautomers, solvates, and pharmaceutically acceptable salts thereof.

The present invention is directed to a compound of Formula (I) wherein:

$R^1$ is a substituent independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl; wherein the heteroatom contained in the quinoline ring of Formula (I) is optionally substituted with an oxo substituent;

m is 0, 1 or 2;

$R^2$ is hydrogen or $C_{1-8}$alkanyl;

L is a direct bond;

$R^3$ is selected from the group consisting of pyrrolyl, pyridyl, furyl, thienyl, and cyclohexyl;

$R^4$ is selected from the group consisting of $C_{1-8}$alkanyl, $C_{4-8}$alkanyloxy, $C_{3-8}$cycloalkanyloxy, $C_{1-8}$alkanylamino, $C_{3-8}$cycloalkanylamino, $C_{3-14}$ cyclic heteroalkanyl, $C_{1-6}$ fluorinated alkyl, and —N($R^5$)($R^6$), wherein the alkanyls in any of the foregoing alkanyl-containing substituents of $R^4$ is optionally substituted with thienyl or phenyl; or when n is 2 or 3, optionally two $R^4$ substituents taken together form a $C_{3-14}$ cyclic heteroalkyl or $C_{3-14}$ cyclic alkanyl;

$R^5$ is hydrogen, $C_{1-16}$alkyl, alkanylcarbonyl or arylcarbonyl;

$R_6$ is $C_{4-16}$ alkyl, alkanylcarbonyl, $C_{1-3}$alkyl substituted with a substituent selected from the group consisting of pyrrolyl, pyridyl, furyl, thienyl, phenyl, and furyl, or arylcarbonyl; or optionally $R^6$ and one of $R^4$ taken together form a saturated or partially unsaturated cyclic heteroalkyl or a heteroaryl; or $R^5$ and $R^6$ optionally taken together form a bridged or non-bridged cyclic heteroalkanyl, wherein said heteroalkanyl is optionally substituted with $C_{1-6}$alkanylcarbonyl;

wherein the alkanyls in any of the foregoing alkanyl-containing substituents of $R^4$, $R^5$ or $R^6$ are optionally and independently substituted with pyrrolyl, pyridyl, furyl, thienyl, phenyl, furyl, $C_{1-4}$alkylpyrrolyl, $C_{1-4}$alkylpyridyl, $C_{1-4}$alkylthienyl, $C_{1-4}$alkylphenyl, or $C_{1-4}$alkylfuryl;

n is 1, 2 or 3;

Z is O or S; and enantiomers, diastereomers, tautomers, solvates, and pharmaceutically acceptable salts thereof.

Embodiments of the present invention also include those wherein for compounds of Formula (I):

a) L is a direct bond;
b) L is $C_{1-4}$alkyldiyl;
c) L is ethen-1,2-diyl;
d) L is ethen-1,2-diyl, and one $R^4$ is $C_{1-6}$ fluorinated alkanyl;
e) L is ethen-1,2-diyl, and one $R^4$ is halogen;
f) L is ethen-1,2-diyl, n is 2, one $R^4$ is halogen and the other $R^4$ is $C_{1-6}$ fluorinated alkanyl;
g) $R^3$ is phenyl;
h) $R^3$ is pyridyl;
i) $R^3$ is thienyl;
j) $R^3$ is furyl;
k) $R^3$ is cyclohexyl;
l) n is 1;
m) n is 2 or 3 and $R^4$ is $C_{1-12}$alkanyl;
n) $R^4$ is —N($R^5$)($R^6$);
o) L is $C_{1-4}$alkyldiyl, $R^3$ is phenyl, n is 1 and $R^4$ is $C_{1-12}$alkanyl;
p) $R^3$ is phenyl, n is 1 and $R^4$ is —N($R^5$)($R^6$);
q) $R^3$ is phenyl, n is 2 or 3, and two $R^4$ substituents taken together form a $C_{3-14}$ cyclic heteroalkyl or $C_{3-14}$ cyclic alkyl;
r) Z is O;

s) m is 0;

t) $R^2$ is hydrogen; and u) combinations of a) through t) above.

The present invention is also directed to a compound selected from the group consisting of 1-Acetyl-2,3-dihydro-1H-indole-5-carboxylic acid quinolin-3-ylamide;
1-Benzoyl-2,3-dihydro-1H-indole-5-carboxylic acid quinolin-3-ylamide;
1-Butyryl-2,3-dihydro-1H-indole-5-carboxylic acid quinolin-3-ylamide;
1-Cyclohexanecarbonyl-2,3-dihydro-1H-indole-5-carboxylic acid quinolin-3-ylamide;
1-Cyclohexyl-2,3-dihydro-1H-indole-5-carboxylic acid quinolin-3-ylamide;
1-Isopropyl-2-trifluoromethyl-1H-benzoimidazole-5-carboxylic acid quinolin-3-ylamide;
1-Methyl-1,2,3,4-tetrahydro-quinoline-6-carboxylic acid quinolin-3-ylamide;
1-Methyl-2,3-dihydro-1H-indole-5-carboxylic acid quinolin-3-ylamide;
1-Pentyl-1,2,3,4-tetrahydro-quinoline-6-carboxylic acid quinolin-3-ylamide;
1-Pentyl-1H-indole-5-carboxylic acid quinolin-3-ylamide;
1-Pentyl-2,3-dihydro-1H-indole-5-carboxylic acid quinolin-3-ylamide;
1-Propyl-2,3-dihydro-1H-indole-5-carboxylic acid quinolin-3-ylamide;
2-(4-Dipentylamino-phenyl)-N-quinolin-3-yl-acetamide;
2-(4-Pentyl-phenyl)-N-quinolin-3-yl-acetamide;
2-(4-tert-Butyl-phenyl)-N-quinolin-3-yl-acetamide;
2-(Heptyl-methyl-amino)-N-quinolin-3-yl-benzamide;
2-(Methyl-pentyl-amino)-N-quinolin-3-yl-benzamide;
2,3-Dihydro-1H-indole-5-carboxylic acid quinolin-3-ylamide;
2-{4-(Methyl-pentyl-amino)-phenyl}-N-quinolin-3-yl-acetamide;
2-Chloro-4-(cyclohexylmethyl-amino)-N-quinolin-3-yl-benzamide;
2-Chloro-4-pentylamino-N-quinolin-3-yl-benzamide;
2-Heptylamino-N-quinolin-3-yl-benzamide;
2-Pentylamino-N-quinolin-3-yl-benzamide;
3-(1-Cyclohexyl-2,3-dihydro-1H-indol-5-yl)-N-quinolin-3-yl-propionamide;
3-(1-Cyclohexylmethyl-2,3-dihydro-1H-indol-5-yl)-N-quinolin-3-yl-propionamide;
3-(1-Propyl-1H-indol-5-yl)-N-quinolin-3-yl-propionamide;
3-(1-Propyl-2,3-dihydro-1H-indol-5-yl)-N-quinolin-3-yl-propionamide;
3-(2,2-Dimethyl-chroman-6-yl)-N-quinolin-3-yl-acrylamide;
3-(2,2-Dimethyl-chroman-6-yl)-N-quinolin-3-yl-propionamide;
3-(4-Azepan-1-yl-phenyl)-N-quinolin-3-yl-acrylamide;
3-(4-Azepan-1-yl-phenyl)-N-quinolin-3-yl-propionamide;
3-(4-Cyclohexylmethyl-phenyl)-N-quinolin-3-yl-propionamide;
3-(4-Dipentylamino-phenyl)-N-quinolin-3-yl-propionamide;
3-(4-Pentyl-phenyl)-N-quinolin-3-yl-acrylamide;
3-(4-Pentyl-phenyl)-N-quinolin-3-yl-propionamide;
3-(4-sec-Butyl-phenyl)-N-quinolin-3-yl-propionamide;
3-(4-tert-Butyl-phenyl)-N-quinolin-3-yl-acrylamide;
3-(4-tert-Butyl-phenyl)-N-quinolin-3-yl-propionamide;
3-(Cyclohexyl-methyl-amino)-N-quinolin-3-yl-benzamide;
3-(Heptyl-methyl-amino)-N-quinolin-3-yl-benzamide;
3-(Methyl-pentyl-amino)-N-quinolin-3-yl-benzamide;
3,4,5,6-Tetrahydro-2H-[1,2']bipyridinyl-5'-carboxylic acid quinolin-3-ylamide;
3,4,5,6-Tetrahydro-2H-{1,2'}bipyridinyl-5'-carboxylic acid quinolin-3-ylamide;
3-[4-(Methyl-phenethyl-amino)-phenyl]-N-quinolin-3-yl-propionamide;
3-{4-(1,1-Dimethyl-3-phenyl-propyl)-phenyl}-N-quinolin-3-yl-propionamide;
3-{4-(1,1-Dimethyl-pentyl)-2,6-dimethoxy-phenyl}-N-quinolin-3-yl-propionamide;
3-{4-(1,1-Dimethyl-pentyl)-phenyl}-N-quinolin-3-yl;
3-{4-(1,1-Dimethyl-propyl)-2,6-dimethoxy-phenyl}-N-quinolin-3-yl-propionamide;
3-{4-(1,1-Dimethyl-propyl)-phenyl}-N-quinolin-3-yl-propionamide;
3-{4-(1-Cyclohexyl-1-methyl-ethyl)-phenyl}-N-quinolin-3-yl-propionamide;
3-{4-(1-Methyl-pentyl)-phenyl}-N-quinolin-3-yl-propionamide;
3-{4-(1-Methyl-pentyl)-phenyl}-N-quinolin-3-yl-propionamide;
3-{4-(Benzyl-methyl-amino)-phenyl}-N-quinolin-3-yl-propionamide;
3-{4-(Cyclohexyl-methyl-amino)-phenyl}-N-quinolin-3-yl-acrylamide;
3-{4-(Cyclohexyl-methyl-amino)-phenyl}-N-quinolin-3-yl-propionamide;
3-{4-(Cyclohexylmethyl-methyl-amino)-phenyl}-N-quinolin-3-yl-propionamide;
3-{4-(Methyl-pentyl-amino)-phenyl}-N-quinolin-3-yl-acrylamide;
3-{4-(Methyl-pentyl-amino)-phenyl}-N-quinolin-3-yl-propionamide;
3-{4-(Methyl-propyl-amino)-phenyl}-N-quinolin-3-yl-propionamide;
3-{5-(1,1-Dimethyl-propyl)-thiophen-2-yl}-N-quinolin-3-yl-propionamide;
3-Cyclohexylamino-N-quinolin-3-yl-benzamide;
3-Dipentylamino-N-quinolin-3-yl-benzamide;
3-Heptylamino-N-quinolin-3-yl-benzamide;
3-Indan-5-yl-N-quinolin-3-yl-propionamide;
3-Methyl-4-(methyl-pentyl-amino)-N-quinolin-3-yl-benzamide;
3-Methyl-4-pentylamino-N-quinolin-3-yl-benzamide;
3-Pentylamino-N-quinolin-3-yl-benzamide;
4-(1,3-Dihydro-isoindol-2-yl)-N-quinolin-3-yl-benzamide;
4-(1,4-Dioxa-8-aza-spiro[4.5]dec-8-yl)-N-quinolin-3-yl-benzamide;
4-(2,6-Dimethyl-morpholin-4-yl)-N-quinolin-3-yl-benzamide;
4-(3,5-Dimethyl-piperidin-1-yl)-N-quinolin-3-yl-benzamide;
4-(3-Aza-bicyclo{3.3.1}non-3-yl)-N-quinolin-3-yl-benzamide;
4-(3-Methyl-piperidin-1-yl)-N-quinolin-3-yl-benzamide;
4-(4-Benzoyl-piperidin-1-yl)-N-quinolin-3-yl-benzamide;
4-(4-Benzyl-piperidin-1-yl)-N-quinolin-3-yl-benzamide;
4-(4-Phenylacetyl-piperazin-1-yl)-N-quinolin-3-yl-benzamide;
4-(4-Phenyl-piperidin-1-yl)-N-quinolin-3-yl-benzamide;
4-(4-Propyl-piperidin-1-yl)-N-quinolin-3-yl-benzamide;
4-(Acetyl-cyclohexyl-amino)-N-quinolin-3-yl-benzamide;
4-(Benzyl-methyl-amino)-N-quinolin-3-yl-benzamide;
4-(Benzyl-pentyl-amino)-N-quinolin-3-yl-benzamide;
4-(Cycloheptyl-methyl-amino)-N-quinolin-3-yl-benzamide;
4-(Cyclohexanecarbonyl-methyl-amino)-N-quinolin-3-yl-benzamide;

4-(Cyclohexyl-ethyl-amino)-N-quinolin-3-yl-benzamide;
4-(Cyclohexylmethyl-amino)-3-methyl-N-quinolin-3-yl-benzamide;
4-(Cyclohexyl-methyl-amino)-3-methyl-N-quinolin-3-yl-benzamide;
4-(Cyclohexyl-methyl-amino)-N-methyl-N-quinolin-3-yl-benzamide;
4-(Cyclohexyl-methyl-amino)-N-quinolin-3-yl-benzamide;
4-(Cyclohexylmethyl-methyl-amino)-3-methyl-N-quinolin-3-yl-benzamide;
4-(Cyclohexylmethyl-methyl-amino)-N-quinolin-3-yl-benzamide;
4-(Cyclohexylmethyl-phenethyl-amino)-N-quinolin-3-yl-benzamide;
4-(Cyclohexyl-propyl-amino)-N-quinolin-3-yl-benzamide;
4-(Cyclopentyl-methyl-amino)-N-quinolin-3-yl-benzamide;
4-(Dec-4-enyl-methyl-amino)-N-quinolin-3-yl-benzamide;
4-(Hept-4-enyl-methyl-amino)-N-quinolin-3-yl-benzamide;
4-(Heptyl-methyl-amino)-N-quinolin-3-yl-benzamide;
4-(Methyl-butyl-amino)-N-quinolin-3-yl-benzamide;
4-(Methyl-hexyl-amino)-N-quinolin-3-yl-benzamide;
4-(Methyl-non-6-enyl-amino)-N-quinolin-3-yl-benzamide;
4-(Methyl-nonyl-amino)-N-quinolin-3-yl-benzamide;
4-(Methyl-pentyl-amino)-N-quinolin-3-yl-benzamide;
4-(Methyl-phenethyl-amino)-N-quinolin-3-yl-benzamide;
4-(Methyl-propyl-amino)-N-quinolin-3-yl-benzamide;
4-(Methyl-tetradecyl-amino)-N-quinolin-3-yl-benzamide;
4-(Octyl-methyl-amino)-N-quinolin-3-yl-benzamide;
4-(Phenethyl-propyl-amino)-N-quinolin-3-yl-benzamide;
4-[1,4']Bipiperidinyl-1'-yl-N-quinolin-3-yl-benzamide;
4-{(3,3-Dimethyl-butyl)-methyl-amino}-N-quinolin-3-yl-benzamide;
4-{4-(1,1-Dimethyl-pentyl)-phenyl}-but-3-enoic acid quinolin-3-ylamide;
4-{4-(1,1-Dimethyl-pentyl)-phenyl}-N-quinolin-3-yl-butyramide;
4-{4-(1,1-Dimethyl-propyl)-phenyl}-but-3-enoic acid quinolin-3-ylamide;
4-{4-(1,1-Dimethyl-propyl)-phenyl}-N-quinolin-3-yl-butyramide;
4-{Methyl-(3-methyl-butyl)-amino}-N-quinolin-3-yl-benzamide;
4-{Methyl-(3-phenyl-allyl)-amino}-N-quinolin-3-yl-benzamide;
4-{Methyl-(3-phenyl-propyl)-amino}-N-quinolin-3-yl-benzamide;
4-{Methyl-(tetrahydro-pyran-4-yl)-amino}-N-quinolin-3-yl-benzamide;
4-{Methyl-{3-(5-methyl-furan-2-yl)-butyl}-amino}-N-quinolin-3-yl-benzamide;
4-Azepan-1-yl-N-quinolin-3-yl-benzamide;
4-Azepan-1-yl-N-quinolin-3-yl-benzamide;
4-Azocan-1-yl-N-quinolin-3-yl-benzamide;
4-Azonan-1-yl-N-quinolin-3-yl-benzamide;
4-Benzyl-3,4,5,6-tetrahydro-2H-{1,2'}bipyridinyl-5'-carboxylic acid quinolin-3-ylamide;
4-Butoxy-N-quinolin-3-yl-benzamide;
4-Butyl-cyclohexanecarboxylic acid quinolin-3-ylamide;
4-Butyl-cyclohexanecarboxylic acid quinolin-3-ylamide;
4-Cycloheptylamino-N-quinolin-3-yl-benzamide;
4-Cyclohexylamino-N-methyl-N-quinolin-3-yl-benzamide;
4-Cyclohexylamino-N-quinolin-3-yl-benzamide;
4-Cyclopentylamino-N-quinolin-3-yl-benzamide;
4-Dibenzylamino-N-quinolin-3-yl-benzamide;
4-Dibutylamino-N-quinolin-3-yl-benzamide;
4-Dihexylamino-N-quinolin-3-yl-benzamide;
4-Dipentylamino-N-quinolin-3-yl-benzamide;
4-Dipropylamino-N-quinolin-3-yl-benzamide;
4-Morpholin-4-yl-N-quinolin-3-yl-benzamide;
4-Pentylamino-N-quinolin-3-yl-benzamide;
4-Phenethylamino-N-quinolin-3-yl-benzamide;
4-piperazin-1-yl-N-quinolin-3-yl-benzamide;
4-Piperidin-1-yl-N-quinolin-3-yl-benzamide;
4-Propyl-3,4,5,6-tetrahydro-2H-{1,2'}bipyridinyl-5'-carboxylic acid quinolin-3-ylamide;
4-Pyrrolidin-1-yl-N-quinolin-3-yl-benzamide;
4-tert-Butyl-cyclohexanecarboxylic acid quinolin-3-ylamide;
4-tert-Butyl-cyclohexanecarboxylic acid quinolin-3-ylamide;
5,5,8,8-Tetramethyl-5,6,7,8-tetrahydro-naphthalene-2-carboxylic acid quinolin-3-ylamide;
5,6,7,8-Tetrahydro-naphthalene-2-carboxylic acid quinolin-3-ylamide;
5-Chloro-1H-indole-2-carboxylic acid quinolin-3-ylamide;
5-Pentyl-thiophene-2-carboxylic acid quinolin-3-ylamide;
6-(3-Aza-bicyclo{3.3.1}non-3-yl)-N-quinolin-3-yl-nicotinamide;
6-(Benzyl-methyl-amino)-N-quinolin-3-yl-nicotinamide;
6-(Cyclohexyl-methyl-amino)-N-quinolin-3-yl-nicotinamide;
6-(Cyclohexyl-methyl-amino)-N-quinolin-3-yl-nicotinamide;
6-(Heptyl-methyl-amino)-N-quinolin-3-yl-nicotinamide;
6-(Methyl-pentyl-amino)-N-quinolin-3-yl-nicotinamide;
6-(Methyl-phenethyl-amino)-N-quinolin-3-yl-nicotinamide;
6-Azepan-1-yl-N-quinolin-3-yl-nicotinamide;
6-Azocan-1-yl-N-quinolin-3-yl-nicotinamide;
6-Cyclohexylamino-N-quinolin-3-yl-nicotinamide;
6-Pentylamino-N-quinolin-3-yl-nicotinamide;
cis-4-(Octahydro-isoquinolin-2-yl)-N-quinolin-3-yl-benzamide;
cis-6-(Octahydro-isoquinolin-2-yl)-N-quinolin-3-yl-nicotinamide;
N-Quinolin-3-yl-3-(3-trifluoromethyl-phenyl)-acrylamide;
N-Quinolin-3-yl-3-(4-tricyclo{5.3.1.13.9}dodec-1-yl-phenyl)-propionamide;
N-Quinolin-3-yl-3-(4-trifluoromethyl-phenyl)-acrylamide;
N-Quinolin-3-yl-3-(5,5,8,8-tetramethyl-5,6,7,8-tetrahydro-naphthalen-2-yl)-propionamide;
N-Quinolin-3-yl-3-(5,6,7,8-tetrahydro-naphthalen-2-yl)-propionamide;
N-Quinolin-3-yl-4-(tetrahydro-pyran-4-ylamino)-benzamide;
N-Quinolin-3-yl-4-thiomorpholin-4-yl-benzamide;
R-4-{(3,7-Dimethyl-oct-6-enyl)-methyl-amino}-N-quinolin-3-yl-benzamide;
S-4-{(3,7-Dimethyl-oct-6-enyl)-methyl-amino}-N-quinolin-3-yl-benzamide;
trans-4-(Octahydro-isoquinolin-2-yl)-N-quinolin-3-yl-benzamide;
trans-6-(Octahydro-isoquinolin-2-yl)-N-quinolin-3-yl-nicotinamide
4-tert-Butyl-N-(4-hydroxy-quinolin-3-yl)-benzamide;
3-(4-tert-Butyl-phenyl)-N-(4-hydroxy-quinolin-3-yl)-acrylamide;
N-Quinolin-3-yl-3-(5,5,8,8-tetramethyl-5,6,7,8-tetrahydro-naphthalen-2-yl)-acrylamide;
N-(4-Chloro-quinolin-3-yl)-3-(5,5,8,8-tetramethyl-5,6,7,8-tetrahydro-naphthalen-2-yl)-acrylamide;
N-(4-Chloro-quinolin-3-yl)-4-(cyclohexyl-methyl-amino)-benzamide;
N-(2-Chloro-quinolin-3-yl)-4-(cyclohexyl-methyl-amino)-benzamide;

4-tert-Butyl-N-(2-methoxy-quinolin-3-yl)-benzamide;
4-Azepan-1-yl-N-(4-chloro-quinolin-3-yl)-benzamide;
4-(3-Aza-bicyclo[3.2.2]non-3-yl)-N-(2-chloro-quinolin-3-yl)-benzamide;
4-Azepan-1-yl-N-(2-chloro-quinolin-3-yl)-benzamide;
4-(3-Aza-bicyclo[3.2.2]non-3-yl)-N-(4-chloro-quinolin-3-yl)-benzamide;
3-(1-Cyclohexyl-2,3-dihydro-1H-indol-5-yl)-N-quinolin-3-yl-acrylamide;
1-Cyclohexyl-2,3-dihydro-1H-indole-5-carboxylic acid (2-chloro-quinolin-3-yl)-amide;
N-(2-Chloro-quinolin-3-yl)-3-(1-cyclohexyl-2,3-dihydro-1H-indol-5-yl)-acrylamide;
3-(1-Cyclohexyl-1H-indol-5-yl)-N-quinolin-3-yl-acrylamide;
N-(4-Chloro-quinolin-3-yl)-3-(1-cyclohexyl-1H-indol-5-yl)-acrylamide;
1-Cyclohexyl-1H-indole-5-carboxylic acid (4-chloro-quinolin-3-yl)-amide;
1-Cyclohexyl-1H-indole-5-carboxylic acid quinolin-3-ylamide;
1-Cyclohexyl-1H-indole-5-carboxylic acid (2-chloro-quinolin-3-yl)-amide;
N-(2-Chloro-quinolin-3-yl)-3-(1-cyclohexyl-1H-indol-5-yl)-acrylamide;
4-(Cyclohexyl-methyl-amino)-N-(8-fluoro-quinolin-3-yl)-benzamide;
4-Azocan-1-yl-N-(8-fluoro-quinolin-3-yl)-benzamide;
4-(3-Aza-bicyclo[3.2.2]non-3-yl)-N-(8-fluoro-quinolin-3-yl)-benzamide;
4-(3-Aza-bicyclo[3.2.2]non-3-yl)-N-(8-trifluoromethyl-quinolin-3-yl)-benzamide;
4-(Cyclohexyl-methyl-amino)-N-(8-trifluoromethyl-quinolin-3-yl)-benzamide;
4-(Cyclohexyl-methyl-amino)-N-(6-fluoro-quinolin-3-yl)-benzamide;
4-Azocan-1-yl-N-(6-fluoro-quinolin-3-yl)-benzamide;
4-(3-Aza-bicyclo[3.2.2]non-3-yl)-N-(6-fluoro-quinolin-3-yl)-benzamide;
4-(3-Aza-bicyclo[3.2.2]non-3-yl)-N-(7-trifluoromethyl-quinolin-3-yl)-benzamide;
4-Azocan-1-yl-N-(7-trifluoromethyl-quinolin-3-yl)-benzamide;
4-(Cyclohexyl-methyl-amino)-N-(7-trifluoromethyl-quinolin-3-yl)-benzamide;
4-Azocan-1-yl-N-(5-fluoro-quinolin-3-yl)-benzamide;
4-(3-Aza-bicyclo[3.2.2]non-3-yl)-N-(5-fluoro-quinolin-3-yl)-benzamide;
3-Phenyl-propynoic acid quinolin-3-ylamide;
trans-2-Phenyl-cyclopropanecarboxylic acid quinolin-3-ylamide;
3-(4-tert-Butyl-phenyl)-propynoic acid quinolin-3-ylamide; and
2-(4-tert-Butyl-phenyl)-cyclopropanecarboxylic acid quinolin-3-ylamide.

The present invention is also directed to a compound selected from the group consisting of
1-Cyclohexyl-2,3-dihydro-1H-indole-5-carboxylic acid quinolin-3-ylamide;
1-Pentyl-1,2,3,4-tetrahydro-quinoline-6-carboxylic acid quinolin-3-ylamide;
1-Pentyl-2,3-dihydro-1H-indole-5-carboxylic acid quinolin-3-ylamide;
1-Propyl-2,3-dihydro-1H-indole-5-carboxylic acid quinolin-3-ylamide;
3-(4-sec-Butyl-phenyl)-N-quinolin-3-yl-propionamide;
3-(4-tert-Butyl-phenyl)-N-quinolin-3-yl-acrylamide;
3-(4-tert-Butyl-phenyl)-N-quinolin-3-yl-propionamide;
3,4,5,6-Tetrahydro-2H-{1,2'}bipyridinyl-5'-carboxylic acid quinolin-3-ylamide;
3-{4-(1,1-Dimethyl-3-phenyl-propyl)-phenyl}-N-quinolin-3-yl-propionamide;
3-{4-(1,1-Dimethyl-pentyl)-2,6-dimethoxy-phenyl}-N-quinolin-3-yl-propionamide;
3-{4-(1,1-Dimethyl-pentyl)-phenyl}-N-quinolin-3-yl;
3-{4-(1,1-Dimethyl-propyl)-2,6-dimethoxy-phenyl}-N-quinolin-3-yl-propionamide;
3-{4-(1,1-Dimethyl-propyl)-phenyl}-N-quinolin-3-yl-propionamide;
3-{4-(1-Cyclohexyl-1-methyl-ethyl)-phenyl}-N-quinolin-3-yl-propionamide;
3-{4-(1-Methyl-pentyl)-phenyl}-N-quinolin-3-yl-propionamide;
3-{5-(1,1-Dimethyl-propyl)-thiophen-2-yl}-N-quinolin-3-yl-propionamide;
4-(3-Aza-bicyclo{3.3.1}non-3-yl)-N-quinolin-3-yl-benzamide;
4-(4-Benzyl-piperidin-1-yl)-N-quinolin-3-yl-benzamide;
4-(Cycloheptyl-methyl-amino)-N-quinolin-3-yl-benzamide;
4-(Cyclohexyl-ethyl-amino)-N-quinolin-3-yl-benzamide;
4-(Cyclohexyl-methyl-amino)-3-methyl-N-quinolin-3-yl-benzamide;
4-(Cyclohexyl-methyl-amino)-N-quinolin-3-yl-benzamide;
4-(Cyclohexylmethyl-methyl-amino)-N-quinolin-3-yl-benzamide;
4-(Cyclopentyl-methyl-amino)-N-quinolin-3-yl-benzamide;
4-(Dec-4-enyl-methyl-amino)-N-quinolin-3-yl-benzamide;
4-(Hept-4-enyl-methyl-amino)-N-quinolin-3-yl-benzamide;
4-(Heptyl-methyl-amino)-N-quinolin-3-yl-benzamide;
4-(Methyl-non-6-enyl-amino)-N-quinolin-3-yl-benzamide;
4-(Methyl-nonyl-amino)-N-quinolin-3-yl-benzamide;
4-(Methyl-phenethyl-amino)-N-quinolin-3-yl-benzamide;
4-(Octyl-methyl-amino)-N-quinolin-3-yl-benzamide;
4-{(3,3-Dimethyl-butyl)-methyl-amino}-N-quinolin-3-yl-benzamide;
4-{Methyl-{3-(5-methyl-furan-2-yl)-butyl}-amino}-N-quinolin-3-yl-benzamide;
4-Azepan-1-yl-N-quinolin-3-yl-benzamide;
4-Azepan-1-yl-N-quinolin-3-yl-benzamide;
4-Azocan-1-yl-N-quinolin-3-yl-benzamide;
4-Azonan-1-yl-N-quinolin-3-yl-benzamide;
4-Benzyl-3,4,5,6-tetrahydro-2H-{1,2'}bipyridinyl-5'-carboxylic acid quinolin-3-ylamide;
5,5,8,8-Tetramethyl-5,6,7,8-tetrahydro-naphthalene-2-carboxylic acid quinolin-3-ylamide;
6-(3-Aza-bicyclo{3.3.1}non-3-yl)-N-quinolin-3-yl-nicotinamide;
6-Azocan-1-yl-N-quinolin-3-yl-nicotinamide;
cis-4-(Octahydro-isoquinolin-2-yl)-N-quinolin-3-yl-benzamide;
cis-6-(Octahydro-isoquinolin-2-yl)-N-quinolin-3-yl-nicotinamide;
N-Quinolin-3-yl-3-(5,5,8,8-tetramethyl-5,6,7,8-tetrahydro-naphthalen-2-yl)-propionamide;
R-4-{(3,7-Dimethyl-oct-6-enyl)-methyl-amino}-N-quinolin-3-yl-benzamide;
S-4-{(3,7-Dimethyl-oct-6-enyl)-methyl-amino}-N-quinolin-3-yl-benzamide;
trans-4-(Octahydro-isoquinolin-2-yl)-N-quinolin-3-yl-benzamide;
trans-6-(Octahydro-isoquinolin-2-yl)-N-quinolin-3-yl-nicotinamide;
4-tert-Butyl-N-(4-hydroxy-quinolin-3-yl)-benzamide;

3-(4-tert-Butyl-phenyl)-N-(4-hydroxy-quinolin-3-yl)-acrylamide;
N-Quinolin-3-yl-3-(5,5,8,8-tetramethyl-5,6,7,8-tetrahydro-naphthalen-2-yl)-acrylamide;
N-(4-Chloro-quinolin-3-yl)-3-(5,5,8,8-tetramethyl-5,6,7,8-tetrahydro-naphthalen-2-yl)-acrylamide;
N-(4-Chloro-quinolin-3-yl)-4-(cyclohexyl-methyl-amino)-benzamide;
N-(2-Chloro-quinolin-3-yl)-4-(cyclohexyl-methyl-amino)-benzamide;
4-tert-Butyl-N-(2-methoxy-quinolin-3-yl)-benzamide;
4-Azepan-1-yl-N-(4-chloro-quinolin-3-yl)-benzamide;
4-(3-Aza-bicyclo[3.2.2]non-3-yl)-N-(2-chloro-quinolin-3-yl)-benzamide;
4-Azepan-1-yl-N-(2-chloro-quinolin-3-yl)-benzamide;
4-(3-Aza-bicyclo[3.2.2]non-3-yl)-N-(4-chloro-quinolin-3-yl)-benzamide;
3-(1-Cyclohexyl-2,3-dihydro-1H-indol-5-yl)-N-quinolin-3-yl-acrylamide;
1-Cyclohexyl-2,3-dihydro-1H-indole-5-carboxylic acid (2-chloro-quinolin-3-yl)-amide;
N-(2-Chloro-quinolin-3-yl)-3-(1-cyclohexyl-2,3-dihydro-1H-indol-5-yl)-acrylamide;
3-(1-Cyclohexyl-1H-indol-5-yl)-N-quinolin-3-yl-acrylamide;
N-(4-Chloro-quinolin-3-yl)-3-(1-cyclohexyl-1H-indol-5-yl)-acrylamide;
1-Cyclohexyl-1H-indole-5-carboxylic acid (4-chloro-quinolin-3-yl)-amide;
1-Cyclohexyl-1H-indole-5-carboxylic acid quinolin-3-ylamide;
1-Cyclohexyl-1H-indole-5-carboxylic acid (2-chloro-quinolin-3-yl)-amide;
N-(2-Chloro-quinolin-3-yl)-3-(1-cyclohexyl-1H-indol-5-yl)-acrylamide;
4-(Cyclohexyl-methyl-amino)-N-(8-fluoro-quinolin-3-yl)-benzamide;
4-Azocan-1-yl-N-(8-fluoro-quinolin-3-yl)-benzamide;
4-(3-Aza-bicyclo[3.2.2]non-3-yl)-N-(8-fluoro-quinolin-3-yl)-benzamide;
4-(3-Aza-bicyclo[3.2.2]non-3-yl)-N-(8-trifluoromethyl-quinolin-3-yl)-benzamide;
4-(Cyclohexyl-methyl-amino)-N-(8-trifluoromethyl-quinolin-3-yl)-benzamide;
4-(Cyclohexyl-methyl-amino)-N-(6-fluoro-quinolin-3-yl)-benzamide;
4-Azocan-1-yl-N-(6-fluoro-quinolin-3-yl)-benzamide;
4-(3-Aza-bicyclo[3.2.2]non-3-yl)-N-(6-fluoro-quinolin-3-yl)-benzamide;
4-(3-Aza-bicyclo[3.2.2]non-3-yl)-N-(7-trifluoromethyl-quinolin-3-yl)-benzamide;
4-Azocan-1-yl-N-(7-trifluoromethyl-quinolin-3-yl)-benzamide;
4-(Cyclohexyl-methyl-amino)-N-(7-trifluoromethyl-quinolin-3-yl)-benzamide;
4-Azocan-1-yl-N-(5-fluoro-quinolin-3-yl)-benzamide;
4-(3-Aza-bicyclo[3.2.2]non-3-yl)-N-(5-fluoro-quinolin-3-yl)-benzamide;
3-Phenyl-propynoic acid quinolin-3-ylamide;
trans-2-Phenyl-cyclopropanecarboxylic acid quinolin-3-ylamide;
3-(4-tert-Butyl-phenyl)-propynoic acid quinolin-3-ylamide; and
2-(4-tert-Butyl-phenyl)-cyclopropanecarboxylic acid quinolin-3-ylamide.

The present invention is also directed to a compound selected from the group consisting of 1-Cyclohexyl-2,3-dihydro-1H-indole-5-carboxylic acid quinolin-3-ylamide;
1-Pentyl-2,3-dihydro-1H-indole-5-carboxylic acid quinolin-3-ylamide;
1-Propyl-2,3-dihydro-1H-indole-5-carboxylic acid quinolin-3-ylamide;
3-(4-sec-Butyl-phenyl)-N-quinolin-3-yl-propionamide;
3-(4-tert-Butyl-phenyl)-N-quinolin-3-yl-acrylamide;
3-(4-tert-Butyl-phenyl)-N-quinolin-3-yl-propionamide;
3,4,5,6-Tetrahydro-2H-{1,2'}bipyridinyl-5'-carboxylic acid quinolin-3-ylamide;
3-{4-(1,1-Dimethyl-3-phenyl-propyl)-phenyl}-N-quinolin-3-yl-propionamide;
3-{4-(1,1-Dimethyl-pentyl)-2,6-dimethoxy-phenyl}-N-quinolin-3-yl-propionamide;
3-{4-(1,1-Dimethyl-propyl)-phenyl}-N-quinolin-3-yl-propionamide;
3-{4-(1-Methyl-pentyl)-phenyl}-N-quinolin-3-yl-propionamide;
3-{5-(1,1-Dimethyl-propyl)-thiophen-2-yl}-N-quinolin-3-yl-propionamide;
4-(3-Aza-bicyclo{3.3.1}non-3-yl)-N-quinolin-3-yl-benzamide;
4-(4-Benzyl-piperidin-1-yl)-N-quinolin-3-yl-benzamide;
4-(Cycloheptyl-methyl-amino)-N-quinolin-3-yl-benzamide;
4-(Cyclohexyl-ethyl-amino)-N-quinolin-3-yl-benzamide;
4-(Cyclohexyl-methyl-amino)-3-methyl-N-quinolin-3-yl-benzamide;
4-(Cyclohexyl-methyl-amino)-N-quinolin-3-yl-benzamide;
4-(Cyclohexylmethyl-methyl-amino)-N-quinolin-3-yl-benzamide;
4-(Cyclopentyl-methyl-amino)-N-quinolin-3-yl-benzamide;
4-(Dec-4-enyl-methyl-amino)-N-quinolin-3-yl-benzamide;
4-(Heptyl-methyl-amino)-N-quinolin-3-yl-benzamide;
4-(Methyl-nonyl-amino)-N-quinolin-3-yl-benzamide;
4-(Methyl-phenethyl-amino)-N-quinolin-3-yl-benzamide;
4-(Octyl-methyl-amino)-N-quinolin-3-yl-benzamide;
4-{(3,3-Dimethyl-butyl)-methyl-amino}-N-quinolin-3-yl-benzamide;
4-Azepan-1-yl-N-quinolin-3-yl-benzamide;
4-Azepan-1-yl-N-quinolin-3-yl-benzamide;
4-Azocan-1-yl-N-quinolin-3-yl-benzamide;
4-Azonan-1-yl-N-quinolin-3-yl-benzamide;
4-Benzyl-3,4,5,6-tetrahydro-2H-{1,2'}bipyridinyl-5'-carboxylic acid quinolin-3-ylamide;
6-(3-Aza-bicyclo{3.3.1}non-3-yl)-N-quinolin-3-yl-nicotinamide;
N-Quinolin-3-yl-3-(5,5,8,8-tetramethyl-5,6,7,8-tetrahydro-naphthalen-2-yl)-propionamide;
R-4-{(3,7-Dimethyl-oct-6-enyl)-methyl-amino}-N-quinolin-3-yl-benzamide; S-4-{(3,7-Dimethyl-oct-6-enyl)-methyl-amino}-N-quinolin-3-yl-benzamide;
4-tert-Butyl-N-(4-hydroxy-quinolin-3-yl)-benzamide;
3-(4-tert-Butyl-phenyl)-N-(4-hydroxy-quinolin-3-yl)-acrylamide;
N-Quinolin-3-yl-3-(5,5,8,8-tetramethyl-5,6,7,8-tetrahydro-naphthalen-2-yl)-acrylamide;
N-(4-Chloro-quinolin-3-yl)-3-(5,5,8,8-tetramethyl-5,6,7,8-tetrahydro-naphthalen-2-yl)-acrylamide;
N-(4-Chloro-quinolin-3-yl)-4-(cyclohexyl-methyl-amino)-benzamide;
N-(2-Chloro-quinolin-3-yl)-4-(cyclohexyl-methyl-amino)-benzamide;
4-tert-Butyl-N-(2-methoxy-quinolin-3-yl)-benzamide;
4-Azepan-1-yl-N-(4-chloro-quinolin-3-yl)-benzamide;
4-(3-Aza-bicyclo[3.2.2]non-3-yl)-N-(2-chloro-quinolin-3-yl)-benzamide;

4-Azepan-1-yl-N-(2-chloro-quinolin-3-yl)-benzamide;
4-(3-Aza-bicyclo[3.2.2]non-3-yl)-N-(4-chloro-quinolin-3-yl)-benzamide;
3-(1-Cyclohexyl-2,3-dihydro-1H-indol-5-yl)-N-quinolin-3-yl-acrylamide;
1-Cyclohexyl-2,3-dihydro-1H-indole-5-carboxylic acid (2-chloro-quinolin-3-yl)-amide;
N-(2-Chloro-quinolin-3-yl)-3-(1-cyclohexyl-2,3-dihydro-1H-indol-5-yl)-acrylamide;
3-(1-Cyclohexyl-1H-indol-5-yl)-N-quinolin-3-yl-acrylamide;
N-(4-Chloro-quinolin-3-yl)-3-(1-cyclohexyl-1H-indol-5-yl)-acrylamide;
1-Cyclohexyl-1H-indole-5-carboxylic acid (4-chloro-quinolin-3-yl)-amide;
1-Cyclohexyl-1H-indole-5-carboxylic acid quinolin-3-ylamide;
1-Cyclohexyl-1H-indole-5-carboxylic acid (2-chloro-quinolin-3-yl)-amide;
N-(2-Chloro-quinolin-3-yl)-3-(1-cyclohexyl-1H-indol-5-yl)-acrylamide;
4-(Cyclohexyl-methyl-amino)-N-(8-fluoro-quinolin-3-yl)-benzamide;
4-Azocan-1-yl-N-(8-fluoro-quinolin-3-yl)-benzamide;
4-(3-Aza-bicyclo[3.2.2]non-3-yl)-N-(8-fluoro-quinolin-3-yl)-benzamide;
4-(3-Aza-bicyclo[3.2.2]non-3-yl)-N-(8-trifluoromethyl-quinolin-3-yl)-benzamide;
4-(Cyclohexyl-methyl-amino)-N-(8-trifluoromethyl-quinolin-3-yl)-benzamide;
4-(Cyclohexyl-methyl-amino)-N-(6-fluoro-quinolin-3-yl)-benzamide;
4-Azocan-1-yl-N-(6-fluoro-quinolin-3-yl)-benzamide;
4-(3-Aza-bicyclo[3.2.2]non-3-yl)-N-(6-fluoro-quinolin-3-yl)-benzamide;
4-(3-Aza-bicyclo[3.2.2]non-3-yl)-N-(7-trifluoromethyl-quinolin-3-yl)-benzamide;
4-Azocan-1-yl-N-(7-trifluoromethyl-quinolin-3-yl)-benzamide;
4-(Cyclohexyl-methyl-amino)-N-(7-trifluoromethyl-quinolin-3-yl)-benzamide;
4-Azocan-1-yl-N-(5-fluoro-quinolin-3-yl)-benzamide;
4-(3-Aza-bicyclo[3.2.2]non-3-yl)-N-(5-fluoro-quinolin-3-yl)-benzamide;
3-Phenyl-propynoic acid quinolin-3-ylamide;
trans-2-Phenyl-cyclopropanecarboxylic acid quinolin-3-ylamide;
3-(4-tert-Butyl-phenyl)-propynoic acid quinolin-3-ylamide; and
2-(4-tert-Butyl-phenyl)-cyclopropanecarboxylic acid quinolin-3-ylamide.

The present invention is also directed to a compound selected from the group consisting of
1-Cyclohexyl-2,3-dihydro-1H-indole-5-carboxylic acid quinolin-3-ylamide;
1-Propyl-2,3-dihydro-1H-indole-5-carboxylic acid quinolin-3-ylamide;
3-(4-sec-Butyl-phenyl)-N-quinolin-3-yl-propionamide;
3-(4-tert-Butyl-phenyl)-N-quinolin-3-yl-acrylamide;
3-(4-tert-Butyl-phenyl)-N-quinolin-3-yl-propionamide;
3-{4-(1,1-Dimethyl-3-phenyl-propyl)-phenyl}-N-quinolin-3-yl-propionamide;
3-{4-(1,1-Dimethyl-pentyl)-2,6-dimethoxy-phenyl}-N-quinolin-3-yl-propionamide;
3-{4-(1,1-Dimethyl-propyl)-phenyl}-N-quinolin-3-yl-propionamide;
3-{4-(1-Methyl-pentyl)-phenyl}-N-quinolin-3-yl-propionamide;
3-{5-(1,1-Dimethyl-propyl)-thiophen-2-yl}-N-quinolin-3-yl-propionamide;
4-(3-Aza-bicyclo{3.3.1}non-3-yl)-N-quinolin-3-yl-benzamide;
4-(4-Benzyl-piperidin-1-yl)-N-quinolin-3-yl-benzamide;
4-(Cycloheptyl-methyl-amino)-N-quinolin-3-yl-benzamide;
4-(Cyclohexyl-ethyl-amino)-N-quinolin-3-yl-benzamide;
4-(Cyclohexyl-methyl-amino)-N-quinolin-3-yl-benzamide;
4-(Cyclohexylmethyl-methyl-amino)-N-quinolin-3-yl-benzamide;
4-(Octyl-methyl-amino)-N-quinolin-3-yl-benzamide;
4-Azepan-1-yl-N-quinolin-3-yl-benzamide;
4-Azepan-1-yl-N-quinolin-3-yl-benzamide;
4-Azocan-1-yl-N-quinolin-3-yl-benzamide;
4-Azonan-1-yl-N-quinolin-3-yl-benzamide;
6-(3-Aza-bicyclo{3.3.1}non-3-yl)-N-quinolin-3-yl-nicotinamide;
N-Quinolin-3-yl-3-(5,5,8,8-tetramethyl-5,6,7,8-tetrahydro-naphthalen-2-yl)-propionamide;
R-4-{(3,7-Dimethyl-oct-6-enyl)-methyl-amino}-N-quinolin-3-yl-benzamide; S-4-{(3,7-Dimethyl-oct-6-enyl)-methyl-amino}-N-quinolin-3-yl-benzamide;
4-tert-Butyl-N-(4-hydroxy-quinolin-3-yl)-benzamide;
3-(4-tert-Butyl-phenyl)-N-(4-hydroxy-quinolin-3-yl)-acrylamide;
N-Quinolin-3-yl-3-(5,5,8,8-tetramethyl-5,6,7,8-tetrahydro-naphthalen-2-yl)-acrylamide;
N-(4-Chloro-quinolin-3-yl)-3-(5,5,8,8-tetramethyl-5,6,7,8-tetrahydro-naphthalen-2-yl)-acrylamide;
N-(4-Chloro-quinolin-3-yl)-4-(cyclohexyl-methyl-amino)-benzamide;
N-(2-Chloro-quinolin-3-yl)-4-(cyclohexyl-methyl-amino)-benzamide;
4-tert-Butyl-N-(2-methoxy-quinolin-3-yl)-benzamide;
4-Azepan-1-yl-N-(4-chloro-quinolin-3-yl)-benzamide;
4-(3-Aza-bicyclo[3.2.2]non-3-yl)-N-(2-chloro-quinolin-3-yl)-benzamide;
4-Azepan-1-yl-N-(2-chloro-quinolin-3-yl)-benzamide;
4-(3-Aza-bicyclo[3.2.2]non-3-yl)-N-(4-chloro-quinolin-3-yl)-benzamide;
3-(1-Cyclohexyl-2,3-dihydro-1H-indol-5-yl)-N-quinolin-3-yl-acrylamide;
1-Cyclohexyl-2,3-dihydro-1H-indole-5-carboxylic acid (2-chloro-quinolin-3-yl)-amide;
N-(2-Chloro-quinolin-3-yl)-3-(1-cyclohexyl-2,3-dihydro-1H-indol-5-yl)-acrylamide;
3-(1-Cyclohexyl-1H-indol-5-yl)-N-quinolin-3-yl-acrylamide;
N-(4-Chloro-quinolin-3-yl)-3-(1-cyclohexyl-1H-indol-5-yl)-acrylamide;
1-Cyclohexyl-1H-indole-5-carboxylic acid (4-chloro-quinolin-3-yl)-amide;
1-Cyclohexyl-1H-indole-5-carboxylic acid quinolin-3-ylamide;
1-Cyclohexyl-1H-indole-5-carboxylic acid (2-chloro-quinolin-3-yl)-amide;
N-(2-Chloro-quinolin-3-yl)-3-(1-cyclohexyl-1H-indol-5-yl)-acrylamide;
4-(Cyclohexyl-methyl-amino)-N-(8-fluoro-quinolin-3-yl)-benzamide;
4-Azocan-1-yl-N-(8-fluoro-quinolin-3-yl)-benzamide;
4-(3-Aza-bicyclo[3.2.2]non-3-yl)-N-(8-fluoro-quinolin-3-yl)-benzamide;
4-(3-Aza-bicyclo[3.2.2]non-3-yl)-N-(8-trifluoromethyl-quinolin-3-yl)-benzamide;

4-(Cyclohexyl-methyl-amino)-N-(8-trifluoromethyl-quinolin-3-yl)-benzamide;
4-(Cyclohexyl-methyl-amino)-N-(6-fluoro-quinolin-3-yl)-benzamide;
4-Azocan-1-yl-N-(6-fluoro-quinolin-3-yl)-benzamide;
4-(3-Aza-bicyclo[3.2.2]non-3-yl)-N-(6-fluoro-quinolin-3-yl)-benzamide;
4-(3-Aza-bicyclo[3.2.2]non-3-yl)-N-(7-trifluoromethyl-quinolin-3-yl)-benzamide;
4-Azocan-1-yl-N-(7-trifluoromethyl-quinolin-3-yl)-benzamide;
4-(Cyclohexyl-methyl-amino)-N-(7-trifluoromethyl-quinolin-3-yl)-benzamide;
4-Azocan-1-yl-N-(5-fluoro-quinolin-3-yl)-benzamide;
4-(3-Aza-bicyclo[3.2.2]non-3-yl)-N-(5-fluoro-quinolin-3-yl)-benzamide;
3-Phenyl-propynoic acid quinolin-3-ylamide;
trans-2-Phenyl-cyclopropanecarboxylic acid quinolin-3-ylamide;
3-(4-tert-Butyl-phenyl)-propynoic acid quinolin-3-ylamide; and
2-(4-tert-Butyl-phenyl)-cyclopropanecarboxylic acid quinolin-3-ylamide.

The present invention is also directed to a compound selected from the group consisting of
1-Cyclohexyl-2,3-dihydro-1H-indole-5-carboxylic acid quinolin-3-ylamide;
3-(4-tert-Butyl-phenyl)-N-quinolin-3-yl-acrylamide;
3-(4-tert-Butyl-phenyl)-N-quinolin-3-yl-propionamide;
3-{4-(1,1-Dimethyl-propyl)-phenyl}-N-quinolin-3-yl-propionamide;
4-(3-Aza-bicyclo{3.3.1}non-3-yl)-N-quinolin-3-yl-benzamide;
4-Azepan-1-yl-N-quinolin-3-yl-benzamide;
6-(3-Aza-bicyclo{3.3.1}non-3-yl)-N-quinolin-3-yl-nicotinamide;
4-tert-Butyl-N-(4-hydroxy-quinolin-3-yl)-benzamide;
3-(4-tert-Butyl-phenyl)-N-(4-hydroxy-quinolin-3-yl)-acrylamide;
N-Quinolin-3-yl-3-(5,5,8,8-tetramethyl-5,6,7,8-tetrahydro-naphthalen-2-yl)-acrylamide;
N-(4-Chloro-quinolin-3-yl)-3-(5,5,8,8-tetramethyl-5,6,7,8-tetrahydro-naphthalen-2-yl)-acrylamide;
N-(4-Chloro-quinolin-3-yl)-4-(cyclohexyl-methyl-amino)-benzamide;
N-(2-Chloro-quinolin-3-yl)-4-(cyclohexyl-methyl-amino)-benzamide;
4-tert-Butyl-N-(2-methoxy-quinolin-3-yl)-benzamide;
4-Azepan-1-yl-N-(4-chloro-quinolin-3-yl)-benzamide;
4-(3-Aza-bicyclo[3.2.2]non-3-yl)-N-(2-chloro-quinolin-3-yl)-benzamide;
4-Azepan-1-yl-N-(2-chloro-quinolin-3-yl)-benzamide;
4-(3-Aza-bicyclo[3.2.2]non-3-yl)-N-(4-chloro-quinolin-3-yl)-benzamide;
3-(1-Cyclohexyl-2,3-dihydro-1H-indol-5-yl)-N-quinolin-3-yl-acrylamide;
1-Cyclohexyl-2,3-dihydro-1H-indole-5-carboxylic acid (2-chloro-quinolin-3-yl)-amide;
N-(2-Chloro-quinolin-3-yl)-3-(1-cyclohexyl-2,3-dihydro-1H-indol-5-yl)-acrylamide;
3-(1-Cyclohexyl-1H-indol-5-yl)-N-quinolin-3-yl-acrylamide;
N-(4-Chloro-quinolin-3-yl)-3-(1-cyclohexyl-1H-indol-5-yl)-acrylamide;
1-Cyclohexyl-1H-indole-5-carboxylic acid (4-chloro-quinolin-3-yl)-amide;
1-Cyclohexyl-1H-indole-5-carboxylic acid quinolin-3-ylamide;
1-Cyclohexyl-1H-indole-5-carboxylic acid (2-chloro-quinolin-3-yl)-amide;
N-(2-Chloro-quinolin-3-yl)-3-(1-cyclohexyl-1H-indol-5-yl)-acrylamide;
4-(Cyclohexyl-methyl-amino)-N-(8-fluoro-quinolin-3-yl)-benzamide;
4-Azocan-1-yl-N-(8-fluoro-quinolin-3-yl)-benzamide;
4-(3-Aza-bicyclo[3.2.2]non-3-yl)-N-(8-fluoro-quinolin-3-yl)-benzamide;
4-(3-Aza-bicyclo[3.2.2]non-3-yl)-N-(8-trifluoromethyl-quinolin-3-yl)-benzamide;
4-(Cyclohexyl-methyl-amino)-N-(8-trifluoromethyl-quinolin-3-yl)-benzamide;
4-(Cyclohexyl-methyl-amino)-N-(6-fluoro-quinolin-3-yl)-benzamide;
4-Azocan-1-yl-N-(6-fluoro-quinolin-3-yl)-benzamide;
4-(3-Aza-bicyclo[3.2.2]non-3-yl)-N-(6-fluoro-quinolin-3-yl)-benzamide;
4-(3-Aza-bicyclo[3.2.2]non-3-yl)-N-(7-trifluoromethyl-quinolin-3-yl)-benzamide;
4-Azocan-1-yl-N-(7-trifluoromethyl-quinolin-3-yl)-benzamide;
4-(Cyclohexyl-methyl-amino)-N-(7-trifluoromethyl-quinolin-3-yl)-benzamide;
4-Azocan-1-yl-N-(5-fluoro-quinolin-3-yl)-benzamide;
4-(3-Aza-bicyclo[3.2.2]non-3-yl)-N-(5-fluoro-quinolin-3-yl)-benzamide;
3-Phenyl-propynoic acid quinolin-3-ylamide;
trans-2-Phenyl-cyclopropanecarboxylic acid quinolin-3-ylamide;
3-(4-tert-Butyl-phenyl)-propynoic acid quinolin-3-ylamide; and
2-(4-tert-Butyl-phenyl)-cyclopropanecarboxylic acid quinolin-3-ylamide.

The compounds of the present invention may also be present in the form of pharmaceutically acceptable salts. For use in medicine, the salts of the compounds of this invention refer to non-toxic "pharmaceutically acceptable salts" (*Ref. International J. Pharm.*, 1986, 33, 201-217; *J. Pharm. Sci.*, 1997 (January), 66, 1, 1). Other salts well known to those in the art may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The present invention includes within its scope prodrugs of the compounds of this invention. In general, such prodrugs will be functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, 3$^{rd}$ Edition, John Wiley & Sons, 1999. The protecting groups may be removed at a convenient subsequent stage using methods known from the art.

Even though the compounds of the present invention (including their pharmaceutically, acceptable salts and pharmaceutically acceptable solvates) can be administered alone, they will generally be administered in admixture with a pharmaceutical carrier, excipient or diluent selected with regard to the intended route of administration and standard pharmaceutical or veterinary practice. Thus, the present invention is directed to pharmaceutical and veterinary compositions comprising compounds of Formula (I) and one or more pharmaceutically acceptable carriers, excipients or diluents.

By way of example, in the pharmaceutical and veterinary compositions of the present invention, the compounds of the present invention may be admixed with any suitable binder(s), lubricant(s), suspending agent(s), coating agent(s), and/or solubilising agent(s).

Tablets or capsules of the compounds may be administered singly or two or more at a time, as appropriate. It is also possible to administer the compounds in sustained release formulations.

Alternatively, the compounds of the general Formula (I) can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin. They can also be incorporated, at a concentration of between 1 and 10% by weight, into an ointment consisting of a white wax or white soft paraffin base together with such stabilisers and preservatives as may be required.

For some applications, preferably the compositions are administered orally in the form of tablets containing excipients such as starch or lactose, or in capsules or ovules either alone or in admixture with excipients, or in the form of elixirs, solutions or suspensions containing flavouring or coloring agents.

The compositions (as well as the compounds alone) can also be injected parenterally, for example intracavernosally, intravenously, intramuscularly or subcutaneously. In this case, the compositions will comprise a suitable carrier or diluent.

For parenteral administration, the compositions are best used in the form of a sterile aqueous solution which may contain other substances, for example enough salts or monosaccharides to make the solution isotonic with blood.

For buccal or sublingual administration the compositions may be administered in the form of tablets or lozenges which can be formulated in a conventional manner.

By way of further example, pharmaceutical and veterinary compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate the major site of absorption. For parenteral administration, the carrier will usually consist of sterile water and other ingredients may be added to increase solubility or preservation. Injectable suspensions or solutions may also be prepared utilizing aqueous carriers along with appropriate additives.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those skilled in that art. To be administered in the form of a transdermal delivery system, the dosage administration will, of course, be continuous rather than intermittent throughout the dosage regimen.

A therapeutically effective amount for use of the instant compounds or a pharmaceutical composition thereof comprises a dose range of from about 0.001 mg to about 1,000 mg, in particular from about 0.1 mg to about 500 mg or, more particularly from about 1 mg to about 250 mg of active ingredient per day for an average (70 kg) human.

For oral administration, a pharmaceutical composition is preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the subject to be treated.

It is also apparent to one skilled in the art that the therapeutically effective dose for active compounds of the invention or a pharmaceutical composition thereof will vary according to the desired effect. Therefore, optimal dosages to be administered may be readily determined and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

Compounds of this invention may be administered in any of the foregoing compositions and dosage regimens or by means of those compositions and dosage regimens established in the art whenever use of the compounds of the invention as vanilloid receptor modulators is required for a subject in need thereof.

The invention also provides a pharmaceutical or veterinary pack or kit comprising one or more containers filled with one or more of the ingredients of the pharmaceutical and veterinary compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

As modulators of the vanilloid VR1 ion channel, the compounds of Formula (I), are useful in methods for treating or preventing a disease or condition in a mammal which disease or condition is affected by the modulation of one or more vanilloid receptors. Such methods comprises administering to a mammal in need of such treatment or prevention a therapeutically effective amount of a compound, salt or solvate of Formula (I). In particular, the compounds of Formula (I) are useful in methods for preventing or treating a chronic- or acute-pain causing diseases or conditions and pulmonary dysfunction, and more particularly, in treating diseases or conditions that cause inflammatory pain, burning pain, itch or urinary incontinence, and chronic obstructive pulmonary disease.

By way of example only, the compounds of Formula (I), are useful for treating diseases and conditions selected from the group consisting of osteoarthritis, rheumatoid arthritis, fibromyalgia, migraine, headache, toothache, burn, sunburn, snake bite (in particular, venomous snake bite), spider bite, insect sting, neurogenic bladder, benign prostatic hypertrophy, interstitial cystitis, urinary tract infection, cough asthma, pharyngitis, mucositis, pancreatitis, enteritis, cellulites, peripheral neuropathy, bilateral peripheral neuropathy, diabetic neuropathy, postherpetic neuralgia, trigeminal neuralgia, causalgia, sciatic neuritis, mandibular joint neuralgia, peripheral neuritis, polyneuritis, stump pain, phantom limb pain, bony fractures, post-operative ileus, Irritable Bowel Syndrome, Inflammatory Bowel Diseases such as Crohn's Disease and ulcerative colitis, cholecystitis, pancreatitis, postmastectomy pain syndrome, oral neuropathic pain, Charcot's pain, reflex sympathetic dystrophy, Guillain-Barre syndrome, meralgia paresthetica, burning-mouth syndrome, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, red neuralgia, Sluder's neuralgia, splenopalatine neuralgia, supraorbital neuralgia, vidian neuralgia, sinus headache, tension headache, labor, childbirth, intestinal gas, menstruation, cancer, and trauma.

Thus, one embodiment of the present invention is a method of treating or preventing ulcerative colitis comprising administering to a mammal in need of such treatment or prevention a therapeutically effective amount of a compound, salt or solvate of formulae (I), (II), (III), or (IV).

While the present invention comprises compositions comprising one or more of the compounds of Formula (I), the present invention also comprises compositions comprising intermediates used in the manufacture of compounds of Formula (I).

GENERAL SYNTHETIC METHODS

Representative compounds of the present invention can be synthesized in accordance with the general synthetic methods described below and are illustrated in the schemes that follows. Since the schemes are an illustration, the invention should not be construed as being limited by the chemical reactions and conditions expressed. The preparation of the various starting materials used in the schemes is well within the skill of persons versed in the art.

It is generally preferred that the respective product of each process step be separated from other components of the reaction mixture and subjected to purification before its use as a starting material in a subsequent step. Separation techniques typically include evaporation, extraction, precipitation and filtration. Purification techniques typically include column chromatography (Still, W. C. et. al., *J. Org. Chem.* 1978, 43, 2921), thin-layer chromatography, crystallization and distillation. The structures of the final products, intermediates and starting materials are confirmed by spectroscopic, spectrometric and analytical methods including nuclear magnetic resonance (NMR), mass spectrometry (MS) and liquid chromatography (HPLC). In the descriptions for the preparation of compounds of this invention, ethyl ether, tetrahydrofuran and dioxane are common examples of an ethereal solvent; benzene, toluene, hexanes and cyclohexane are typical hydrocarbon solvents and dichloromethane and dichloroethane are representative halogenhydrocarbon solvents. In those cases wherein the product is isolated as the acid addition salt the free base may be obtained by techniques known to those skilled in the art. In those cases in which the product is isolated as an acid addition salt, the salt may contain one or more equivalents of the acid.

Protecting group manipulations well know to those skilled in the art may be needed at various stages of the syntheses depending upon substituents and functional groups that are present on the reactants.

| | |
|---|---|
| HBTU = | O-benzotriazol-1-yl-N,N,N',N'-tetramethyluronium hexafluorophospate |
| CDI = | 1,1'--carbonyldiimidazole |
| HATU = | O-(7-azabenzotriazol-1-yl)-N,N,N',N'-tetramethyluronium hexafluorophosphate |
| TEA = | triethylamine |
| DIEA = | N,N-diisopropylethylamine |
| DMF = | N,N-dimethylformamide |
| TFA = | trifluoroacetic acid |
| DMSO = | dimethyl sulfoxide |
| mCPBA = | 3-chloroperoxybenzoic acid |

Scheme A

Certain target compounds of the present invention may be prepared according to the process outlined in Scheme A below.

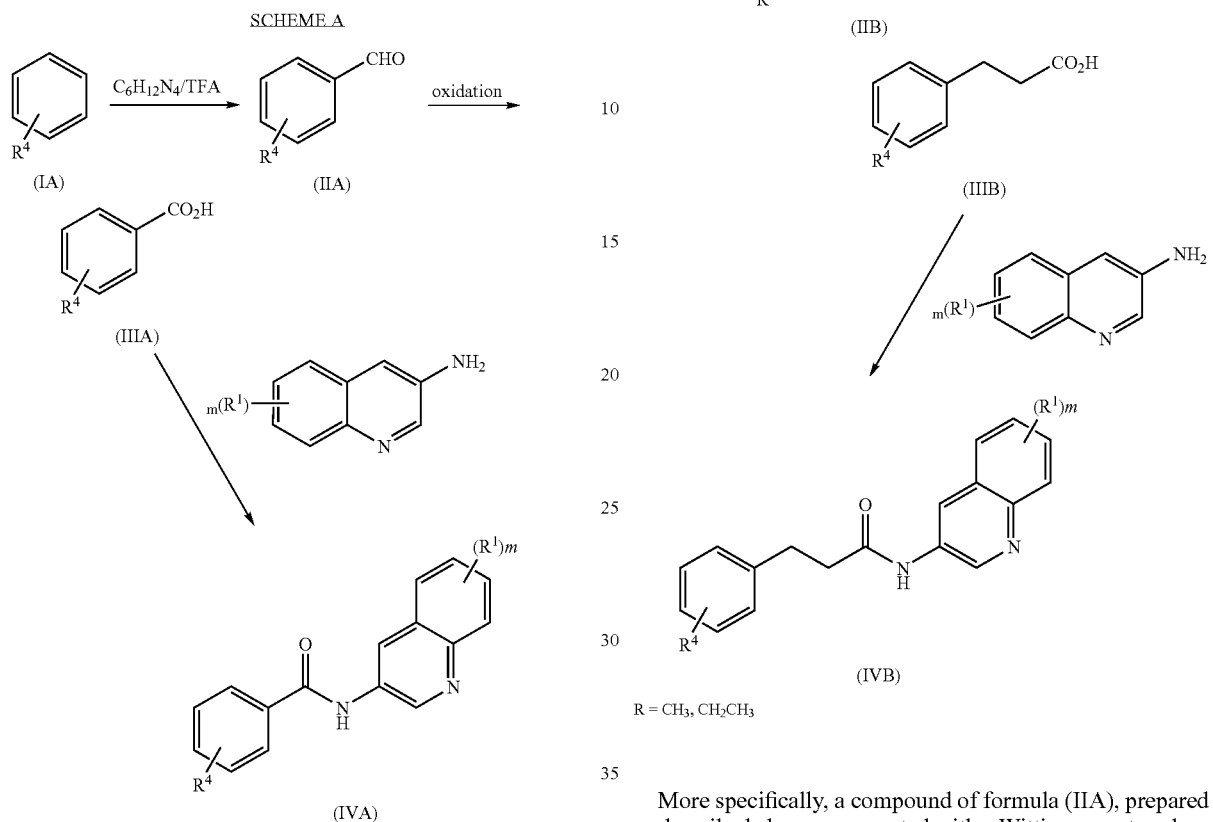

More specifically, a suitably substituted benzene (IA) was reacted with hexamethylenetetramine and an acid such as trifluoroacetic acid at an elevated temperature preferably at a temperature in the range of 80-100° C., to yield the corresponding compound of formula (IIA).

The compound of formula (IIA) was reacted with an oxidizing agent such as manganese dioxide, Jones reagent and the like in a suitable solvent such as acetone, dichloromethane and the like to yield the corresponding compound of formula (IIIA).

The compound of formula (IIIA) was then reacted with a suitably substituted 3-aminoquinoline using peptide coupling methods known to those skilled in the art to provide a compound of formula (IVA).

Scheme B

Certain target compounds of the present invention may be prepared according to the process outlined in Scheme B below.

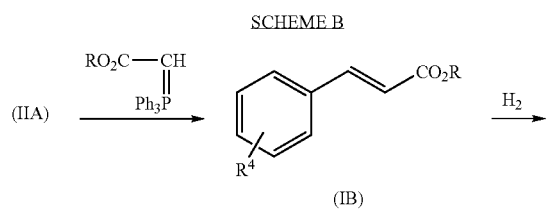

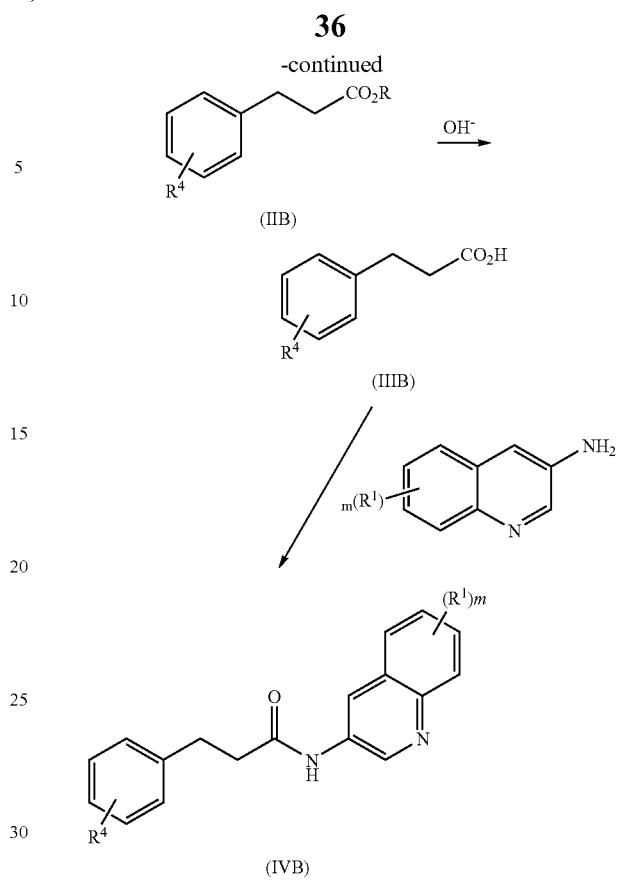

More specifically, a compound of formula (IIA), prepared as described above was reacted with a Wittig reagent such as ethyl(triphenylphosphoranylidene)acetate (purchased from Aldrich Chemicals) in a suitable solvent such as benzene or toluene at an elevated temperature, preferably at a temperature in a range of 80-100° C. to yield the compound of formula (IB).

The compound of formula (IB) was reduced by treating with hydrogen gas at an elevated pressure in the range of about 40-50 psi in a suitable solvent such as ethanol or methanol and the like, in the presence of a catalyst such as 10% palladium on carbon at ambient temperature to yield the corresponding compound of formula (IIB).

The compound of formula (IIB) was saponified by reaction with suitable base such as sodium hydroxide, potassium hydroxide, lithium hydroxide, sodium carbonate, potassium carbonate and the like in a solvent such as ethanol, methanol, aqueous tetrahydrofuran and the like, at a temperature from ambient temperature to a temperature of about 70-100° C. to yield the corresponding compound of formula (IIIB).

The compound of formula (IIIB) was then reacted with a suitably substituted 3-aminoquinoline using peptide coupling methods known to those skilled in the art to provide a compound of formula (IVB).

Scheme C

Certain target compounds of the present invention may be prepared according to the process outlined in Scheme C below.

SCHEME C

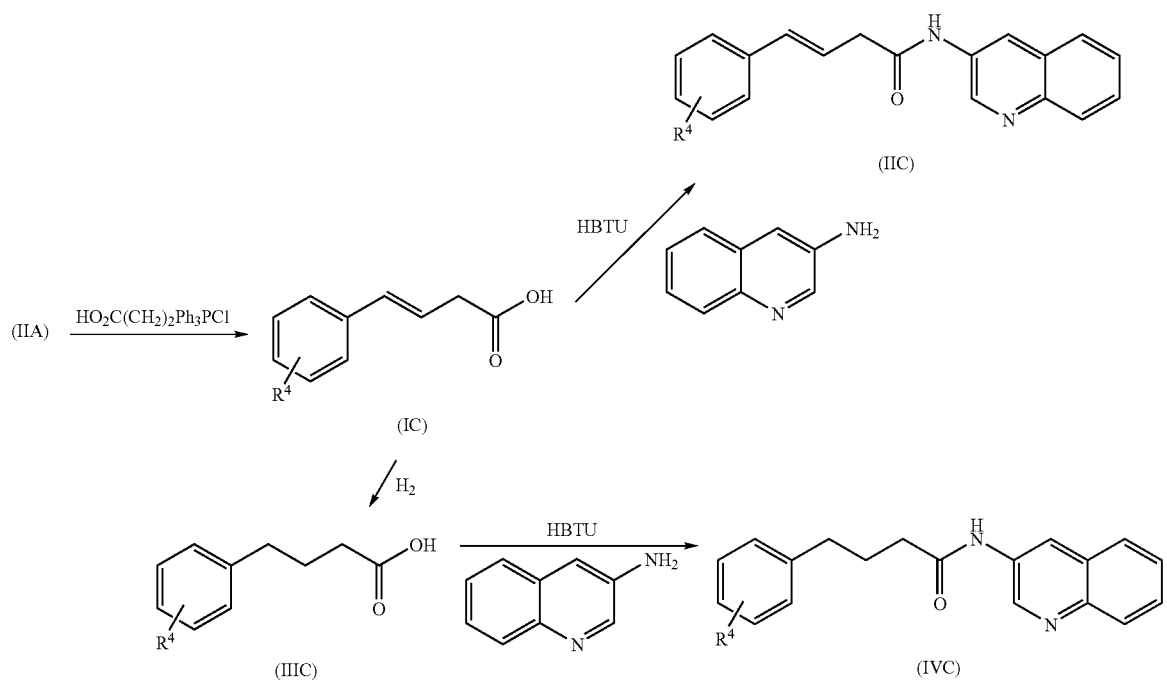

More specifically, a compound of formula (IIA), prepared as described above, was reacted with a Wittig reagent such as (2-carboxyethyl)-triphenylphosphonium chloride (prepared as described in the literature, *Journal of Organic Chemistry* 1962, 3407) in the presence of a strong base such as potassium t-butoxide in a suitable solvent such a tetrahydrofuran or diethylether and the like at a temperature ranging from 0° C. to ambient temperature to yield the compound of formula (IC).

The compound of formula (IC) was reduced by treating with hydrogen gas at an elevated pressure in the range of about 40-50 psi in a suitable solvent such as ethanol or methanol and the like, in the presence of a catalyst such as 10% palladium on carbon at ambient temperature to yield the corresponding compound of formula (IIIC).

The compound of formula ((IIIC) was reacted with a suitably substituted 3-aminoquinoline using peptide coupling methods known to those skilled in the art to provide a compound of formula (IVC).

In addition, a compound of formula (IC) was reacted with a suitably substituted 3-aminoquinoline using peptide coupling methods known to those skilled in the art to provide a compound of formula (IIC).

Scheme D

Certain target compounds of the present invention may be prepared according to the process outlined in Scheme D below.

SCHEME D

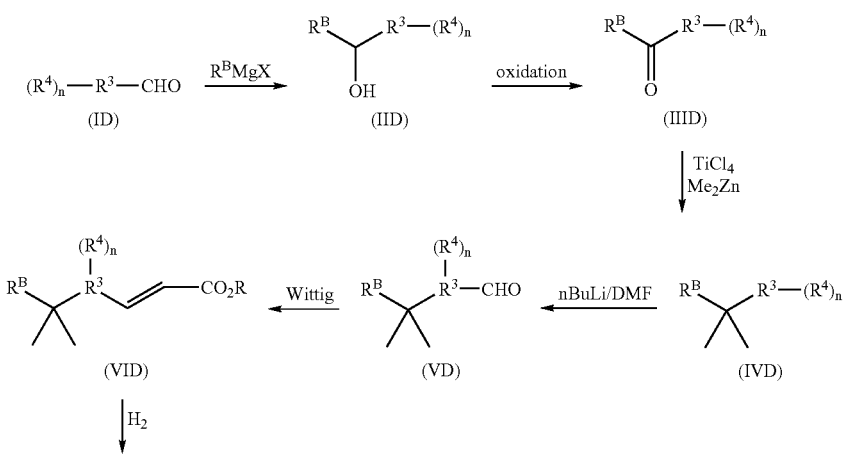

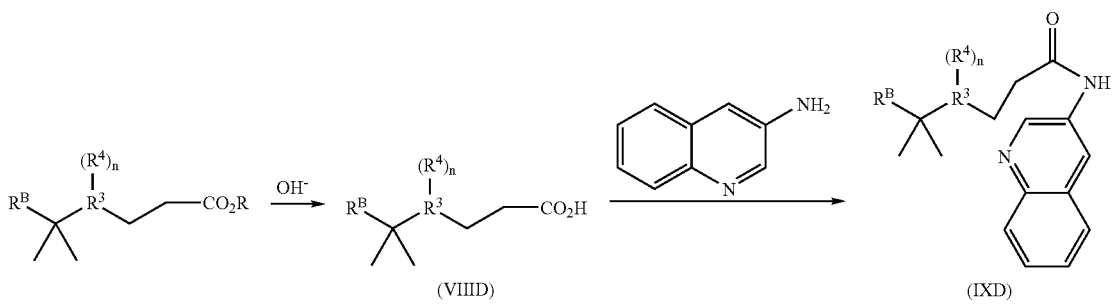

(VIIID)  (IXD)

wherein R and $R^B$ = $C_{1-4}$alkanyl

More specifically, a suitably substituted aldehyde of formula (ID) was reacted with a Grignard reagent such as ethylmagnesium bromide in a suitable solvent such as tetrahydrofuran or diethylether to yield the corresponding compound of formula (IID).

The compound of formula (IID) was reacted with an oxidizing agent such as manganese dioxide or Jones reagent in a suitable solvent such as acetone, dichloromethane and the like at a temperature of 0° C. to room temperature to yield the corresponding compound of formula (IIID).

The compound of formula (IIID) was reacted with titanium tetrachloride and dimethylzinc in a suitable solvent such as dichloromethane at a temperature in the range of −50° C. to ambient temperature to yield the corresponding compound of formula (IVD).

The compound of formula (IVD) was reacted with n-butyllithium and DMF in a suitable solvent such as diethylether or tetrahydrofuran and the like at about 0° C. to yield the corresponding aldehyde of formula (VD).

The compound of formula (VD) was reacted with a Wittig reagent such as ethyl(triphenylphosphoranylidene)acetate (purchased from Aldrich Chemicals) in a suitable solvent such a benzene or toluene at an elevated temperature, preferably at a temperature in a range of 80-100° C. to yield the compound of formula (VID).

The compound of formula (VID) was reduced by treating with hydrogen gas at an elevated pressure in the range of about 40-50 psi in a suitable solvent such as ethanol or methanol and the like, in the presence of a catalyst such as 10% palladium on carbon at ambient temperature to yield the corresponding compound of formula (VIID).

The compound of formula (VIID) was saponified by reaction with suitable base such as sodium hydroxide, potassium hydroxide, lithium hydroxide, sodium carbonate, potassium carbonate and the like in a solvent such as ethanol, methanol, aqueous tetrahydrofuran and the like, at a temperature from ambient temperature to a temperature of about 70-100° C. to yield the corresponding compound of formula (VIIID).

The compound of formula (VIIID) was then reacted with a suitably substituted 3-aminoquinoline using peptide coupling methods known to those skilled in the art to provide a compound of formula (IXD).

Scheme E

Certain target compounds of the present invention may be prepared according to the process outlined in Scheme E below.

SCHEME E

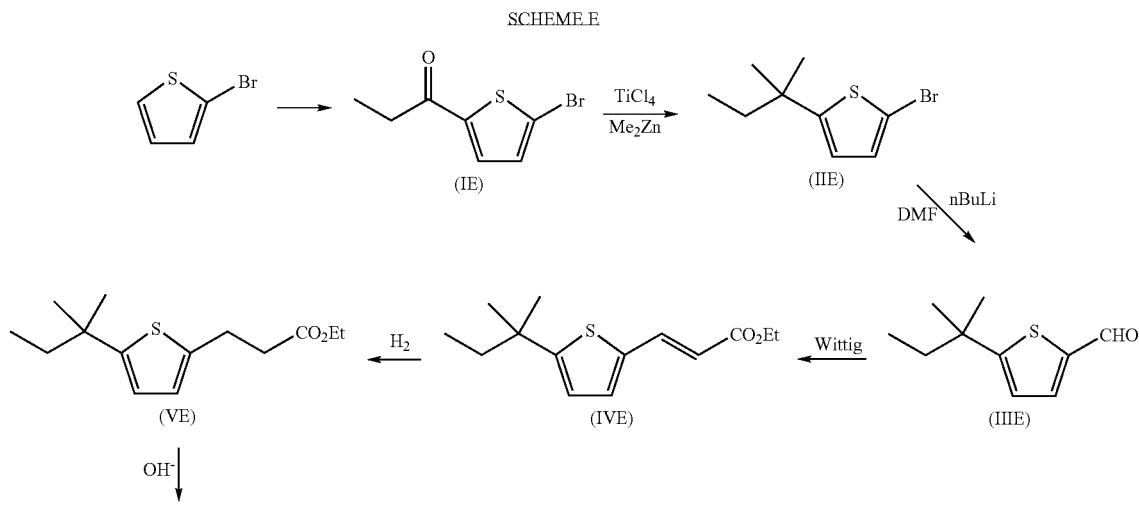

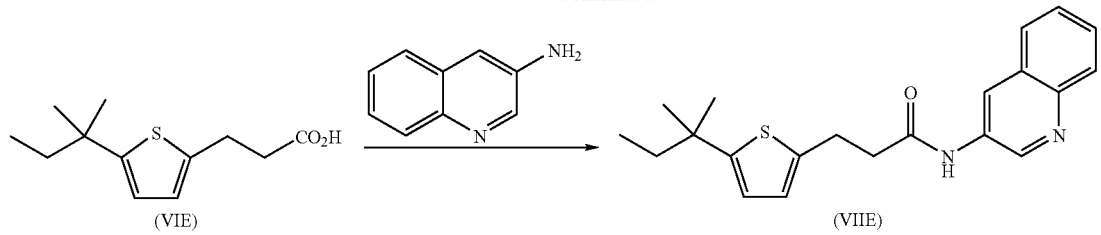

More specifically, 2-bromothiophene was converted to 1-(5-bromo-thiophe-2-yl)-propan-1-one (IE) as described in the literature (*JACS* 1950, 3695). The compound of formula (IE) was reacted with titanium tetrachloride and dimethylzinc in a suitable solvent such as dichloromethane at a temperature in the range of −50° C. to ambient temperature to yield the corresponding compound of formula (IIE). The compound of formula (IIE) was reacted with n-butyllithium and DMF in a suitable solvent such as diethylether or tetrahydrofuran and the like at about 0° C. to yield the corresponding aldehyde of formula (IIIE).

The compound of formula (IIIE) was reacted with a Wittig reagent such as ethyl(triphenylphosphoranylidene)acetate (purchased from Aldrich Chemicals) in a suitable solvent such a benzene or toluene at an elevated temperature, preferably at a temperature in a range of 80-100° C. to yield the compound of formula (IVE).

The compound of formula (IVE) was reduced by treating with hydrogen gas at an elevated pressure in the range of about 40-50 psi in a suitable solvent such as ethanol or methanol and the like, in the presence of a catalyst such as 10% palladium on carbon at ambient temperature to yield the corresponding compound of formula (VE).

The compound of formula (VE) was saponified by reaction with suitable base such as sodium hydroxide, potassium hydroxide, lithium hydroxide, sodium carbonate, potassium carbonate and the like in a solvent such as ethanol, methanol, aqueous tetrahydrofuran and the like, at a temperature from ambient temperature to a temperature of about 70-100° C. to yield the corresponding compound of formula (VIE).

The compound of formula (VIE) was then reacted with a suitably substituted 3-aminoquinoline using peptide coupling methods known to those skilled in the art to provide a compound of formula (VIIE).

Scheme F

Certain target compounds of the present invention may be prepared according to the process outlined in Scheme F below.

SCHEME F

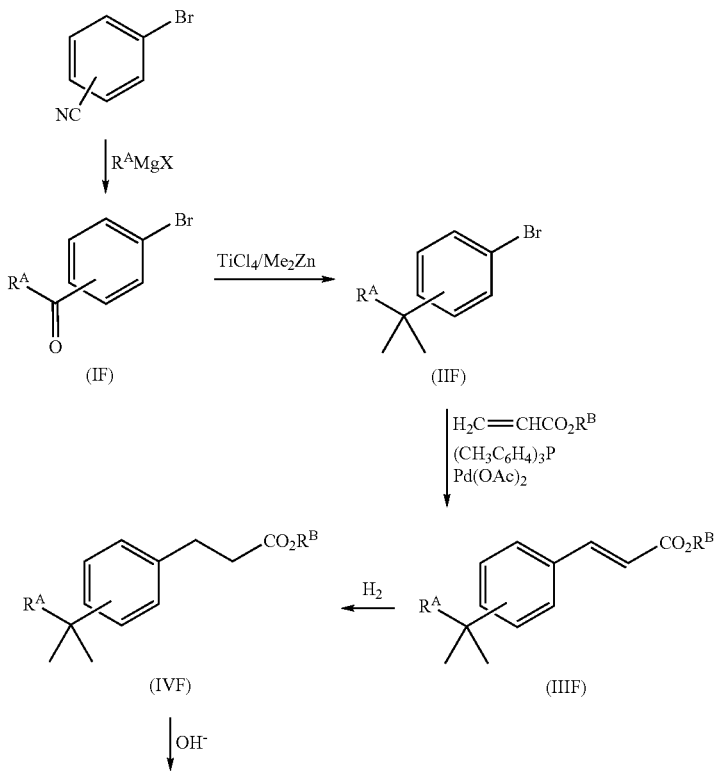

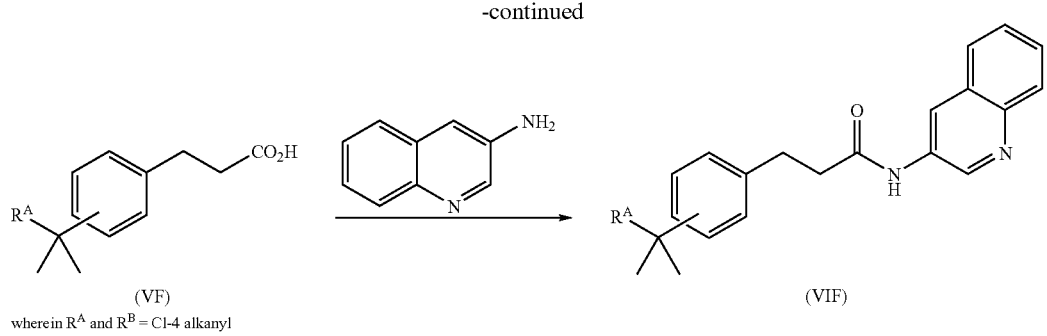

(VF)

wherein $R^A$ and $R^B$ = Cl-4 alkanyl (VIF)

More specifically, a suitably substituted cyano-bromobenzene was reacted with a Grignard reagent such as phenethyl magnesium chloride in a suitable solvent such as diethylether, tetrahydrofuran and the like to yield the corresponding ketone of formula (IF).

The compound of formula (IF) was reacted with titanium tetrachloride and dimethylzinc in a suitable solvent such as dichloromethane at a temperature in the range of −50° C. to ambient temperature to yield the corresponding compound of formula (IIF).

The compound of formula (IIF) underwent a Heck reaction with an unsaturated substrate such as methyl acrylate in the presence of a palladium catalyst such as palladium acetate and a ligand such as tri-o-tolylphosphine or triphenylphosphine in a solvent such as THF, ether and the like at an elevated temperature, preferably at a temperature in a range of 80-100° C. to yield the corresponding compound of formula (IIIF).

The compound of formula (IIIF) was reduced by treating with hydrogen gas at an elevated pressure in the range of about 40-50 psi in a suitable solvent such as ethanol or methanol and the like, in the presence of a catalyst such as 10% palladium on carbon at ambient temperature to yield the corresponding compound of formula (IVF).

The compound of formula (IVF) was saponified by reaction with suitable base such as sodium hydroxide, potassium hydroxide, lithium hydroxide, sodium carbonate, potassium carbonate and the like in a solvent such as ethanol, methanol, aqueous tetrahydrofuran and the like, at a temperature from ambient temperature to a temperature of about 70-100° C. to yield the corresponding compound of formula (VF).

The compound of formula (VF) was then reacted with a suitably substituted 3-aminoquinoline using peptide coupling methods known to those skilled in the art to provide a compound of formula (VIF).

Scheme G

Certain target compounds of the present invention may be prepared according to the process outlined in Scheme G below.

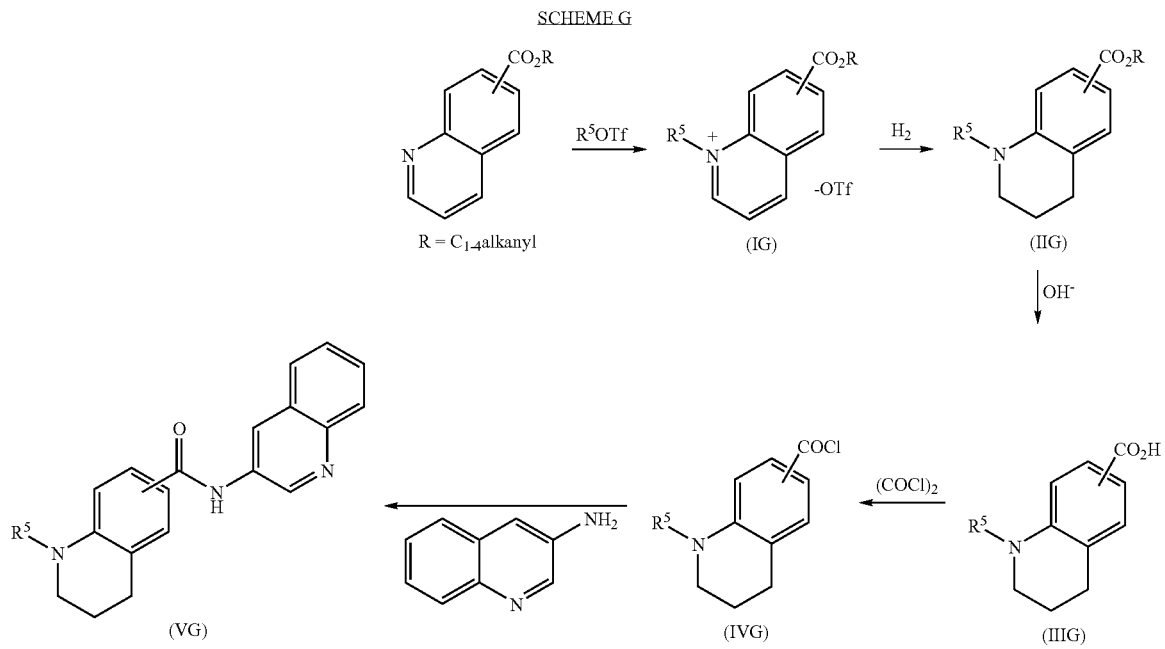

More specifically, a suitably substituted quinoline ester is reacted with an alkyl triflate such as methyl, n-butyl or n-pentyl triflate to yield the corresponding compound of formula (IG).

The compound of formula (IG) was reduced by treating with hydrogen gas at an elevated pressure in the range of about 40-50 psi in a suitable solvent such as ethanol or methanol and the like, in the presence of a catalyst such as 10% palladium on carbon at ambient temperature to yield the corresponding compound of formula (IIG).

The compound of formula (IIG) was saponified by reaction with suitable base such as sodium hydroxide, potassium hydroxide, lithium hydroxide, sodium carbonate, potassium carbonate and the like in a solvent such as ethanol, methanol, aqueous tetrahydrofuran and the like, at a temperature from ambient temperature to a temperature of about 70-100° C. to yield the corresponding compound of formula (IIIG).

The compound of formula (IIIG) was reacted with a chlorinating agent such as oxalyl chloride or thionyl chloride in the presence of an acylation catalyst such as DMF in a suitable solvent such as methylene chloride, chloroform or dichloroethane and the like at a temperature of about 0° C. to yield the corresponding compound of formula (IVG).

The compound of formula (IVG) was reacted with a suitably substituted 3-aminoquinoline in the presence of an organic base such as diisopropylethylamine or triethylamine and the like, in a suitable solvent such as methylene chloride, dichloroethane, DMF and the like, to yield the corresponding compound of formula (VG).

Scheme H

Certain target compounds of the present invention may be prepared according to the process outlined in Scheme H below.

More specifically, a suitably substituted nitro-cinnamate was reduced by treating with hydrogen gas at an elevated pressure in the range of about 40-50 psi in a suitable solvent such as ethanol or methanol and the like, in the presence of a catalyst such as 10% palladium on carbon at ambient temperature to yield the corresponding compound of formula (IH).

The compound of formula (IH) was reacted with an appropriately substituted aldehyde or ketone in the presence of a reducing agent such as tetramethylammonium triacetoxyborohydride, sodium triacetoxyborohydride, sodium cyanoborohydride and the like in a suitable solvent such as dichloroethane, dichloromethane, chloroform, methanol, tetrahydrofuran and the like at a temperature in the range of ambient temperature to a temperature of about 70-100° C. to yield the corresponding amine of formula (IIH).

The compound of formula (IIH) could be reacted with a suitably substituted aldehyde and a reducing agent such as tetramethylammonium triacetoxyborohydride, sodium triacetoxyborohydride, sodium cyanoborohydride and the like in a suitable solvent such as dichloroethane, dichloromethane, chloroform, methanol, tetrahydrofuran and the like at a temperature in the range of ambient temperature to a temperature of about 70-100° C. to yield the corresponding amine of formula (IIIH).

The compound of formula (IIIH) was saponified by reaction with suitable base such as sodium hydroxide, potassium hydroxide, lithium hydroxide, sodium carbonate, potassium carbonate and the like in a solvent such as ethanol, methanol, aqueous tetrahydrofuran and the like, at a temperature from ambient temperature to a temperature of about 70-100° C. to yield the corresponding compound of formula (IVH).

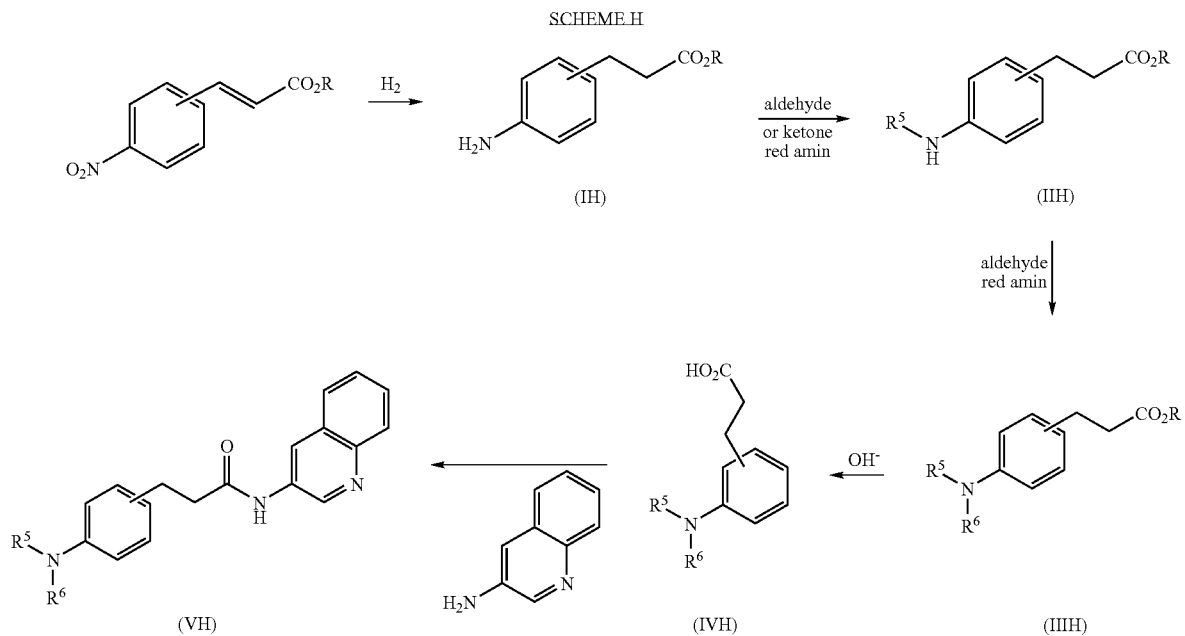

wherein R = $C_{1-4}$alkanyl

The compound of formula (IVH) was then reacted with a suitably substituted 3-aminoquinoline using peptide coupling methods known to those skilled in the art to provide a compound of formula (VH).

Scheme I

Certain target compounds of the present invention may be prepared according to the process outlined in Scheme I below.

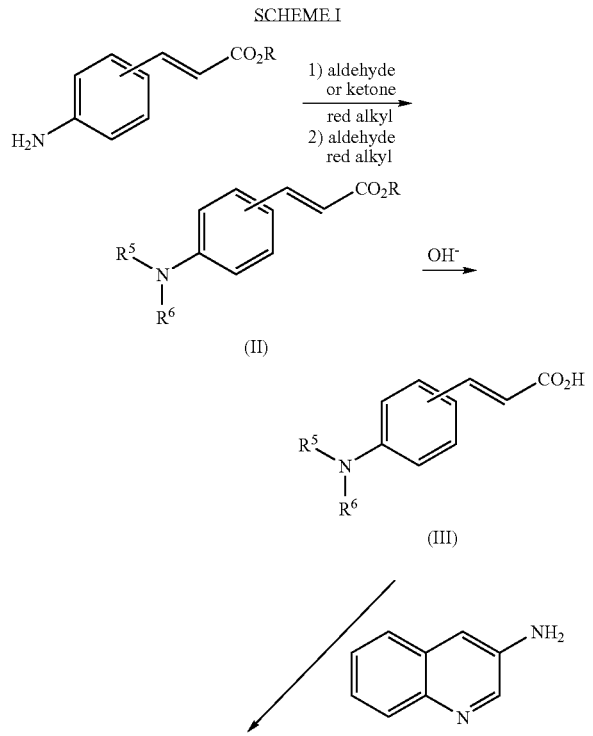

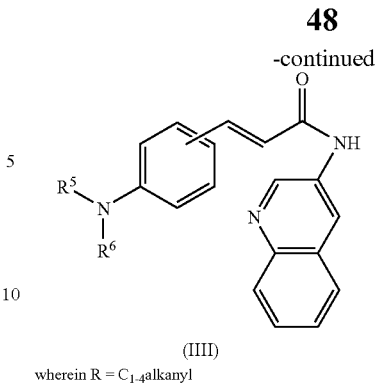

wherein R = C$_{1-4}$alkanyl

More specifically, a suitably substituted amino-cinnamate was reacted initially with a suitably substituted aldehyde or ketone and a reducing agent such as tetramethylammonium triacetoxyborohydride, sodium triacetoxyborohydride, sodium cyanoborohydride and the like in a suitable solvent such as dichloroethane, dichloromethane, chloroform, methanol, tetrahydrofuran and the like at a temperature in the range of ambient temperature to a temperature of about 70-100° C. This reaction could be followed, in the same reaction vessel, by reaction with a suitably substituted aldehyde and a reducing agent such as tetramethylammonium triacetoxyborohydride, sodium triacetoxyborohydride, sodium cyanoborohydride and the like in a suitable solvent such as dichloroethane, dichloromethane, chloroform, methanol, tetrahydrofuran and the like at a temperature in the range of ambient temperature to a temperature of about 70-100° C. to yield the corresponding amine of formula (II).

The compound of formula (II) was saponified by reaction with suitable base such as sodium hydroxide, potassium hydroxide, lithium hydroxide, sodium carbonate, potassium carbonate and the like in a solvent such as ethanol, methanol, aqueous tetrahydrofuran and the like, at a temperature from ambient temperature to a temperature of about 70-100° C. to yield the corresponding compound of formula (III).

The compound of formula (III) was then reacted with a suitably substituted 3-aminoquinoline using peptide coupling methods known to those skilled in the art to provide a compound of formula (IIII).

Scheme J

Certain target compounds of the present invention may be prepared according to the process outlined in Scheme J below.

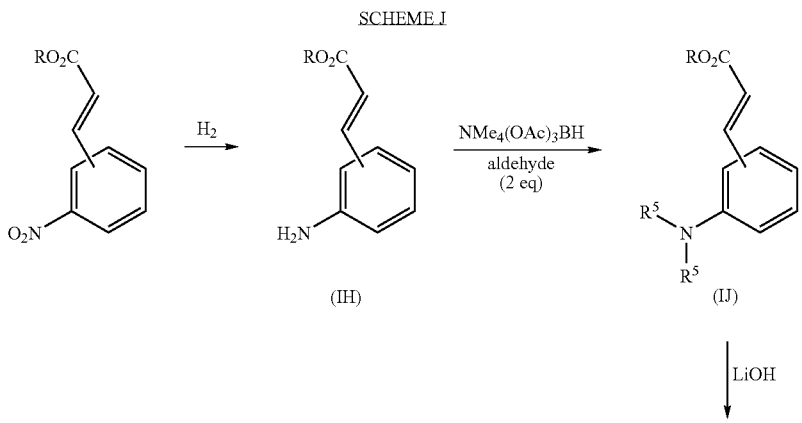

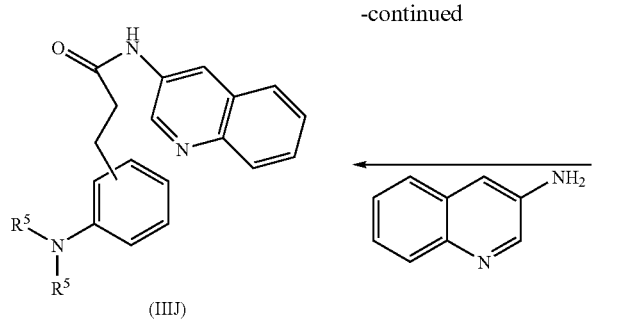

More specifically, a compound of formula (IH), obtained as described above, was reacted with a suitably substituted aldehyde and a reducing agent such as tetramethylammonium triacetoxyborohydride, sodium triacetoxyborohydride, sodium cyanoborohydride and the like in a suitable solvent such as dichloroethane, dichloromethane, chloroform, methanol, tetrahydrofuran and the like at a temperature in the range of ambient temperature to a temperature of about 70-100° C. to yield the corresponding tertiary amine of formula (IJ).

The compound of formula (IJ) was saponified by reaction with suitable base such as sodium hydroxide, potassium hydroxide, lithium hydroxide, sodium carbonate, potassium carbonate and the like in a solvent such as ethanol, methanol, aqueous tetrahydrofuran and the like, at a temperature from ambient temperature to a temperature of about 70-100° C. to yield the corresponding compound of formula (IIJ).

The compound of formula (IIJ) was then reacted with a suitably substituted 3-aminoquinoline using peptide coupling methods known to those skilled in the art to provide a compound of formula (IIIJ).

Scheme K

Certain target compounds of the present invention may be prepared according to the process outlined in Scheme K below.

More specifically, a compound of formula (IIA), prepared as described above, was saponified by reaction with suitable base such as sodium hydroxide, potassium hydroxide, lithium hydroxide, sodium carbonate, potassium carbonate and the like in a solvent such as ethanol, methanol, aqueous tetrahydrofuran and the like, at a temperature from ambient temperature to a temperature of about 70-100° C. to yield the corresponding compound of formula (IK).

The compound of formula (IK) was then reacted with a suitably substituted 3-aminoquinoline using peptide coupling methods known to those skilled in the art to provide a compound of formula (IIK).

Scheme L

Certain target compounds of the present invention may be prepared according to the process outlined in Scheme L below.

SCHEME L

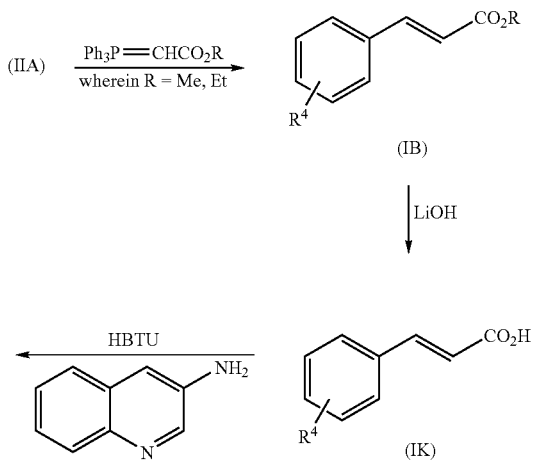

SCHEME K

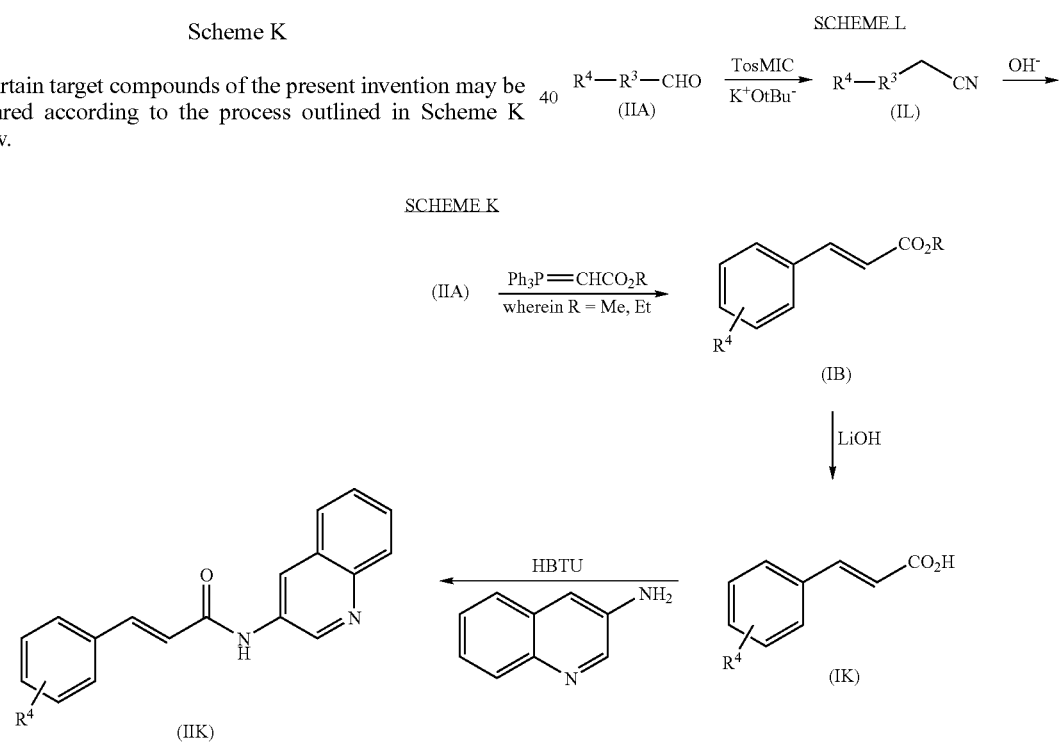

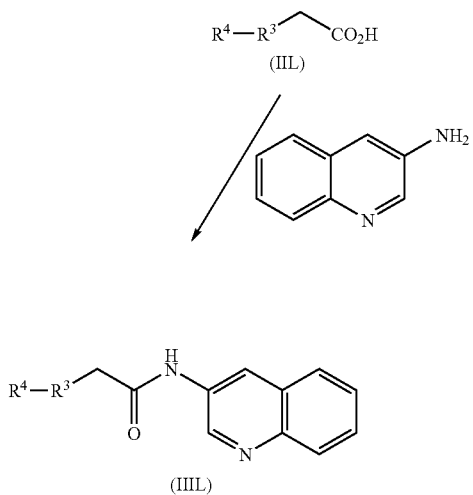

More specifically, a suitable substituted aldehyde of formula (IIA) was reacted with the reagent tosylmethylisocyanide (TosMIC) in the presence of a strong base such as potassium t-butoxide or sodium t-butoxide in a solvent such as dimethoxyethane or tetrahydrofuran and the like at a temperature in the range of −50° C. to 100° C. to yield the corresponding compound of formula (IL).

The compound of formula (IL) was hydrolyzed by reaction with suitable base such as sodium hydroxide, potassium hydroxide and the like in a solvent such as ethanol, methanol, aqueous tetrahydrofuran and the like, at an elevated temperature, preferably a temperature in the range of about 70-100° C. to yield the corresponding compound of formula (IIL).

The compound of formula (IIL) was reacted with a suitably substituted 3-aminoquinoline with a suitable coupling agent such as HATU, HBTU, 1,1'-carbonyl diimidazole and the like in the presence of an organic base such as diisopropylethylamine or triethylamine and the like, in a suitable solvent such as methylene chloride, dichloroethane, DMF and the like, to yield the corresponding compound of formula (IIIL).

Scheme M

Certain target compounds of the present invention may be prepared according to the process outlined in Scheme M below.

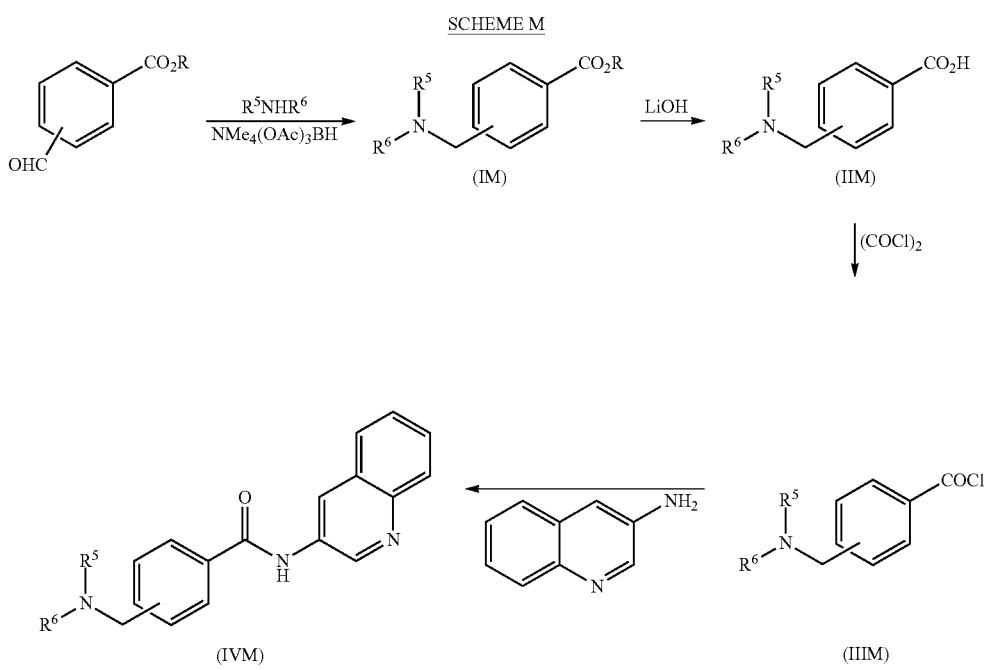

wherein R = $C_{1-4}$alkanyl

More specifically, a suitably substituted benzaldehyde ester and the aldehyde portion was reductively animated with an appropriately substituted amine in the presence of a reducing agent such as tetramethylammonium triacetoxyborohydride, sodium triacetoxyborohydride, sodium cyanoborohydride and the like in a suitable solvent such as dichloroethane, dichloromethane, chloroform, methanol, tetrahydrofuran and the like at a temperature in the range of ambient temperature to a temperature of about 70-100° C. to yield the corresponding amine of formula (IM).

The compound of formula (IM) was then saponified by reaction with suitable base such as sodium hydroxide, potassium hydroxide, lithium hydroxide, sodium carbonate, potassium carbonate and the like in a solvent such as ethanol, methanol, aqueous tetrahydrofuran and the like, at a temperature from ambient temperature to a temperature of about 70-100° C. to yield the corresponding compound of formula (IIM).

The compound of formula (IIM) was reacted with a chlorinating agent such as oxalyl chloride or thionyl chloride in the presence of an acylation catalyst such as DMF in a suitable solvent such as methylene chloride, chloroform, dichloroethane and the like at a temperature of about 0° C. to yield the corresponding compound of formula (IIIM).

The compound of formula (IIIM) was reacted with a suitably substituted 3-aminoquinoline in the presence of an organic base such as diisopropylethylamine or triethylamine and the like, in a suitable solvent such as methylene chloride, dichloroethane, DMF and the like, to yield the corresponding compound of formula (IVM).

Scheme N

Certain target compounds of the present invention may be prepared according to the process outlined in Scheme N below.

SCHEME N

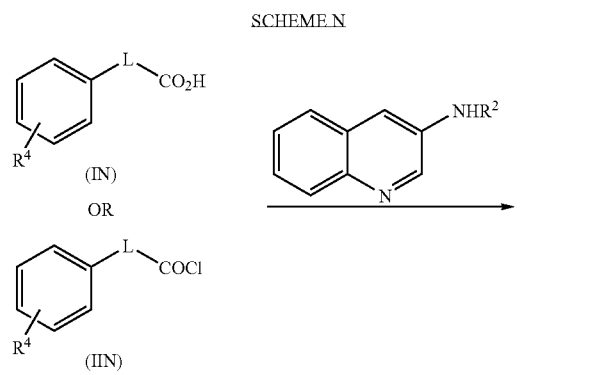

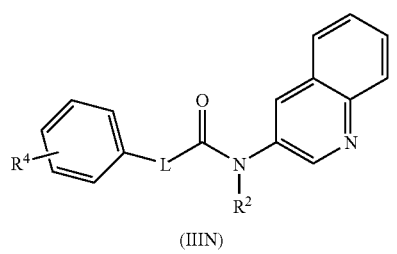

More specifically, a compound of formula (IN) was reacted with a suitably substituted 3-aminoquinoline with a suitable coupling agent such as HATU, HBTU, 1,1'-carbonyl diimidazole and the like in the presence of an organic base such as diisopropylethylamine or triethylamine and the like, in a suitable solvent such as methylene chloride, dichloroethane, DMF and the like, to yield the corresponding compound of formula (IIIN).

Alternatively a compound of formula (IIN) was reacted with a suitably substituted 3-aminoquinoline in the presence of an organic base such as diisopropylethylamine or triethylamine and the like, in a suitable solvent such as methylene chloride, dichloroethane, DMF and the like, to yield the corresponding compound of formula (IIIN).

Scheme O

Certain target compounds of the present invention may be prepared according to the process outlined in Scheme O below.

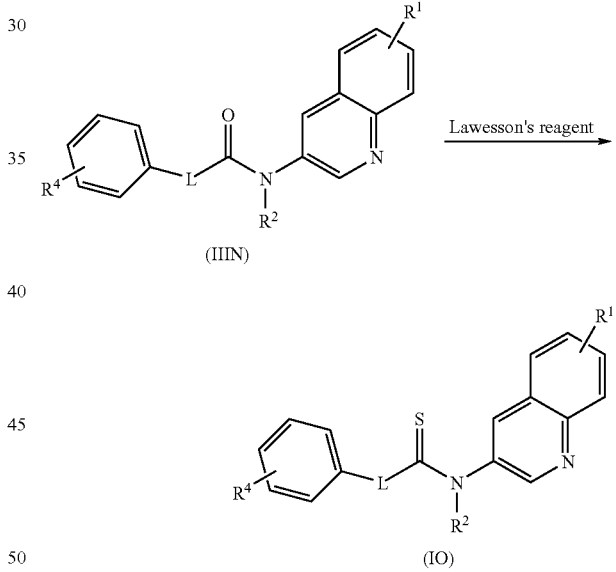

More specifically, a compound of formula (IIIN) was reacted with a sulfurizing agent such as Lawesson's reagent or phosphorous pentasulfide in a suitable solvent such as benzene, toluene and the like at an elevated temperature, preferably a temperature in the range of about 70-100° C. to yield the corresponding compound of formula (IO).

Scheme P

Certain target compounds of the present invention may be prepared according to the process outlined in Scheme P below.

Scheme O

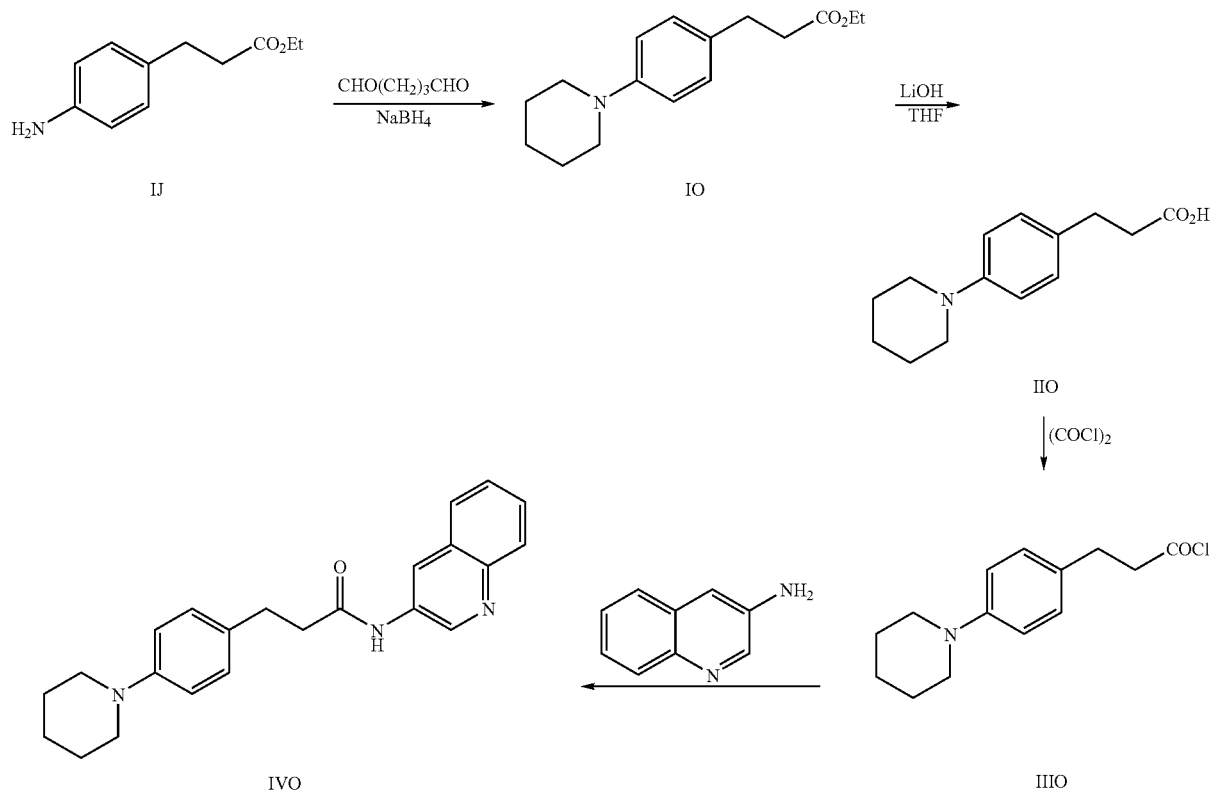

More specifically, a compound of formula (IJ), obtained as described above, was reacted with glutaraldehyde in the presence of a reducing agent such as sodium borohydride, tetramethylammonium triacetoxyborohydride, sodium triacetoxyborohydride, sodium cyanoborohydride and the like in a suitable solvent such as dichloroethane, dichloromethane, chloroform, methanol, tetrahydrofuran and the like at a temperature in the range of ambient temperature to a temperature of about 70-100° C. to yield the corresponding tertiary amine of formula (IO).

The compound of formula (IO) was saponified by reaction with suitable base such as lithium hydroxide, sodium hydroxide, potassium hydroxide, sodium carbonate, potassium carbonate and the like in a solvent such as ethanol, methanol, aqueous tetrahydrofuran and the like, at a temperature from ambient temperature to a temperature of about 70-100° C. to yield the corresponding carboxylic acid of formula (IIO).

The compound of formula (IIO) was reacted with a chlorinating agent such as oxalyl chloride or thionyl chloride in the presence of an acylation catalyst such as DMF in a suitable solvent such as methylene chloride, chloroform, dichloroethane and the like at a temperature of about 0° C. to yield the corresponding compound of formula (IIIO).

The compound of formula (IIIO) was reacted with a suitably substituted 3-aminoquinoline in the presence of an organic base such as diisopropylethylamine or triethylamine and the like, in a suitable solvent such as methylene chloride, dichloroethane, DMF and the like, to yield the corresponding compound of formula (IVO).

Scheme AA

Certain target compounds of the present invention may be prepared according to the process outlined in Scheme AA below.

SCHEME AA

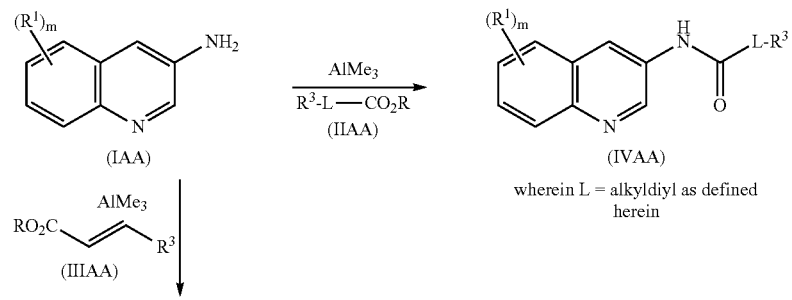

wherein L = alkyldiyl as defined herein

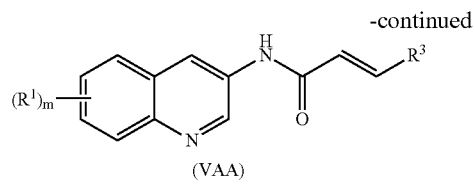

(VAA)

wherein R = C$_{1-4}$alkanyl

More specifically, a suitably substituted 3-aminoquinoline (IAA) and a suitably substituted ester was treated with trimethylaluminum in an aprotic solvent, such as 1,2-dichloroethane or toluene, at a temperature in the range of 0-100° C., to yield the corresponding compound of the formula IVAA or VAA.

Scheme BB

Certain target compounds of the present invention may be prepared according to the process outlined in Scheme BB below.

The compound of the formula (IIIBB) was treated with an acid, such as TFA or hydrochloric acid, in a suitable solvent, such as dichloromethane or methanol, at a temperature range of 0-100° C., to yield the corresponding compound of the formula (IVBB).

The compound of the formula (IVBB) and a suitably substituted ketone or aldehyde was treated with a suitable reducing agent, such as tetramethylammonium triacetoxyborohydride or sodium cyanoborohydride, in a suitable solvent, such as 1,2-dichloroethane or methanol, at a temperature range of 0-100° C., to yield the corresponding compound of the formula (VBB).

SCHEME BB

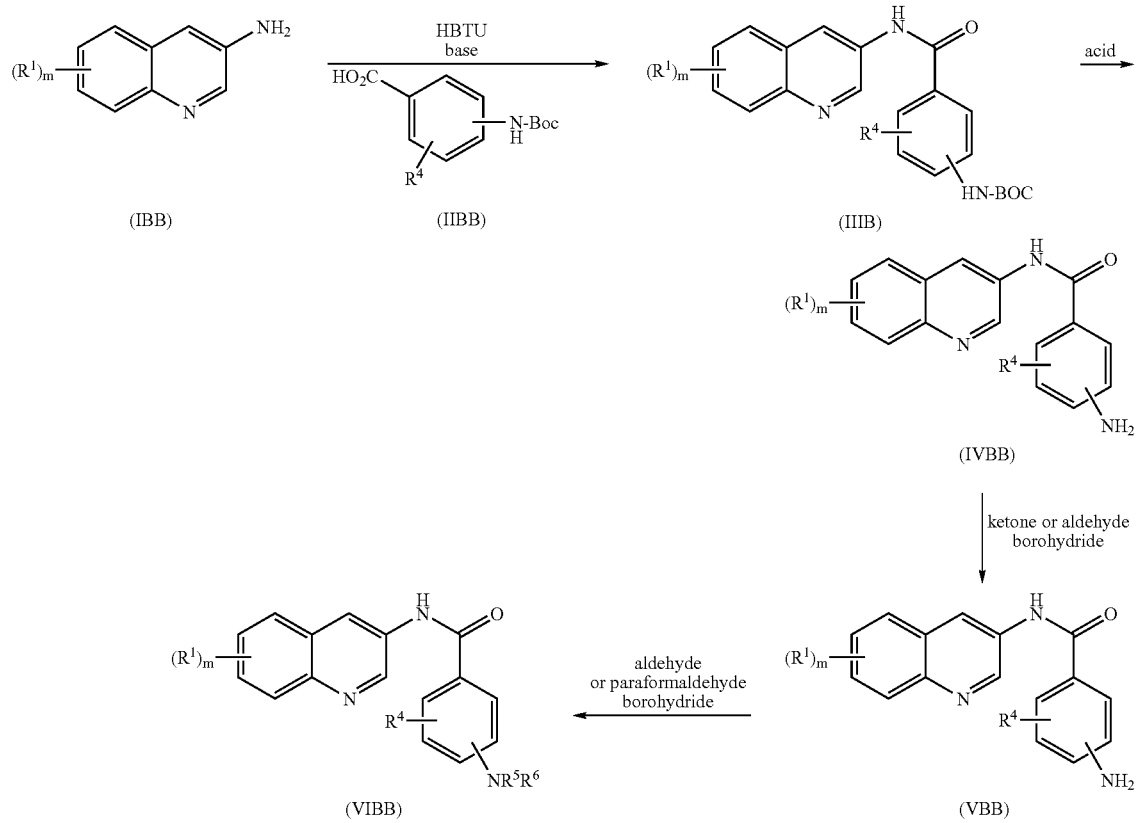

More specifically, an acid of the formula (IIBB) was activated with a suitable activating reagent, such as HBTU or CDI or HATU, and a suitable base, such as TEA or DIEA, in a suitable solvent, such as acetonitrile or DMF or dichloromethane, at a temperature range 0-200° C., and subsequently treated with a suitably substituted 3-aminoquinoline (IBB), at a temperature range of 0-200° C. to yield the corresponding compound of the formula (IIIBB).

The compound of the formula (VBB) and a suitably substituted aldehyde or paraformaldehyde was treated with a suitable reducing agent, such as tetramethylammonium triacetoxyborohydride or sodium cyanoborohydride, in a suitable solvent, such as 1,2-dichloroethane or methanol, at a temperature range of 0-100° C., to yield the corresponding compound of the formula (VIBB).

Scheme CC

Certain target compounds of the present invention may be prepared according to the process outlined in Scheme CC below.

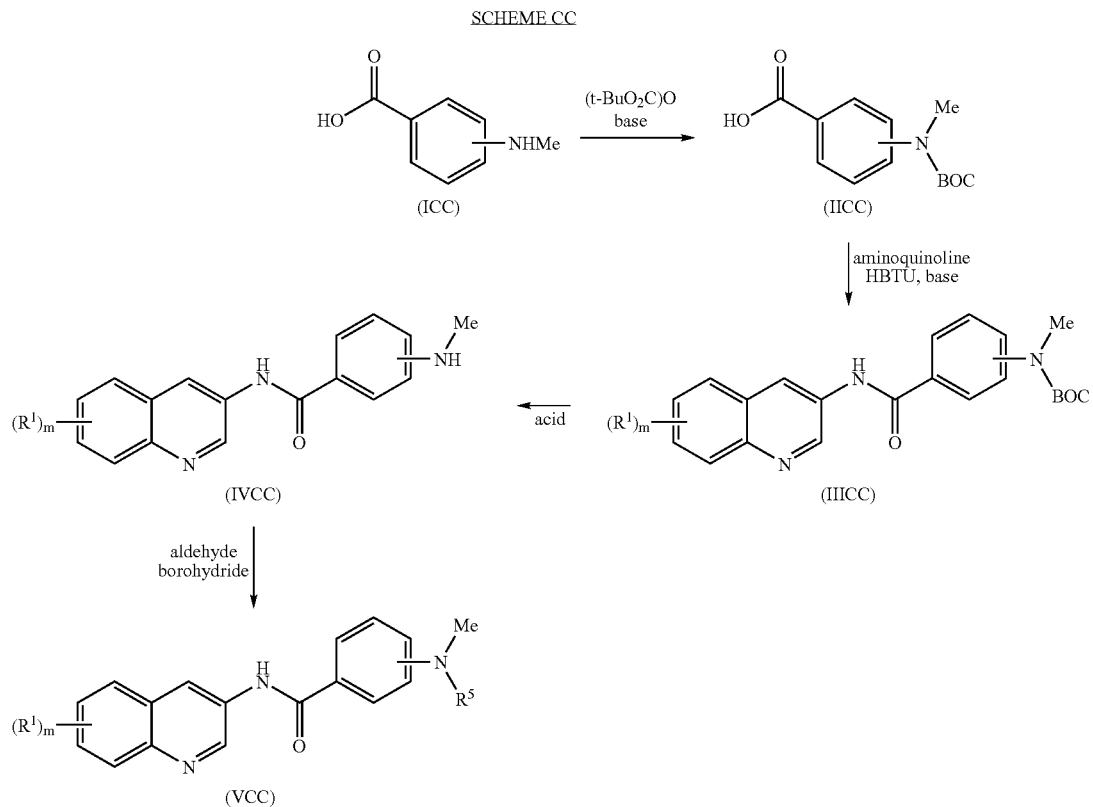

More specifically, a suitably substituted aminobenzoic acid (ICC) was treated with di-tert-butyl dicarbonate and a suitable base, such as sodium hydroxide or sodium carbonate, in a suitable solvent, such as water or dioxane, at a temperature range of 0-100° C., to yield the corresponding compound of the formula (IICC).

An acid of the formula (IICC) was activated with and a suitable activating reagent, such as HBTU or CDI or HATU, and a suitable base, such as TEA or DIEA, in a suitable solvent, such as acetonitrile or DMF or dichloromethane, at a temperature range 0-200° C., and subsequently treated with a suitably substituted 3-aminoquinoline, at a temperature range of 0-200° C. to yield the corresponding compound of the formula (IIICC).

The compound of the formula (IIICC) was treated with an acid, such as TFA or hydrochloric acid, in a suitable solvent, such as dichloromethane or methanol, at a temperature range of 0-100° C., to yield the corresponding compound of the formula (IVCC).

The compound of the formula (IVCC) and a suitably substituted aldehyde was treated with a suitable reducing agent, such as tetramethylammonium triacetoxyborohydride or sodium cyanoborohydride, in a suitable solvent, such as 1,2-dichloroethane or methanol, at a temperature range of 0-100° C., to yield the corresponding compound of the formula (VCC).

Scheme DD

Certain target compounds of the present invention may be prepared according to the process outlined in Scheme DD below.

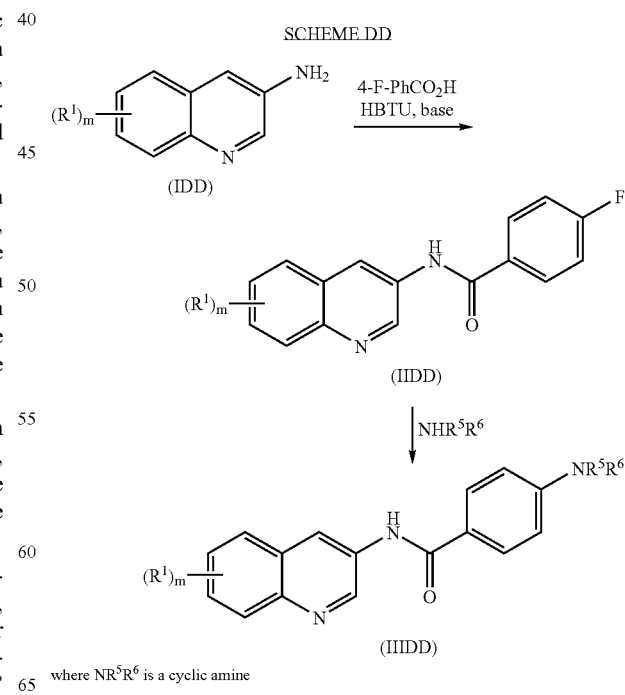

where $NR^5R^6$ is a cyclic amine

More specifically, 4-fluorobenzoic acid was activated with a suitable activating reagent, such as HBTU or CDI or HATU, and a suitable base, such as TEA or DIEA, in a suitable solvent, such as acetonitrile or DMF or dichloromethane, at a temperature range 0-200° C., and subsequently treated with a suitably substituted 3-aminoquinoline (IDD), at a temperature range of 0-200° C., to yield the corresponding compound of the formula (IIDD).

The compound of the formula (IIDD) was treated with an amine (NHR⁵R⁶) in a suitable solvent, such as DMSO or DMF or methanol or toluene, at a temperature of 50-200° C., to yield the corresponding compound of the formula (IIIDD).

Scheme EE

Certain target compounds of the present invention may be prepared according to the process outlined in Scheme EE below.

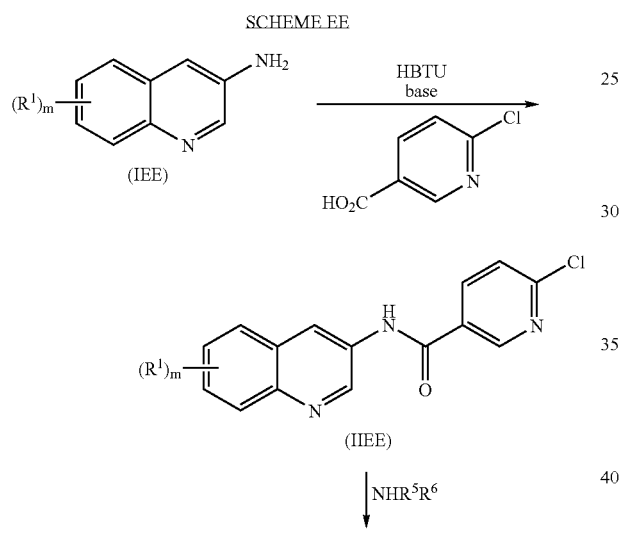

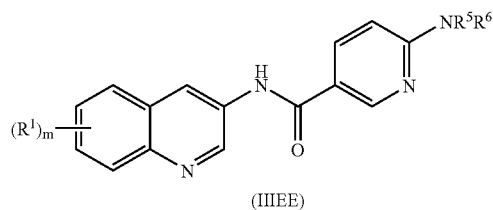

More specifically, 6-chloronicotinic acid was activated with a suitable activating reagent, such as HBTU or CDI or HATU, and a suitable base, such as TEA or DIEA, in a suitable solvent, such as acetonitrile or DMF or dichloromethane, at a temperature range 0-200° C., and subsequently treated with a suitably substituted 3-aminoquinoline (IEE), at a temperature range of 0-200° C., to yield the corresponding compound of the formula (IIEE).

The compound of the formula (IIEE) was treated with an amine (NHR⁵R⁶) in a suitable solvent, such as DMSO or DMF or methanol or toluene, at a temperature of 50-200° C., to yield the corresponding compound of the formula (IIIEE).

Scheme FF

Certain target compounds of the present invention may be prepared according to the process outlined in Scheme FF below.

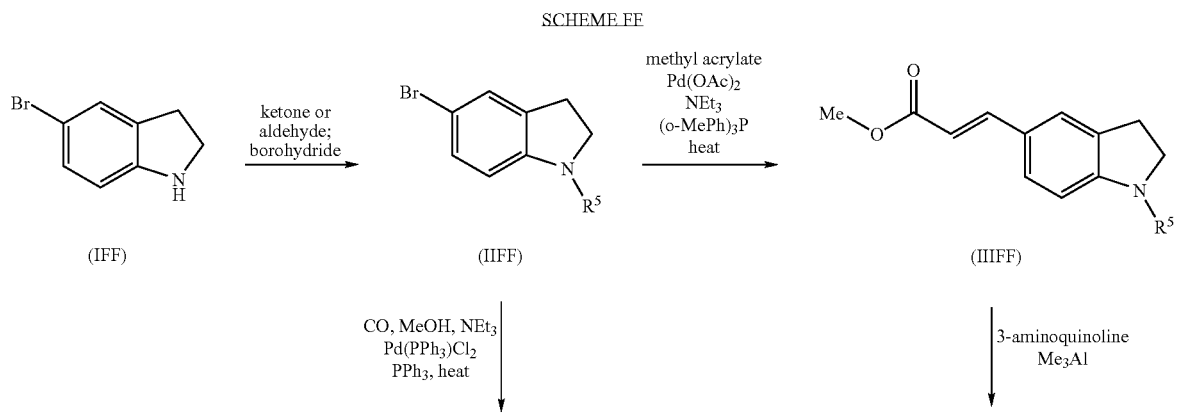

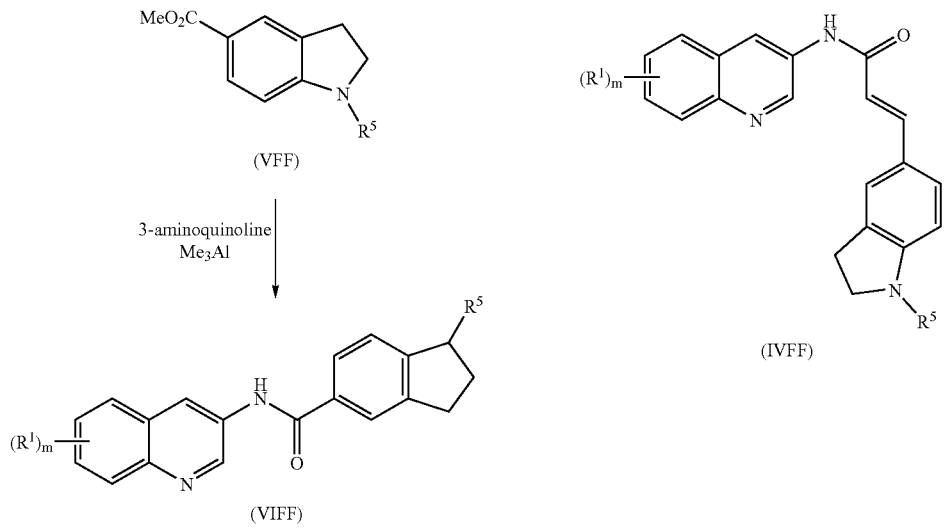

More specifically, 5-bromoindoline (IFF) was treated with a suitable ketone or aldehyde and a suitable reducing agent, such as tetramethylammonium triacetoxyborohydride or sodium cyanoborohydride, in a suitable solvent, such as 1,2-dichloroethane or methanol, at a temperature range of 0-100° C., to yield the corresponding compound of the formula (IIFF).

The compound of the formula (IIFF), methyl acrylate, a suitable catalyst, such as palladium(II) acetate, a suitable phosphine ligand, such as tri-(o-tolyl)phosphine, a suitable base, such as TEA or DIEA, was heated to a temperature of 50-200° C., to yield the corresponding compound of the formula (IIIFF).

A compound of the formula (IIIFF) and suitably substituted 3-aminoquinoline was treated with trimethylaluminum in an aprotic solvent, such as 1,2-dichloroethane or toluene, at a temperature in the range of 0-200° C., to yield the corresponding compound of the formula (IVFF).

The compound of the formula (IIFF), a suitable catalyst, such as bis-(triphenylphosphine)palladium(II)chloride, a suitable phosphine ligand, such as triphosphine, a suitable base, such as TEA or DIEA, in the presence of carbon monoxide (20-200 psi) was heated to a temperature of 50-200° C., to yield the corresponding compound of the formula (VFF).

A compound of the formula (VFF) and suitably substituted 3-aminoquinoline was treated with trimethylaluminum in an aprotic solvent, such as 1,2-dichloroethane or toluene, at a temperature in the range of 0-200° C., to yield the corresponding compound of the formula (VIFF).

Scheme GG

Certain target compounds of the present invention may be prepared according to the process outlined in Scheme GG below.

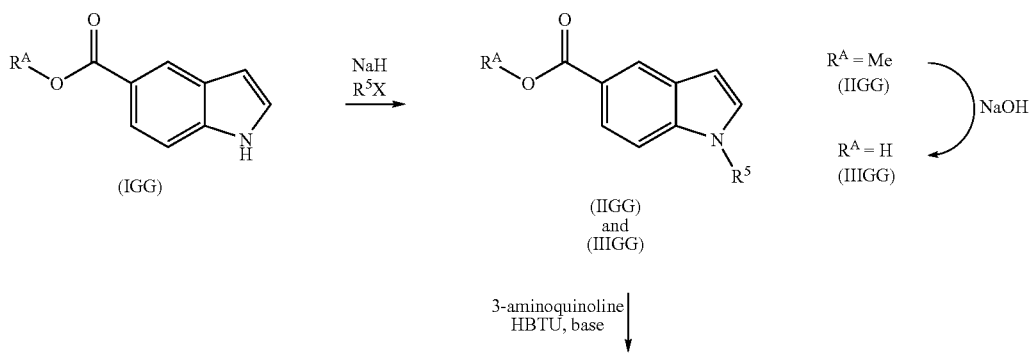

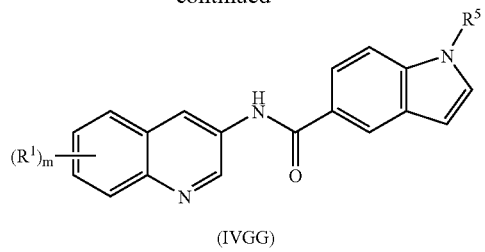

(IVGG)

More specifically, a compound of the formula (IGG) was treated with a suitable base, such as sodium hydride, and an alkyl halide, in a suitable solvent, such as DMF or THF or DMSO, at a temperature range of 0-200° C., to yield the corresponding compound of the formula (IIGG, $R^4$=Me).

A compound of the formula (IIGG, $R^4$=Me) was saponified with a suitable source of hydroxide, such as sodium hydroxide or potassium hydroxide, in a suitable solvent, such as methanol or water or THF, at a temperature range of 0-200° C., to yield the corresponding compound of the formula (IIIGG, $R^4$=H).

An acid of the formula (IIIGG, $R^4$=H) was activated with a suitable activating reagent, such as HBTU or CDI or HATU, and a suitable base, such as TEA or DIEA, in a suitable solvent, such as acetonitrile or DMF or dichloromethane, at a temperature range 0-200° C., and subsequently treated with a suitably substituted 3-aminoquinoline, at a temperature range of 0-200° C., to yield the corresponding compound of the formula (IVGG).

Scheme HH

Certain target compounds of the present invention may be prepared according to the process outlined in Scheme HH below.

SCHEME HH

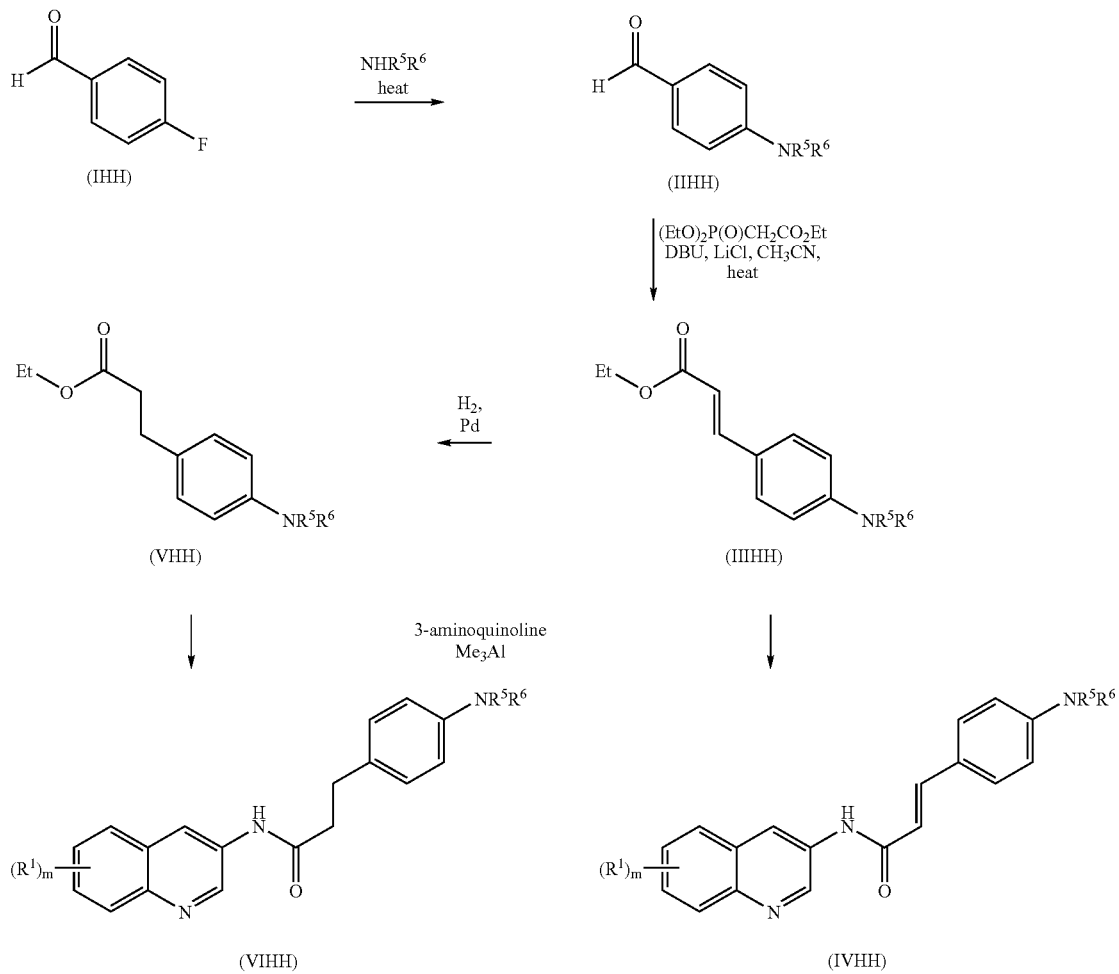

More specifically, 4-fluorobenzaldehyde was treated with an amine (NHR⁵R⁶) in a suitable solvent, such as acetonitrile or DMSO or toluene, at a temperature range of 50-200° C., to yield a compound of the formula (IIHH).

A compound of the formula (IIHH) was treated with a suitable Wittig reagent, such as triethyl phosphonoacetate, a suitable base, such as DBU, and lithium chloride, in a suitable solvent, such as acetonitrile or dichloromethane, at a temperature of 50-200° C., to yield a compound of the formula (IIIHH).

A compound of the formula (IIIHH) and a suitably substituted 3-aminoquinoline was treated with trimethyl aluminum in a suitable solvent, such as 1,2-dichloroethane or toluene, at a temperature range of 0-200° C., to yield a compound of the formula (IVHH).

A compound of the formula (IIIHH) was hydrogenated at 20-80 psi, with a suitable catalyst, such as palladium, in a suitable solvent, such as methanol, at a temperature range of 0-200° C., to yield a compound of the formula (VHH).

A compound of the formula (VHH) and a suitably substituted 3-aminoquinoline was treated with trimethylaluminum in a suitable solvent, such as 1,2-dichloroethane or toluene, at a temperature range of 0-200° C., to yield a compound of the formula (VIHH).

Scheme JJ

Certain target compounds of the present invention may be prepared according to the process outlined in Scheme JJ below.

SCHEME JJ

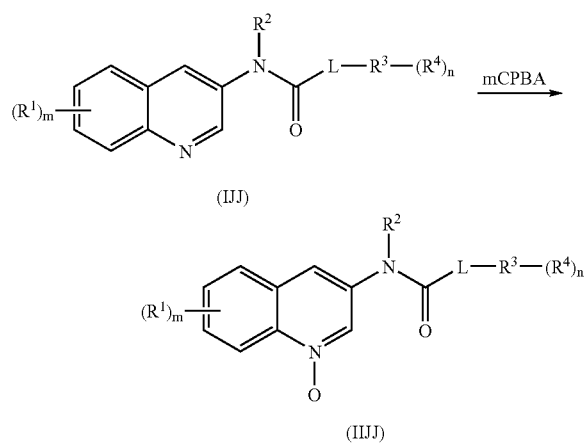

More specifically, a compound of the formula (IJJ) was treated with a suitable oxidizing agent, such as mCPBA, in a suitable solvent, such as dichloromethane, at a temperature range of −40-100° C., to yield a compound of the formula (IIJJ).

Scheme KK

Certain target compounds of the present invention may be prepared according to the process outlined in Scheme KK below.

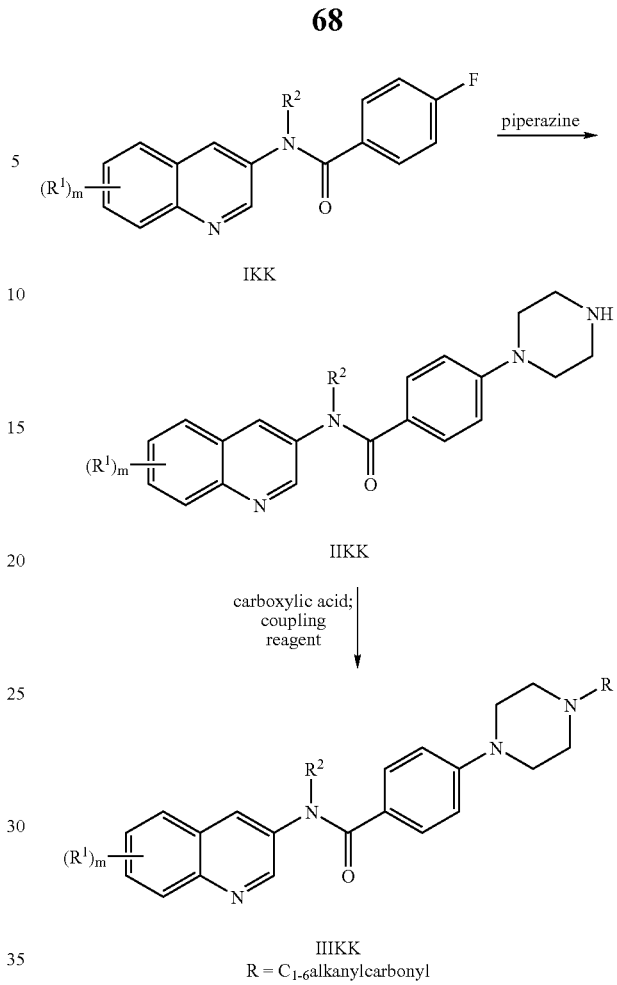

More specifically, a compound of formula (IKK) was treated with piperazine in a suitable solvent, such as dimethylsulfoxide, at a temperature in the range of 50-250° C., to yield the corresponding compound of the formula (IIKK).

The compound of the formula (IIKK) was coupled to a suitable organic carboxylic acid, using coupling methods known to those skilled in the art to provide the compound of the formula (IIIKK).

Scheme LL

Certain target compounds of the present invention may be prepared according to the process outlined in Scheme LL below.

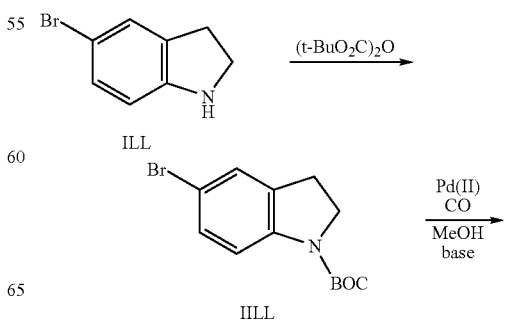

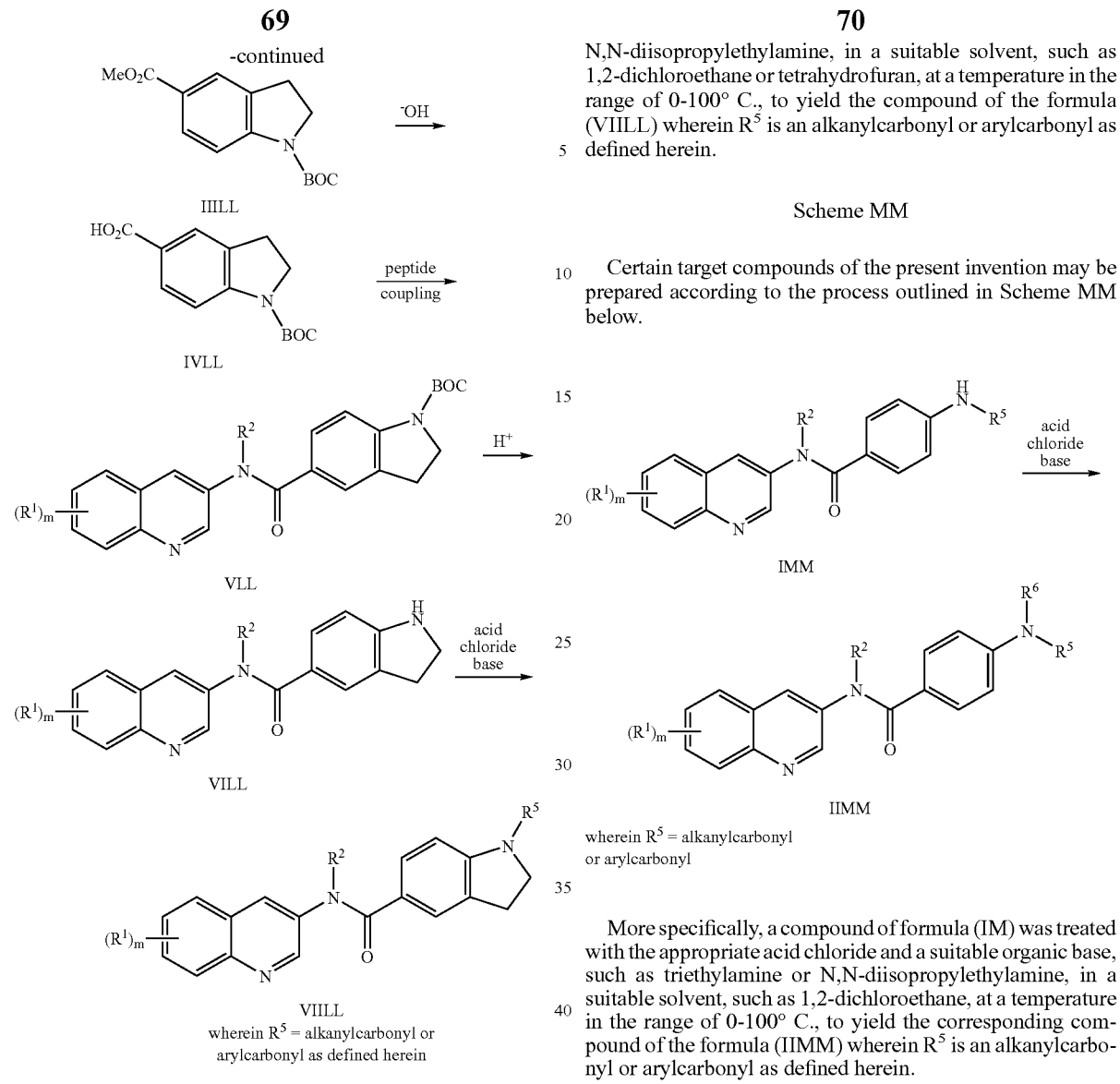

More specifically, 5-bromoindoline (ILL) was treated with di-tert-butyldicarbonate in a suitable solvent, such as dichloromethane, at a temperature in the range of 0-100° C., to yield the corresponding BOC-protected 5-bromoindoline (IILL).

The compound of the formula (IILL) was treated with an appropriate catalyst, such as bistriphenylphosphinopalladium(II) chloride, an appropriate organic base, such as tributylamine, in the presence of carbon monoxide gas at 10 to 1000 psi, in methanol, at a temperature in the range of 20-200° C., to yield a the ester of the formula (IIILL).

The ester of the formula (IIILL) was converted to the corresponding acid of the formula (IVLL) using saponification methods known to those skilled in the art.

The acid of the formula (IVLL) was coupled to an appropriately substituted 3-aminoquinoline, using methods known to those skilled in the art, to yield a compound of the formula (VLL).

A BOC-protected compound of the formula (VLL) was deprotected using an appropriate organic or inorganic acid, such as trifluoroacetic acid or hydrochloric acid, in a suitable solvent, such as dichloromethane or dioxane, at a temperature in the range of 0-100° C., to yield the compound of the formula (VILL).

A compound of the formula (VILL) was treated with an appropriate acid chloride and a suitable organic base, such as N,N-diisopropylethylamine, in a suitable solvent, such as 1,2-dichloroethane or tetrahydrofuran, at a temperature in the range of 0-100° C., to yield the compound of the formula (VIILL) wherein $R^5$ is an alkanylcarbonyl or arylcarbonyl as defined herein.

Scheme MM

Certain target compounds of the present invention may be prepared according to the process outlined in Scheme MM below.

More specifically, a compound of formula (IM) was treated with the appropriate acid chloride and a suitable organic base, such as triethylamine or N,N-diisopropylethylamine, in a suitable solvent, such as 1,2-dichloroethane, at a temperature in the range of 0-100° C., to yield the corresponding compound of the formula (IIMM) wherein $R^5$ is an alkanylcarbonyl or arylcarbonyl as defined herein.

Scheme NN

Certain target compounds of the present invention may be prepared according to the process outlined in Scheme NN below.

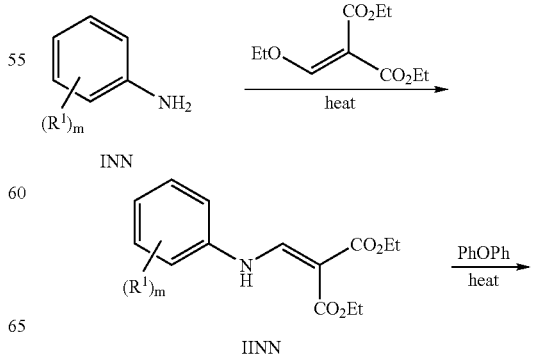

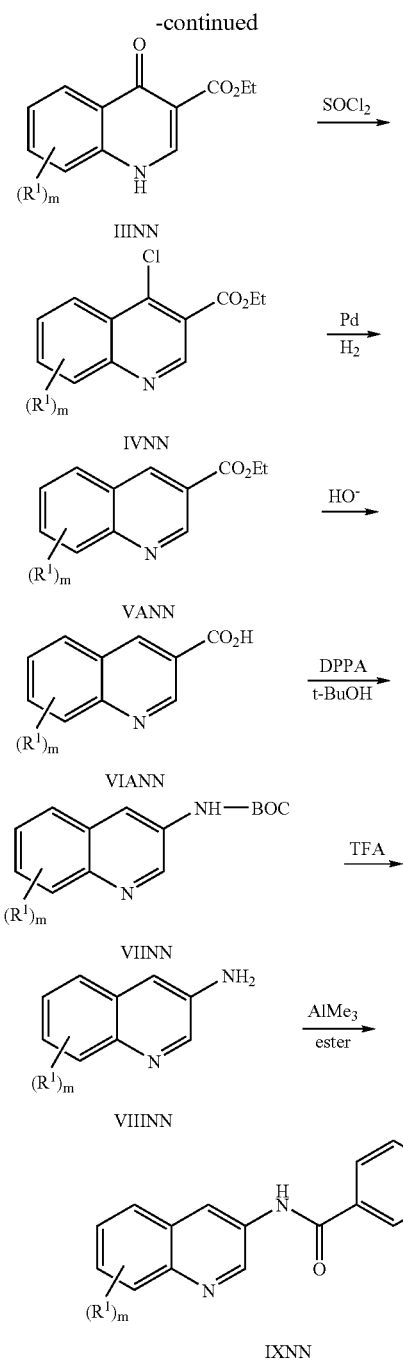

appropriate solvent, such as ethanol or ethyl acetate or tetrahydrofuran at a temperature in the range of 25-200° C., to yield the corresponding compound of the formula (VNN).

A compound of the formula (VNN) was treated with a source of hydroxide ion, such as sodium hydroxide, in an appropriate solvent, such as methanol or water, or mixture of solvents, such as methanol and water, at a temperature in the range of 0-200° C., to yield the corresponding compound of the formula (VINN). A compound of the formula (VINN) was treated with diphenylphosphoryl azide in the presence of a base, such as TEA or diisopropylethylamine, in t-butanol at a temperature in the range of 25-300° C. to yield the corresponding compound of the formula (VIINN).

A compound of the formula (VIINN) was treated with an acid, such as trifluoroacetic acid or hydrochloric acid or trifluoroacetic acid with water, with or without a solvent, such as DCE or DCM or THF or methanol, at a temperature in the range of 0-200° C., to yield the corresponding compound of the formula (VIIINN).

A compound of the formula (VIIINN) was treated with the appropriate ester and trimethylaluminum in an appropriate aprotic solvent or mixture of solvents, such as DCE or DCM or toluene at a temperature in the range of 25-300° C., to yield the corresponding compound of the formula (IXNN).

Scheme OO

Certain target compounds of the present invention may be prepared according to the process outlined in Scheme OO below.

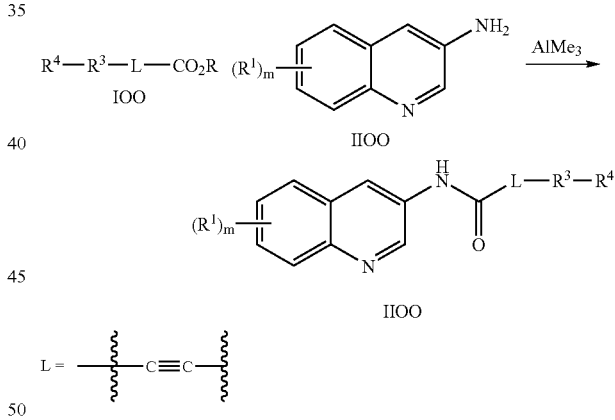

More specifically, a suitably substituted compound of formula (INN) was treated with diethyl ethoxymethylenemalonate and heated to a temperature in the range of 0-300° C., to yield the corresponding compound of the formula (IINN). A compound of formula (IINN) was added to a high boiling solvent such as diphenylether at a temperature in the range of 200-400° C. to yield the corresponding compound of the formula (IIINN).

A compound of formula (IIINN) was treated with thionyl chloride or phosphorous oxychloride at a temperature in the range of 25-200° C., to yield the corresponding compound of the formula (IVNN).

A compound of formula (IVNN) was treated in with hydrogen gas over an appropriate catalyst, such as palladium, in an More specifically, an ester of the formula (IOO) and an aminoquinoline of the formula (IIOO) was treated with the trimethylaluminum in an appropriate aprotic solvent or mixture of solvents, such as DCE or DCM or toluene, at a temperature in the range of 25-300° C., to yield the corresponding compound of the formula (IIIOO).

SPECIFIC SYNTHETIC EXAMPLES

Specific compounds which are representative of the invention may be prepared as per the following examples offered by way of illustration and not by way of limitation. No attempt has been made to optimize the yields obtained in any of the reactions. One skilled in the art would know how to increase such yields through routine variations in reaction times, temperatures, solvents and/or reagents.

Unless otherwise indicated, $^1$H NMR's were run on a Bruker AC-300 instrument. Mass spectral analyses were performed on a Fisons instrument (Hewlett-Packard HPLC driven electrospray MS instrument).

Preparation of Hydrocarbon Starting Materials (1-Methyl-pentyl)-benzene

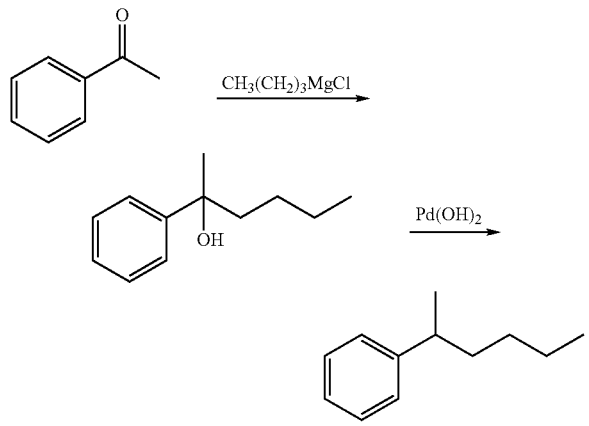

A. To 25 mL anhydrous THF in a round bottom flask equipped with a stir bar under a nitrogen atmosphere was added butylmagnesium chloride (2M in Et$_2$O, 20 mL, 40 mmol). Acetophenone (4.2 mL, 36.0 mmol) was dissolved in 25 mL anhydrous THF and added dropwise via addition funnel to the reaction over a period of 17 minutes. The reaction was then stirred overnight and quenched by addition of saturated ammonium chloride solution (50 mL) and extracted once with 100 mL diethylether. The organics were washed once with additional saturated ammonium chloride (50 mL), once with water (50 mL) and once with brine (50 mL). The organics were then dried over Na$_2$SO$_4$, filtered and concentrated in vacuo to yield the product as a nearly colorless oil (6.33 g, 35.5 mmol). This product was carried on to the next step without further purification.

B. The tertiary alcohol from step A, 2-phenyl-hexan-2-ol (35.5 mmol), was dissolved in 50 mL ethanol along with Pd(OH)$_2$ (0.695 g). The mixture was hydrogenated at ~50 psi overnight, filtered over a pad of celite and the reaction was found to be incomplete. Fresh Pd(OH)$_2$ (0.741 g) was added and the hydrogenation was continued overnight. The reaction mixture was filtered over a pad of celite and evaporated in vacuo to yield the title product as a tan liquid (3.874 g, 23.9 mmol). $^1$H NMR (CDCl$_3$): δ 7.28 (m, 2H), 7.18 (m, 3H), 2.68 (h, 1H), 1.57 (m, 2H), 1.34-1.03 (m, 7H), 0.87 (t, 3H).

Cyclohexylmethyl-benzene

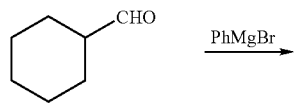

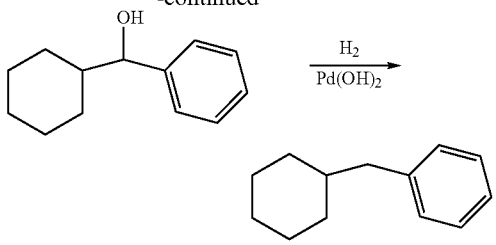

A. To a nitrogen flushed 3-neck round bottom flask equipped with a stir bar and addition funnel was added 25 mL anhydrous THF and phenylmagnesium bromide (3M in Et$_2$O, 10.0 mL, 30.0 mmol). A solution of cyclohexanecarboxaldehyde (3.3 mL, 27.2 mmol) in 15 mL anhydrous THF was added to the reaction mixture via addition funnel over a period of 6 minutes. The reaction was allowed to stir for 48 hours at which time it was quenched with saturated ammonium chloride (25 mL) and then extracted with 100 mL diethylether. The organics were washed once with additional saturated ammonium chloride (50 mL), once with water (50 mL) and once with brine (50 mL). The organics were then dried over Na$_2$SO$_4$, filtered and concentrated in vacuo to yield the crude product, which was carried on without further purification B. The secondary alcohol from step A, was dissolved in 50 mL ethanol along with Pd(OH)$_2$ (0.546 g). The mixture was hydrogenated at ~50 psi overnight at which time an additional amount of Pd(OH)$_2$ (1.08 g) was added and the hydrogenation was continued overnight. The reaction mixture was filtered over a pad of celite and evaporated in vacuo to yield the title product as a nearly colorless oil (4.560 g, 26.2 mmol). $^1$H NMR (CDCl$_3$): δ 7.28 (m, 2H), 7.17 (m, 3H), 2.49 (d, 2H), 1.81-1.35 (m, 6H), 1.30-1.03 (m, 3H), 1.02-0.79 (m, 2H).

(1-Cyclohexyl-1-methyl-ethyl)-benzene

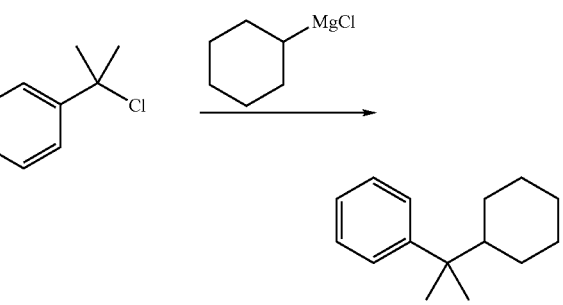

To a nitrogen flushed 3-neck round bottom flask equipped with a stir bar and addition funnel was added cyclohexylmagnesium chloride (2M in Et$_2$O, 7.5 mL, 15 mmol). The solution was evaporated under a stream of nitrogen then slightly warmed under vacuum to remove any residual ether. The dried Grignard reagent was then dissolved in 25 mL methylene chloride and cooled in an ice bath. A solution of α,α-dimethylbenzylchloride in 25 mL methylene chloride was added to the reaction mixture via addition funnel over a period of 6 minutes. The ice bath was then allowed to melt and the reaction was allowed to warm up overnight. The reaction mixture was diluted with 100 mL diethylether and washed once with saturated ammonium chloride (50 mL), once with 1N HCl (50 mL), once with 1N NaOH (50 mL) and once with (1,1-Dimethyl-pentyl)-benzene

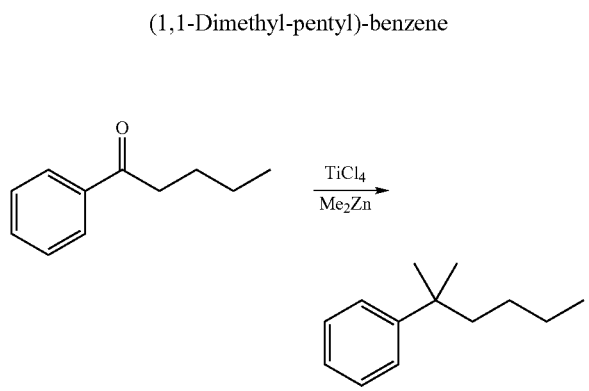

To a nitrogen flushed round bottom flask equipped with a stir bar and addition funnel was added 80 mL dichloromethane. TiCl$_4$ (4.6 mL, 41.9 mmol) was added and the mixture was cooled in a dry ice-acetonitrile bath to ~−50° C. To this was added Me$_2$Zn (2M in toluene, 21 mL, 42 mmol). The resulting thick slurry was allowed to stir for ~10 minutes. A solution of valerophenone (3.3 mL, 20.1 mmol) in 20 mL methylene chloride was added to the reaction mixture via addition funnel over a period of 16 minutes. The ice bath was then allowed to melt and the reaction was allowed to warm up overnight at which time the reaction was carefully poured into 500 mL ice/water and then extracted twice with 100 mL methylene chloride. The combined organics were washed twice with 1N HCl (100 mL) and once with brine (100 mL). The organics were then dried over Na$_2$SO$_4$, filtered and concentrated in vacuo to yield the crude product, which was used without further purification. $^1$H NMR (CDCl$_3$): δ 7.37-7.08 (m, 5H), 1.62 (m, 2H), 7.31 (s, 6H), 1.22 (t, 2H), 1.05 (m, 2H), 0.82 (t, 3H).

Example (1)

3-[4-(1-Methyl-pentyl)-phenyl]-N-quinolin-3-yl-benzamide

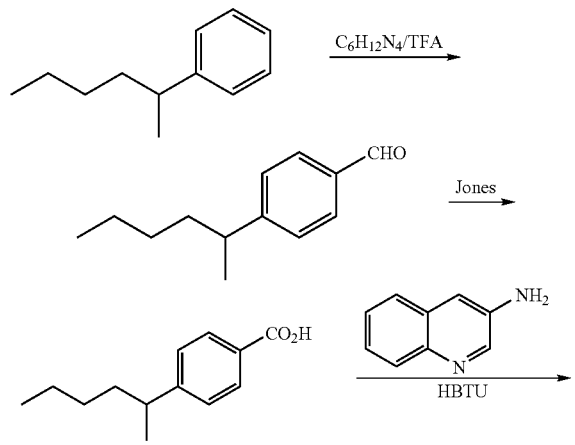

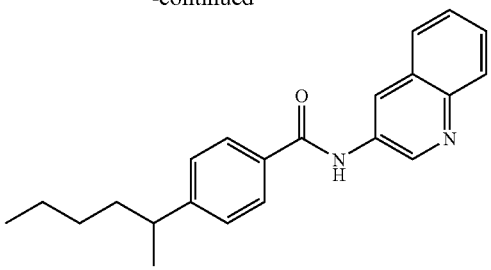

A. 4-(1-Methyl-pentyl)-benzaldehyde. (1-Methyl-pentyl)-benzene (3.771 g, 21.15 mmol) was stirred under nitrogen with trifluoroacetic acid (25 mL) in a round bottom flask equipped with a reflux condenser. To this was added hexamethylenetetramine (3.29 g, 23.5 mmol) and then the mixture was heated at reflux for 9 hours. Concentration of the reaction mixture under vacuum gave a residue that was carefully partitioned between 250 mL diethylether and 50 mL saturated NaHCO$_3$. The aqueous was removed and the organics were washed twice more with 50 mL saturated NaHCO$_3$ solution. The organics were then dried over Na$_2$SO$_4$, filtered and concentrated in vacuo to yield the crude product as a brown oil (4.245 g, 20.8 mmol) which was carried on without further purification. $^1$H NMR (CDCl$_3$): 9.99 (s, 1H), 7.82 (d, 2H), 7.34 (d, 2H), 2.78 (h, 1H), 1.60 (q, 2H), 1.38-1.03 (m, 7H), 0.87 (t, 3H).

B. 4-(1-Methyl-pentyl)-benzoic acid. 4-(1-Methyl-pentyl)-benzaldehyde obtained in step A (0.615 g, 3.01 mmol) was stirred with 10 mL acetone in a round bottom flask. Jones reagent (0.7 M, 10 mL, 7 mmol) was added and the reaction was stirred for 48 hours. The reaction was quenched by addition of 2 mL iPrOH and then diluted with 50 mL water. The mixture was then extracted three times with diethylether (25 mL) and the combined organics washed once with 25 mL water, dried over Na$_2$SO$_4$, treated with charcoal, filtered and then evaporated in vacuo. The residue was then dissolved in 25 mL 1N NaOH solution and washed twice with 25 mL diethylether. The aqueous solution was partially evaporated to remove the residual diethylether then acidified with 25 mL 2N HCl. The mixture was extracted once with 20 mL diethylether. The organics were dried over Na$_2$SO$_4$, filtered, and concentrated in vacuo to yield the product as a light tan thick oil (0.353 g, 1.71 mmol). $^1$H NMR (DMSO-d$_6$): 12.74 (s, 1H), 7.88 (d, 2H), 7.34 (d, 2H), 2.76 (h, 1H), 1.55 (q, 2H), 1.32-0.96 (m, 7H), 0.82 (t, 3H); MS: m/z 205 (M-H)$^-$.

C. 3-[4-(1-Methyl-pentyl)-phenyl]-N-quinolin-3-yl-propionamide. 4-(1-Methyl-pentyl)-benzoic acid from step B (0.114 g, 0.55 mmol) was dissolved in 5 mL DMF with stirring. To this was added Et$_3$N (0.10 mL, 0.72 mmol), 3-aminoquinoline (0.082 g, 0.57 mmol) and lastly HBTU (0.224 g, 0.59 mmol). The reaction was allowed to stir overnight then poured into 25 mL EtOAc and washed with saturated NaHCO$_3$ solution (25 mL) then brine (25 mL). The organics were dried over Na$_2$SO$_4$, filtered, evaporated in vacuo and the residue chromatographed over silica gel eluting with 0% to 40% EtOAc in hexanes. Evaporation of the proper fractions yielded the title product (0.120 g, 0.36 mmol). $^1$H NMR (DMSO-d$_6$): 8.93 (d, 1H), 8.86 (d, 1H), 8.09 (m, 2H), 7.88 (m, 3H), 7.67 (dt, 1H), 7.57 (t, 1H), 7.35 (d, 2H), 2.79 (h, 1H), 1.61 (q, 2H), 1.37-1.04 (m, 7H), 0.87 (t, 3H); MS: m/z 333.4 (MH$^+$).

Following the procedure described above for Example 1 and the appropriate reagents, starting materials and purification methods known to those skilled in the art, the following compounds were prepared:

| Example # | Compound name | MS (calc) | MS (obs) |
|---|---|---|---|
| (2) | 4-(1,1-Dimethyl-propyl)-N-quinolin-3-yl-benzamide | 318.4 | 319.2 |
| (3) | 4-Cyclohexylmethyl-N-quinolin-3-yl-benzamide | 344.6 | 345.6 |
| (4) | N-Quinolin-3-yl-4-tricyclo[5.3.1.13,9]dodec-1-yl-benzamide | 382.5 | 383.7 |
| (5) | 4-sec-Butyl-N-quinolin-3-yl-benzamide | 304.4 | 305.2 |
| (6) | 4-(1,1-Dimethyl-pentyl)-N-quinolin-3-yl-benzamide | 346.5 | 347.1 |
| (7) | Indan-5-carboxylic acid quinolin-3-ylamide | 288.4 | 289.1 |
| (8) | 5,6,7,8-Tetrahydro-naphthalene-2-carboxylic acid quinolin-3-ylamide | 302.4 | 303.1 |
| (9) | 4-(1-Cyclohexyl-1-methyl-ethyl)-N-quinolin-3-yl-benzamide | 372.5 | 373.2 |
| (10) | 5,5,8,8-Tetramethyl-5,6,7,8-tetrahydro-naphthalene-2-carboxylic acid quinolin-3-ylamide | 358.5 | 359.1 |
| (11) | 4-tert-Butyl-cyclohexanecarboxylic acid quinolin-3-ylamide | 310.4 | 311.1 |
| (12) | 1-Isopropyl-2-trifluoromethyl-1H-benzoimidazole-5-carboxylic acid quinolin-3-ylamide | 398.3 | 399.3 |
| (13) | 4-Butyl-cyclohexanecarboxylic acid quinolin-3-ylamide | 310.4 | 311.1 |

Example (14)

3-[4-(1,1-Dimethyl-propyl)-phenyl]-N-quinolin-3-yl-propionamide

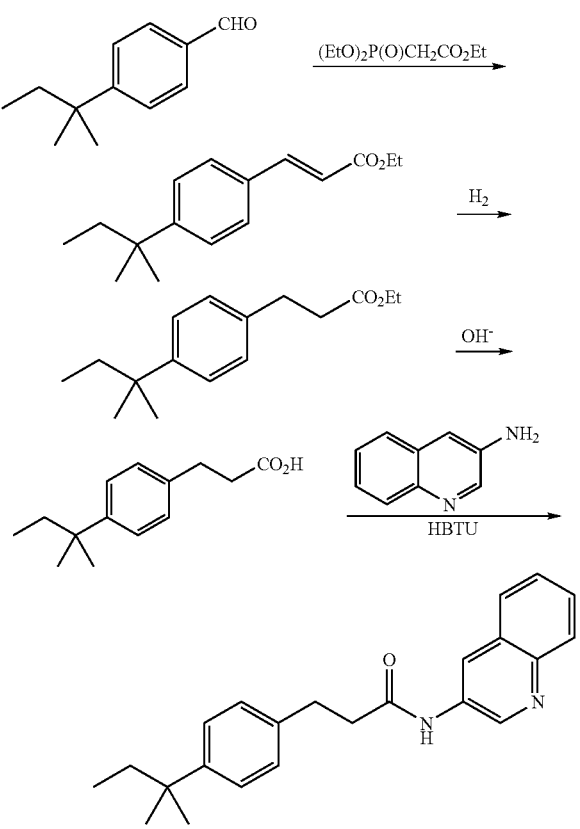

A. 3-[4-(1,1-Dimethyl-propyl)-phenyl]-acrylic acid ethyl ester. To a nitrogen flushed round bottom flask equipped with a stir bar and reflux condenser was added 4-(1,1-dimethyl-propyl)-benzaldehyde (1.767 g, 10.02 mmol) and 25 mL benzene. (Carbethoxymethylene)triphenylphosphorane (3.497 g, 10.03 mmol) was added and the solution was heated at reflux for 4 hours. The reaction was evaporated in vacuo and the residue triturated with 50 mL $Et_2O$ and then filtered. The filtrate was evaporated in vacuo and chromatographed over silica gel eluting with 0% to 5% EtOAc in hexanes. Evaporation of the appropriate fractions yielded the product as a yellow oil (2.138 g, 8.68 mmol). $^1$H NMR ($CDCl_3$): δ 7.70 (d, 1H), 7.49 (d, 2H), 7.37 (d, 2H), 6.42 (d, 1H), 4.28 (q, 2H), 1.67 (q, 2H), 1.36 (t, 3H), 1.28 (s, 6H), 0.69 (t, 3H)

B. 3-[4-(1,1-dimethyl-propyl)-phenyl]-propionic acid ethyl ester. 3-[4-(1,1-Dimethyl-propyl)-phenyl]-acrylic acid ethyl ester obtained in step A (2.138 g, 8.68 mmol) was dissolved in 50 mL ethanol along with 10% Pd/C (0.216 g) and hydrogenated at ~50 psi for 4.5 hours. Filtration of the reaction mixture over a pad of celite and evaporation of the filtrate yielded the product as a pale yellow oil (2.060 g, 8.29 mmol). $^1$H NMR ($CDCl_3$): δ 7.27 (d, 2H), 7.13 (d, 2H), 4.14 (q, 2H), 2.93 (t, 2H), 2.62 (t, 2H), 1.64 (q, 2H), 1.28 (s, 6H), 1.24 (t, 3H), 0.68 (t, 3H).

C. 3-[4-(1,1-dimethyl-propyl)-phenyl]-propionic acid. To a round bottom flask equipped with a stir bar was added the ester obtained in step B, 3-[4-(1,1-dimethyl-propyl)-phenyl]-propionic acid ethyl ester (2.050 g, 8.25 mmol), 50 mL THF, 10 mL water and $LiOH \cdot H_2O$ (0.692 g, 16.5 mmol). The reaction was stirred for 48 hours then evaporated in vacuo to an aqueous residue which was diluted with 50 mL water and acidified with 25 mL 1N HCl. The precipitate solid was collected by filtration, rinsed with water and dried under vacuum at 50° C. The product was obtained as a waxy white solid (1.697 g, 7.70 mmol). $^1$H NMR (DMSO-$d_6$): δ12.07 (br s, 1H), 7.22 (d, 2H), 7.13 (d, 2H), 2.80 (t, 2H), 2.52 (t, 2H), 1.60 (q, 2H), 1.22 (s, 6H), 0.61 (t, 3H); MS: m/z 279.3 (M-H)$^-$.

D. 3-[4-(1,1-Dimethyl-propyl)-phenyl]-N-quinolin-3-yl-propionamide. 3-Aminoquinoline (0.144 g, 1.00 mmol), $Et_3N$ (0.16 mL, 1.15 mmol) and 3-[4-(1,1-dimethyl-propyl)-phenyl]-propionic acid from step C (0.220 g, 1.00 mmol) were dissolved in 5 mL DMF with stirring. HBTU (0.384 g, 1.01 mmol) was added and the reaction was stirred for 48 hours. The reaction mixture was then partitioned between 100 mL 50% saturated $NaHCO_3$ and 100 mL $Et_2O$. The organics were then washed twice with 100 mL water, once with 100 mL brine, dried over $Na_2SO_4$, filtered and evaporated in vacuo. The residue was chromatographed over silica gel eluting with 0% to 40% EtOAc in hexanes. Evaporation of the proper fractions yielded the product (0.286 g, 0.83 mmol). $^1$H NMR ($CDCl_3$): δ 8.73 (s, 1H), 8.59 (s, 1H), 8.04 (d, 1H), 7.81 (d, 1H), 7.65 (t, 1H), 7.55 (t, 1H), 7.29 (d, 2H), 7.22 (d, 2H), 3.09 (t, 2H), 2.79 (t, 2H), 1.66 (q, 2H), 1.28 (s, 6H), 0.68 (t, 3H); MS: m/z 347.7 (MH$^+$).

Following the procedure described above for Example 13 and the appropriate reagents, starting materials and purification methods known to those skilled in the art, the following compounds of the present invention were prepared:

| Example # | Compound name | MS (calc) | MS (obs) |
|---|---|---|---|
| (15) | N-Quinolin-3-yl-3-(5,5,8,8-tetramethyl-5,6,7,8-tetrahydro-naphthalen-2-yl)-propionamide | 386.5 | 387.2 |

-continued

| Example # | Compound name | MS (calc) | MS (obs) |
|---|---|---|---|
| (16) | 3-(4-sec-Butyl-phenyl)-N-quinolin-3-yl-propionamide | 332.4 | 333.4 |
| (17) | 3-[4-(1-Methyl-pentyl)-phenyl]-N-quinolin-3-yl-propionamide | 360.5 | 361.5 |
| (18) | 3-[4-(1-Cyclohexyl-1-methyl-ethyl)-phenyl]-N-quinolin-3-yl-propionamide | 400.6 | 401.2 |
| (19) | 3-[4-(1,1-Dimethyl-pentyl)-phenyl]-N-quinolin-3-yl-propionamide | 374.5 | 375.2 |
| (20) | 3-(4-Cyclohexylmethyl-phenyl)-N-quinolin-3-yl-propionamide | 372.5 | 373.6 |
| (21) | 3-Indan-5-yl-N-quinolin-3-yl-propionamide | 316.4 | 317.1 |
| (22) | N-Quinolin-3-yl-3-(4-tricyclo[5.3.1.13,9]dodec-1-yl-phenyl)-propionamide | 410.6 | 411.8 |
| (23) | 3-(4-Pentyl-phenyl)-N-quinolin-3-yl-propionamide | 346.5 | 347.0 |
| (24) | N-Quinolin-3-yl-3-(5,6,7,8-tetrahydro-naphthalen-2-yl)-propionamide | 330.4 | 331.1 |

Example (25)

4-[4-(1,1-Dimethyl-pentyl)-phenyl]-but-3-enoic acid quinolin-3-ylamide

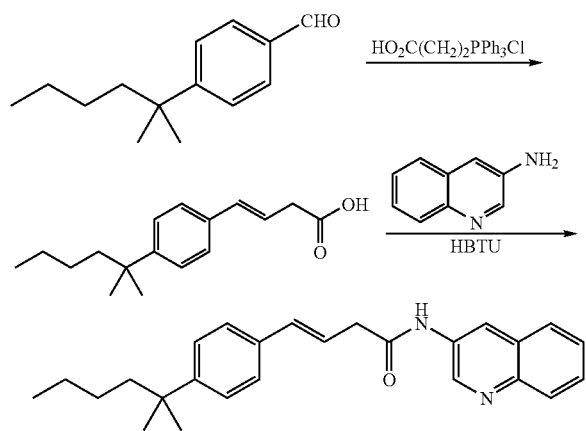

A. 4-[4-(1,1-Dimethyl-pentyl)-phenyl]-but-3-enoic acid. To a nitrogen flushed round bottom flask equipped with a stir bar and addition funnel was added 4-(1,1-dimethyl-pentyl)-benzaldehyde (3.399 g, 16.64 mmol), 50 mL THF and (2-carboxyethyl)-triphenylphosphonium chloride (*Journal of Organic Chemistry* 1962, 3407). The reaction mixture was cooled on an ice bath and a solution of potassium t-butoxide (1M in THF, 35 mL, 35 mmol) was added dropwise via addition funnel over a period of 16 minutes. The ice was allowed to melt and the reaction was allowed to warm up overnight. The thick slurry was then poured into 500 mL water and washed once with 200 mL diethyl ether. The aqueous layer was then acidified with 2.5 mL concentrated HCl and extracted twice with 100 mL diethylether. The combined organics were dried over $Na_2SO_4$, filtered and then evaporated in vacuo. The residue was chromatographed by reverse-phase HPLC($C_{18}$ eluted with acetonitrile/water+0.1% TFA). The proper fractions were collected and lyophilized to yield the product as a cream colored powder (1.303 g, 5.00 mmol). $^1$H NMR (DMSO-$d_6$): δ12.33 (s, 1H), 7.31 (q, 4H), 6.48 (d, 1H), 6.27 (dt, 1H), 3.20 (d, 2H), 1.58 (m, 2H), 1.25 (s, 6H), 1.18 (m, 2H), 0.98 (m, 2H), 0.78 (t, 3H); MS: m/z 258.9 (M-H)$^-$.

B. 4-[4-(1,1-Dimethyl-pentyl)-phenyl]-but-3-enoic acid quinolin-3-ylamide. The 4-[4-(1,1-dimethyl-pentyl)-phenyl]-but-3-enoic acid from step A (0.130 g, 0.50 mmol) was dissolved in 5 mL DMF with stirring. To this was added $Et_3N$ (0.08 mL, 0.57 mmol), 3-aminoquinoline (0.077 g, 0.53 mmol) and lastly HBTU (0.204 g, 0.54 mmol). The reaction was allowed to stir for 48 hours then poured into 25 mL EtOAc and washed with saturated $NaHCO_3$ solution (25 mL) and then brine (25 mL). The organics were dried over $Na_2SO_4$, filtered and then evaporated in vacuo and the residue chromatographed over silica gel eluting with 0% to 60% EtOAc in hexanes. Evaporation of the proper fractions yielded the title compound (0.156 g, 0.40 mmol). $^1$H NMR (CDCl$_3$): δ 8.74 (m, 2H), 8.04 (d, 1H), 7.81 (d, 1H), 7.64 (m, 2H), 7.55 (t, 1H), 7.40 (d, 2H), 7.33 (d, 2H), 6.70 (d, 1H), 6.40 (d of t, 1H), 3.43 (d, 2H), 1.61 (m, 2H), 1.32 (s, 6H), 1.24 (m, 2H), 1.07 (m, 2H), 0.83 (t, 3H); MS: m/z 387.4 (MH$^+$).

Following the procedure described above for Example 25 and the appropriate reagents, starting materials and purification methods known to those skilled in the art, the following compounds of the present invention were prepared:

| Example # | Compound name | MS (calc) | MS (obs) |
|---|---|---|---|
| (26) | 4-[4-(1,1-Dimethyl-propyl)-phenyl]-but-3-enoic acid quinolin-3-ylamide | 358.5 | 359.5 |

Example (27)

4-[4-(1,1-Dimethyl-pentyl)-phenyl]-N-quinolin-3-yl-butyramide

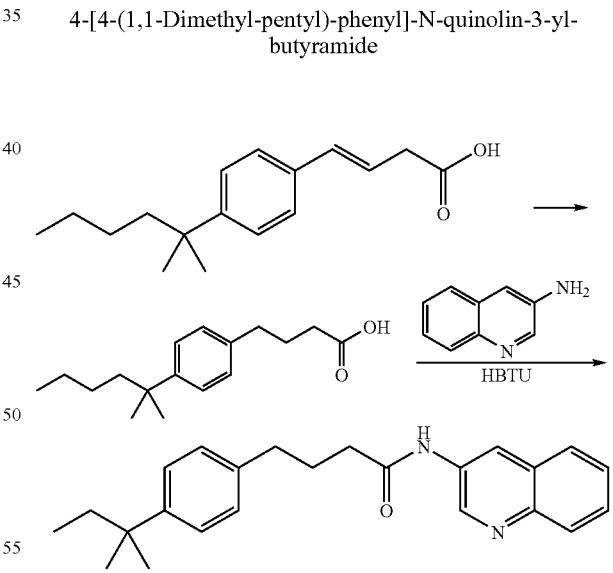

A. 4-[4-(1,1-Dimethyl-pentyl)-phenyl]-butyric acid. 4-[4-(1,1-Dimethyl-pentyl)-phenyl]-but-3-enoic acid (1.03 g, 4.0 mmol), prepared as described above, was dissolved in 50 mL ethanol along with 10% Pd/C (0.103 g) and hydrogenated at ~50 psi overnight. Filtration of the reaction mixture over a pad of celite and evaporation of the filtrate yielded the product as a light yellow oil (1.014 g, 3.86 mmol). $^1$H NMR (CDCl$_3$): δ 7.25 (d, 2H), 7.12 (d, 2H), 2.66 (t, 2H), 2.39 (t, 2H), 1.98 (p, 2H), 1.58 (m, 2H), 1.28 (s, 6H), 1.22 (m, 2H), 1.04 (m, 2H), 0.82 (t, 3H); MS: m/z 261.0 (M-H)$^-$.

B. 4-[4-(1,1-Dimethyl-pentyl)-phenyl]-N-quinolin-3-yl-butyramide. 4-[4-(1,1-Dimethyl-pentyl)-phenyl]-butyric acid from the previous reaction (0.264 g, 1.01 mmol) was dissolved in 5 mL DMF with stirring. To this was added Et₃N (0.16 mL, 1.15 mmol), 3-aminoquinoline (0.147 g, 1.02 mmol) and lastly HBTU (0.403 g, 1.06 mmol). The reaction was allowed to stir overnight then poured into 25 mL EtOAc and washed with saturated NaHCO₃ solution (25 mL) then brine (25 mL). The organics were dried over Na₂SO₄, filtered and then evaporated in vacuo. The residue was chromatographed over silica gel eluting with 0% to 55% EtOAc in hexanes. Evaporation of the proper fractions yielded the title product (0.186 g, 0.48 mmol). ¹H NMR (CDCl₃): δ 8.82 (s, 1H), 8.69 (d, 1H), 8.05 (d, 1H), 7.82 (d, 1H), 7.64 (t, 1H), 7.56 (t, 1H), 7.33 (br s, 1H), 7.28 (d, 2H), 7.17 (d, 2H), 2.72 (t, 2H), 2.48 (t, 2H), 2.14 (p, 2H), 1.59 (m, 2H), 1.28 (s, 6H), 1.23 (m, 2H), 1.05 (m, 2H), 0.84 (t, 3H); MS: m/z 389.5 (MH⁺).

Following the procedure described above for Example 27 and the appropriate reagents, starting materials and purification methods known to those skilled in the art, the following compounds were prepared:

| Example # | Compound name | MS (calc) | MS (obs) |
|---|---|---|---|
| (28) | 4-[4-(1,1-Dimethyl-propyl)-phenyl]-N-quinolin-3-yl-butyramide | 360.5 | 361.5 |

Example (29)

3-[4-(1-Dimethyl-propyl)-2,6-dimethoxy-phenyl]-N-quinolin-3-yl-propionamide

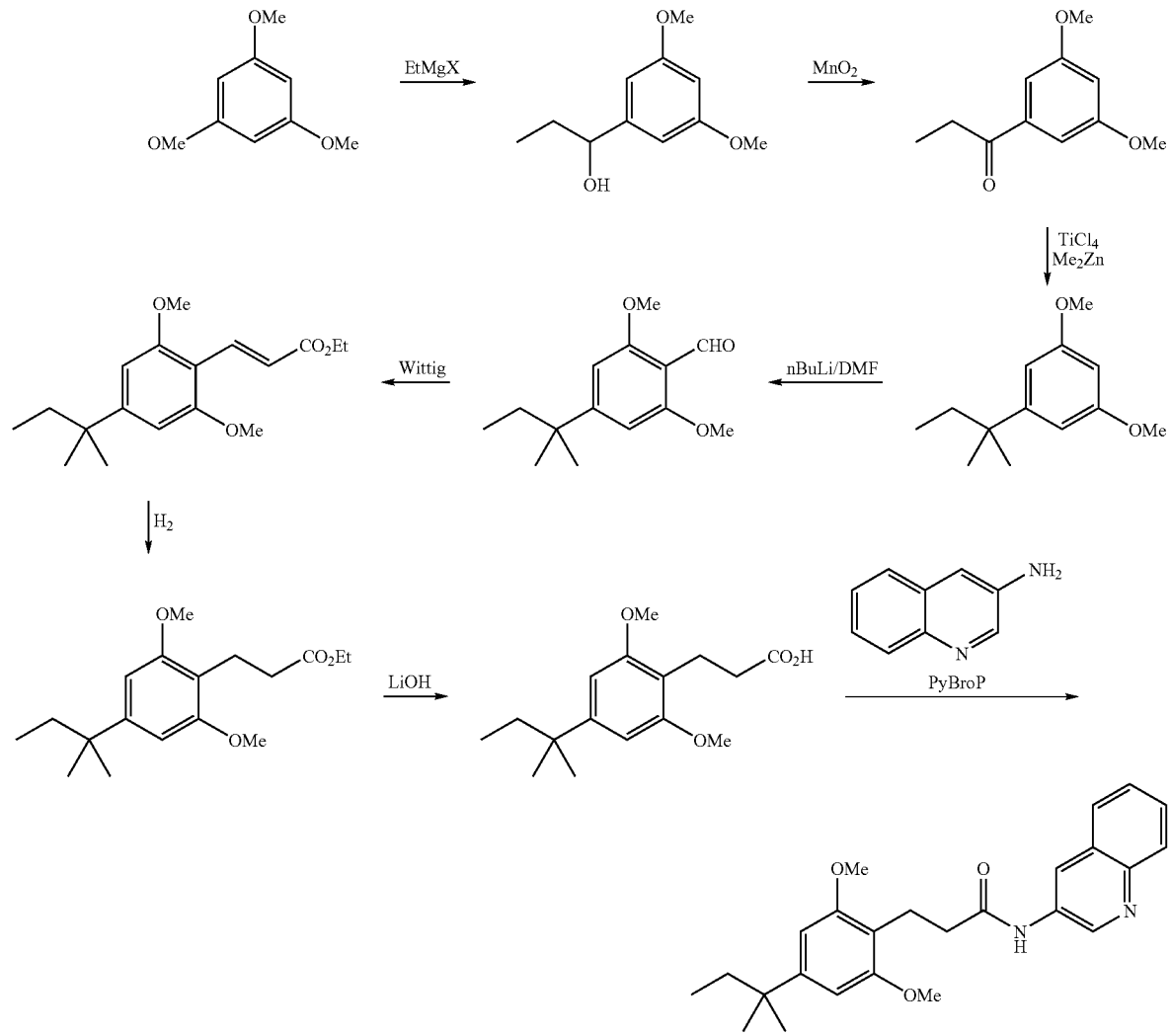

A. 1-(3,5-Dimethoxy-phenyl)-propan-1-ol. To a nitrogen flushed 3-neck round bottom flask equipped with a stir bar and addition funnel was added 25 mL THF and EtMgBr (3M in Et₂O, 11.0 mL, 33.0 mmol). A solution of 3,5-dimethoxybenzaldehyde (4.99 g, 30.0 mmol) in 25 mL anhydrous THF was added dropwise via addition funnel to the reaction mixture which was then allowed to stir overnight. The reaction was diluted with 100 mL Et₂O, washed twice with 50 mL saturated NH₄Cl solution, once with 50 mL water and once with 50 mL brine. The organics were dried over Na₂SO₄, filtered and evaporated in vacuo to yield the product as a yellow oil (5.657 g, 28.83 mmol). ¹H NMR (CDCl₃): δ 6.52

(m, 2H), 6.38 (m, 1H), 4.54 (m, 1H), 3.81 (s, 6H), 1.84 (d, 1H), 1.78 (m, 2H), 0.95 (t, 3H).

B. 1-(3,5-Dimethoxy-phenyl)-propan-1-one. To a round bottom flask equipped with a stir bar was added the product from step A, 1-(3,5-dimethoxy-phenyl)-propan-1-ol (5.657 g, 28.8 mmol), 100 mL dichloromethane and activated $MnO_2$ (12.51 g, 143.9 mmol). The reaction was stirred at room temperature overnight then a reflux condenser was installed and the reaction was heated at reflux for 2 days. The reaction mixture was filtered over a pad of celite and evaporated in vacuo to give a residue that was chromatographed over silica gel eluting with 0% to 7.5% EtOAc in hexanes. Evaporation of the proper fractions yielded the product as a colorless solid (2.050 g, 10.6 mmol). $^1H$ NMR ($CDCl_3$): δ 7.10 (m, 2H), 6.64 (m, 1H), 3.85 (s, 6H), 2.98 (q, 2H), 1.22 (t, 3H).

C. 1-(1,1-Dimethyl-propyl)-3,5-dimethoxy-benzene. To a nitrogen flushed round bottom flask equipped with a stir bar and addition funnel was added 80 mL methylene chloride. $TiCl_4$ (2.3 mL, 21.0 mmol) was added and the reaction mixture was cooled in a dry ice-acetonitrile bath to −50° C. To this was added $Me_2Zn$ (2M in toluene, 10.5 mL, 21 mmol) and the resulting thick slurry was allowed to stir for ~10 minutes. A solution of 1-(3,5-dimethoxy-phenyl)-propan-1-one, the product from step B, (1.951 g, 10.0 mmol) in 20 mL methylene chloride was added to the reaction mixture via addition funnel over a period of 25 minutes. After 3 hours the ice bath was removed and the reaction was allowed to warm up to room temperature overnight. The reaction was then carefully poured into 300 mL ice/water and extracted twice with 100 mL methylene chloride. The combined organics were washed twice with 1N HCl (100 mL) and once with brine (100 mL). The organics were then dried over $Na_2SO_4$, filtered and concentrated to a residue that was chromatographed over silica gel eluting with 0% to 2.5% EtOAc in hexanes. Evaporation of the proper fractions yielded the product as a colorless liquid (1.077 g, 5.17 mmol). $^1H$ NMR ($CDCl_3$): δ 6.49 (m, 2H), 6.29 (m, 1H), 3.81 (s, 6H), 1.62 (q, 2H), 1.27 (s, 6H), 0.71 (t, 3H).

D. 4-(1,1-Dimethyl-propyl)-2,6-dimethoxy-benzaldehyde. To a nitrogen flushed round bottom flask equipped with a stir bar was added 1-(1,1-dimethyl-propyl)-3,5-dimethoxy-benzene, obtained in step C, (1.071 g, 5.14 mmol) and 10 mL $Et_2O$. The reaction was cooled in an ice bath and n-butyllithium (2.5 M in hexanes, 2.7 mL 6.75 mmol) was added dropwise to the reaction. The reaction mixture was then stirred at 0° C. for one hour, the ice bath was removed and the reaction was allowed to warm up to room temperature overnight. The tan slurry was then re-cooled in an ice bath and DMF (0.68 mL, 8.78 mmol) was added drop wise. The reaction was stirred on the ice bath for 2 hours then for an additional 3 hours at room temp. The reaction mixture was quenched with 50 mL 3% $H_2SO_4$ and extracted twice with 25 mL $Et_2O$. The combined organics were dried over $Na_2SO_4$, filtered and evaporated in vacuo to yield the product aldehyde as a yellow oil (1.2 g, 5.1 mmol). $^1H$ NMR ($CDCl_3$): δ 10.46 (s, 1H), 6.53 (s, 2H), 3.92 (s, 6H), 1.67 (q, 2H), 1.29 (s, 6H), 0.73 (t, 3H).

E. 3-[4-(1,1-Dimethyl-propyl)-2,6-dimethoxy-phenyl]-acrylic acid ethyl ester. To a nitrogen flushed round bottom flask was added 15 mL acetonitrile and the aldehyde obtained in step D, 4-(1,1-dimethyl-propyl)-2,6-dimethoxy-benzaldehyde (0.711 g, 3.01 mmol). LiCl (0.199 g, 4.69 mmol), triethyl phosphonoacetate (0.72 mL, 3.63 mmol) and lastly DBU (0.51 mL, 3.41 mmol) were added and the reaction was stirred overnight. The reaction mixture was then partitioned between 10 mL water and 25 mL $Et_2O$. The organics were washed twice with 10 mL 1N HCl, once with 10 mL water, dried over $Na_2SO_4$, filtered and evaporated to a residue that was chromatographed over silica gel eluting with 0% to 7.5% EtOAc in hexanes. Evaporation of the proper fractions yielded the product as a white solid (0.626 g, 2.04 mmol). $^1H$ NMR ($CDCl_3$): δ 8.13 (d, 1H), 6.86 (d, 1H), 6.53 (s, 2H), 4.27 (q, 2H), 3.88 (s, 6H), 1.66 (q, 2H), 1.35 (t, 3H), 1.30 (s, 6H), 0.72 (s, 3H); MS: m/z 307.2 ($MH^+$).

F. 3-[4-(1,1-Dimethyl-propyl)-2,6-dimethoxy-phenyl]-propionic acid ethyl ester. 3-[4-(1,1-Dimethyl-propyl)-2,6-dimethoxy-phenyl]-acrylic acid ethyl ester (0.621 g, 2.03 mmol), obtained in step E, was dissolved in 25 mL ethanol along with 10% Pd/C (0.068 g) and hydrogenated at ~50 psi for 48 hours for 48 hours. Filtration of the reaction mixture over a pad of celite and evaporation of the filtrate yielded the product as a pale tan oil (0.623 g, 2.02 mmol). $^1H$ NMR ($CDCl_3$): δ 6.49 (s, 2H), 4.13 (q, 2H), 3.79 (s, 6H), 2.94 (dd, 2H), 2.48 (dd, 2H), 1.64 (q, 2H), 1.27 (m, 9H), 0.72 (t, 3H); MS: m/z 309.1 ($MH^+$).

G. 3-[4-(1,1-Dimethyl-propyl)-2,6-dimethoxy-phenyl]-propionic acid. To a round bottom flask equipped with a stir bar was added 3-[4-(1,1-dimethyl-propyl)-2,6-dimethoxy-phenyl]-propionic acid ethyl ester (0.605 g, 1.96 mmol), obtained in step F, 25 mL THF, 5 mL water and $LiOH \cdot H_2O$ (0.164 g, 3.91 mmol). The reaction was stirred until complete by reverse phase HPLC then evaporated in vacuo to an aqueous residue which was diluted with 25 mL water and then acidified with 5 mL 2N HCl. The precipitated solid was collected by filtration, rinsed with water and dried under vacuum at 50° C. to yield the product as a white powder (0.495 g, 1.77 mmol). $^1H$ NMR (DMSO-$d_6$): δ 12.04 (s, 1H), 6.53 (s, 2H), 3.78 (s, 6H), 2.76 (dd, 2H), 2.26 (dd, 2H), 1.62 (q, 2H), 1.24 (s, 6H), 0.67 (t, 3H).

H. 3-[4-(1,1-Dimethyl-propyl)-2,6-dimethoxy-phenyl]-N-quinolin-3-yl-propionamide. Into a round bottom flask equipped with a stir bar was added 10 mL acetonitrile, the product obtained in step G 3-[4-(1,1-dimethyl-propyl)-2,6-dimethoxy-phenyl]-propionic acid (0.422 g, 1.51 mmol), $iPr_2NEt$ (0.29 mL, 1.66 mmol), 3-aminoquinoline (0.218 g, 1.51 mmol) and lastly PyBroP (0.713 g, 1.53 mmol). The reaction was stirred overnight at room temperature, an additional amount of PyBroP was added (0.145 g, 0.31 mmol) and the reaction was stirred for an additional 2 hours at room temperature. The reaction mixture was then diluted with 100 mL $Et_2O$ and washed once with 25 mL saturated $NaHCO_3$ and twice with 25 mL water. The organics were dried over $Na_2SO_4$, filtered and evaporated to a residue that was chromatographed over silica gel eluting with 0% to 50% EtOAc in hexanes. Evaporation of the proper fractions yielded, after trituration with hexanes, the title compound which was dried under vacuum at 50° C. (0.301 g, 0.74 mmol). $^1H$ NMR ($CDCl_3$): δ 8.81 (s, 1H), 8.58 (d, 1H), 8.03 (m, 2H), 7.80 (d, 1H), 7.62 (t, 1H), 7.53 (t, 1H), 6.57 (s, 2H), 3.88 (s, 6H), 3.10 (t, 2H), 2.80 (t, 2H), 1.64 (q, 2H), 1.29 (s, 6H), 0.72 (t, 3H); MS: m/z 407.6 ($MH^+$).

Following the procedure described above for Example 29 and the appropriate reagents, starting materials and purification methods known to those skilled in the art, the following compounds of the present invention were prepared:

| Example # | Compound name | MS (calc) | MS (obs) |
|---|---|---|---|
| (30) | 3-[4-(1,1-Dimethyl-pentyl)-2,6-dimethoxy-phenyl]-N-quinolin-3-yl-propionamide | 406.5 | 407.6 |

Example (31)

3-[5-(1,1-Dimethyl-propyl)-thiophen-2-yl]-N-quinolin-3-yl-propionamide

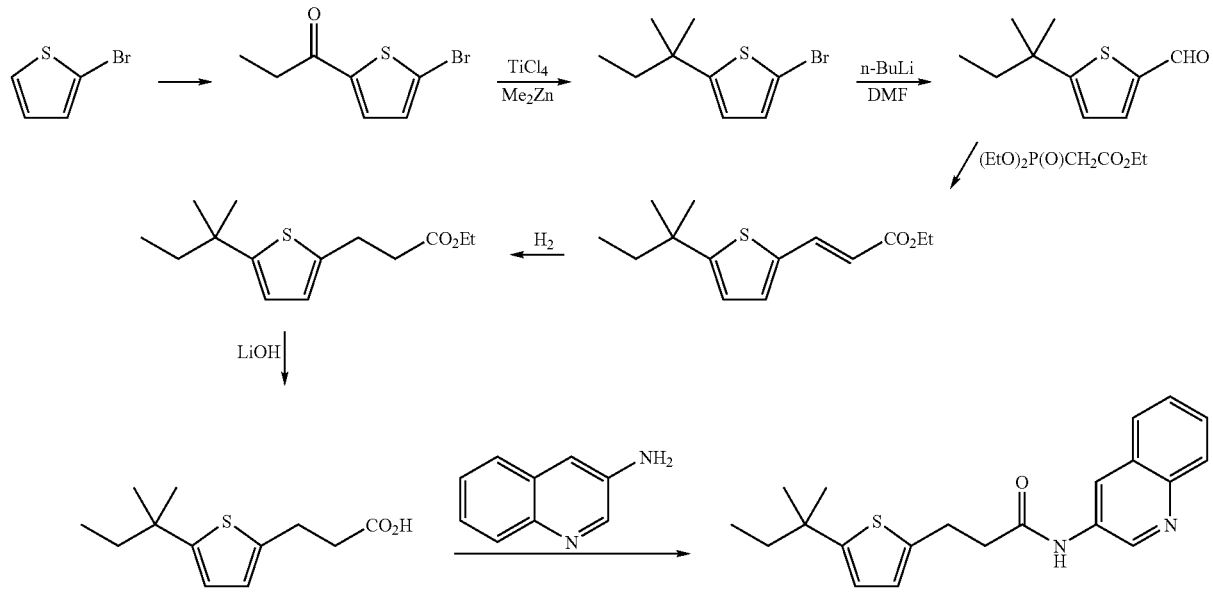

A. 2-Bromo-5-(1,1-dimethyl-propyl)-thiophene. To a nitrogen flushed round bottom flask equipped with a stir bar and addition funnel was added 80 mL methylene chloride. TiCl$_4$ (2.3 mL, 21.0 mmol) was added and the mixture cooled with a dry ice-acetonitrile bath to about −50° C. To this was added Me$_2$Zn (2M in toluene, 10.5 mL, 21 mmol). The resulting thick slurry was allowed to stir for at least 10 minutes. A solution of 1-(5-bromo-thiophen-2-yl)-propan-1-one [prepared as described in *JACS* 1950, 3695] (2.191 g, 10.1 mmol) in 20 mL methylene chloride was added to the reaction mixture via addition over a period of 35 minutes. The ice bath was allowed to melt and the reaction was allowed to warm up overnight. The reaction was then carefully poured into 500 mL ice/water and then extracted three times with 100 mL methylene chloride. The combined organics were washed twice with 1N HCl (100 mL) and once with brine (100 mL). The organics were then dried over Na$_2$SO$_4$, treated with charcoal, filtered and concentrated to a residue that was chromatographed over silica gel eluting with 100% hexanes. Evaporation of the proper fractions yielded the product as a colorless liquid (1.256 g, 5.39 mmol). $^1$H NMR (CDCl$_3$): δ 6.85 (d, 1H), 6.53 (d, 1H), 1.62 (q, 2H), 1.31 (s, 6H), 0.81 (t, 3H).

B. 5-(1,1-Dimethyl-propyl)-thiophene-2-carboxaldehyde. To a nitrogen flushed round bottom flask equipped with a stir bar was added 50 mL anhydrous THF and 2-bromo-5-(1,1-dimethyl-propyl)-thiophene (1.25 g, 5.36 mmol) prepared in step A. The reaction was cooled in a dry ice-acetone bath and n-butyllithium solution (2.5 M in hexanes, 2.4 mL, 6.0 mmol) was added drop wise. The ice bath was allowed to melt and the reaction was allowed to warm up overnight. The reaction was then cooled in a dry ice-acetone bath and a solution of 1 mL DMF in 4 mL anhydrous THF was added dropwise. After the ice bath had melted over 6.5 hours the reaction was diluted with 200 mL Et$_2$O and washed twice with 50 mL saturated NH$_4$Cl, 50 mL water and 50 mL brine. The organics were dried over Na$_2$SO$_4$, filtered and evaporated to a residue that was chromatographed over silica gel eluting with 5% to 10% EtOAc in hexanes. Evaporation of the proper fractions yielded the product aldehyde as a yellow liquid (0.249 g, 1.37 mmol). $^1$H NMR (CDCl$_3$): δ 9.82 (s, 1H), 7.62 (d, 1H), 6.93 (d, 1H), 1.70 (q, 2H), 1.38 (s, 6H), 0.81 (t, 3H).

C. 3-[5-(1,1-Dimethyl-propyl)-thiophen-2-yl]-acrylic acid ethyl ester. To a nitrogen flushed round bottom flask equipped with a stir bar was added 10 mL acetonitrile, 5-(1,1-dimethyl-propyl)-thiophene-2-carboxaldehyde (0.236 g, 1.29 mmol) obtained in step B, LiCl (0.086 g, 2.03 mmol), DBU (0.23 mL, 1.54 mmol) and lastly triethyl phosphonoacetate (0.31 mL, 1.56 mmol). The reaction was stirred overnight and then evaporated in vacuo. The residue was partitioned between 10 mL water and 25 mL Et$_2$O. The organics were then washed twice with 10 mL 1N HCl, once with 10 mL brine and evaporated to a residue that was chromatographed over silica gel eluting with 0% to 10% EtOAc in hexanes. Evaporation of the proper fractions yielded the product as a yellow oil (0.296 g, 1.17 mmol). $^1$H NMR (CDCl$_3$): δ 7.72 (d, 1H), 7.08 (d, 1H), 6.77 (d, 1H), 6.13 (d, 1H), 4.26 (q, 2H), 1.68 (q, 2H), 1.32 (m, 9H), 0.80 (t, 3H).

D. 3-[5-(1,1-Dimethyl-propyl)-thiophen-2-yl]-propionic acid ethyl ester. 3-[5-(1,1-Dimethyl-propyl)-thiophen-2-yl]-acrylic acid ethyl ester (0.292 g, 1.16 mmol), obtained in the previous step, was dissolved in 25 mL ethanol along with 10% Pd/C (0.053 g) and hydrogenated at ~50 psi for 48 hours. Filtration of the reaction mixture over a pad of celite and evaporation of the filtrate showed the reaction to be incomplete. The hydrogenation was then re-started with fresh 25 mL EtOH and 10% Pd/C (0.256 g) for 3 more days. Filtration of the reaction mixture over a pad of celite and evaporation of the filtrate yielded the product as a yellow oil (quant). $^1$H NMR (CDCl$_3$): δ 6.59 (m, 2H), 4.16 (q, 2H), 3.11 (t, 2H), 2.67 (t, 2H), 1.63 (q, 2H), 1.28 (m, 9H), 0.80 (t, 3H).

E. 3-[5-(1,1-Dimethyl-propyl)-thiophen-2-yl]-propionic acid. To a round bottom flask equipped with a stir bar was added 3-[5-(1,1-dimethyl-propyl)-thiophen-2-yl]-propionic acid ethyl ester (1.16 mmol), obtained in step D, 25 mL THF, 5 mL water and LiOH.H$_2$O (0.107 g, 2.55 mmol). The reaction was stirred for 48 hours then evaporated in vacuo to an aqueous residue which was diluted with 25 mL water, acidified with 10 mL 1N HCl and extracted twice with 25 mL Et$_2$O. The combined organics were dried over Na$_2$SO$_4$, filtered and evaporated to yield the product as a thick yellow-orange oil (0.229 g, 1.01 mmol). $^1$H NMR (CDCl$_3$): δ 6.64 (d, 1H), 6.58 (d, 1H), 3.12 (t, 2H), 2.73 (t, 2H), 1.62 (q, 2H), 1.30 (s, 6H), 0.78 (t, 3H); MS: m/z 224.9 (MH)$^-$.

F. 3-[5-(1,1-Dimethyl-propyl)-thiophen-2-yl]-N-quinolin-3-yl-propionamide. To a round bottom flask equipped with a stir bar add 10 mL dichloromethane 3-[5-(1,1-dimethyl-propyl)-thiophen-2-yl]-propionic acid (0.228 g, 1.01 mmol) from step E, iPr$_2$NEt (0.39 mL, 2.2 mmol), 3-aminoquinoline (0.146 g, 1.01 mmol) and lastly 2-chloro-1,3-dimethylimidazolinium chloride (0.199 g, 1.18 mmol). The reaction was stirred overnight, diluted with 15 mL dichloromethane and washed twice with 25 mL 1N HCl and twice with 25 mL saturated NaHCO$_3$. Evaporation of the organics gave a residue that was chromatographed over silica gel eluting with 0% to 45% EtOAc in hexanes. Evaporation of the proper fractions yielded the title compound as a yellow-tan solid (0.190 g, 0.54 mmol). $^1$H NMR (CDCl$_3$): δ 8.76 (s, 1H), 8.58 (d, 1H), 8.03 (d, 1H), 7.81 (d, 1H), 7.64 (t, 1H), 7.54 (t, 1H), 7.39 (br s, 1H), 6.68 (d, 1H), 6.61 (d, 1H), 3.26 (t, 2H), 2.81 (t, 2H), 1.63 (q, 2H), 1.29 (s, 6H), 0.77 (t, 3H); MS: m/z 353.5 (MH$^+$).

Example (32)

3-[4-(1,1-Dimethyl-3-phenyl-propyl)-phenyl]-N-quinolin-3-yl-propionamide

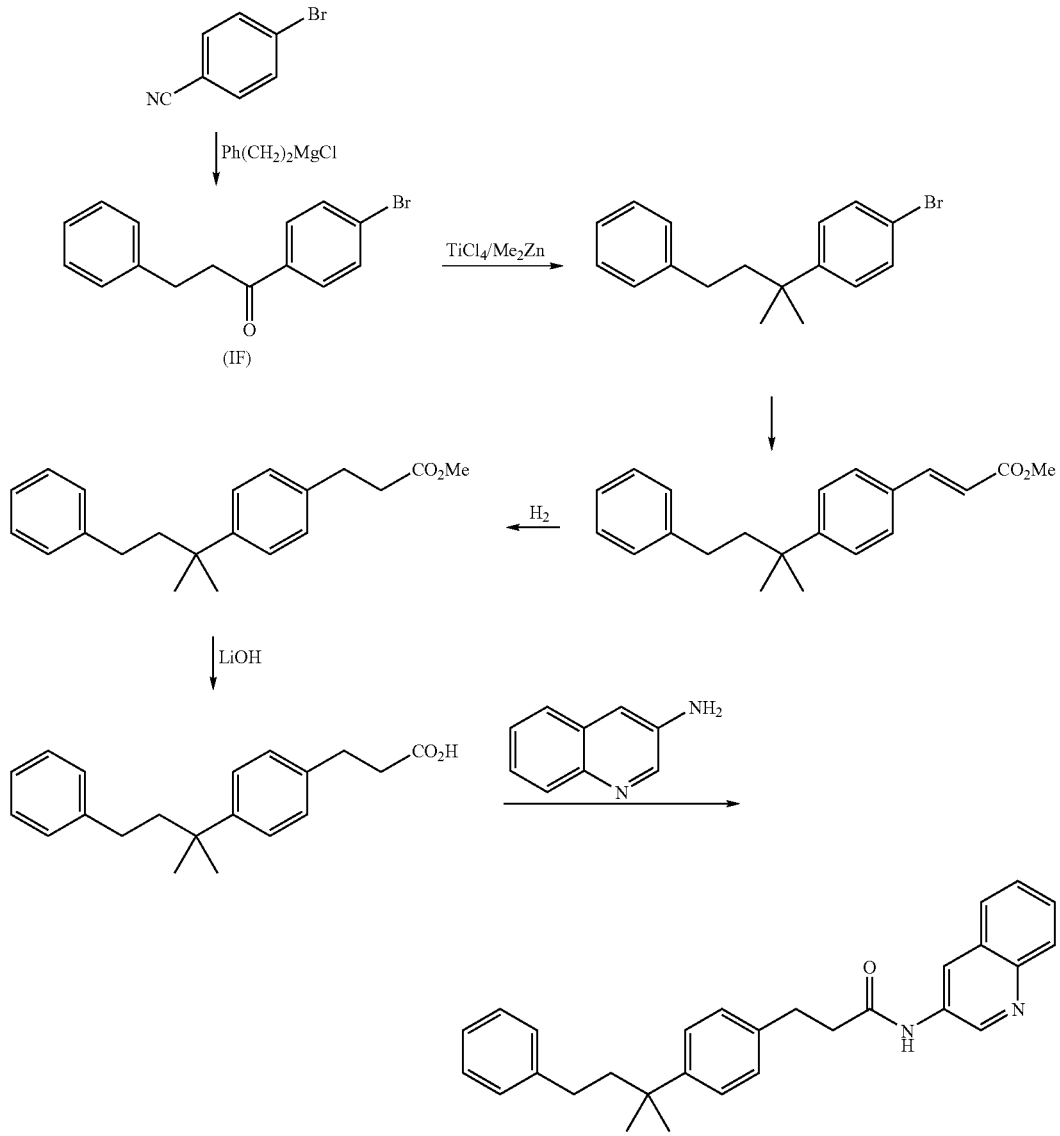

A. 1-(4-Bromo-phenyl)-3-phenyl-propan-1-one. Into a nitrogen flushed 3-neck round bottom flask equipped with a stir bar, addition funnel and reflux condenser was added 25 mL anhydrous THF, phenethylmagnesium chloride (1M in THF, 30 mL, 30 mmol) and CuBr catalyst (0.083 g). Into the addition funnel was added a solution of 4-bromobenzonitrile (4.97 g, 27.3 mmol) in 50 mL anhydrous THF. This was added dropwise to the Grignard solution over 7.5 minutes. When the addition was complete the reaction was heated at reflux overnight. After cooling, the reaction was quenched with 100 mL 15% H₂SO₄ and extracted twice with 100 mL Et₂O. The combined organics were washed once with 100 mL saturated NH₄Cl, once with 100 mL brine, dried over Na₂SO₄, treated with charcoal, filtered, evaporated to a solid. This crude solid was triturated with 20 mL EtOH, filtered off and rinsed with an additional 10 mL EtOH. Drying the solid under vacuum yielded the product as an off-white crystalline powder (3.529 g, 12.2 mmol). ¹H NMR (CDCl₃): δ 7.84 (d, 2H), 7.62 (d, 2H), 7.29 (m, 5H), 3.30 (t, 2H), 3.09 (t, 2H).

B. 4-(1,1-Dimethyl-3-phenyl-propyl)-bromobenzene. To a nitrogen flushed round bottom flask equipped with a stir bar and addition funnel was added 80 mL methylene chloride. TiCl₄ (2.7 mL, 24.6 mmol) was added and the mixture cooled with a dry ice-acetonitrile bath to about −50° C. To this was added Me₂Zn (2M in toluene, 12.5 mL, 25.0 mmol). The resulting thick slurry was allowed to stir for at least 10 minutes. A solution of 1-(4-bromo-phenyl)-3-phenyl-propan-1-one (3.385 g, 11.7 mmol) obtained in step A in 20 mL methylene chloride was put into the addition funnel and this was added dropwise to the reaction over 24 minutes. The ice bath was allowed to melt and the reaction mixture was allowed to warm up overnight. The reaction was then carefully poured into 500 mL ice/water and extracted twice with 100 mL methylene chloride. The combined organics were then washed twice with 1N HCl (100 mL) and once with brine (100 mL). The organics were dried over Na₂SO₄, treated with charcoal, filtered and concentrated to a residue that was chromatographed over silica gel eluting with 100% hexanes. Evaporation of the proper fractions yielded the product as a colorless oil (0.858 g, 2.83 mmol). ¹H NMR (CDCl₃): δ 7.48 (d, 2H), 7.27 (m, 5H), 7.09 (d, 2H), 2.34 (m, 2H), 1.92 (m, 2H), 1.37 (s, 6H).

C. 3-[4-(1,1-Dimethyl-3-phenyl-propyl)-phenyl]-acrylic acid methyl ester. Into a small pressure tube was added 1.5 mL Et₃N and a stir bar. To this was added 4-(1,1-dimethyl-3-phenyl-propyl)-bromobenzene obtained in step A (0.858 g, 2.83 mmol), methyl acrylate (0.32 mL, 3.55 mmol), Pd(OAc)₂ (0.008 g, 0.036 mmol) and tri-o-tolylphosphine (0.034 g, 0.11 mmol). The reaction mixture was deoxygenated by bubbling argon through the solution. The vessel was then capped and heated at 100° C. for 3.5 hours. After cooling, the reaction was partitioned between 25 mL Et₂O and 25 mL 1N HCl. The organics were then washed once with 25 mL 1N HCl, dried over Na₂SO₄, filtered and evaporated in vacuo to yield the product as a yellow oil (0.873 g, 2.83 mmol). This oil was then chromatographed over silica gel with 5% EtOAc in hexanes. Evaporation of the proper fractions gave the title compound as an oil. ¹H NMR (CDCl₃): δ 7.72 (d, 1H), 7.52 (d, 2H), 7.43 (d, 2H), 7.23 (d, 2H), 7.17 (d, 1H), 7.08 (d, 2H), 3.82 (s, 3H), 2.37 (m, 2H), 1.94 (m, 2H), 1.38 (s, 6H).

D. 3-[4-(1,1-Dimethyl-3-phenyl-propyl)-phenyl]-propionic acid methyl ester. The cinnamate ester obtained in step C, 3-[4-(1,1-dimethyl-3-phenyl-propyl)-phenyl]-acrylic acid methyl ester (0.867 g, 2.81 mmol) was dissolved in 25 mL methanol along with 10% Pd/C (0.161 g) and hydrogenated at ~50 psi for 48 hours. Filtration of the reaction mixture over a pad of celite and evaporation of the filtrate yielded the product as colorless oil (0.647 g, 2.08 mmol). ¹H NMR (CDCl₃): δ 7.32 (d, 2H), 7.26 (d, 2H), 7.19 (m, 3H), 7.12 (m, 2H), 3.68 (s, 3H), 2.96 (t, 2H), 2.67 (t, 2H), 2.37 (m, 2H), 1.92 (m, 2H), 1.34 (s, 6H).

E. 3-[4-(1,1-Dimethyl-3-phenyl-propyl)-phenyl]-propionic acid. To a round bottom flask equipped with a stir bar was added 3-[4-(1,1-dimethyl-3-phenyl-propyl)-phenyl]-propionic acid methyl ester obtained in step D (0.640 g 2.06 mmol), 25 mL THF, 5 mL water and LiOH·H₂O (0.174 g, 4.15 mmol). The reaction was stirred for 3 days then evaporated in vacuo to an aqueous residue which was diluted with 50 mL water, acidified with 10 mL 1N HCl. The precipitated solid was collected by filtration, rinsed with water and dried under vacuum to yield the product as a white powder (0.536 g, 1.81 mmol). ¹H NMR (DMSO-d₆): δ 7.33 (d, 2H), 7.21 (m, 5H), 7.11 (d, 2H), 2.82 (t, 2H), 2.56 (t, 2H), 2.28 (m, 2H), 1.86 (m, 2H), 1.31 (s, 6H); MS: m/z 294.9 (MH)⁻.

F. 3-[4-(1,1-Dimethyl-3-phenyl-propyl)-phenyl]-N-quinolin-3-yl-propionamide. The carboxylic acid obtained in step E, 3-[4-(1,1-dimethyl-3-phenyl-propyl)-phenyl]-propionic acid, (0.150 g, 0.51 mmol) was dissolved in 5 mL DMF with stirring. To this was added Et₃N (0.08 mL, 0.57 mmol), 3-aminoquinoline (0.075 g, 0.52 mmol) and lastly HBTU (0.207 g, 0.55 mmol). The reaction was allowed to stir overnight then poured into 25 mL EtOAc and washed with saturated NaHCO₃ solution (25 mL) then brine (25 mL). The organics were evaporated in vacuo and the residue chromatographed over silica gel eluting with 0% to 55% EtOAc in hexanes. Evaporation of the proper fractions yielded the title product (0.126 g, 0.298 mmol). ¹H NMR (CDCl₃): δ 8.73 (s, 1H), 8.61 (d, 1H), 8.03 (d, 1H), 7.80 (d, 1H), 7.64 (t, 1H), 7.55 (t, 1H), 7.37 (d, 2H), 7.28-7.10 (m, 6H), 7.07 (d, 2H), 3.10 (t, 2H), 2.78 (t, 2H), 2.36 (m, 2H), 1.92 (m, 2H), 1.37 (s, 6H); MS: m/z 423.5 (MH⁺).

Example (33)

1-Pentyl-1,2,3,4-tetrahydro-quinoline-6-carboxylic acid quinolin-3-ylamide

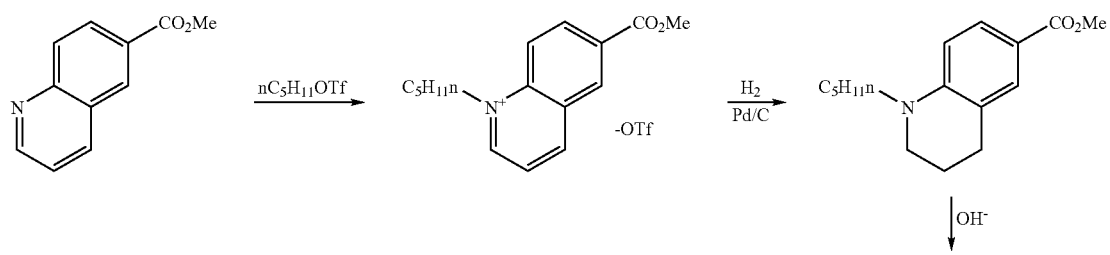

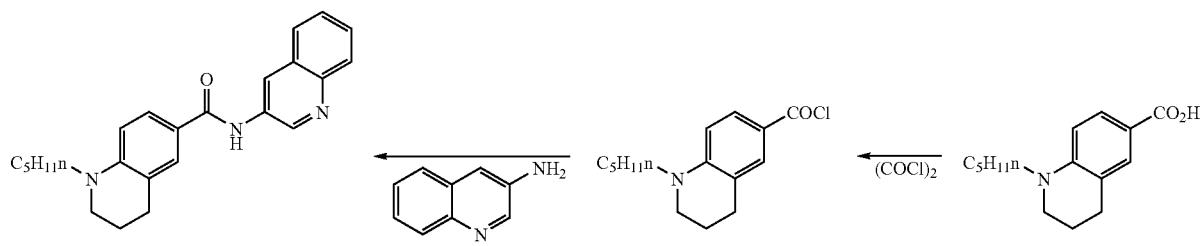

n-Pentyltriflate. To a nitrogen flushed round bottom flask equipped with a stir bar was added pyridine (0.81 mL, 10.0 mmol) and n-pentanol (1.09 mL, 10.0 mmol). The reaction was cooled in an ice bath and triflic anhydride (1.69 mL, 10.0 mmol) was added dropwise. The ice bath was allowed to melt over two hours at which time the entire reaction mixture was filtered over a column of silica gel eluting with dichloromethane. The filtrate was carefully evaporated in vacuo then carried on without further purification(1.11 g, 5.04 mmol).

A. Triflate salt of 1-pentyl-quinoline-6-carboxylic acid methyl ester. To a nitrogen flushed round bottom flask equipped with a stir bar was added 10 mL EtOAc and quinoline-6-carboxylic acid methyl ester (0.729 g, 3.89 mmol). A solution of the pentyltriflate prepared as described above (5.04 mmol) in 10 mL EtOAc was then added and the reaction mixture was stirred overnight. The reaction mixture was evaporated in vacuo and carried on without further purification.

B. 1-Pentyl-1,2,3,4-tetrahydro-quinoline-6-carboxylic acid methyl ester. The triflate salt of 1-pentyl-quinoline-6-carboxylic acid methyl ester (3.89 mmol) obtained in step A was dissolved in 50 mL ethanol along with 10% Pd/C (0.162 g) and hydrogenated at ~50 psi overnight. Filtration of the reaction mixture over a pad of celite and evaporation of the filtrate gave a residue which was dissolved in 50 mL dichloromethane, washed twice with 25 mL saturated NaHCO$_3$, once with 25 mL brine, dried over Na$_2$SO$_4$ and evaporated. The residue was chromatographed over silica gel eluting with 0% to 7.5% EtOAc in hexanes. Evaporation of the proper fractions yielded the product (0.756 g, 2.89 mmol) as a yellow oil. $^1$H NMR (CDCl$_3$): δ 7.73 (dd, 1H), 7.62 (d, 1H), 6.52 (d, 1H), 3.88 (s, 3H), 3.36 (t, 2H), 3.30 (t, 2H), 2.79 (t, 2H), 1.96 (m, 2H), 1.62 (m, 2H), 1.37 (m, 4H), 0.94 (t, 3H); MS: m/z 262.5 (MH$^+$).

C. 1-Pentyl-1,2,3,4-tetrahydro-quinoline-6-carboxylic acid. Into a round bottom flask equipped with a stir bar and reflux condenser was added a solution of 1-pentyl-1,2,3,4-tetrahydro-quinoline-6-carboxylic acid methyl ester obtained in step B (0.748 g, 2.86 mmol) in 25 mL EtOH. NaOH solution (1N, 10.0 mL, 10.0 mmol) was added and the reaction mixture was heated at reflux overnight then evaporated in vacuo to an aqueous residue which was diluted with 25 mL water and acidified with 10 mL 1N HCl. The precipitated solid was collected by filtration, rinsed with water and dried to yield the product as a pale tan powder (quant). $^1$H NMR (DMSO-d$_6$): δ 11.89 (br s, 1H), 7.58 (dd, 1H), 7.47 (d, 1H), 6.57 (d, 1H), 3.32 (m, 4H), 2.69 (t, 2H), 1.84 (m, 2H), 1.53 (m, 2H), 1.31 (m, 4H), 0.88 (t, 3H); MS: m/z 248.4 (MH$^+$).

D. 1-Pentyl-1,2,3,4-tetrahydro-quinoline-6-carbonyl chloride. Into a nitrogen flushed round bottom flask equipped with a stir bar was suspended the acid obtained in step C, 1-pentyl-1,2,3,4-tetrahydro-quinoline-6-carboxylic acid (0.554 g, 2.20 mmol), in 25 mL dichloromethane. To the suspension was added two drops of DMF followed by oxalyl chloride (0.58 mL, 6.65 mmol). The reaction was stirred for 1.5 hours then evaporated in vacuo to give the acid chloride that was carried on without further purification.

E. 1-Pentyl-1,2,3,4-tetrahydro-quinoline-6-carboxylic acid quinolin-3-ylamide. The acid chloride obtained in step D, 1-pentyl-1,2,3,4-tetrahydro-quinoline-6-carbonyl chloride (1.10 mmol), was dissolved in 5 mL acetonitrile with stirring. To the solution was added Et$_3$N (0.35 mL, 2.51 mmol) and 3-aminoquinoline (0.144 g, 1.00 mmol). The reaction was stirred overnight, diluted with 50 mL Et$_2$O, extracted twice with 50 mL 1N NaOH and once with 100 mL brine. The organics were dried over Na$_2$SO$_4$, filtered, evaporated and then chromatographed over silica gel eluting with 0% to 7.5% EtOAc in hexanes. Evaporation of the proper fractions yielded the product as a freebase which was converted to its hydrochloride salt by treatment with ethereal HCl. Evaporation of the ether in vacuo and drying under vacuum at 50° C. yielded the product as an orange powder (0.078 g, 0.17 mmol). $^1$H NMR (CDCl$_3$): δ 10.80 (s, 1H), 10.39 (s, 1H), 9.98 (s, 1H), 8.61 (d, 1H), 8.17 (dd, 1H), 8.04 (m, 2H), 7.87 (t, 1H), 7.78 (t, 1H), 6.64 (d, 1H), 3.38 (t, 2H), 3.31 (t, 2H), 2.87 (t, 2H), 1.98 (m, 2H), 1.63 (m, 2H), 1.36 (m, 4H), 0.93 (t, 3H); MS: m/z 374.7 (MH$^+$).

Following the procedure described above for Example 33 and the appropriate reagents, starting materials and purification methods known to those skilled in the art, the following compound was prepared:

| Example # | Compound name | MS (calc) | MS (obs) |
|---|---|---|---|
| (34) | 1-Methyl-1,2,3,4-tetrahydro-quinoline-6-carboxylic acid quinolin-3-ylamide | 317.4 | 318.5 |

Example (35)

3-[4-(Cyclohexylmethyl-methyl-amino)-phenyl]-N-quinolin-3-yl-propionamide

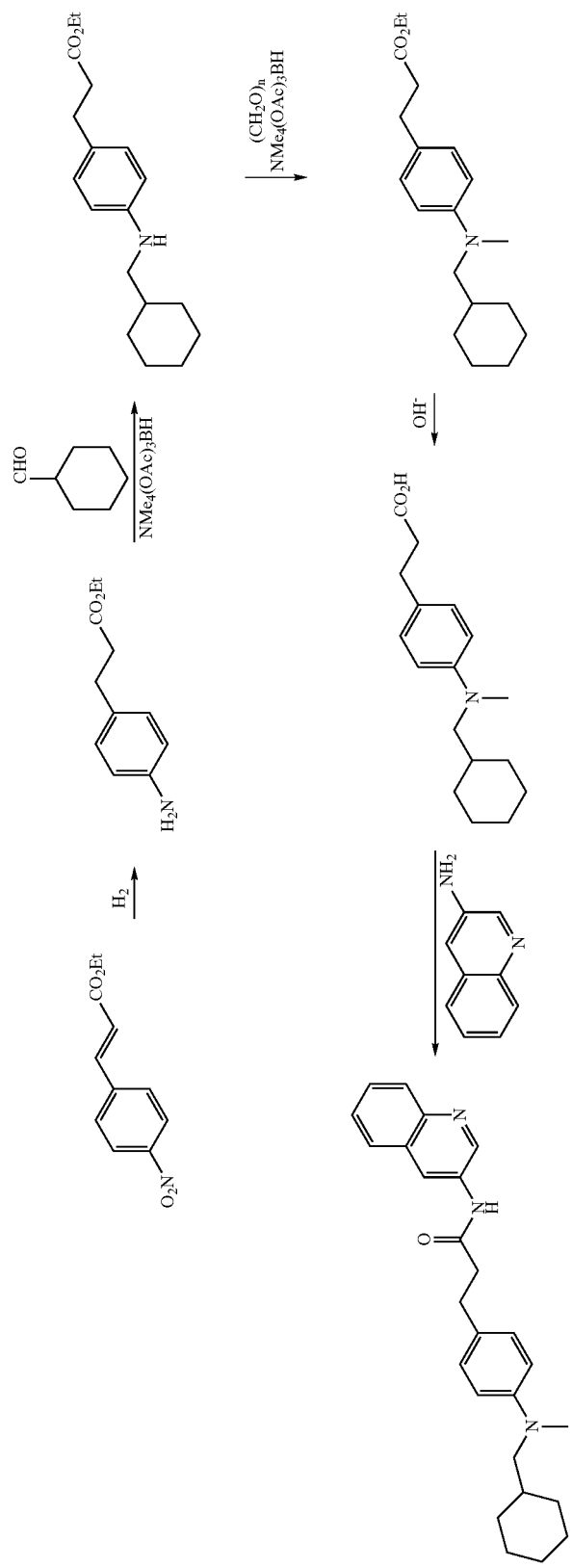

A. 3-(4-Amino-phenyl)-propionic acid ethyl ester. Ethyl 4-nitrocinnamate (6.66 g, 30.1 mmol) was dissolved in 60 mL EtOH along with 5% Pd/C (0.667 g) and hydrogenated at ~50 psi for 1.5 hours. Filtration of the reaction mixture over a pad of celite and evaporation of the filtrate gave the product as a pale peach colored liquid (5.776 g, 29.9 mmol). $^1$H NMR (CDCl$_3$): δ 6.99 (d, 2H), 6.62 (d, 2H), 4.12 (q, 2H), 3.64 (br s, 2H), 2.85 (t, 2H), 2.58 (t, 2H), 1.23 (t, 3H).

B. 3-[4-(Cyclohexylmethyl-amino)-phenyl]-propionic acid ethyl ester. Into a nitrogen flushed round bottom flask equipped with a stir bar was added 30 mL dichloroethane, the aniline obtained in step A, 3-(4-amino-phenyl)-propionic acid ethyl ester (1.451 g, 7.51 mmol), cyclohexanecarboxaldehyde (0.91 mL, 7.51 mmol), and tetramethylammonium triacetoxyborohydride (3.982 g, 15.13 mmol). The reaction was stirred overnight then diluted with 25 mL dichloromethane, extracted twice with 50 mL water, once with 50 mL saturated NaHCO$_3$ and once with 50 mL brine. The organics were dried over Na$_2$SO$_4$, filtered and evaporated in vacuo to yield the crude product which was carried on without further purification (2.161 g, 7.47 mmol). MS: m/z 290.1 (MH$^+$).

C. 3-[4-(Cyclohexylmethyl-methyl-amino)-phenyl]-propionic acid ethyl ester. To a round bottom flask equipped with a stir bar and reflux condenser was added 50 mL dichloromethane, the product from step B, 3-[4-(cyclohexylmethyl-amino)-phenyl]-propionic acid ethyl ester (2.161 g, 7.47 mmol), paraformaldehyde (1.130 g, 37.6 mmol) and tetramethylammonium triacetoxyborohydride (3.950 g, 15.0 mmol). The reaction was heated at reflux overnight, cooled and diluted with 50 mL dichloromethane. The mixture was then extracted twice with 50 mL water, once with 50 mL saturated NaHCO$_3$ and once with 50 mL brine. The organics were dried over Na$_2$SO$_4$, filtered, evaporated and chromatographed over silica gel eluting with 0% to 5% EtOAc in hexanes. Evaporation of the proper fractions yielded the product as a colorless oil (1.611 g, 5.31 mmol). $^1$H NMR (CDCl$_3$): δ 7.06 (d, 2H), 6.62 (d, 2H), 4.13 (q, 2H), 3.08 (d, 2H), 2.93 (s, 3H), 2.86 (t, 2H), 2.58 (t, 2H), 1.72 (m, 6H), 1.22 (m, 6H), 0.93 (m, 2H); MS: m/z 304.1 (MH$^+$).

D. 3-[4-(Cyclohexylmethyl-methyl-amino)-phenyl]-propionic acid. To a round bottom flask equipped with a stir bar was added the propionate ester obtained in step C, 3-[4-(cyclohexylmethyl-methyl-amino)-phenyl]-propionic acid ethyl ester (1.611 g, 5.31 mmol), 50 mL THF, 10 mL water and LiOH.H$_2$O (0.252 g, 6.01 mmol). The reaction was stirred for 2 days, evaporated in vacuo to an aqueous residue which was then diluted with 50 mL water and acidified with 6.0 mL 1N HCl. The precipitated solid was collected by filtration, rinsed with water and dried under vacuum at 50° C. The product was obtained as an off-white powder (1.299 g, 4.72 mmol). $^1$H NMR (DMSO-d$_6$): δ 12.02 (s, 1H), 6.99 (d, 2H), 6.55 (d, 2H), 3.08 (d, 2H), 2.86 (s, 3H), 2.70 (t, 2H), 2.46 (t, 2H), 1.66 (m, 6H), 1.17 (m, 3H), 0.92 (m, 2H); MS: m/z 276.1 (MH$^+$).

E. 3-[4-(Cyclohexylmethyl-methyl-amino)-phenyl]-N-quinolin-3-yl-propionamide. The propionic acid obtained in step D, 3-[4-(cyclohexylmethyl-methyl-amino)-phenyl]-propionic acid (0.282 g, 1.02 mmol) was dissolved in 5 mL DMF with stirring. To this was added Et$_3$N (0.16 mL, 1.15 mmol), 3-aminoquinoline (0.147 g, 1.02 mmol) and lastly HBTU (0.396 g, 1.04 mmol). The reaction was allowed to stir for 48 hours then poured into 25 mL Et$_2$O and washed three times with 10 mL water. The organic layers were dried over Na$_2$SO$_4$, filtered and the solution was allowed to stand and partially evaporate which caused a solid to form. This solid was collected, rinsed with a small amount of Et$_2$O, and dried under vacuum to give the product as a cream colored powder (0.267 g, 0.66 mmol). $^1$H NMR (CDCl$_3$): δ 8.77 (s, 1H), 8.55 (s, 1H), 8.04 (d, 1H), 7.83 (d, 1H), 7.66 (t, 1H), 7.55 (t, 1H), 7.27 (s, 1H), 7.14 (d, 2H), 6.64 (d, 2H), 3.12 (d, 2H), 3.02 (t, 2H), 2.95 (s, 3H), 2.73 (t, 2H), 1.67 (m, 6H), 1.20 (m, 3H), 0.93 (m, 2H); MS: m/z 402.1 (MH$^+$).

Following the procedure described above for Example 35 and the appropriate reagents, starting materials and purification methods known to those skilled in the art, the following compounds of the present invention were prepared:

| Example # | Compound name | MS (calc) | MS (obs) |
|---|---|---|---|
| (36) | 3-[4-(Benzyl-methyl-amino)-phenyl]-N-quinolin-3-yl-propionamide | 395.5 | 396.1 |
| (37) | 3-[4-(Methyl-pentyl-amino)-phenyl]-N-quinolin-3-yl-propionamide | 375.5 | 376.2 |
| (38) | 3-[4-(Heptyl-methyl-amino)-phenyl]-N-quinolin-3-yl-propionamide | 403.6 | 404.2 |
| (39) | 3-[4-(Methyl-propyl-amino)-phenyl]-N-quinolin-3-yl-propionamide | 347.5 | 348.1 |
| (40) | 3-[4-(Cyclohexyl-methyl-amino)-phenyl]-N-quinolin-3-yl-propionamide | 387.5 | 388.1 |
| (41) | 2-[4-(Methyl-pentyl-amino)-phenyl]-N-quinolin-3-yl-acetamide | 361.5 | 362.1 |

Example (42)

3-[4-(Cyclohexyl-methyl-amino)-phenyl]-N-quinolin-3-yl-acrylamide

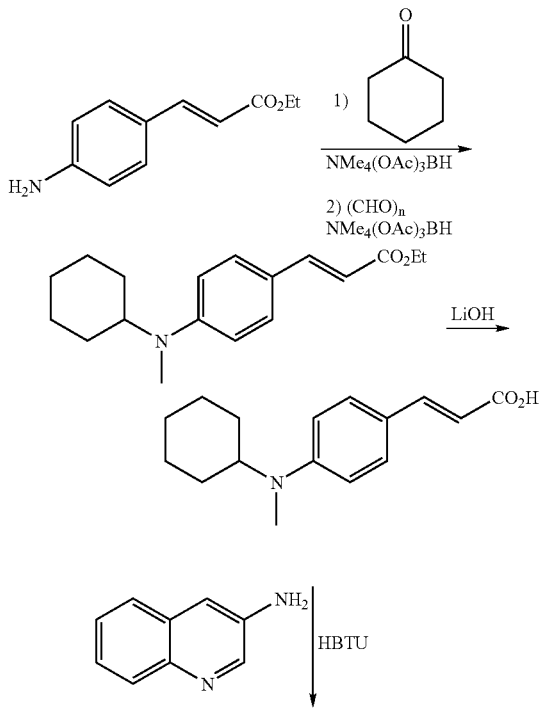

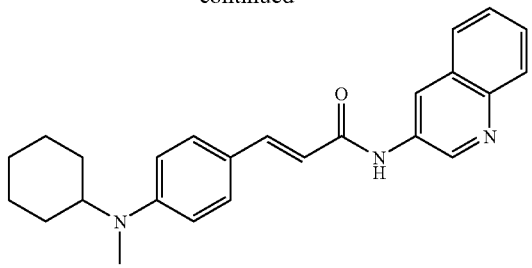

A. 3-[4-(Cyclohexyl-methyl-amino)-phenyl]-acrylic acid ethyl ester. Into a round bottom flask equipped with a stir bar and reflux condenser was added 30 mL dichloroethane, ethyl 4-aminocinnamate (1.914 g, 10.01 mmol), cyclohexanone (1.04 mL, 10.03 mmol) and tetramethylammonium triacetoxyborohydride (5.325 g, 20.2 mmol). The reaction was heated at reflux overnight, cooled and paraformaldehyde (1.505 g, 50.1 mmol) was added along with additional tetramethylammonium triacetoxyborohydride (5.276 g, 20.1 mmol). The reaction was then heated at reflux overnight. Upon cooling, the reaction mixture was diluted with 50 mL dichloromethane, washed twice with 50 mL water, once with 50 mL saturated NaHCO$_3$ and once with 50 mL brine. The organics were dried over Na$_2$SO$_4$, filtered, evaporated and chromatographed over silica gel eluting with 0% to 7.5% EtOAc in hexanes. Evaporation of the proper fractions yielded the product as a thick yellow liquid (1.680 g, 5.85 mmol).

$^1$H NMR (CDCl$_3$): δ 7.62 (d, 1H), 7.40 (d, 2H), 6.70 (d, 2H), 6.21 (d, 1H), 4.23 (q, 2H), 3.63 (m, 1H), 2.83 (s, 3H), 1.92-7.66 (m, 5H), 1.58-1.23 (m, 7H), 1.16 (m, 1H).

B. 3-[4-(Cyclohexyl-methyl-amino)-phenyl]-acrylic acid. To a round bottom flask equipped with a stir bar was added the cinnamate ester obtained in step A, 3-[4-(cyclohexyl-methyl-amino)-phenyl]-acrylic acid ethyl ester (1.672 g, 5.82 mmol), 50 mL THF, 10 mL water and LiOH.H$_2$O (0.252 g, 6.01 mmol). The reaction was stirred for 4 days at room temperature. The reaction mixture was then heated at reflux overnight, additional LiOH.H$_2$O was added (0.084 g, 2.00 mmol) and the refluxing was continued overnight. The reaction mixture was evaporated in vacuo to give an aqueous residue which was diluted with 50 mL water and acidified with 8.0 mL 1N HCl. The precipitated solid was collected by filtration, rinsed with water and hexanes and dried under vacuum at 50° C. The product was obtained as a yellow powder (1.274 g, 4.91 mmol). $^1$H NMR (DMSO-d$_6$): 11.92 (s, 1H), 7.48 (m, 3H), 6.78 (d, 2H), 6.22 (d, 1H), 3.70 (m, 1H), 2.80 (s, 3H), 1.78 (br d, 2H), 1.65 (br s, 3H), 1.58-1.29 (m, 4H), 1.13 (m, 1H); MS: m/z 260.1 (MH$^+$).

C. 3-[4-(Cyclohexyl-methyl-amino)-phenyl]-N-quinolin-3-yl-acrylamide. The cinnamic acid obtained in step B, 3-[4-(cyclohexyl-methyl-amino)-phenyl]-acrylic acid (0.259 g, 1.00 mmol) was dissolved in 5 mL DMF with stirring. To this was added Et$_3$N (0.16 mL, 1.15 mmol), 3-aminoquinoline (0.144 g, 1.00 mmol) and lastly HBTU (0.389 g, 1.03 mmol). The reaction was allowed to stir for 17 days then poured into a mixture of Et$_2$O and NaHCO$_3$. The solid that formed was collected by filtration, washed with additional Et$_2$O and water then dried under vacuum at 40° C. to give the product as an orange powder (0.215 g, 0.56 mmol). $^1$H NMR (CDCl$_3$): δ 8.98 (s, 1H), 8.89 (s, 1H), 8.13 (br s, 1H), 8.07 (d, 1H), 7.83 (d, 1H), 7.74 (d, 1H), 7.63 (t, 1H), 7.56 (t, 1H), 7.43 (d, 2H), 6.72 (d, 2H), 6.47 (d, 1H), 3.63 (m, 1H), 2.85 (s, 3H), 1.93-1.64 (m, 5H), 1.58-1.29 (m, 4H), 1.21 (m, 1H); MS: m/z 386 (MH$^+$).

Following the procedure described above for Example 42 and the appropriate reagents, starting materials and purification methods known to those skilled in the art, the following compounds of the present invention were prepared:

| Example # | Compound name | MS (calc) | MS (obs) |
|---|---|---|---|
| (43) | 3-[4-(Methyl-pentyl-amino)-phenyl]-N-quinolin-3-yl-acrylamide | 373.5 | 374 |

Example (44)

3-(4-Dipentylamino-phenyl)-N-quinolin-3-yl-propionamide

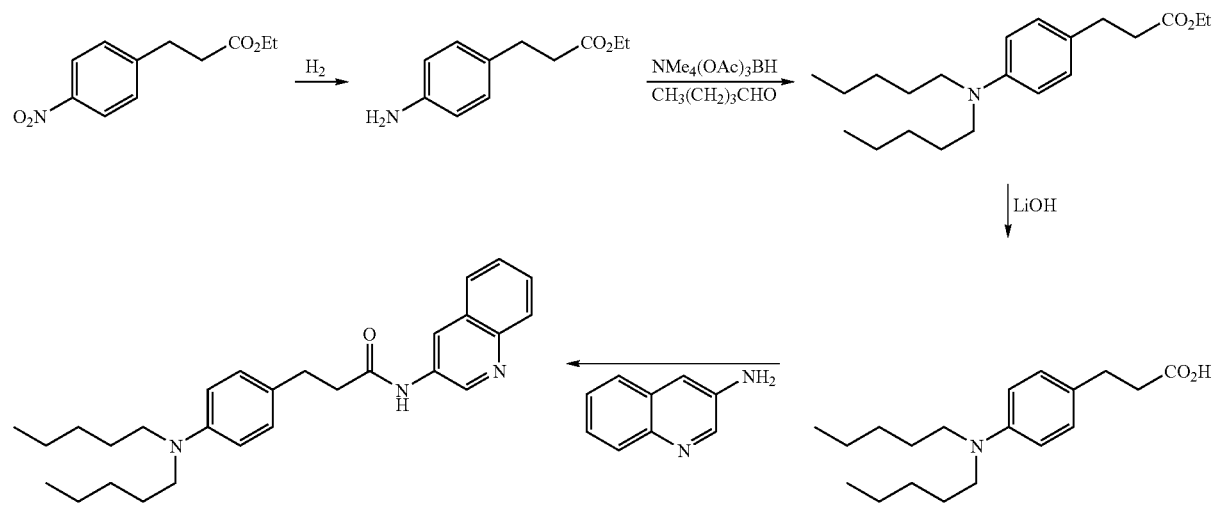

A. 3-(4-Dipentylamino-phenyl)-propionic acid ethyl ester. To a round bottom flask equipped with a stir bar and reflux condenser was added 25 mL dichloroethane, 3-(4-aminophenyl)-propionic acid ethyl ester prepared as described above (1.163 g, 6.02 mmol), valeraldehyde (1.30 mL, 12.2 mmol) and tetramethylammonium triacetoxyborohydride (6.34 g, 24.1 mmol). The reaction was heated at reflux overnight, cooled and diluted with 25 mL dichloroethane. The mixture was then washed once with 50 mL brine, once with 50 mL saturated $NaHCO_3$ and once more with 50 mL brine. The organics were dried over $Na_2SO_4$, filtered, evaporated in vacuo and chromatographed over silica gel eluting with 0% to 5% EtOAc in hexanes. Evaporation of the proper fractions yielded the product as a pale yellow oil (1.091 g, 3.27 mmol).

Following the procedure described above for Example 44 and the appropriate reagents, starting materials and purification methods known to those skilled in the art, the following compounds of the present invention were prepared:

| Example # | Compound name | MS (calc) | MS (obs) |
|---|---|---|---|
| (45) | 2-(4-Dipentylamino-phenyl)-N-quinolin-3-yl-acetamide | 417.6 | 418.2 |

Example (46)

3-(4-Pentyl-phenyl)-N-quinolin-3-yl-acrylamide

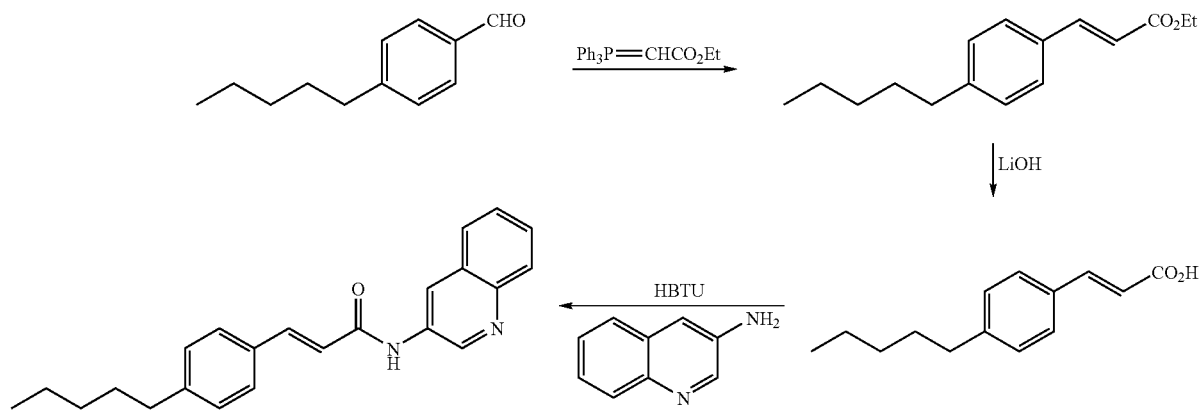

$^1$H NMR (CDCl$_3$): δ 7.04 (d, 2H), 6.58 (d, 2H), 4.13 (q, 2H), 3.23 (t, 4H), 2.86 (t, 2H), 2.58 (t, 2H), 1.58 (m, 4H), 1.43-1.18 (m, 11H), 0.92 (t, 6H); MS: m/z 334.1 (MH$^+$).

B. 3-(4-Dipentylamino-phenyl)-propionic acid. To a round bottom flask equipped with a stir bar was added the propionate ester obtained in step A, 3-(4-dipentylamino-phenyl)-propionic acid ethyl ester (1.078 g, 3.23 mmol), 40 mL THF, 8 mL water and LiOH.H$_2$O (0.168 g, 4.00 mmol). The reaction was stirred for 48 hours then evaporated in vacuo to an aqueous residue which was diluted with 20 mL water and acidified with 4.0 mL 1N HCl. The mixture was then evaporated in vacuo and the oily residue triturated with water, decanted and dried under vacuum at 50° C. to give the product as an orange oil (0.965 g, 3.16 mmol). $^1$H NMR (CDCl$_3$): δ 7.08 (br d, 2H), 6.71 (br s, 2H), 3.23 (t, 4H), 2.88 (t, 2H), 2.63 (t, 2H), 1.58 (br s, 4H), 1.31 (m, 8H), 0.90 (t, 6H).

C. 3-(4-Dipentylamino-phenyl)-N-quinolin-3-yl-propionamide. The carboxylic acid obtained in step B, 3-(4-dipentylamino-phenyl)-propionic acid (0.318 g, 1.04 mmol) was dissolved in 5 mL DMF with stirring. To this was added Et$_3$N (0.16 mL, 1.15 mmol), 3-aminoquinoline (0.150 g, 1.04 mmol) and lastly HBTU (0.405 g, 1.07 mmol). The reaction was allowed to stir overnight then poured into a mixture of 100 mL aqueous NaHCO$_3$ containing a small amount of NaOH. The precipitated solid was collected by filtration, rinsed with 3N NaOH then with water and dried under vacuum to yield the title product as an orange-brown solid (0.224 g, 0.52 mmol). $^1$H NMR (CDCl$_3$): δ 8.73 (s, 1H), 8.55 (d, 1H), 8.02 (d, 1H), 7.81 (d, 1H), 7.63 (t, 1H), 7.55 (t, 1H), 7.39 (s, 1H), 7.11 (d, 2H), 6.62 (d, 2H), 3.25 (t, 4H), 3.02 (t, 2H), 2.75 (t, 2H), 1.57 (m, 4H), 1.32 (m, 8H), 0.90 (t, 6H); MS: m/z 432.2 (MH$^+$).

A. 3-(4-Pentyl-phenyl)-acrylic acid ethyl ester. To a nitrogen flushed round bottom flask equipped with a stir bar and reflux condenser was added 4-pentyl-benzaldehyde (1.782 g, 10.11 mmol) and 25 mL benzene. (Carbethoxymethylene)triphenylphosphorane (3.539 g, 10.16 mmol) was added and the solution was heated at reflux overnight. The reaction mixture was evaporated in vacuo. The resulting residue was triturated with 50 mL Et$_2$O and filtered. The filtrate was evaporated in vacuo and chromatographed over silica gel eluting with 0% to 5% EtOAc in hexanes. Evaporation of the proper fractions yielded the product as a colorless oil (2.126 g, 8.63 mmol). $^1$H NMR (CDCl$_3$): δ 7.68 (d, 1H, J=16.0 Hz), 7.45 (d, 2H), 7.20 (d, 2H), 6.41 (d, 1H, J=16.0 Hz), 4.28 (q, 2H), 2.64 (t, 2H), 1.62 (m, 2H), 1.33 (m, 7H), 0.89 (t, 3H); MS: m/z 247 (MH$^+$).

B. 3-(4-Pentyl-phenyl)-acrylic acid. To a round bottom flask equipped with a stir bar was added the cinnamate ester obtained in step A, 3-(4-pentyl-phenyl)-acrylic acid ethyl ester (1.052 g, 4.27 mmol), 50 mL THF, 10 mL water and LiOH.H$_2$O (0.187 g, 4.46 mmol). The reaction was stirred overnight then an additional amount of LiOH.H$_2$O was added (0.179 g, 4.27). The reaction was stirred for an additional 5 days then evaporated in vacuo, diluted with 50 mL water and acidified with 25 mL 1N HCl. The precipitated solid was collected by filtration, rinsed with water and dried under vacuum at 50° C. to give the product as a white powder (0.636 g, 2.91 mmol). $^1$H NMR (DMSO-d$_6$): 12.32 (s, 1H), 7.60 (m, 3H), 7.25 (d, 2H), 6.48 (d, 1H), 2.61 (t, 2H), 1.60 (m, 2H), 1.30 (m, 4H), 0.87 (t, 3H); MS: m/z 217.0 (M-H)$^-$.

C. 3-(4-Pentyl-phenyl)-N-quinolin-3-yl-acrylamide. The carboxylic acid obtained in step B, 3-(4-pentyl-phenyl)-acrylic acid (0.220 g, 1.01 mmol), was dissolved in 5 mL DMF with stirring. To this was added Et$_3$N (0.16 mL, 1.15 mmol), 3-aminoquinoline (0.147 g, 1.02 mmol) and lastly HBTU (0.383 g, 1.01 mmol). The reaction was allowed to stir overnight then poured into 100 mL aqueous NaHCO$_3$ containing a small amount of NaOH. The solid was collected by filtration, rinsed with water and chromatographed over silica gel eluting with 0% to 50% EtOAc in hexanes. Evaporation of the proper fractions yielded the title product as a pale tan powder (0.125 g, 0.36 mmol). $^1$H NMR (CDCl$_3$): δ 8.92 (s, 1H), 8.83 (d, 1H), 8.05 (d, 1H), 7.82 (m, 3H), 7.65 (t, 1H), 7.57 (t, 1H), 7.48 (d, 2H), 7.21 (d, 2H), 6.62 (d, 1H), 2.63 (t, 2H), 1.64 (m, 2H), 1.33 (m, 4H), 0.89 (t, 3H); MS: m/z 345.0 (MH$^+$).

Example (47)

2-(4-Pentyl-phenyl)-N-quinolin-3-yl-acetamide

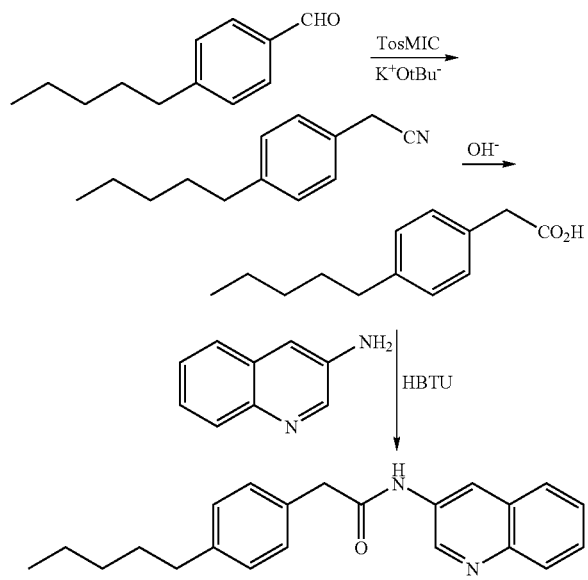

A. (4-Pentyl-phenyl)-acetonitrile. Into a 3-neck round bottom flask equipped with a stir bar, reflux condenser and addition funnel was added potassium t-butoxide solution (1M in THF, 31 mL, 31 mmol). The flask was cooled in a dry ice-acetonitrile bath and a solution of tolylmethyl isocyanide (TosMIC) in 15 mL DME was added (3.179 g, 16.3 mmol). The reaction was stirred for a few minutes then a solution of 4-pentyl-benzaldehyde (2.593 g, 14.7 mmol) in 15 mL DME was added dropwise over 35 minutes. The reaction was stirred in the ice bath for 2 hours then removed and allowed to warm to room temperature. Methanol (40 mL) was then added and the solution was heated at reflux for 25 minutes. The reaction mixture was evaporated in vacuo, dissolved in 150 mL dichloromethane, washed twice with 100 mL 5% HOAc, once with 100 mL saturated NaHCO$_3$ and finally with 100 mL brine. The organics were dried over Na$_2$SO$_4$, filtered, evaporated and chromatographed over silica gel eluting with 0% to 7.5% EtOAc in hexanes. Evaporation of the proper fractions yielded the product as a brown oil with a distinctive odor (0.949 g, 5.07 mmol). $^1$H NMR (CDCl$_3$): δ 7.22 (m, 4H), 3.72 (s, 2H), 2.60 (t, 2H), 1.61 (m, 2H), 1.32 (m, 4H), 0.90 (t, 3H).

B. (4-Pentyl-phenyl)-acetic acid. Into a round bottom flask equipped with a stir bar and reflux condenser was added 25 mL EtOH, (4-pentyl-phenyl)-acetonitrile prepared in step A (0.945 g, 5.05 mmol), and NaOH solution (1N, 5 mL, 5 mmol). The reaction was heated at reflux for 2 days then an additional amount of NaOH solution was added (1N, 5 mL, 5 mmol) and reaction mixture was heated at reflux for an additional 5 days. The reaction mixture was evaporated in vacuo, dissolved in 50 mL water then filtered over a pad of celite. The aqueous filtrate was acidified with 25 mL 1N HCl and the precipitated solid was collected by filtration. The solid was rinsed with water and dried under vacuum at 50° C. to give the product as an orange powder (0.917 g, 4.45 mmol). $^1$H NMR (DMSO-d$_6$): δ 12.25 (s, 1H), 7.13 (m, 4H), 3.52 (s, 2H), 2.54 (t, 2H), 1.57 (m, 2H), 1.28 (m, 4H), 0.85 (t, 3H); MS: m/z 205 (M-H.)$^-$ C. 2-(4-Pentyl-phenyl)-N-quinolin-3-yl-acetamide. The carboxylic acid obtained in step B (4-pentyl-phenyl)-acetic acid (0.208 g, 1.01 mmol) was dissolved in 5 mL DMF with stirring. To this was added Et$_3$N (0.15 mL, 1.08 mmol), 3-aminoquinoline (0.147 g, 1.02 mmol) and lastly HBTU (0.390 g, 1.03 mmol). The reaction was allowed to stir overnight then poured into 100 mL aqueous NaHCO$_3$ containing a small amount of NaOH. The precipitated solid was collected by filtration, rinsed with water and dried under vacuum to yield the product as a tan powder (0.256 g, 0.77 mmol). $^1$H NMR (CDCl$_3$): δ 8.74 (d, 1H), 8.58 (d, 1H), 8.02 (d, 1H), 7.78 (d, 1H), 7.63 (t, 1H), 7.53 (t, 1H), 7.44 (s, 1H), 7.28 (m, 4H), 3.82 (s, 2H), 2.64 (t, 2H), 1.63 (m, 2H), 1.33 (m, 4H), 0.90 (t, 3H); MS: m/z 333.0 (MH$^+$).

Example (48)

4-[(Hexyl-methyl-amino)-methyl]-N-quinolin-3-yl-benzamide

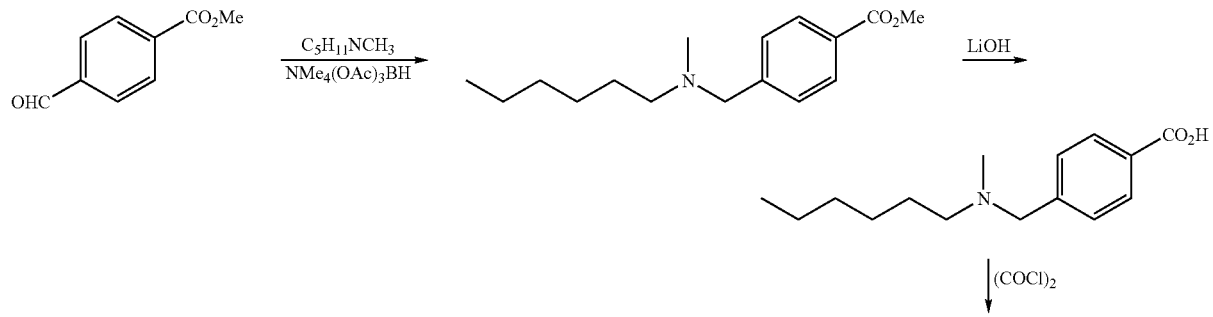

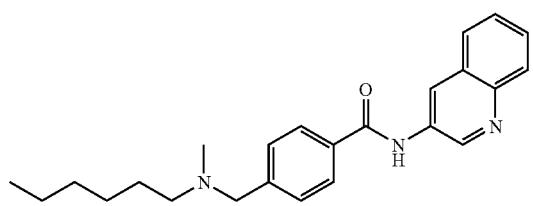 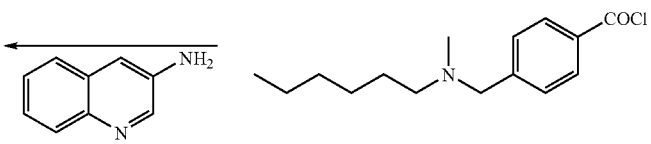

A. 4-[(Hexyl-methyl-amino)-methyl]-benzoic acid methyl ester. Into a round bottom flask equipped with a stir bar was added 25 mL dichloroethane, methyl 4-formylbenzoate (1.235 g, 7.52 mmol), N-methylhexylamine (1.14 mL, 7.52 mmol) and tetramethylammonium triacetoxyborohydride (3.975 g, 15.1 mmol). The reaction was stirred overnight then diluted with 25 mL dichloromethane, washed twice with 50 mL water, once with 50 mL saturated NaHCO$_3$ and once with brine. The organics were dried over Na$_2$SO$_4$, filtered, evaporated and then chromatographed over silica gel eluting with 0% to 20% EtOAc in hexanes. Evaporation of the proper fractions yielded the product as a colorless oil (1.386 g, 5.26 mmol). $^1$H NMR (CDCl$_3$): δ 8.01 (d, 2H), 7.42 (d, 2H), 3.92 (s, 3H), 3.52 (s, 2H), 2.37 (t, 2H), 2.19 (s, 3H), 1.52 (m, 2H), 1.30 (m, 6H), 0.89 (t, 3H); MS: m/z 264.1 (MH$^+$).

B. 4-[(Hexyl-methyl-amino)-methyl]-benzoic acid. To a round bottom flask equipped with a stir bar was added the benzoate ester prepared in step A, 4-[(hexyl-methyl-amino)-methyl]-benzoic acid methyl ester (1.386 g, 5.26 mmol), 50 mL THF, 10 mL water and LiOH.H$_2$O (0.252 g, 6.01 mmol). The reaction was stirred 48 hours then evaporated in vacuo to give an aqueous residue which was diluted with 50 mL water and then acidified with 6.0 mL 1N HCl. The solution was filtered over a pad of celite to remove the turbidity then evaporated in vacuo and dried under vacuum at 50° C. to give the product as a mixture with LiCl. No further attempts were made to remove the inorganic salt from the carboxylic acid. $^1$H NMR (DMSO-d$_6$): 7.90 (d, 2H), 7.42 (d, 2H), 3.53 (s, 2H), 2.32 (t, 2H), 2.12 (s, 3H), 1.46 (m, 2H), 1.25 (m, 6H), 0.83 (t, 3H); MS: m/z 250.1 (MH$^+$).

C. 4-[(Hexyl-methyl-amino)-methyl]-benzoyl chloride. Into a nitrogen flushed round bottom flask equipped with a stir bar was suspended the benzoic acid prepared in step B, 4-[(hexyl-methyl-amino)-methyl]-benzoic acid (0.298 g, 1.00 mmol) in 20 mL dichloromethane. To the suspension was added one drop of DMF followed by oxalyl chloride (0.26 mL, 2.98 mmol). The reaction was stirred for one hour then an additional amount of oxalyl chloride was added (0.26 mL, 2.98 mmol) and the reaction was stirred overnight. The reaction mixture was then evaporated in vacuo to give the acid chloride that was carried on without further purification.

D. 4-[(Hexyl-methyl-amino)-methyl]-N-quinolin-3-yl-benzamide. The acid chloride obtained in step C, 4-[(hexyl-methyl-amino)-methyl]-benzoyl chloride (1.00 mmol), was dissolved in 10 mL acetonitrile with stirring. To the solution was added iPr$_2$NEt (0.38 mL, 2.18 mmol) and 3-aminoquinoline (0.145 g, 1.01 mmol). The reaction was stirred for 2 hours then evaporated in vacuo. The resulting residue was suspended in 50 mL dichloromethane, washed twice with 25 mL 1N NaOH, once with 25 mL water and once with 25 mL brine. The organics were dried over Na$_2$SO$_4$, filtered, evaporated and chromatographed over silica gel eluting with 5% MeOH/NH$_3$: 95% dichloromethane. Evaporation of the proper fractions yielded the title product as a yellow-tan powder (0.249 g, 0.66 mmol). $^1$H NMR (CDCl$_3$): δ 8.94 (s, 1H), 8.88 (d, 1H), 8.20 (s, 1H), 8.07 (d, 1H), 7.91 (d, 2H), 7.83 (d, 1H), 7.67 (t, 1H), 7.57 (t, 1H), 7.48 (d, 2H), 3.55 (s, 2H), 2.38 (t, 2H), 2.20 (s, 3H), 1.52 (m, 2H), 1.31 (m, 6H), 0.90 (t, 3H); MS: m/z 376.1. (MH$^+$)

Following the procedure described above for Example 48 and the appropriate reagents, starting materials and purification methods known to those skilled in the art, the following compounds of the present invention were prepared:

| Example # | Compound name | MS (calc) | MS (obs) |
|---|---|---|---|
| (49) | 2-[4-(Cyclohexyl-methyl-amino)-phenyl]-N-quinolin-3-yl-acetamide | 373.5 | 374.1 |

Example (50)

3-(4-tert-Butyl-phenyl)-N-quinolin-3-yl-propionamide 4-t-Butylphenylacetic acid To a round bottom flask equipped with a stir bar was added methyl 4-t-butylphenylacetate (5.185 g, 25.13 mmol), 125 mL THF, 25 mL water and LiOH.H$_2$O (1.054 g, 25.12 mmol). The reaction was stirred overnight then evaporated in vacuo to give an aqueous residue which was diluted with 25 mL water. The solution was then filtered over a nylon disk and the filtrate acidified with 50 mL 1N HCl. The precipitated solid that formed was collected by filtration, rinsed with water and dried to yield the product, 4-t-butylphenylacetic acid, as a white powder (4.572 g, 23.8 mmol). $^1$H NMR (DMSO-d$_6$): δ 12.28 (br s, 1H), 7.33 (d, 2H), 7.18 (d, 2H), 3.51 (s, 2H), 1.28 (s, 9H); MS: m/z 191.0 (M-H)$^-$.

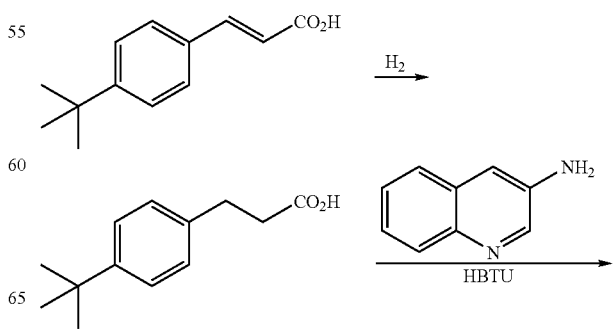

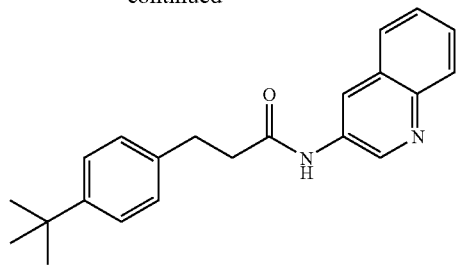

A. 3-(4-tert-Butyl-phenyl)-propionic acid. 3-(4-tert-Butyl-phenyl)-acrylic acid (3.06 g, 15.0 mmol) was dissolved in 50 mL EtOH along with 10% Pd/C (0.308 g) and hydrogenated at ~50 psi overnight. Filtration of the reaction mixture over a pad of celite and evaporation of the filtrate gave the title product as a white crystalline powder (3.021 g, 14.6 mmol). $^1$H NMR (DMSO-d$_6$): δ 12.11 (br s, 1H), 7.30 (d, 2H), 7.14 (d, 2H), 2.78 (t, 2H), 2.52 (t, 2H), 1.27 (s, 9H); MS: m/z 205.0 (M-H)$^-$.

B. 3-(4-tert-Butyl-phenyl)-N-quinolin-3-yl-propionamide. The carboxylic acid obtained in step A, 3-(4-tert-butyl-phenyl)-propionic acid (0.208 g, 1.01 mmol), was dissolved in 5 mL DMF with stirring. Triethylamine (0.16 mL, 1.15 mmol) was then added followed by 3-aminoquinoline (0.147 g, 1.02 mmol) and lastly HBTU (0.404 g, 1.07 mmol). The reaction mixture was stirred at room temperature for 48 hours then poured into 25 mL EtOAc, washed with 25 mL saturated NaHCO$_3$ solution then 25 mL brine. The organics were evaporated in vacuo and the residue was chromatographed over silica gel eluting with 0% to 60% EtOAc in hexanes. Evaporation of the proper fractions yielded the title product as an off-white powder (0.294 g, 0.88 mmol). $^1$H NMR (CDCl$_3$): δ 8.72 (s, 1H), 8.55 (d, 1H), 8.03 (d, 1H), 7.81 (d, 1H), 7.63 (t, 1H), 7.53 (t, 1H), 7.37 (d, 2H), 7.21 (m, 3H), 3.09 (t, 2H), 2.78 (t, 2H), 1.31 (s, 9H); MS: m/z 333.5 (MH$^+$).

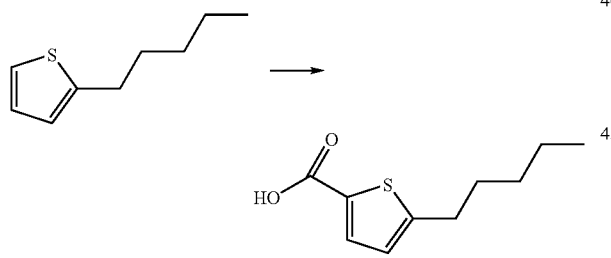

5-Pentyl-thiophene-2-carboxylic acid. n-Butyllithium (2.0 M in cyclohexane, 6.2 mL, 12.4 mmol) was added to a solution of 2-pentyl-thiophene (1.75 g, 11.3 mmol) in diethyl ether (40 mL) at –10° C. The resultant solution was stirred at 0° C. for 30 minutes, then cooled to –10° C. Carbon dioxide was bubbled through the solution at –5 to –10° C. for 45 minutes. The solution was washed with 2N hydrochloric acid, then brine and dried over sodium sulfate. The solvent was evaporated in vacuo to give an oil which crystallized from cold hexane, to give a colorless solid, 0.553 g (25%). MS: m/z 199 (MH$^+$). $^1$H NMR (CDCl$_3$): δ 0.90 (t, 3 H), 1.29-1.41 (m, 4 H), 1.65-1.75 (m, 2 H), 2.85 (t, 2 H), 6.82 (d, 1 H) and 7.72 (d, 1 H).

The preceding carboxylic acids were coupled to 3-amino-quinolines according to the procedure of step B of Example 48.

Following the procedure described above for Example 50 and the appropriate reagents, starting materials and purification methods known to those skilled in the art, the following compounds of the present invention were prepared:

| Example # | Compound name | MS (calc) | MS (obs) |
| --- | --- | --- | --- |
| (51) | 3-(4-tert-Butyl-phenyl)-N-quinolin-3-yl-acrylamide | 330.4 | 331.4 |
| (52) | 2-(4-tert-Butyl-phenyl)-N-quinolin-3-yl-acetamide | 318.4 | 319.4 |
| (53) | 4-tert-Butyl-N-quinolin-3-yl-benzamide | 304.4 | 305.4 |
| (54) | N-Quinolin-3-yl-4-trifluoromethyl-benzamide | 316.28 | 317.1 |
| (55) | N-Quinolin-3-yl-3-(4-trifluoromethyl-phenyl)-acrylamide | 342.32 | 342.00 |
| (56) | 3-(4-Chloro-3-trifluoromethyl-phenyl)-N-quinolin-3-yl-acrylamide | 376.77 | 377.00 |
| (57) | 3-(3,4-Dichloro-phenyl)-N-quinolin-3-yl-acrylamide | 343.21 (342) | 343.00 |
| (58) | N-Quinolin-3-yl-3-(3-trifluoromethyl-phenyl)-acrylamide | 342.31 | 343.20 |
| (59) | 5-Butyl-pyridine-2-carboxylic acid quinolin-3-ylamide | 305.38 | 306 |
| (60) | 5-Pentyl-thiophene-2-carboxylic acid quinolin-3-ylamide | 324.45 | 325 |
| (61) | N-Quinolin-3-yl-3-(4-trifluoromethyl-phenyl)-propionamide | 344.34 | 345 |
| (62) | 2-Methyl-3-phenyl-N-quinolin-3-yl-acrylamide | 288.35 | 289 |

Example (63)

4-Butoxy-N-quinolin-3-yl-benzamide

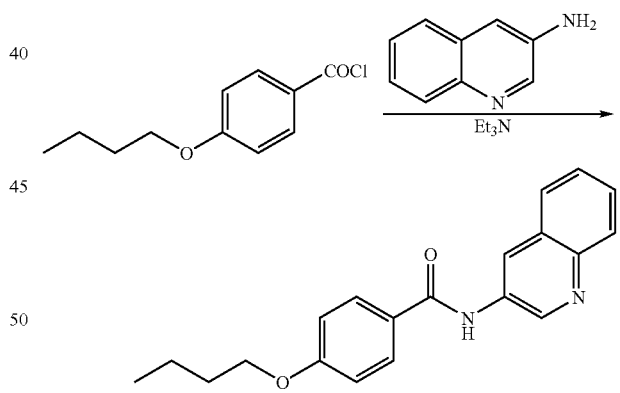

4-Butoxy-N-quinolin-3-yl-benzamide. 4-Butoxy-benzoyl chloride (0.21 mL, 1.11 mmol), Et$_3$N (0.16 mL, 1.15 mL) and 3-aminoquinoline (0.153 g, 1.06 mmol) were stirred together in 10 mL acetonitrile in a round bottom flask for 4 hours. The reaction mixture was then evaporated in vacuo and the residue was triturated with 5 mL acetonitrile. The resulting solid was collected by filtration, rinsed with acetonitrile and dried to yield the title product as a cream-colored powder (0.284 g, 0.89 mmol). $^1$H NMR (CDCl$_3$): δ 8.91 (s, 2H), 8.20 (s, 1H), 8.08 (d, 1H), 7.94 (d, 2H), 7.84 (d, 1H), 7.67 (t, 1H), 7.57 (t, 1H), 7.01 (d, 2H), 4.05 (t, 2H), 1.83 (p, 2H), 1.52 (h, 2H), 1.01 (t, 3H); MS: m/z 321.0 (MH$^+$).

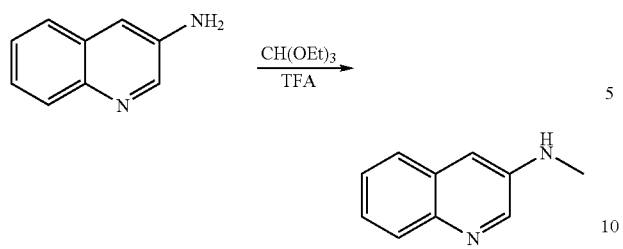

Methyl-quinolin-3-yl-amine. A solution of quinolin-3-ylamine (5.2 g, 36.1 mmol) and trifluoroacetic acid (catalytic) in triethyl orthoformate (30 mL) was heated at reflux for 6 hours. The solvent was evaporated in vacuo, and the residue was dissolved in ethanol (50 mL). Sodium borohydride tablets (2.5 g, 0.203 mol) was added to the solution, and the resultant mixture was stirred at room temperature for 2.5 days. The mixture was partitioned between water and dichloromethane. The organic layer was separated, washed with water and dried over sodium sulfate. The solvent was evaporated in vacuo, to give the product, 5.35 g (94%), an oil, which crystallized on standing. MS: m/z 159 (MH$^+$). $^1$H NMR (CDCl$_3$): δ 2.90 (d, 3 H), 4.15 (br s, 1 H), 6.97 (d, 1 H), 7.36-7.47 (m, 2 H), 7.55-7.65 (m, 1 H), 7.91-7.96 (m, 1 H) and 8.42 (d, 1 H).

Following the procedure described above for Example 63 and the appropriate reagents, starting materials and purification methods known to those skilled in the art, the following compounds of the present invention were prepared:

| Example # | Compound name | MS (calc) | MS (obs) |
|---|---|---|---|
| (64) | 4-Pentyl-N-quinolin-3-yl-benzamide | 318.41 | 319 |
| (65) | 4-Methyl-N-quinolin-3-yl-benzamide | 262.31 | 263 |
| (66) | 4-Ethyl-N-quinolin-3-yl-benzamide | 276.337 | 277 |
| (67) | 4-Propyl-N-quinolin-3-yl-benzamide | 290.36 | 291 |
| (68) | 4-Butyl-N-quinolin-3-yl-benzamide | 304.391 | 305 |
| (69) | 4-Hexyl-N-quinolin-3-yl-benzamide | 332.44 | 333 |
| (70) | 4-Decyl-N-quinolin-3-yl-benzamide | 388.552 | 389 |
| (71) | 4-Heptyl-N-quinolin-3-yl-benzamide | 346.47 | 347 |
| (72) | 4-Octyl-N-quinolin-3-yl-benzamide | 360.498 | 361 |
| (73) | 4-Nonyl-N-quinolin-3-yl-benzamide | 374.52 | 375 |
| (74) | Biphenyl-4-carboxylic acid quinolin-3-ylamide | 324.381 | 325 |
| (75) | 4-Butyl-N-methyl-N-quinolin-3-yl-benzamide | 318.42 | 319 |
| (76) | 4-Ethoxy-N-quinolin-3-yl-benzamide | 292.336 | 293 |

Preparation of substituted 3-aminoquinolines

2-Chloro-quinolin-3-ylamine

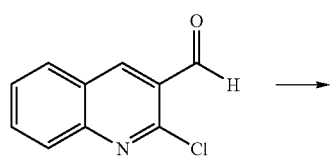

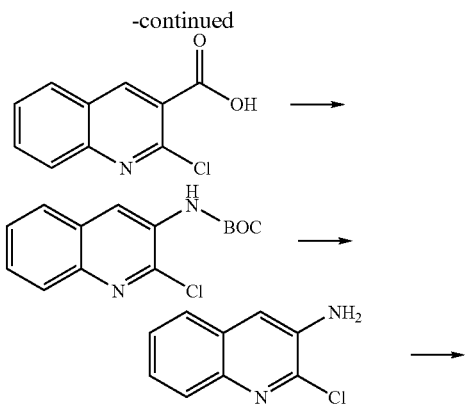

A. 2-Chloro-quinoline-3-carboxylic acid. A suspension of silver nitrate (6.8 g, 40 mmol) in ethanol (100 mL) was added to a solution of 2-chloro-quinoline-3-carbaldehyde (4.8 g, 25 mmol) in ethanol (200 mL). A solution of sodium hydroxide (5 g, 125 mmol) in 80% ethanol (100 mL) was added over 15 minutes. The resulting black suspension was stirred at ambient temperature for 4 hours. The mixture was filtered through a pad of celite, and the pad was washed generously with ethanol. The combined ethanolic solutions were concentrated in vacuo and diluted with water. The aqueous solution was neutralized with concentrated hydrochloric acid, and the product precipitated. The product was collected by filtration and washed with water. The solid was triturated in hot ethanol, cooled and collected by filtration to give a colorless solid, 3.5 g (67%). MS: m/z 208 (MH$^+$). $^1$H NMR (DMSO-d$_6$): δ 7.74 (d of d, 1 H), 7.94 (d of d, 1 H), 8.01 (d, 1 H), 8.18 (d, 1 H), 8.95 (s, 1 H) and 13.81 (s, 1 H).

B. (2-Chloro-quinolin-3-yl)-carbamic acid tert-butyl ester. Diphenyphosphoryl azide (2.72 mL, 12.6 mmol) was added to a mixture of 2-chloro-quinoline-3-carboxylic acid (2.5 g, 12.0 mmol) and triethylamine (1.84 mL, 13.2 mmol) in tert-butanol (30 mL). The resultant solution was heated at reflux for 2 hours. The solvent was evaporated in vacuo, and the residue was partitioned between ethyl acetate and water. The organic layer was washed successively with water (3×), a saturated aqueous solution of sodium bicarbonate, and brine. The solution was dried over sodium sulfate, and the solvent was evaporated in vacuo. The product was purified by flash chromatography on silica gel, eluted with 2% to 7.5% ethyl acetate in hexane to give the product, 2.1 g (63%). MS: m/z 279 (MH$^+$). $^1$H NMR (DMSO-d$_6$): δ 1.58 (s, 9 H), 7.23 (br s, 1 H), 7.51 (d of d, 1 H), 7.58 (d of d, 1 H), 7.78 (d, 1 H), 7.93 (d, 1 H) and 8.90 (s, 1 H).

C. 2-Chloro-quinolin-3-ylamine A solution of 2-chloro-quinolin-3-yl)-carbamic acid tert-butyl ester (2.0 g, 7.18 mmol) in 1,2-dichloroethane (20 mL) and trifluoroacetic acid (12 mL) was stirred at ambient temperature for 20 hours. The solvents were evaporated in vacuo, and the residue was triturated in an aqueous solution of sodium bicarbonate. The product was collected by filtration, washed with water, and dried in vacuo to give the product as a pale yellow solid, 1.2 g (94%). MS: m/z 179 (MH$^+$). $^1$H NMR (DMSO-d$_6$): δ 5.8 (br s, 2 H), 7.41 (m, 3 H), 7.71 (m, 2 H).

4-Chloro-quinolin-3-ylamine was prepared as described in "Synthesis of Some 3-Nitro- and 3-Amino-4-dialkylamino-quinoline Derivatives" Surrey, A. R.; Cutler, R. A. J. Amer. Chem. Soc. 1951, 73, 2413.

Preparation of Substituted tert-butoxycarbonylamino-benzoic acid derivatives 4-tert-Butoxyamino-3-methyl-benzoic acid. A solution of di-tert-butyl dicarbonate (18.7 g, 85.8 mmol) in dioxane (50 mL) was added to a solution of 4-amino-3-methylbenzoic acid (9.95 g, 65.8 mmol) in 3 N aqueous sodium hydroxide (22 mL, 66 mmol). The resultant solution was stirred at ambient temperature, and additional portions of di-tert-butyl dicarbonate (14 g and 7 g) were added at 18 and 42 hours respectively. The solution was stirred an additional 2 days. The solution was diluted with water and neutralized with 1N hydrochloric acid. The precipitate was collected by filtration, washed with water and dried in vacuo, to give the product as a colorless solid, 12.75 g (77%). $^1$H NMR (DMSO-$d_6$): δ 1.48 (s, 9 H), 3.47 (s, 3 H), 7.60 (d, 1 H), 7.70-7.74 (m, 2 H), 8.70 (s, 1 H) and 12.69 (s, 1 H).

4-tert-Butoxyamino-2-chloro-benzoic acid. 4-amino-2-chloro-benzoic acid was converted to product in 79% yield, using the procedure described for the synthesis of 4-tert-Butoxyamino-3-methyl-benzoic acid. $^1$H NMR (DMSO-$d_6$): δ 1.49 (s, 9 H), 7.46 (d of d, 1 H), 7.71 (br s, 1 H), 7.80 (d, 1 H), 9.87 (s, 1 H) and 13.00 (br s, 1 H).

Preparation of Substituted Nicotinic Acid Derivatives

Pyridyl carboxylates were prepared according to the method of Comins, D. L.; Stroud, E. D.; Herrick, J. Heterocyles, 1984, 22, 151.

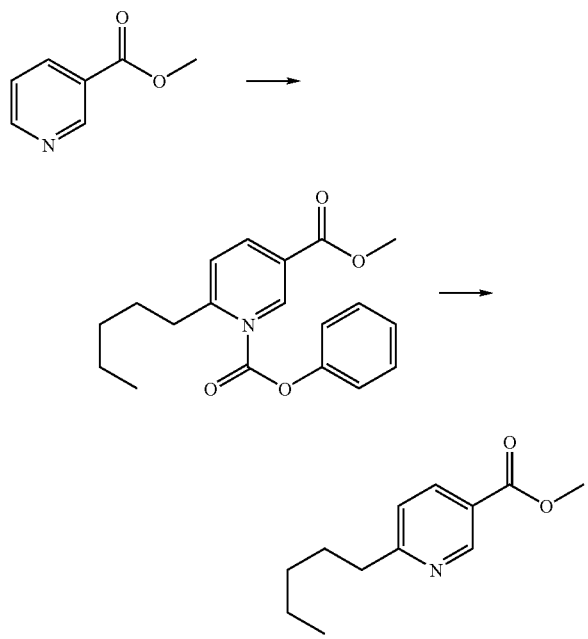

6-Pentyl-6H-pyridine-1,3-dicarboxylic acid 3-methyl ester 1-phenyl ester. Phenylchloroformate (1.83 mL, 14.6 mmol) was added dropwise to a solution of Nicotinic acid methyl ester (2.0 g, 14.6 mmol) in tetrahydrofuran (30 mL) at −20° C., and stirred for ten minutes. A solution of pentylmagnesium bromide (2 M in diethyl ether, 7.3 mL, 14.6 mmol) was added dropwise to the solution and stirred for 30 min at −20° C. The resulting solution was washed successively with saturated aqueous ammonium chloride and brine. The solution was dried over sodium sulfate, and the solvent was evaporated in vacuo to give the product mixed with another isomer. The crude mixture was used without purification in the subsequent step. MS: m/z 330 (MH$^+$).

6-Pentyl-nicotinic acid methyl ester. The crude mixture from above with naphthalene (27.5 g), and sulfur (0.5 g, 15.6 mmol) was heated for 3 hours. The naphthalene was distilled off in vacuo, and the residue was partitioned between diethyl ether and 2N hydrochloric acid. The aqueous extracts were combined and made basic with 3N sodium hydroxide. The product was extracted into dichloromethane and preabsorbed onto silica gel. The product was separated from its isomer by flash chromatography, using ethyl acetate (15-20%) in hexane as the eluant, to give the product, 0.30 g (10% for 2 steps). MS: m/z 208 (MH$^+$). $^1$H NMR (CDCl$_3$): δ 0.90 (t, 3 H), 1.31-1.48 (m, 4 H), 1.67-1.78 (m, 2 H), 2.85 (t, 2 H), 3.94 (s, 3 H), 7.22 (d, 1 H), 8.18 (d of d, 1 H) and 9.13 (d, 1 H).

Example (77)

4-tert-Butyl-N-(2-chloro-quinolin-3-yl)-benzamide

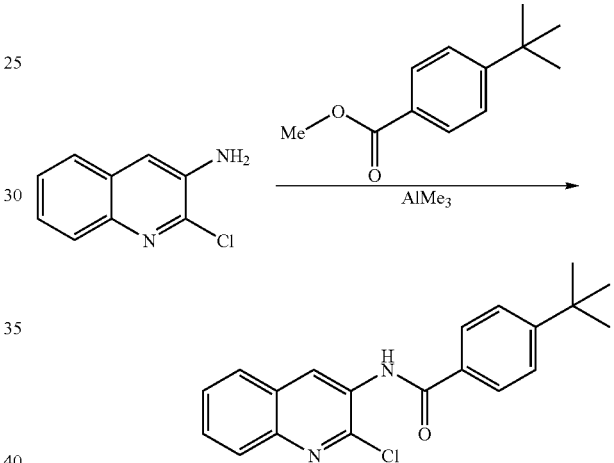

A solution of trimethylaluminum in toluene (2.0 M, 0.56 mL, 1.12 mmol) was added to a solution of 2-chloro-quinolin-3-ylamine (0.2 g, 1.12 mmol) and methyl 4-tert-butylbenzoate (0.227 mL, 1.18 mmol) in 1,2-dichloroethane (10 mL). The solution was heated at reflux for 6 hours, cooled to room temperature and treated with methanol (~1 mL). The product was preabsorbed onto silica gel, and purified by flash chromatography, using 10% ethyl acetate in hexane as the eluant to give the product as a colorless solid, 0.32 g (84%). MS: m/z 339 (MH$^+$). $^1$H NMR (DMSO-$d_6$): δ 1.34 (s, 9 H), 7.60 (d, 2 H), 7.69 (d of d, 1 H), 7.82 (d of d, 1 H), 7.99 (d, 3 H), 8.09 (d, 1 H), 8.67 (s, 1 H) and 10.31 (s, 1 H).

The following compounds were prepared according to the method of Example 77:

| Example # | Compound name | M Wt | MH$^+$ |
|---|---|---|---|
| (78) | 4-tert-Butyl-N-(2-chloro-quinolin-3-yl)-benzamide | 338.84 | 339 |
| (79) | 4-tert-Butyl-N-(4-chloro-quinolin-3-yl)-benzamide | 338.83 | 339.1 |
| (80) | 6-Pentyl-N-quinolin-3-yl-nicotinamide | 319.41 | 320 |

Example (81)

3-(4-tert-Butyl-phenyl)-N-(2-chloro-quinolin-3-yl)-acrylamide

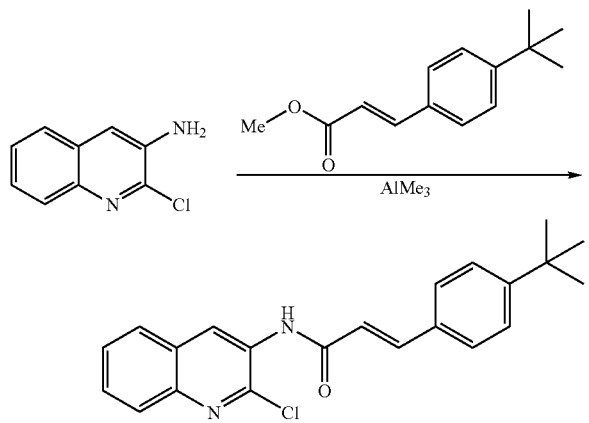

A solution of trimethylaluminum (2.0 M, 0.61 mL, 1.22 mmol) was added to a solution of 2-chloro-quinolin-3-ylamine (0.2 g, 1.12 mmol) and methyl 4-tert-butylcinnamate (0.241 g, 1.11 mmol) in 1,2-dichloroethane (10 mL). The solution was heated at reflux for 6 hours. The solution was cooled and treated with methanol (~1 mL). The product was preabsorbed on silica gel and eluted with 20% ethyl acetate in hexane, to give the product as a colorless solid, 0.288 g (71%). MS: m/z 365 (MH$^+$). $^1$H NMR (DMSO-d$_6$): δ 1.31 (m, 9 H), 7.16 (d, 1 H), 7.50 (d, 2 H), 7.59-7.69 (m, 4 H), 7.75 (t, 1 H), 7.95 (d, 1 H), 8.05 (d, 1 H), 8.94 (s, 1 H), and 9.97 (s, 1 H).

The following compounds were prepared according to the method of Example 81:

| Example # | Compound name | M Wt | MH$^+$ |
|---|---|---|---|
| (82) | 3-(4-tert-Butyl-phenyl)-N-(4-chloro-quinolin-3-yl)-acrylamide | 364.87 | 365.00 |
| (83) | 3-(4-Cyano-phenyl)-N-quinolin-3-yl-acrylamide | 299.33 | 300.10 |
| (84) | 3-(4-tert-Butyl-phenyl)-N-(2-chloro-quinolin-3-yl)-acrylamide | 364.87 | 365.10 |
| (85) | N-(2-Chloro-quinolin-3-yl)-3-[4-(1,1-dimethyl-propyl)-phenyl]-acrylamide | 378.90 | 379.00 |
| (86) | N-(4-Chloro-quinolin-3-yl)-3-[4-(1,1-dimethyl-propyl)-phenyl]-acrylamide | 378.90 | 379.20 |
| (87) | 3-[4-(1,1-Dimethyl-propyl)-phenyl]-N-quinolin-3-yl-acrylamide | 344.46 | 345.00 |
| (87a) | 4-tert-Butyl-N-(4-hydroxy-quinolin-3-yl)-benzamide | 320.39 | 321 |
| (87b) | 3-(4-tert-Butyl-phenyl)-N-(4-hydroxy-quinolin-3-yl)-acrylamide | 346.43 | 347 |
| (87c) | N-Quinolin-3-yl-3-(5,5,8,8-tetramethyl-5,6,7,8-tetrahydro-naphthalen-2-yl)-acrylamide | 384.53 | 385 |
| (87d) | N-(4-Chloro-quinolin-3-yl)-3-(5,5,8,8-tetramethyl-5,6,7,8-tetrahydro-naphthalen-2-yl)-acrylamide | 418.97 | 419 |
| (87e) | N-(4-Chloro-quinolin-3-yl)-4-(cyclohexyl-methyl-amino)-benzamide | 393.92 | 394 |
| (87f) | N-(2-Chloro-quinolin-3-yl)-4-(cyclohexyl-methyl-amino)-benzamide | 393.92 | 394 |
| (87g) | 4-tert-Butyl-N-(2-methoxy-quinolin-3-yl)-benzamide | 334.31 | 335 |
| (87h) | 4-Azepan-1-yl-N-(4-chloro-quinolin-3-yl)-benzamide | 379.89 | 380 |
| (87i) | 4-Azepan-1-yl-N-(2-chloro-quinolin-3-yl)-benzamide | 379.89 | 380 |
| (87j) | 4-(3-Aza-bicyclo[3.2.2]non-3-yl)-N-(2-chloro-quinolin-3-yl)-benzamide | 405.93 | 406 |
| (87k) | 4-(3-Aza-bicyclo[3.2.2]non-3-yl)-N-(4-chloro-quinolin-3-yl)-benzamide | 405.93 | 406 |

Example (88)

4-Phenethylamino-N-quinolin-3-yl-benzamide

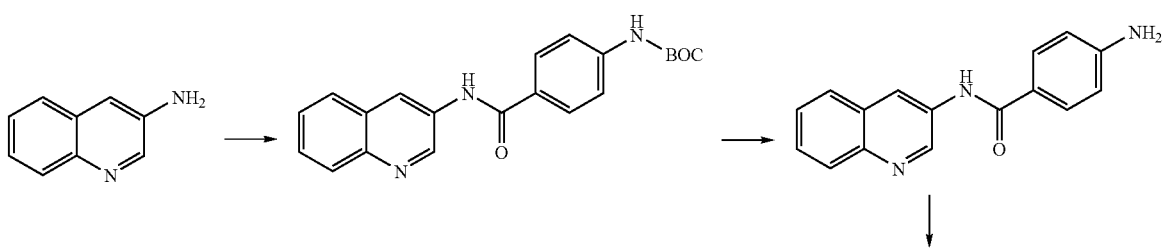

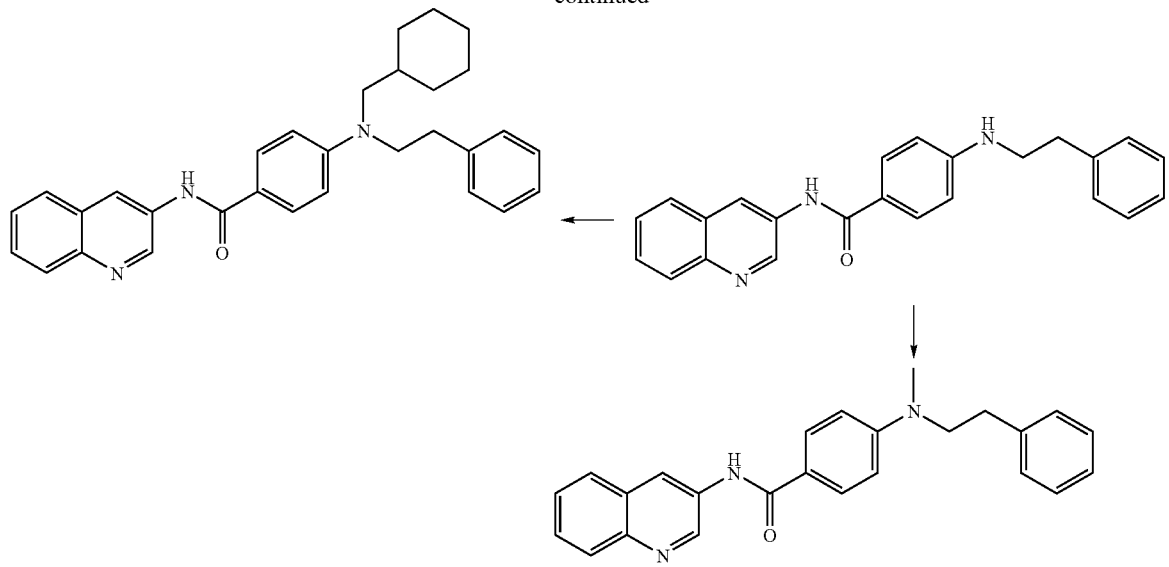

{4-(Quinolin-3-ylcarbamoyl)-phenyl}-carbamic acid tert-butyl ester. N,N-diisopropylethyl amine (12.1 mL, 69.4 mmol) was added to a solution of 4-tert-butoxycarbony-lamino-benzoic acid (9.05 g, 38.1 mmol), quinolin-3-ylamine (5.0 g, 34.7 mmol) and O-benzotriazol-1-yl-N,N,N', N'-tetramethyluronium hexafluorophospate (HBTU) (14.5 g, 38.1 mmol) in acetonitrile (200 mL) and was stirred at ambient temperature for ten minutes. The solution was heated at reflux for approximately 18 hours. Upon cooling to room temperature, the product crystallized and was collected by filtration, to give a colorless solid, 7.9 g (63%). MS: m/z 364 (MH$^+$). $^1$H NMR (DMSO-d$_6$): δ 1.51 (s, 9 H), 7.57-7.70 (m, 4 H), 7.75-8.00 (m, 4 H), 8.83 (d, J=2 Hz, 1 H), 9.15 (d, J=2 Hz, 1 H), 9.75 (br s, 1 H) and 10.54 (br s, 1 H).

4-Amino-N-quinolin-3-yl-benzamide. A solution of [4-(quinolin-3-ylcarbamoyl)-phenyl]-carbamic acid tert-butyl ester (7.2 g, 19.8 mmol) in dichloromethane (70 mL), trifluoroacetic acid (70 mL) and water (7 mL) was stirred at ambient temperature for approximately 18 hours. The solvent was evaporated in vacuo, and the resultant residue was triturated in water (100 mL) and saturated aqueous sodium bicarbonate (100 mL). The product was collected by filtration, washed with water and dried in vacuo, to give a colorless solid, 4.36 g (84%). MS: m/z 264 (MH$^+$). $^1$H NMR (DMSO-d$_6$): δ 5.87 (br s, 2 H), 6.64 (d, 2 H), 7.55-7.67 (m, 2 H), 7.81 (d, 2 H), 7.94 (t, 2 H), 8.81 (d, J=2 Hz, 1 H), 9.14 (d, J=2 Hz, 1 H) and 10.22 (br s, 1 H).

4-Phenethylamino-N-quinolin-3-yl-benzamide. A solution of 4-amino-N-quinolin-3-yl-benzamide (1.0 g, 3.8 mmol), phenylacetaldehyde (0.49 mL, 4.18 mmol), tetramethylammonium triacetoxyborohydride (2.0 g, 7.60 mmol) and acetic acid (a catalytic amount) in 1,2-dichloroethane (40 mL) was heated at reflux for approximately 18 hours. The resultant solution was cooled to room temperature and washed with a saturated solution of aqueous sodium bicarbonate. The solution was applied to a flash silica gel column, and the product was eluted with ethyl acetate (40% to 75%) in hexane to give the product, 0.67 g (48%), as a colorless solid. MS: m/z 368 (MH$^+$). $^1$H NMR (DMSO-d$_6$): δ 2.88 (t, 2 H), 3.35 (t, 2 H), 6.51 (br t, 1 H), 6.7 (d, 2 H), 7.20-7.27 (m, 1 H), 7.30-7.33 (m, 4 H), 7.55-7.67 (m, 2 H), 7.87 (d, 2 H), 7.95 (m, 2 H), 8.82 (d, J=2 Hz, 1 H), 9.15 (d, J=2 Hz, 1H) and 10.25 (s, 1 H).

Example (89)

4-(Methyl-phenethyl-amino)-N-quinolin-3-yl-benzamide

A mixture of 4-phenethylamino-N-quinolin-3-yl-benzamide (0.213 g, 0.57 mmol), paraformaldehyde (0.17 g, 5.8 mmol) and tetramethylammonium triacetoxyborohydride (0.37 g, 1.42 mmol) in 1,2-dichloroethane (~10 mL) was heated at reflux for 6 hours. The resultant solution was washed with saturated aqueous sodium bicarbonate and applied to a flash silica gel column. The product was eluted with ethyl acetate (40%) in hexanes to give the product, 0.2 g (92%). MS: m/z 382 (MH$^+$). $^1$H NMR (DMSO-d$_6$): δ 2.90 (t, 2 H), 2.93 (s, 3 H), 3.66 (t, 2 H), 6.73 (d, 2 H), 7.21-7.35 (m, 5 H), 7.53 (d of t, 1 H), 7.63 (d of t, 1 H), 7.80-7.87 (m, 3 H), 8.05 (m, 1 H), 8.85 (d, 1H) and 8.91 (d, 1 H).

Example (90)

4-(Cyclohexylmethyl-phenethyl-amino)-N-quinolin-3-yl-benzamide

A solution of 4-phenethylamino-N-quinolin-3-yl-benzamide (73 mg, 0.199 mmol) cyclohexane carboxaldehyde (0.072 mL, 0.596 mmol), tetramethylammonium triacetoxyborohydride (78 mg, 0.299 mmol) and catalytic acetic acid in 1,2-dichloroethane was heated at reflux 1 day. Cyclohexane carboxaldehyde (0.15 mL) and tetramethylammonium triacetoxyborohydride (0.25 g) was added, and the solution was refluxed an additional 2 days. The reaction was cooled and washed with a saturated solution of aqueous sodium bicarbonate. The solution was applied to a flash silica gel column and the product was eluted with ethyl acetate in hexane. The product was further purified by preparative reverse phase (C$_{18}$) chromatography and eluted with a gradient of acetonitrile in water with 0.1% trifluoroacetic acid, to give the product as the trifluoroacetate salt, a colorless solid, 0.040 g (29%). MS: m/z 464 (MH$^+$). $^1$H NMR (DMSO-d$_6$): δ 0.91-1.05 (m, 2 H), 1.07-1.19 (m, 3 H), 1.57-1.73 (m, 6 H), 2.83 (t, 2 H), 3.15 (d, 2 H), 3.62 (t, 2 H), 6.84 (d, 2 H), 7.21-7.35 (m, 5 H), 7.62-7.74 (m, 2 H), 7.93 (d, 2 H), 8.01 (d, 2 H), 8.94 (d, 1 H), 9.26 (d, 1 H) and 10.41 (s, 1 H).

The following compounds were prepared according to the methods of the Examples 88-90:

| Example # | Compound name | M Wt | MH$^+$ |
|---|---|---|---|
| (91) | 4-Dipropylamino-N-quinolin-3-yl-benzamide | 347.46 | 348 |
| (92) | 4-Dibutylamino-N-quinolin-3-yl-benzamide | 375.51 | 376 |
| (93) | 4-Benzylamino-N-quinolin-3-yl-benzamide | 353.42 | 354 |
| (94) | 4-Dibenzylamino-N-quinolin-3-yl-benzamide | 443.55 | 444 |
| (95) | 4-Amino-N-quinolin-3-yl-benzamide | 263.30 | 264 |
| (96) | 4-Pentylamino-N-quinolin-3-yl-benzamide | 333.43 | 334 |
| (97) | 4-Dipentylamino-N-quinolin-3-yl-benzamide | 403.57 | 404 |
| (98) | 4-Propylamino-N-quinolin-3-yl-benzamide | 305.38 | 306 |
| (99) | 4-Cyclohexylamino-N-quinolin-3-yl-benzamide | 345.44 | 346 |
| (100) | 4-Dihexylamino-N-quinolin-3-yl-benzamide | 431.62 | 432 |
| (101) | 4-(Benzyl-pentyl-amino)-N-quinolin-3-yl-benzamide | 423.56 | 424 |
| (102) | 4-(Cyclohexyl-methyl-amino)-N-quinolin-3-yl-benzamide | 359.47 | 360.3 |
| (103) | 4-(Cyclopentyl-methyl-amino)-N-quinolin-3-yl-benzamide | 345.44 | 346 |
| (104) | 4-Cycloheptylamino-N-quinolin-3-yl-benzamide | 359.47 | 360 |
| (105) | 4-(Cycloheptyl-methyl-amino)-N-quinolin-3-yl-benzamide | 373.50 | 374 |
| (106) | 4-Phenethylamino-N-quinolin-3-yl-benzamide | 367.45 | 368 |
| (107) | 4-Cyclopentylamino-N-quinolin-3-yl-benzamide | 331.42 | 332 |
| (108) | 4-(Cyclohexyl-propyl-amino)-N-quinolin-3-yl-benzamide | 387.52 | 388 |
| (109) | 4-(Phenethyl-propyl-amino)-N-quinolin-3-yl-benzamide | 409.53 | 410 |
| (110) | 4-(Cyclohexylmethyl-phenethyl-amino)-N-quinolin-3-yl-benzamide | 463.62 | 464 |
| (111) | 4-Amino-3-methyl-N-quinolin-3-yl-benzamide | 277.33 | 278 |
| (112) | 3-Methyl-4-pentylamino-N-quinolin-3-yl-benzamide | 347.46 | 348 |
| (113) | 3-Methyl-4-(methyl-pentyl-amino)-N-quinolin-3-yl-benzamide | 361.49 | 362 |
| (114) | 3-Methyl-4-propylamino-N-quinolin-3-yl-benzamide | 319.41 | 320 |
| (115) | 3-Methyl-4-(methyl-propyl-amino)-N-quinolin-3-yl-benzamide | 333.43 | 334 |
| (116) | N-Quinolin-3-yl-4-(tetrahydro-pyran-4-ylamino)-benzamide | 347.42 | 348 |
| (117) | 4-[Methyl-(tetrahydro-pyran-4-yl)-amino]-N-quinolin-3-yl-benzamide | 361.44 | 362 |
| (118) | 4-Amino-2-chloro-N-quinolin-3-yl-benzamide | 297.74 | 298 |
| (119) | 2-Chloro-4-cyclohexylamino-N-quinolin-3-yl-benzamide | 379.89 | 380 |
| (120) | 4-(Cyclohexyl-ethyl-amino)-N-quinolin-3-yl-benzamide | 373.50 | 374 |
| (121) | 2-Chloro-4-pentylamino-N-quinolin-3-yl-benzamide | 367.88 | 368 |
| (122) | 2-Chloro-4-(cyclohexylmethyl-amino)-N-quinolin-3-yl-benzamide | 393.92 | 394 |
| (123) | 2-Chloro-4-isopropylamino-N-quinolin-3-yl-benzamide | 339.82 | 340 |
| (124) | 4-(Cyclohexylmethyl-amino)-3-methyl-N-quinolin-3-yl-benzamide | 373.50 | 374 |
| (125) | 2-Chloro-4-(cyclohexyl-methyl-amino)-N-quinolin-3-yl-benzamide | 393.92 | 394 |
| (126) | 2-Chloro-4-propylamino-N-quinolin-3-yl-benzamide | 339.82 | 340 |
| (127) | 4-(Cyclohexylmethyl-methyl-amino)-3-methyl-N-quinolin-3-yl-benzamide | 387.52 | 388 |
| (128) | 4-(Cyclohexyl-methyl-amino)-3-methyl-N-quinolin-3-yl-benzamide | 373.50 | 374 |
| (129) | 2-Chloro-4-(methyl-propyl-amino)-N-quinolin-3-yl-benzamide | 353.85 | 354 |
| (130) | 2-Chloro-4-(methyl-pentyl-amino)-N-quinolin-3-yl-benzamide | 381.91 | 382 |
| (131) | 2-Chloro-4-(cyclohexylmethyl-methyl-amino)-N-quinolin-3-yl-benzamide | 407.94 | 408 |
| (132) | 2-Chloro-4-(isopropyl-methyl-amino)-N-quinolin-3-yl-benzamide | 353.85 | 354 |
| (133) | 3-(Methyl-pentyl-amino)-N-quinolin-3-yl-benzamide | 347.46 | 348 |
| (134) | 3-Heptylamino-N-quinolin-3-yl-benzamide | 361.49 | 362 |
| (135) | 3-Cyclohexylamino-N-quinolin-3-yl-benzamide | 345.44 | 346 |
| (136) | 3-Propylamino-N-quinolin-3-yl-benzamide | 305.38 | 306 |
| (137) | 3-Dipropylamino-N-quinolin-3-yl-benzamide | 347.46 | 348 |
| (138) | 3-Amino-N-quinolin-3-yl-benzamide | 263.30 | 264 |
| (139) | 3-Pentylamino-N-quinolin-3-yl-benzamide | 333.43 | 334 |
| (140) | 3-Dipentylamino-N-quinolin-3-yl-benzamide | 403.57 | 404 |
| (141) | 3-(Methyl-propyl-amino)-N-quinolin-3-yl-benzamide | 319.41 | 320 |
| (142) | 3-(Heptyl-methyl-amino)-N-quinolin-3-yl-benzamide | 375.51 | 376 |
| (143) | 3-(Cyclohexyl-methyl-amino)-N-quinolin-3-yl-benzamide | 359.47 | 360 |
| (144) | 2-(Heptyl-methyl-amino)-N-quinolin-3-yl-benzamide | 375.51 | 376 |
| (145) | 2-Pentylamino-N-quinolin-3-yl-benzamide | 333.43 | 334 |
| (146) | 2-Heptylamino-N-quinolin-3-yl-benzamide | 361.49 | 362 |
| (147) | 2-Amino-N-quinolin-3-yl-benzamide | 263.30 | 264 |
| (148) | 2-(Methyl-pentyl-amino)-N-quinolin-3-yl-benzamide | 347.46 | 348 |
| (149) | 4-Amino-N-methyl-N-quinolin-3-yl-benzamide | 277.33 | 278 |
| (150) | 4-Cyclohexylamino-N-methyl-N-quinolin-3-yl-benzamide | 359.47 | 360 |
| (151) | 4-(Cyclohexyl-methyl-amino)-N-methyl-N-quinolin-3-yl-benzamide | 373.50 | 374 |

Example (152)

4-Methylamino-N-quinolin-3-yl-benzamide

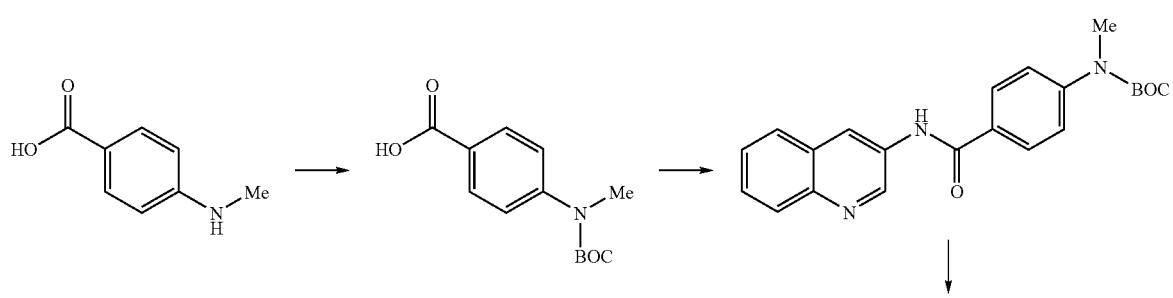

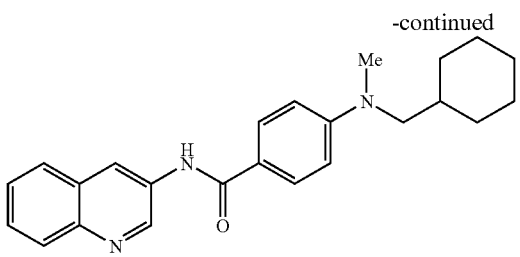 ← 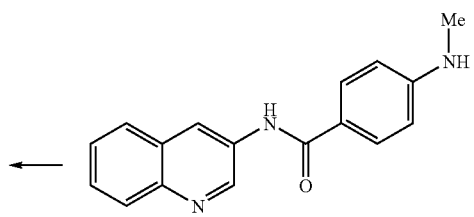

4-(tert-Butoxycarbonyl-methyl-amino)-benzoic acid. A solution of di-tert-butyl dicarbonate (8.0 g, 36.7 mmol) in dioxane (15 mL) was added, via an addition funnel, to a solution of 4-methylamino-benzoic acid (5.0 g, 33.1 mmol) in 1N aqueous sodium hydroxide (35 mL, 35 mmol) and stirred at ambient temperature for 6 hours. Di-tert-butyl dicarbonate (2.7 g, 12.4 mmol) was added and stirring was continued an additional 18 hours. Di-tert-butyl dicarbonate (1.5 g, 6.8 mmol) was added and stirring was continued an additional day. The solution was diluted with water (100 mL) and cooled on an ice bath. The solution was neutralized with 1 N hydrochloric acid, and the resultant precipitate was collected by filtration, washed with water and dried on the filter funnel, to give the product as a colorless solid, 7.25 g (87%). $^1$H NMR (DMSO-$d_6$): δ 1.42 (s, 9 H), 3.23 (s, 3 H), 7.42 (d, 2 H), 7.90 (d, 2 H) and 12.86 (br s, 1 H).

Methyl-[4-(quinolin-3-ylcarbamoyl)-phenyl]-carbamic acid tert-butyl ester. A solution of 4-(tert-butoxycarbonyl-methyl-amino)-benzoic acid (3.36 g, 13.4 mmol), O-benzotriazol-1-yl-N,N,N',N'-tetramethyluronium hexafluorophospate (HBTU) (5.22 g, 13.8 mmol) and N,N-diisopropylethyl (4.8 mL, 27.5 mmol) in acetonitrile (200 mL) was stirred at ambient temperature for ten minutes. Quinolin-3-ylamine (1.93 g, 13.4 mmol) was added, and the solution was heated at reflux for 20 hours. The solvent was evaporated in vacuo, and the residue was partitioned between 1 N aqueous sodium hydroxide and dichloromethane. The product was purified by flash silica gel chromatography, using 67% ethyl acetate in hexane as the eluant to give the product as a colorless solid, 4 g (80%). MS: m/z 378 (MH$^+$). $^1$H NMR (CDCl$_3$): δ 1.51 (s, 9 H), 3.29 (s, 3 H), 7.33 (d, 2 H), 7.53 (d of d, 1 H), 7.65 (d of d, 1 H), 7.85 (d, 2 H), 8.04 (d, 1 H), 8.70 (br s, 1 H) and 8.86-8.91 (m, 2 H).

4-Methylamino-N-quinolin-3-yl-benzamide. A solution of methyl-[4-(quinolin-3-ylcarbamoyl)-phenyl]-carbamic acid tert-butyl ester (8.5 g, 22.5 mmol) in dichloromethane (100 ml), trifluoroacetic acid (100 mL) and water (10 mL) was stirred at room temperature for 6 hours. The solvent was evaporated in vacuo, and the residue was suspended in 1 N aqueous sodium hydroxide (200 mL). The product was collected by filtration, washed with water and dried in vacuo, to give a colorless solid, 5.4 g (87%). MS: m/z 278 (MH$^+$). $^1$H NMR (DMSO-$d_6$): δ 2.77 (d, 3 H), 6.44 (br d, 1 H), 6.63 (d, 2 H), 7.54-7.67 (m, 2 H), 7.89 (d, 2 H) superimposed on 7.95 (t, 2 H), 8.82 (d, 1 H), 9.16 (d, 1 H) and 10.26 (s, 1 H).

Example (153)

4-(Cyclohexylmethyl-methyl-amino)-N-quinolin-3-yl-benzamide

A solution of 4-methylamino-N-quinolin-3-yl-benzamide (0.075 g, 0.27 mmol), cyclohexylcarboxaldehyde (0.049 mL, 0.405 mmol) and tetramethylammonium triacetoxyborohydride (0.213 g, 0.81 mmol) in 1,2-dichloroethane was heated to 85° C. in a sealed tube for 18 hours. The solution was cooled to room temperature and washed with a solution of ammonium hydroxide in water. The product was preabsorbed on silica gel and purified by flash chromatography, using ethyl acetate/hexane (1/1) as the eluant, to give the product as a colorless solid, 0.051 g (51%). MS: m/z 374 (MH$^+$). $^1$H NMR (DMSO-$d_6$): δ 0.90-1.05 (m, 2 H), 1.10-1.23 (m, 3 H), 1.58-1.77 (m, 6 H), 3.02 (s, 3 H), 3.27 (d, 2 H), 6.77 (d, 2 H), 7.54-7.67 (m, 2 H), 7.91 (d, 2 H) superimposed on 7.95 (t, 2 H), 8.81 (d, 1 H), 9.15 (d, 1 H) and 10.28 (s, 1 H).

The following compounds were prepared according to the methods of Examples 152 and 153:

| Example # | Compound name | M Wt | MH$^+$ |
|---|---|---|---|
| (154) | 4-(Methyl-pentyl-amino)-N-quinolin-3-yl-benzamide | 347.46 | 348 |
| (155) | 4-[Methyl-(3-methyl-butyl)-amino]-N-quinolin-3-yl-benzamide | 347.46 | 348.1 |
| (156) | 4-[Methyl-(3-phenyl-propyl)-amino]-N-quinolin-3-yl-benzamide | 395.50 | 396.1 |
| (157) | 4-(Methyl-propyl-amino)-N-quinolin-3-yl-benzamide | 319.41 | 320 |
| (158) | 4-(Methyl-butyl-amino)-N-quinolin-3-yl-benzamide | 333.43 | 334 |
| (159) | 4-(Methyl-hexyl-amino)-N-quinolin-3-yl-benzamide | 361.49 | 362 |
| (160) | 4-(Methyl-nonyl-amino)-N-quinolin-3-yl-benzamide | 403.57 | 404 |
| (161) | 4-(Methyl-tetradecyl-amino)-N-quinolin-3-yl-benzamide | 473.70 | 474 |
| (153) | 4-(Cyclohexylmethyl-methyl-amino)-N-quinolin-3-yl-benzamide | 373.50 | 374 |
| (162) | 4-(Methyl-phenethyl-amino)-N-quinolin-3-yl-benzamide | 381.48 | 382 |
| (163) | 4-[Methyl-(3-phenyl-allyl)-amino]-N-quinolin-3-yl-benzamide | 393.49 | 394 |
| (164) | 4-{Methyl-[3-(5-methyl-furan-2-yl)-butyl]-amino}-N-quinolin-3-yl-benzamide | 413.52 | 414 |
| (165) | 4-(Heptyl-methyl-amino)-N-quinolin-3-yl-benzamide | 375.51 | 376 |
| (166) | 4-(Octyl-methyl-amino)-N-quinolin-3-yl-benzamide | 389.54 | 390 |
| (167) | 4-[(3,3-Dimethyl-butyl)-methyl-amino]-N-quinolin-3-yl-benzamide | 361.49 | 362 |
| (168) | 4-(Hept-4-enyl-methyl-amino)-N-quinolin-3-yl-benzamide | 373.50 | 374 |
| (169) | 4-(Methyl-non-6-enyl-amino)-N-quinolin-3-yl-benzamide | 401.55 | 402 |
| (170) | 4-(Dec-4-enyl-methyl-amino)-N-quinolin-3-yl-benzamide | 415.58 | 416 |
| (171) | 4-{Methyl-[4-(quinolin-3-ylcarbamoyl)-phenyl]-amino}-but-2-enoic acid ethyl ester | 389.45 | 390 |
| (172) | 4-{Methyl-[4-(quinolin-3-ylcarbamoyl)-phenyl]-amino}-butyric acid ethyl ester | 391.47 | 392 |
| (173) | 4-{Methyl-[4-(quinolin-3-ylcarbamoyl)-phenyl]-amino}-butyric acid | 363.42 | 364 |
| (174) | 4-{Methyl-[4-(quinolin-3-ylcarbamoyl)-phenyl]-amino}-but-2-enoic acid | 361.39 | 362 |

-continued

| Example # | Compound name | M Wt | MH+ |
|---|---|---|---|
| (175) | 4-(Benzyl-methyl-amino)-N-quinolin-3-yl-benzamide | 367.45 | |
| (176) | R-4-[(3,7-Dimethyl-oct-6-enyl)-methyl-amino]-N-quinolin-3-yl-benzamide | 415.58 | 416 |
| (177) | S-4-[(3,7-Dimethyl-oct-6-enyl)-methyl-amino]-N-quinolin-3-yl-benzamide | 415.58 | 416 |

Example (178)

4-(3-Aza-bicyclo[3.3.1]non-3-yl)-N-quinolin-3-yl-benzamide

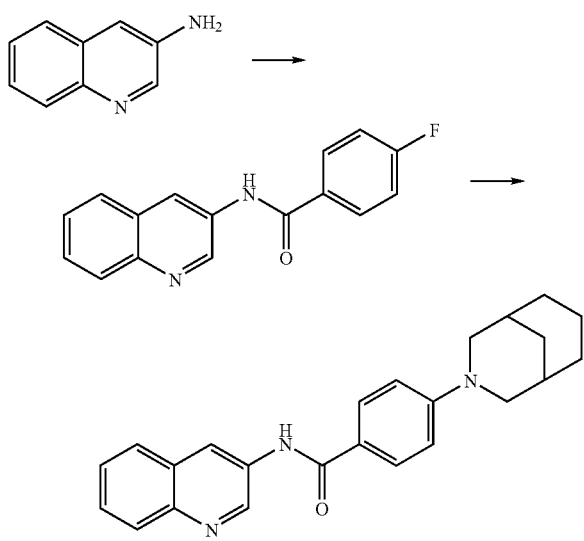

4-Fluoro-N-quinolin-3-yl-benzamide. A solution of 4-fluorobenzoic acid (2.57 g, 18.3 mmol), quinolin-3-ylamine (2.5 g, 17.4 mmol), O-benzotriazol-1-benzotriazol-1-yl-N,N,N',N'-tetramethyluronium hexafluorophospate (HBTU) (7.3 g, 19.3 mmol) and N,N-diisopropylethylamine (6.4 mL, 36.7 mmol) in acetonitrile (75 mL) was stirred at ambient temperature for ten minutes, then heated at reflux for 20 hours. The solution was cooled to 0° C., and the product crystallized. The product was collected by filtration and washed with acetonitrile, to give a colorless solid, 3.86 g (79%). MS: m/z 267 (MH+). $^1$H NMR(DMSO-d$_6$): δ 7.39-7.46 (m, 2 H), 7.58-7.71 (m, 2 H), 7.97-8.01 (m, 2 H), 8.11-8.16 (m, 2 H), 8.85 (d, 1 H), 9.15 (d, 1 H) and 10.73 (s, 1 H).

4-(3-Aza-bicyclo[3.3.1]non-3-yl)-N-quinolin-3-yl-benzamide. A solution of 4-fluoro-N-quinolin-3-yl-benzamide (0.080 g, 0.299 mmol), 3-aza-bicyclo[3.3.1]nonane (0.200 g, 1.60 mmol) and N,N-diisopropylethylamine (0.10 mL, 0.57 mmol) in dimethyl sulfoxide (2 mL) was heated to 100° C. for 11 days. The DMSO solution was applied to a preparative reverse phase C$_{18}$ column, and the product was eluted with a gradient of acetonitrile in water with 0.1% trifluoroacetic acid, to give the product as a trifluoroacetate salt, a yellow solid, 0.065 g (36%). MS: m/z 372 (MH+). $^1$H NMR (DMSO-d$_6$): δ 1.40-1.50 (m, 1 H), 1.58-1.93 (m, 7 H), 2.05 (br s, 2 H), 3.04-3.08 (m, 2 H), 3.85 (d, 2 H), 7.00 (d, 2 H), 7.62-7.76 (m, 2 H), 7.96 (d, 2 H), 8.02 (d, 2 H), 8.95 (d, 1 H), 9.28 (d, 1 H) and 10.45 (s, 1 H).

The following compounds were prepared according to the method of Example 178:

| Example # | Compound name | M Wt | MH+ |
|---|---|---|---|
| (179) | 4-Pyrrolidin-1-yl-N-quinolin-3-yl-benzamide | 317.38 | 318 |
| (180) | 4-(4-Benzyl-piperidin-1-yl)-N-quinolin-3-yl-benzamide | 421.53 | 422.1 |
| (181) | 4-(3,5-Dimethyl-piperidin-1-yl)-N-quinolin-3-yl-benzamide | 359.46 | 360.1 |
| (182) | 4-Piperidin-1-yl-N-quinolin-3-yl-benzamide | 331.41 | 332 |
| (183) | 4-[1,4']Bipiperidinyl-1'-yl-N-quinolin-3-yl-benzamide | 414.54 | 415 |
| (184) | 4-(3-Methyl-piperidin-1-yl)-N-quinolin-3-yl-benzamide | 345.44 | 346 |
| (185) | 4-(4-Phenyl-piperidin-1-yl)-N-quinolin-3-yl-benzamide | 407.51 | 408 |
| (186) | 1-[4-(Quinolin-3-ylcarbamoyl)-phenyl]-piperidine-3-carboxylic acid diethylamide | 430.54 | 431 |
| (187) | 4-(1,4-Dioxa-8-aza-spiro[4.5]dec-8-yl)-N-quinolin-3-yl-benzamide | 389.45 | 390 |
| (188) | 1-[4-(Quinolin-3-ylcarbamoyl)-phenyl]-piperidine-2-carboxylic acid | 375.42 | 376 |
| (189) | 4-(4-Oxo-piperidin-1-yl)-N-quinolin-3-yl-benzamide | 345.4 | 346 |
| (178) | 4-(3-Aza-bicyclo[3.3.1]non-3-yl)-N-quinolin-3-yl-benzamide | 371.47 | 372 |
| (190) | cis-4-(Octahydro-isoquinolin-2-yl)-N-quinolin-3-yl-benzamide | 385.5 | 386.1 |
| (191) | 4-(4-Benzoyl-piperidin-1-yl)-N-quinolin-3-yl-benzamide | 435.52 | 436 |
| (192) | 4-(4-Propyl-piperidin-1-yl)-N-quinolin-3-yl-benzamide | 373.49 | 374 |
| (193) | trans-4-(Octahydro-isoquinolin-2-yl)-N-quinolin-3-yl-benzamide | 385.5 | 386 |
| (194) | 4-Azonan-1-yl-N-quinolin-3-yl-benzamide | 373.49 | 374 |
| (195) | 4-Azepan-1-yl-N-quinolin-3-yl-benzamide | 345.44 | 346 |
| (196) | 4-Azepan-1-yl-N-quinolin-3-yl-benzamide | 371.47 | 372 |
| (197) | 4-Azocan-1-yl-N-quinolin-3-yl-benzamide | 359.46 | 360.1 |
| (198) | 4-Morpholin-4-yl-N-quinolin-3-yl-benzamide | 333.39 | 334 |
| (199) | 4-(1,3-Dihydro-isoindol-2-yl)-N-quinolin-3-yl-benzamide | 365.43 | 366 |
| (200) | N-Quinolin-3-yl-4-thiomorpholin-4-yl-benzamide | 349.46 | 350 |
| (201) | 4-(2,6-Dimethyl-morpholin-4-yl)-N-quinolin-3-yl-benzamide | 361.44 | 362 |
| (202) | 4-(3,4-Dihydro-1H-isoquinolin-2-yl)-N-quinolin-3-yl-benzamide | 379.46 | 380 |
| (203) | 4-(4-Benzhydryl-piperazin-1-yl)-N-quinolin-3-yl-benzamide | 498.63 | 499 |
| (204) | 4-Piperazin-1-yl-N-quinolin-3-yl-benzamide | 332.41 | 333 |
| (205) | 4-(4-Benzyl-piperazin-1-yl)-N-quinolin-3-yl-benzamide | 422.53 | 423 |
| (206) | 4-(4-Phenyl-piperazin-1-yl)-N-quinolin-3-yl-benzamide | 408.50 | 409 |
| (207) | 4-(4-Methyl-piperazin-1-yl)-N-quinolin-3-yl-benzamide | 346.43 | 347 |

Example (208)

6-Azocan-1-yl-N-quinolin-3-yl-nicotinamide

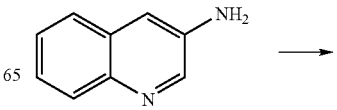

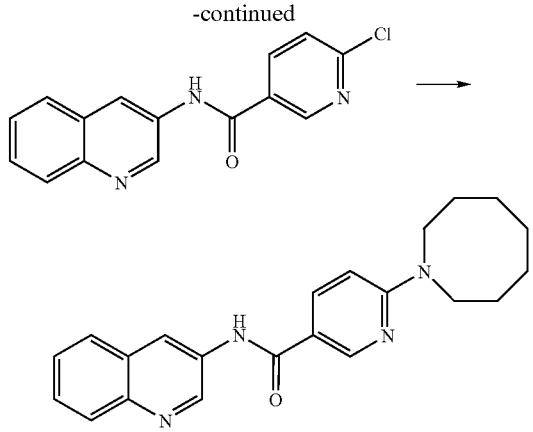

6-Chloro-N-quinolin-3-yl-nicotinamide. A solution of 6-chloro-nicotinic acid (2.95 g, 18.7 mmol), O-benzotriazol-1-yl-N,N,N',N'-tetramethyluronium hexafluorophospate (HBTU) (7.09 g, 18.7 mmol), quinolin-3-ylamine (2.7 g, 18.7 mmol), and N,N-diisopropylethylamine (8.2 mL, 46.7 mmol) in acetonitrile was heated at reflux. The resultant mixture was cooled, and the crystalline product was collected by filtration, to give a colorless solid, 3.1 g (58%). MS: m/z 284 (MH$^+$). $^1$H NMR (DMSO-d$_6$): δ 7.61 (t, 1 H), 7.70 (d of t, 1 H), 7.77, (d, 1 H), 8.00 (d, 2 H), 8.43 (d of d, 1 H), 8.85 (d, 1 H), 9.05 (d, 1 H), 9.14 (d, 1 H) and 10.95 (s, 1 H).

6-Azocan-1-yl-N-quinolin-3-yl-nicotinamide. A solution of 6-chloro-N-quinolin-3-yl-nicotinamide (0.10 g, 0.35 mmol) and heptamethyleneimine (0.40 mL, 3.17 mmol) in dimethyl sulfoxide (1 mL) was heated to 82° C. for 5 hours. The resultant solution was poured into water, and the product was extracted with dichloromethane. The organic solution was washed several times with water, and applied to a flash silica gel column. The product was eluted with an ethyl acetate/hexane mixture (1/1), to give the product as a colorless solid, 92 mg (72%). MS: m/z 361 (MH$^+$). $^1$H NMR (DMSO-d$_6$): δ 1.38-1.57 (m, 6 H), 1.69-1.78 (m, 4 H), 3.69 (br s, 4 H), 6.71 (d, 1 H), 7.56-7.68 (m, 2 H), 7.96 (t, 2 H), 8.09 (d of d, 1 H), 8.81 (s, 2 H), 9.13 (d, 1 H) and 10.39 (s, 1 H).

The following compounds were prepared according to the method of Example 208:

| Example # | Compound name | M Wt | MH$^+$ |
|---|---|---|---|
| (209) | 3,4,5,6-Tetrahydro-2H-[1,2']bipyridinyl-5'-carboxylic acid quinolin-3-ylamide | 332.41 | 333 |
| (210) | 6-Pentylamino-N-quinolin-3-yl-nicotinamide | 334.42 | 335 |
| (211) | 6-(Methyl-pentyl-amino)-N-quinolin-3-yl-nicotinamide | 348.45 | 349 |
| (212) | 6-Azepan-1-yl-N-quinolin-3-yl-nicotinamide | 346.43 | 347 |
| (213) | 6-Cyclohexylamino-N-quinolin-3-yl-nicotinamide | 346.43 | 347 |
| (214) | 6-(Cyclohexyl-methyl-amino)-N-quinolin-3-yl-nicotinamide | 360.45 | 361 |
| (215) | 6-(3-Aza-bicyclo[3.3.1]non-3-yl)-N-quinolin-3-yl-nicotinamide | 372.47 | 373 |
| (216) | 6-(Heptyl-methyl-amino)-N-quinolin-3-yl-nicotinamide | 376.49 | 377 |
| (208) | 6-Azocan-1-yl-N-quinolin-3-yl-nicotinamide | 360.46 | 361 |
| (217) | 3,4,5,6-Tetrahydro-2H-[1,2']bipyridinyl-5'-carboxylic acid quinolin-3-ylamide | 372.46 | 373 |
| (218) | 6-(Methyl-phenethyl-amino)-N-quinolin-3-yl-nicotinamide | 382.47 | 383 |
| (219) | 4-Propyl-3,4,5,6-tetrahydro-2H-[1,2']bipyridinyl-5'-carboxylic acid quinolin-3-ylamide | 374.48 | 375 |
| (220) | 4-Benzyl-3,4,5,6-tetrahydro-2H-[1,2']bipyridinyl-5'-carboxylic acid quinolin-3-ylamide | 422.53 | 423 |
| (221) | 6-(Benzyl-methyl-amino)-N-quinolin-3-yl-nicotinamide | 368.43 | 369 |
| (222) | cis-6-(Octahydro-isoquinolin-2-yl)-N-quinolin-3-yl-nicotinamide | 386.50 | 387 |
| (223) | trans-6-(Octahydro-isoquinolin-2-yl)-N-quinolin-3-yl-nicotinamide | 386.50 | 387 |

Example (224)

1-Cyclohexyl-2,3-dihydro-1H-indole-5-carboxylic acid (4-chloro-quinolin-3-yl)-amide

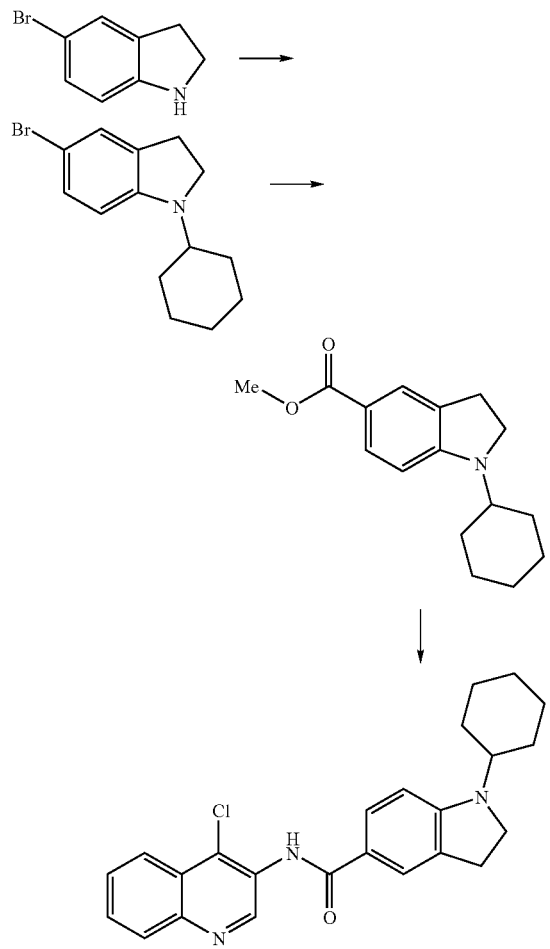

5-Bromo-1-cyclohexyl-2,3-dihydro-1H-indole. A solution of 5-bromo-2,3-dihydro-1H-indole (94.0 g, 20.2 mmol), cyclohexanone (4.6 mL, 44.4 mmol) and sodium cyanoborohydride (1.6 g, 25.5 mmol) in methanol (100 mL) was heated at reflux for 16 hours. More cyclohexanone (2.3 mL, 22.2 mmol) and sodium cyanoborohydride (1.6 g, 25.5 mmol) were added. Heating was continued for 1 day. The solvent was evaporated in vacuo, and the residue was treated with ammonium hydroxide in water. The product was extracted into dichloromethane, and dried over sodium sulfate. The solvent was evaporated in vacuo, and the product was purified by flash silica gel chromatography, eluted with ethyl acetate (1% to 2%) in hexane to give an oil, 7.49 g (37%). MS: m/z 280 (MH+). $^1$H NMR (CDCl$_3$): δ 1.08-1.20 (m, 1 H), 1.25-1.42 (m, 4 H), 1.64-1.74 (m, 1 H), 1.76-1.88 (m, 4 H), 2.91 (t, 2 H), 3.24-3.32 (m, 1 H), 3.36 (t, 2 H), 6.23 (d, 1 H) and 7.08-7.11 (m, 2 H).

1-Cyclohexyl-2,3-dihydro-1H-indole-5-carboxylic acid methyl ester. In a steel pressure reactor, pressurized with carbon monoxide (250 psi), a solution of 5-bromo-1-cyclohexyl-2,3-dihydro-1H-indole (2.1 g, 7.49 mmol), bis(triphenylphosphine)palladium(II)chloride (0.263 g, 0.375 mmol), triphenylphosphine (0.196 g, 0.749 mmol) and N,N-diisopropylethylamine (2.9 mL, 16.5 mmol) in methanol (40 mL) was heated to 100° C. for 3 days. The reactor was cooled, and the gas was carefully vented. Insoluble material was removed by filtration, and the solvent was evaporated in vacuo. The residue was purified by flash silica gel chromatography, eluted with 5% ethyl acetate in heptane, to give the product, 1.56 g (80%), a colorless oil. $^1$H NMR (CDCl$_3$): δ 1.08-1.20 (m, 1 H), 1.27-1.47 (m, 4 H), 1.68-1.76 (m, 1 H), 1.80-1.89 (m, 4 H), 2.97 (t, 2 H), 3.34-3.45 (m, 1 H), 3.51 (t, 2 H), 3.83 (s, 3 H), 6.29 (d, 1 H), 7.65 (d, 1 H) and 7.78 (d of d, 1 H).

1-Cyclohexyl-2,3-dihydro-1H-indole-5-carboxylic acid (4-chloro-quinolin-3-yl)-amide. Trimethylaluminum (2.0 M in toluene, 0.6 mL, 1.2 mmol) was added to a solution of 1-cyclohexyl-2,3-dihydro-1H-indole-5-carboxylic acid methyl ester (0.14 g, 0.54 mmol) and 4-chloro-quinolin-3-ylamine (0.097 g, 0.543 mmol) in 1,2-dichloroethane. The resultant solution was heated at reflux for 4 hours. Methanol (~1 mL) was added and the product was preabsorbed onto silica gel and purified by flash chromatography, using 30% ethyl acetate in heptane as the eluant. The product was further purified by reverse phase (C$_{18}$) chromatography using a gradient of acetonitrile in water with 0.1% trifluoroacetic acid as the eluant, to give the product as it's trifluoroacetate salt, 0.090 g (32%). MS: m/z 406 (MH+). $^1$H NMR (DMSO-d$_6$): δ 1.07-1.23 (m, 1 H), 1.29-1.49 (m, 4 H), 1.62-1.84 (m, 5 H), 3.51 (t, 2 H), 3.45 (m, 3 H), 6.52 (d, 1 H), 7.72 (s, 1 H), 7.77-7.88 (m, 3 H), 8.11 (d, 1 H), 8.23 (d, 1 H), 9.00 (s, 1 H) and 10.02 (s, 1 H).

Example (225)

3-(1-Cyclohexyl-2,3-dihydro-1H-indol-5-yl)-N-quinolin-3-yl-acrylamide

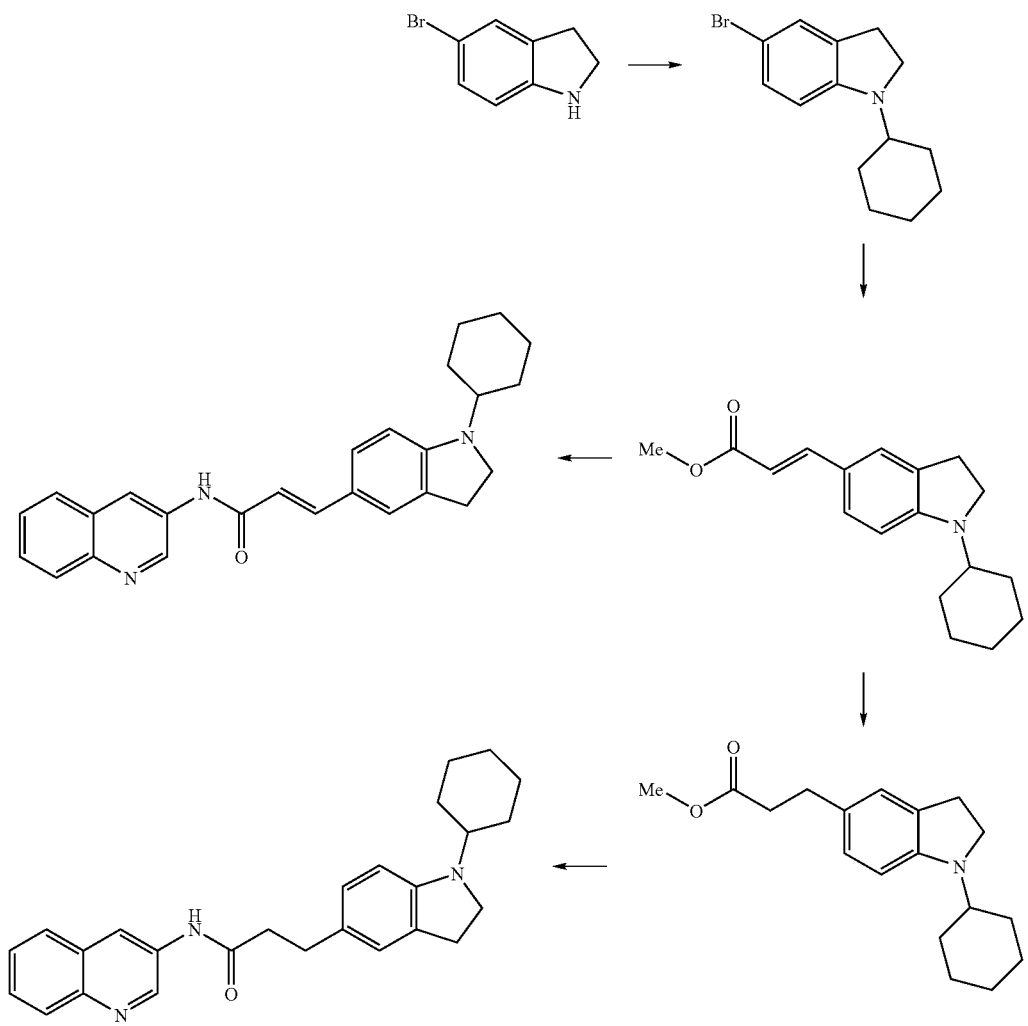

3-(1-Cyclohexyl-2,3-dihydro-1H-indol-5-yl)-acrylic acid methyl ester. In a sealed tube, a solution of 5-bromo-1-cyclohexyl-2,3-dihydro-1H-indole (2.2 g, 7.85 mmol), methyl acrylate (0.848 mL, 9.42 mmol) and palladium(II)acetate in triethylamine (4.7 mL, 33.8 mmol) was heated to 100° C. for 2 hours. The resultant suspension was diluted with methanol and transferred into a round bottom flask. The solvents were evaporated in vacuo, and the residue was partitioned between dichloromethane and saturated aqueous sodium bicarbonate. The product was preabsorbed onto silica gel and purified by flash chromatography, using ethyl acetate (5% to 10%) in heptane as the eluant, to give the product as a yellow solid, 1.86 g (83%). MS: m/z 286 (MH$^+$). $^1$H NMR (CDCl$_3$): δ 1.17-1.22 (m, 1 H), 1.28-1.45 (m, 4 H), 1.64-1.74 (m, 1 H), 1.77-1.99 (m, 4 H), 2.96 (t, 2 H), 3.29-3.44 (m, 1 H), 3.49 (t, 2 H), 3.76 (s, 3 H), 6.14 (d, 1 H), 6.31 (d, 1 H), 7.19 (br d, 1 H), 7.25 (d, 1 H) and 7.59 (d, 1 H).

3-(1-Cyclohexyl-2,3-dihydro-1H-indol-5-yl)-N-quinolin-3-yl-acrylamide A solution of trimethylaluminum (2.0 M in toluene, 1.05 mL, 2.1 mmol) was added to a solution of quinolin-3-ylamine (0.15 g, 1.04 mmol) and 3-(1-cyclohexyl-2,3-dihydro-1H-indol-5-yl)-acrylic acid methyl ester (0.30 g, 1.04 mmol) in 1,2-dichloroethane (10 mL). The resultant solution was heated at reflux for 2 hours. The solution was cooled and treated with methanol (~1 mL). The product was preabsorbed onto silica gel and eluted with ethyl acetate (35% to 50%) in heptane, to give the product as a yellow solid, 0.35 g (85%). MS: m/z 398 (MH$^+$). $^1$H NMR (DMSO-d$_6$): δ 1.03-1.20 (m, 1 H), 1.29-1.47 (m, 4 H), 1.60-1.81 (m, 5 H), 2.50 (t, 2 H), 3.38-3.51 (m, 3 H), 6.47 (d, 1 H), 6.53 (d, 1 H), 7.27 (d, 1 H) superimposed on 7.29 (s, 1 H), 7.51 (d, 1 H), 7.57-7.66 (m, 2 H), 7.92 (d, 1 H), 7.95 (d, 1 H), 8.80 (d, 1 H), 8.97 (d, 1 H) and 10.43 (s, 1H).

Example (226)

3-(1-Cyclohexyl-2,3-dihydro-1H-indol-5-yl)-N-quinolin-3-yl-propionamide 3-(1-Cyclohexyl-2,3-dihydro-1H-indol-5-yl)-propionic acid methyl ester. A solution of 3-(1-cyclohexyl-2,3-dihydro-1H-indol-5-yl)-acrylic acid methyl ester (1.60 g, 5.61 mmol) in methanol (30 mL) with 10% palladium on carbon (0.16 g) was hydrogenated at 55 psi and room temperature for 20 hours. The catalyst was removed by filtration, and the solvent was evaporated in vacuo. The crude product was purified by flash chromatography, using 7.5% ethyl acetate in hexane as the eluant, to give the product, 1.36 g (84%), an oil. MS: m/z 288 (MH$^+$). $^1$H NMR (CDCl$_3$): δ 1.04-1.21 (m, 1 H), 1.26-1.43 (m, 4 H), 1.64-1.73 (m, 1 H), 1.78-1.86 (m, 4 H), 2.82 (t, 2 H), 2.84-2.92 (m, 4 H), 3.29 (m, 1 H) super imposed on 3.34 (t, 2 H), 3.66 (s, 3 H), 6.31 (d, 1 H), 6.85 (d, 1 H) and 6.87 (s, 1 H).

3-(1-Cyclohexyl-2,3-dihydro-1H-indol-5-yl)-N-quinolin-3-yl-propionamide. A solution of trimethylaluminum (2.0 M in toluene, 0.26 mL, 0.52 mmol) was added to a solution of 3-(1-cyclohexyl-2,3-dihydro-1H-indol-5-yl)-propionic acid methyl ester (0.147 g, 0.511 mmol) and quinolin-3-ylamine (0.074 g, 0.511 mmol) in 1,2-dichloroethane (2 mL). The resultant solution was heated to 85° C. in a sealed tube for 2 hours. The cooled solution was treated with several drops of methanol. The product was preabsorbed onto silica gel and purified via flash chromatography, using ethyl acetate/hexane (1/1) as the eluant. The product was dissolved in tetrahydrofuran and treated with ethereal hydrogen chloride. The solvents were evaporated in vacuo to give the product as the hydrochloride salt, 0.110 g (46%), a colorless solid. MS: m/z 400 (MH$^+$). $^1$H NMR (DMSO-d$_6$): δ 1.01-1.47 (m, 5 H), 1.56-1.80 (m, 5 H), 2.79 (t, 2 H), 3.00 (t, 2 H), 3.10 (t, 2 H), 3.62-3.77 (m, 3 H), 7.29-7.32 (m, 3 H), 7.73 (t, 1 H), 7.81 (d of t, 1 H), 8.12 (d, 2 H), 8.99 (d, 1 H), 9.22 (d, 1 H) and 11.09 (s, 1H).

The following compounds were prepared according to the method of Example 226:

| Example # | Compound name | M Wt | MH$^+$ |
|---|---|---|---|
| (227) | 1-Pentyl-2,3-dihydro-1H-indole-5-carboxylic acid quinolin-3-ylamide | 359.47 | 360 |
| (228) | 3-(1-Cyclohexylmethyl-2,3-dihydro-1H-indol-5-yl)-N-quinolin-3-yl-propionamide | 413.55 | 414 |
| (229) | 1-Propyl-2,3-dihydro-1H-indole-5-carboxylic acid quinolin-3-ylamide | 331.41 | 332 |
| (230) | 1-Cyclohexyl-2,3-dihydro-1H-indole-5-carboxylic acid quinolin-3-ylamide | 371.47 | 372 |
| (231) | 1-Methyl-2,3-dihydro-1H-indole-5-carboxylic acid quinolin-3-ylamide | 303.36 | 304 |
| (226) | 3-(1-Cyclohexyl-2,3-dihydro-1H-indol-5-yl)-N-quinolin-3-yl-propionamide | 399.53 | 400 |
| (232) | 3-(1-Propyl-2,3-dihydro-1H-indol-5-yl)-N-quinolin-3-yl-propionamide | 359.47 | 360.1 |
| (233) | 1-Cyclohexyl-2,3-dihydro-1H-indole-5-carboxylic acid (4-chloro-quinolin-3-yl)-amide | 405.93 | 406.2 |
| (234) | 3-(1-Cyclohexyl-2,3-dihydro-1H-indol-5-yl)-N-quinolin-3-yl-acrylamide | 397.51 | 398.3 |
| (234a) | 3-(1-Cyclohexyl-2,3-dihydro-1H-indol-5-yl)-N-quinolin-3-yl-acrylamide | 397.52 | 398 |
| (234b) | 1-Cyclohexyl-2,3-dihydro-1H-indole-5-carboxylic acid (2-chloro-quinolin-3-yl)-amide | 405.93 | 406 |
| (234c) | N-(2-Chloro-quinolin-3-yl)-3-(1-cyclohexyl-2,3-dihydro-1H-indol-5-yl)-acrylamide | 431.97 | 432 |

Example (235)

1-Pentyl-1H-indole-5-carboxylic acid quinolin-3-ylamide

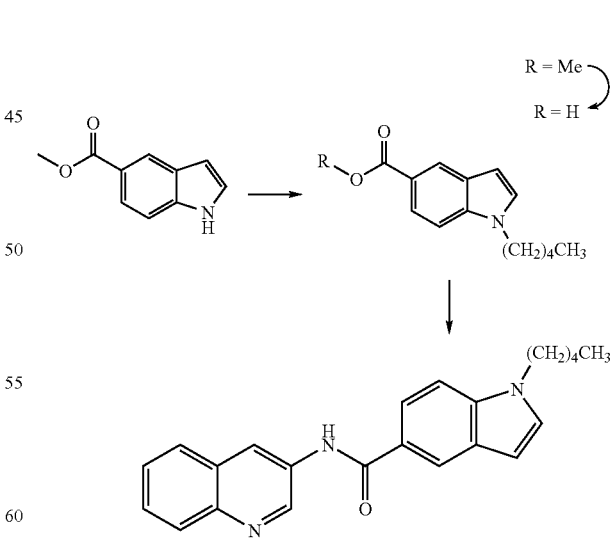

1-Pentyl-1H-indole-5-carboxylic acid methyl ester. Methyl indole-5-carboxylate (0.875 g, 5.0 mmol) was added to a suspension of sodium hydride (60% in oil, 0.22 g, 5.5 mmol) in N,N-dimethylformamide (15 mL) at 0° C. The resultant solution was stirred at room temperature for 30 min.

Bromopentane (0.706 mL, 5.69 mmol) was added to the solution, and stirring was continued for 4 hours. The solution was poured into ice water (100 mL), and the product was extracted into dichloromethane. The organic solution was washed several times with water and dried over sodium sulfate. The solvent was evaporated in vacuo, and the residue was purified by flash silica gel chromatography using 5% ethyl acetate in hexane as the eluant, to give the product, 0.975 g (79%), as an oil. MS: m/z 280 (MH$^+$). $^1$H NMR (CDCl$_3$): δ 0.87 (t, 3 H), 1.22-1.40 (m, 4 H), 1.77-1.87 (m, 2 H), 3.92 (s, 3 H), 4.11 (t, 2 H), 6.58 (d, 1 H), 7.14 (d, 1 H), 7.32 (d, 1 H), 7.90 (d of d, 1 H) and 8.40 (d, 1 H).

1-Pentyl-1H-indole-5-carboxylic acid. Aqueous sodium hydroxide (1N, 3.4 mL, 3.4 mmol) was added to a solution of 1-pentyl-1H-indole-5-carboxylic acid methyl ester (0.79 g, 3.09 mmol) in methanol (30 mL). The resultant solution was heated at reflux for 4 hours. Additional aqueous sodium hydroxide (3.4 mL) was added and heating was continued for 4 hours. The solution was cooled, neutralized with 1N hydrochloric acid. The solvent was evaporated in vacuo. The residue was partitioned between water dichloromethane. The organic solution was dried over sodium sulfate and the solvent was evaporated in vacuo, to give the product, 0.715 g (100%). MS: m/z 232 (MH$^+$). $^1$H NMR (CDCl$_3$): δ 0.88 (t, 3 H), 1.24-1.42 (m, 4 H), 1.80-1.89 (m, 2 H), 4.14 (t, 2 H), 6.61 (d, 1 H), 7.16 (d, 1 H), 7.36 (d, 1 H), 7.99 (d of d, 1 H) and 8.50 (s, 1 H).

1-Pentyl-1H-indole-5-carboxylic acid quinolin-3-ylamide. A solution of 1-pentyl-1H-indole-5-carboxylic acid (0.687, 2.97 mmol), O-benzotriazol-1-yl-N,N,N',N'-tetramethyluronium hexafluorophospate (HBTU) (1.18 g, 3.11 mmol) and N,N-diisopropylethyl (1.14 mL, 6.53 mmol) in acetonitrile (20 mL) was stirred at ambient temperature for 5 minutes. Quinolin-3-ylamine (1.93 g, 13.4 mmol) was added, and the solution was heated at reflux for 18 hours. The solvent was evaporated in vacuo, and the residue was partitioned between dichloromethane and water. The product was preabsorbed onto silica gel and purified by flash chromatography using ethyl acetate in hexane as the eluant, to give the product, 0.40 g (38%). MS: m/z 358 (MH$^+$). $^1$H NMR (DMSO-d$_6$): δ 0.84 (t, 3 H), 1.23-1.34 (m, 4 H), 1.73-1.83 (m, 2 H), 4.24 (t, 2 H), 6.64 (d, 1 H), 7.53 (d, 1 H), 7.56-7.69 (m, 3 H), 7.86 (d, 1 H), 7.98 (t, 2 H), 8.37 (s, 1 H), 8.89 (d, 1 H), 9.21 (d, 1 H) and 10.60 (s, 1 H).

The following compounds were prepared according to the method of Example 235:

| Example # | Compound name | M Wt | MH$^+$ |
|---|---|---|---|
| (235) | 1-Pentyl-1H-indole-5-carboxylic acid quinolin-3-ylamide | 357.46 | 358 |
| (236) | 1-Propyl-1H-indole-5-carboxylic acid (2-chloro-quinolin-3-yl)-amide | 363.85 | 364 |
| (237) | 1-Propyl-1H-indole-5-carboxylic acid (4-chloro-quinolin-3-yl)-amide | 363.85 | 364 |
| (238) | 1-Propyl-1H-indole-5-carboxylic acid quinolin-3-ylamide | 329.40 | 330 |
| (238a) | 3-(1-Cyclohexyl-1H-indol-5-yl)-N-quinolin-3-yl-acrylamide | 395.51 | 396 |
| (238b) | N-(4-Chloro-quinolin-3-yl)-3-(1-cyclohexyl-1H-indol-5-yl)-acrylamide | 429.95 | 430 |
| (238c) | 1-Cyclohexyl-1H-indole-5-carboxylic acid (4-chloro-quinolin-3-yl)-amide | 403.92 | 404 |
| (238d) | 1-Cyclohexyl-1H-indole-5-carboxylic acid quinolin-3-ylamide | 369.47 | 370 |
| (238e) | 1-Cyclohexyl-1H-indole-5-carboxylic acid (2-chloro-quinolin-3-yl)-amide | 403.92 | 404 |
| (238f) | N-(2-Chloro-quinolin-3-yl)-3-(1-cyclohexyl-1H-indol-5-yl)-acrylamide | 429.95 | 430 |

Example (239)

3-(4-Azepan-1-yl-phenyl)-N-quinolin-3-yl-acrylamide

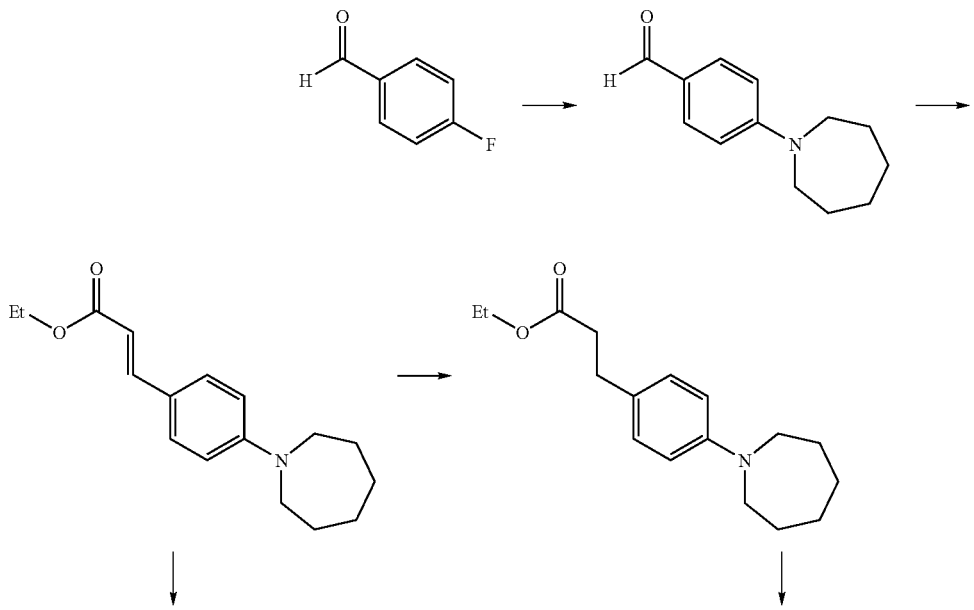

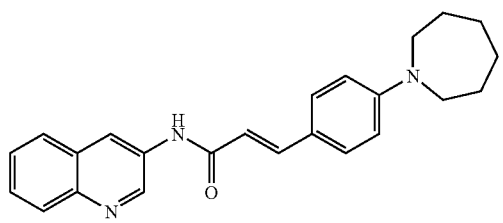

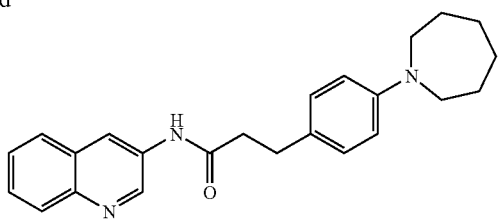

4-Azepan-1-yl-benzaldehyde. A solution of 4-fluoro-benzaldehyde (2.59 mL, 24.2 mmol) and hexamethyleneimine (8.2 mL, 72 mmol) in acetonitrile (40 mL) was heated at reflux for 16 hours. The product was preabsorbed onto silica gel and purified by flash silica gel chromatography, using ethyl acetate (10-15%) in hexane as the eluant, to give the product, 5.0 g (100%). MS: m/z 204 (MH$^+$). $^1$H NMR (CDCl$_3$): δ 1.53-1.59 (m, 4 H), 1.78-1.82 (m, 4 H), 3.53 (t, 4 H), 6.70 (d, 2 H), 7.70 (d, 2 H) and 9.70 (s, 1 H).

3-(4-Azepan-1-yl-phenyl)-acrylic acid ethyl ester. Triethyl phosphonoacetate (2.4 mL, 12.1 mmol) was added to a solution of 4-azepan-1-yl-benzaldehyde (2.05 g, 10.1 mmol), 1,8-diazabicyclo[5.4.0]undec-7-ene (DBU) (1.81 mL, 12.1 mmol) and lithium chloride (0.641 g, 15.1 mmol) in acetonitrile (40 mL) was heated at reflux for 2 hours. Triethyl phosphonoacetate (0.24 mL, 1.2 mmol), 1,8-diazabicyclo[5.4.0]undec-7-ene (DBU) (0.18 mL, 1.2 mmol) and lithium chloride (0.065 g, 1.5 mmol) was added, and the solution was refluxed an additional 18 hours. The solvent was evaporated in vacuo. The product was preabsorbed onto silica gel and purified by flash chromatography, using ethyl acetate (5%) in hexane as the eluant, to give the product, 1.941 g (70%), as a yellow crystalline solid. MS: m/z 274 (MH$^+$). $^1$H NMR (CDCl$_3$): δ 1.32 (t, 3 H), 1.52-1.56 (m, 4 H), 1.78 (m, 4 H), 3.49 (t, 4 H), 4.23 (q, 2 H), 6.19 (d, 1 H), 6.65 (d, 2 H), 7.39 (d, 2 H) and 7.61 (d, 1 H).

3-(4-Azepan-1-yl-phenyl)-N-quinolin-3-yl-acrylamide. A solution of trimethylaluminum (2.0 M in toluene, 0.274 mL, 0.54 mmol) was added to a solution of (3-(4-azepan-1-yl-phenyl)-acrylic acid ethyl ester (0.15 g, 0.55 mmol) and quinolin-3-ylamine (0.072 g, 0.49 mmol) in 1,2-dichloroethane. The solution was sealed in a tube and heated to 80° C. for 6 hours. The solution was cooled, and the product was preabsorbed onto silica gel. The product was eluted with methanol (3%) in dichloromethane. Further purification by reverse phase (C$_{18}$) chromatography, using a gradient of acetonitrile (30-90%) in water with 0.1% trifluoroacetate, gave the product as the bis-trifluoroacetate salt, an orange solid, 0.045 g (14%). MS: m/z 372 (MH$^+$). $^1$H NMR (DMSO-d$_6$): δ 1.46 (m, 4 H), 1.73 (m, 4 H), 3.51 (t, 4 H), 6.58 (d, 1 H), 6.75 (d, 2 H), 7.45 (d, 2 H), 7.54-7.66 (m, 3 H), 7.94 (t, 2 H), 8.81 (d, 1 H), 8.98 (d, 1 H) and 10.48 (s, 1 H).

Example (240)

3-(4-Azepan-1-yl-phenyl)-N-quinolin-3-yl-propionamide 3-(4-Azepan-1-yl-phenyl)-propionic acid ethyl ester. A solution of 3-(4-azepan-1-yl-phenyl)-acrylic acid ethyl ester (1.0 g, 3.65 mmol) in ethanol (20 Ml) was hydrogenated at 55 psi over 10% palladium (0.1 g) for 18 hours. The catalyst was removed by filtration, and the solvent was evaporated in vacuo. The crude product was purified by flash silica gel chromatography, using 5% ethyl acetate in hexane as the eluant, to give the product, 1.0 g (99%), a color less oil. MS: m/z 276 (MH$^+$). $^1$H NMR (CDCl$_3$): δ 1.24 (t, 3 H), 1.48-1.61 (m, 4 H), 1.76 (m, 4 H), 2.56 (t, 2 H), 2.84 (t, 2 H), 3.42 (t, 4 H), 4.13 (q, 2 H), 6.61 (d, 2 H) and 7.03 (d, 2 H).

3-(4-Azepan-1-yl-phenyl)-N-quinolin-3-yl-propionamide. A solution of trimethylaluminum (2.0 M in toluene, 0.50 mL, 1.0 mmol) was added to a solution of 3-(4-Azepan-1-yl-phenyl)-propionic acid ethyl ester (0.20 g, 0.73 mmol) and quinoline-3-ylamine (0.087 g, 0.61 mmol) in 1,2-dichloroethane (2 mL). The resultant solution was heated to 85° C. in a sealed tube. The solution was cooled and treated with several drops of methanol. The product was preabsorbed onto silica gel and purified by flash chromatography, using ethyl acetate/hexane (1/2) as the eluant. The product was dissolved in tetrahydrofuran and treated with 1N ethereal hydrogen chloride. The solvents were evaporated in vacuo to give the product as the hydrochloride salt, 0.23 g (70%). MS: m/z 374 (MH$^+$). $^1$H NMR (DMSO-d$_6$): δ 1.57-1.72 (m, 4 H), 1.87-2.03 (m, 4 H), 2.80 (t, 2 H), 2.97 (t, 2 H), 3.47-3.62 (m, 4 H), 7.34 (br s, 2 H) superimposed on 7.45 (br s, 1 H), 7.77 (d of d, 1 H), 7.87 (d of d, 1 H), 8.17 (d, 2 H), 9.07 (d, 1 H), 9.30 (d, 1 H) and 11.25 (s, 1 H).

The following compounds were prepared according to the method of Example 240:

| Example # | Compound name | M Wt | MH$^+$ |
|---|---|---|---|
| (241) | 3-(4-Azepan-1-yl-phenyl)-N-quinolin-3-yl-acrylamide | 371.48 | 372 |
| (242) | 3-(4-Azepan-1-yl-phenyl)-N-(4-chloro-quinolin-3-yl)-acrylamide | 405.927 | 406 |
| (243) | 3-(4-Azepan-1-yl-phenyl)-N-(2-chloro-quinolin-3-yl)-acrylamide | 405.93 | 406 |
| (240) | 3-(4-Azepan-1-yl-phenyl)-N-quinolin-3-yl-propionamide | 373.5 | 374 |

Example (244)

4-tert-Butyl-N-(1-oxy-quinolin-3-yl)-benzamide

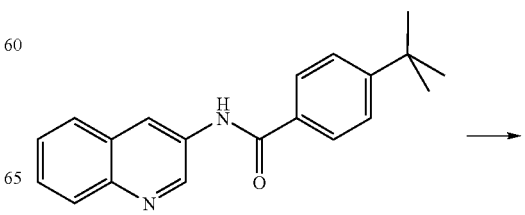

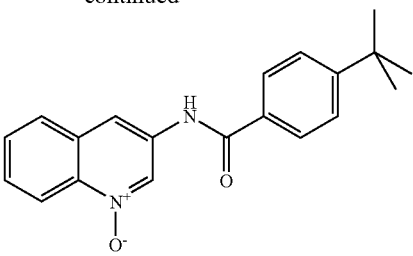

4-tert-Butyl-N-(1-oxy-quinolin-3-yl)-benzamide. meta-Chloroperbenzoic acid (50-87%, 0.578 g, ~2.2 mmol) was added to a solution of 4-tert-butyl-N-quinolin-3-yl-benzamide (0.51 g, 1.68 mmol) in dichloromethane (10 mL) and stirred at room temperature for 20 hours. The product was preabsorbed onto silica gel and purified by flash chromatography, using methanol (3-5%) in dichloromethane as the eluant, to give the product, 0.411 g (76%), an off white solid. MS: m/z 321 (MH$^+$). $^1$H NMR (DMSO-d$_6$): δ 1.34 (s, 9 H), 7.60 (d, 2 H), 7.69-7.74 (m, 2 H), 7.94 (d, 2 H), 8.05-8.08 (m, 1 H), 8.42 (br s, 1 H), 8.45-8.48 (m, 1 H), 9.02 (d, 1 H) and 10.60 (s, 1 H).

The following compounds were prepared according to the method of Example 244:

| Example # | Compound name | M Wt | MH$^+$ |
|---|---|---|---|
| (245) | N-(1-Oxy-quinolin-3-yl)-4-trifluoromethyl-benzamide | 332.28 | 333 |
| (244) | 4-tert-Butyl-N-(1-oxy-quinolin-3-yl)-benzamide | 320.39 | 321 |

Example (246)

3-(4-Piperidin-1-yl-phenyl)-N-quinolin-3-yl-propionamide

A. 3-(4-Amino-phenyl)-propionic acid ethyl ester. Ethyl 4-nitrocinnamate (6.66 g, 30.1 mmol) was dissolved in 60 mL EtOH along with 5% Pd/C (0.667 g) and hydrogenated at ~50 psi for 1.5 hours. Filtration over a pad of celite and evaporation of the filtrate gave the product as a pale peach colored liquid (5.776 g, 29.9 mmol).

B. 3-(4-Piperidin-1-yl-phenyl)-propionic acid ethyl ester. Into a nitrogen flushed round bottom flask equipped with a stir bar was added the aniline from step A, 3-(4-amino-phenyl)-propionic acid ethyl ester, (1.342 g, 6.94 mmol) and 13 mL of dichloroethane. The flask was cooled on an ice bath and into an addition funnel was introduced an aqueous solution of glutaraldehyde (4.0 mL, 50 wt. % aqueous solution), sulfuric acid (3M, 12 mL), 19 mL MeOH and 13 mL THF. A 0.4 g tablet of NaBH$_4$ was introduced to the solution of the aniline and at the same time the glutaraldehyde mixture was added dropwise to the reaction mixture over a period of 6 minutes. An additional 0.4 g tablet of NaBH$_4$ was added and the reaction mixture was allowed to warm up overnight. The reaction mixture was then partitioned between 100 mL Et$_2$O and 100 mL 10% aqueous Na$_2$CO$_3$ solution. The organics were separated and washed with 100 mL brine. The organics were dried over Na$_2$SO$_4$, filtered and evaporated in vacuo. The residue was purified by chromatography over silica gel eluting with 0% to 10% EtOAc in hexanes. Evaporation of the proper fractions yielded the product as a colorless oil (0.693 g, 2.65 mmol). $^1$H NMR (CDCl$_3$): δ 7.09 (d, 2H), 6.88 (d, 2H), 4.13 (q, 2H), 3.11 (t, 4H), 2.88 (t, 2H), 2.58 (t, 2H), 1.71 (m, 4H), 1.57 (m, 2H), 1.24 (t, 3H); MS: m/z 262.1 (MH$^+$).

C. 3-(4-Piperidin-1-yl-phenyl)-propionic acid. To a round bottom flask equipped with a stir bar was added the propionate ester IR (0.687 g, 2.63 mmol), 25 mL THF, 5 mL water and LiOH.H$_2$O (0.126 g, 3.00 mmol). The reaction was stirred for 48 hours then evaporated in vacuo to an aqueous residue which was diluted with 10 mL water and acidified with 3.0 mL 1N HCl. Evaporation of the clear solution in vacuo yielded a solid residue theoretically containing 83% product and 17% LiCl by weight. $^1$H NMR (DMSO-d$_6$): δ 12.08 (s, 1H), 7.06 (d, 2H), 6.83 (d, 2H), 3.08 (br s, 4H), 2.72 (t, 2H), 2.46 (t, 2H), 1.71-1.43 (m, 6H); MS: m/z 234.1 (MH$^-$).

D. 3-(4-Piperidin-1-yl-phenyl)-propionyl chloride. Into a nitrogen flushed round bottom flask equipped with a stir bar 3-(4-piperidin-1-yl-phenyl)-propionic acid, obtained in step C, was suspended (0.286 g, 1.02 mmol) in 20 mL DCM. To the suspension was added one drop of DMF followed by

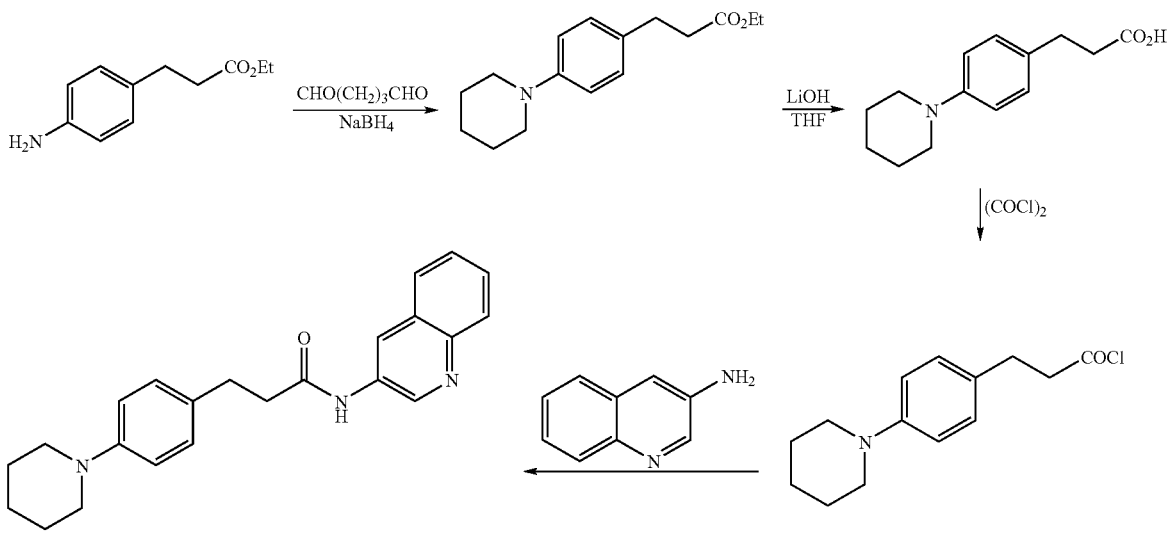

oxalyl chloride (0.30 mL, 3.4 mmol). The reaction was stirred overnight then evaporated in vacuo to give the acid chloride which was carried on without further purification.

E. 3-(4-Piperidin-1-yl-phenyl)-N-quinolin-3-yl-propionamide. The acid chloride obtained in step D, 3-(4-piperidin-1-yl-phenyl)-propionyl chloride, (1.02 mmol) was dissolved in 10 mL acetonitrile with stirring. To the solution was added iPr$_2$NEt (0.39 mL, 2.24 mmol) and 3-aminoquinoline (0.119 g, 0.83 mmol). The reaction was stirred for 5 hours, evaporated in vacuo and suspended in 50 mL Et$_2$O. The ether suspension was washed twice with 25 mL 1N NaOH and twice with 25 mL brine. At this point a solid had formed. Both the solid and organic extract were combined and evaporated in vacuo to yield a residue that was purified by silica gel chromatography eluting with 3% MeOH/NH$_3$: 97% DCM. Evaporation of the proper fractions yielded the product as a tan powder (0.148 g, 0.412 mmol). $^1$H NMR (CDCl$_3$): δ 8.74 (s, 1H), 8.53 (d, 1H), 8.02 (d, 1H), 7.80 (d, 1H), 7.63 (t, 1H), 7.53 (t, 1H), 7.23 (m, 1H), 7.17 (d, 2H), 6.89 (d, 2H), 3.12 (t, 4H), 3.04 (t, 2H) 2.74 (t, 2H), 1.71 (m, 4H), 1.58 (m, 2H); MS: m/z 360.1 (MH$^+$).

Example (247)

3-[4-(Methyl-phenethyl-amino)-phenyl]-N-quinolin-3-yl-propionamide

Synthesis of 3-phenylpropionic & 3-phenylacrylic esters

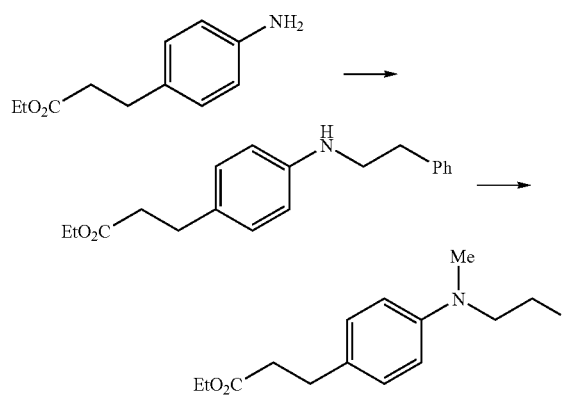

3-[4-(Methyl-phenethyl-amino)-phenyl]-N-quinolin-3-yl-propionamide

3-[4-(Phenethyl-amino)-phenyl]-propionic acid ethyl ester. Tetramethylammonium triacetoxyborohydride (4.9 g, 18.6 mmol) was added to a solution of 3-(4-aminophenyl)-propionic acid ethyl ester (3.0 g, 15.5 mmol) and phenylacetaldehyde (1.08 mL, 15.5 mmol) in 1,2-dichloroethane (50 mL). The resultant solution was stirred at room temperature for ten minutes, then heated at reflux overnight. The solution was treated with a 1:1 solution of water:ammonium hydroxide. The organic layer was applied to a silica gel column and eluted with ethyl acetate/hexane (⅛) to give the product as an oil, 1.3 g (28%). MS: m/z 298 (MH$^+$). $^1$H NMR (CDCl$_3$): δ 1.24 (t, 3 H), 2.58 (t, 2 H), 2.86 (s, 3 H), 3.53 (t, 2 H), 3.67 (t, 2 H), 4.13 (q, 2 H), 4.32 (t, 2 H), 6.67 (d, 2 H), 7.09 (d, 2 H), 7.19-7.32 (m, 5 H).

3-[4-(Methyl-phenethyl-amino)-phenyl]-propionic acid ethyl ester. Paraformaldehyde (0.89 g, 30.5 mmol) was added to a solution of 3-[4-(Phenethyl-amino)-phenyl]-propionic acid ethyl ester (1.3 g, 4.37 mmol) in 1,2-dichloroethane (25 mL). The resultant suspension was stirred at room temperature for 15 minutes. Tetramethylammonium triacetoxyborohydride (2.0 g, 8.74 mmol) was added, and the suspension was heated at reflux for 6 hours. The mixture was cooled to room temperature and treated with ammonium hydroxide (20 mL). The organic layer was separated and applied to a silica gel column. The product was eluted with ethyl acetate/hexane (1/20) to give an oil, 0.80 g (59%). MS: m/z 312 (MH$^+$). $^1$H NMR (CDCl$_3$): δ 1.23 (t, 3 H), 2.55 (t, 2 H), 2.90 (t, 2 H), 3.37 (t, 2 H), 3.59 (br s, 1 H), 4.11 (q, 2 H), 6.55 (d, 2 H), 7.01 (d, 2 H), 7.20-7.37 (m, 5 H).

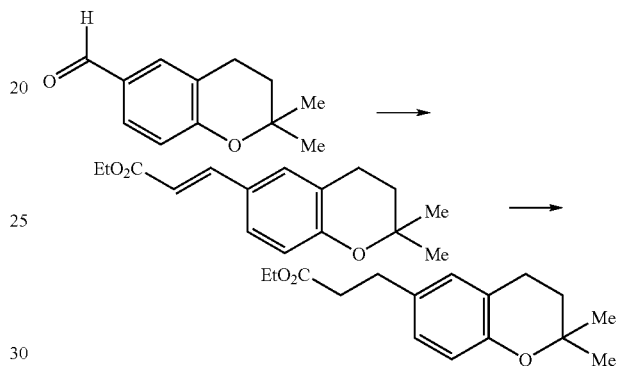

3-(2,2-Dimethyl-chroman-6-yl)-acrylic acid ethyl ester. A mixture of 2,2-Dimethyl-chroman-6-carbaldehyde (1.87 g, 9.82 mmol), lithium chloride (0.73 g, 17.2 mmol), triethyl phosphonoacetate (2.92 mL, 14.7 mmol) and 1,8-diazabicyclo[5.4.0]undec-7-ene (DBU) (2.2 mL, 14.7 mmol) in acetonitrile (30 mL) was heated at reflux for 2 hours. The solvent was evaporated in vacuo, and the residue was partitioned between dichloromethane and water. The product was preabsorbed onto silica gel and purified by flash chromatography, using 5-10% ethyl acetate in hexane as the eluant to give 2.2 g (86%). MS: m/z 261 (MH$^+$). $^1$H NMR (CDCl$_3$): δ 1.32 (t, 3 H), 1.34 (s, 6 H), 1.81 (t, 2 H), 2.77 (t, 2 H), 4.24 (q, 2 H), 6.26 (d, 1 H), 6.77 (d, 1 H), 7.24-7.30 (m, 2 H) and 7.60 (d, 1 H).

3-(2,2-Dimethyl-chroman-6-yl)-propionic acid ethyl ester. A suspension of 3-(2,2-Dimethyl-chroman-6-yl)-acrylic acid ethyl ester (1.2 g, 4.61 mmol) in methanol (25 mL) was hydrogenated with 10% palladium on carbon at 60 psi of hydrogen for 6 hours. The catalyst was removed by filtration, and the solvent was evaporated in vacuo to give the product 0.95 g (79%). MS: m/z 263 (MH$^+$). $^1$H NMR (CDCl$_3$): δ 1.15 (t, 3 H), 1.24 (s, 6 H), 1.70 (t, 2 H), 2.49 (t, 2 H), 2.65 (t, 2 H), 2.76 (t, 2 H), 4.04 (q, 2 H), 6.62 (d, 1 H) and 6.81-6.86 (m, 2 H).

The esters above were converted to the following products according to the conditions set forth in scheme AA:

| Example | Compound name | M Wt | MH$^+$ |
|---|---|---|---|
| (247) | 3-[4-(Methyl-phenethyl-amino)-phenyl]-N-quinolin-3-yl-propionamide | 409.53 | 410 |
| (248) | 3-(2,2-Dimethyl-chroman-6-yl)-N-quinolin-3-yl-acrylamide | 358.44 | 359 |
| (249) | 3-(2,2-Dimethyl-chroman-6-yl)-N-quinolin-3-yl-propionamide | 360.45 | 361 |

Example (250)

4-(4-Phenylacetyl-piperazin-1-yl)-N-quinolin-3-yl-benzamide 4-piperazin-1-yl-N-quinolin-3-yl-benzamide. A solution of 4-fluoro-N-quinolin-3-yl-benzamide (2.0 g, 3.76 mmol) and piperazine (6.2 g, 72 mmol) in methylsulfoxide (30 mL) was heated 100° C. for 1.5 days, to give the product 2.53 g (100%).

4-(4-Phenylacetyl-piperazin-1-yl)-N-quinolin-3-yl-benzamide. A solution of 4-piperazin-1-yl-N-quinolin-3-yl-benzamide (75 mg, 0.284 mmol), phenylacetic acid (51 mg, 0.375 mmol), O-benzotriazol-1-yl-N,N,N',N'-tetramethyluronium hexafluorophosphate (HBTU)(118 mg, 0.30 mmol) and N,N—N,N-diisopropylethylamine (0.110 mL, 0.626 mmol) in acetonitrile (2 mL) was heated to 80° C. The solution was cooled to room temperature and the product crystallized. The product was collected by filtration washed with acetonitrile to give 63 mg (49%). MS: m/z 451 (MH$^+$). $^1$H NMR (DMSO-d$_6$): δ 3.24-3.34 (m, 4 H), 3.63-3.69 (m, 4 H), 3.79 (s, 2 H), 7.05 (d, 2 H), 7.22-7.46 (m, 5 H), 7.54-7.67 (m, 2 H), 7.92-7.99 (m, 4 H), 8.82 (d, 1 H), 9.15 (d, 1 H) and 10.40 (s, 1 H).

Example (251)

2,3-Dihydro-1H-indole-5-carboxylic acid quinolin-3-ylamide

5-Bromo-2,3-dihydro-indole-1-carboxylic acid tert-butyl ester. A solution of 5-bromo-2,3-dihydro-1H-indole (4.97 g, 25.1 mmol), di-tert-butyl dicarbonate (6.0 g, 27.5 mmol) and 4-dimethylaminopyridine (catalytic) in dichloromethane (70 mL) was stirred at room temperature until the starting material was consumed. The solvent was evaporated in vacuo, and the residue was purified by flash chromatography on silica gel, eluted with ethyl acetate/hexane to give the product, 4.1 g (55%). $^1$H NMR (CDCl$_3$): δ 1.55 (s, 9 H), 3.06 (t, 2 H), 3.97 (t, 2 H), 7.23-7.27 (m, 2 H) and 7.72 (br m, 1 H).

2,3-Dihydro-indole-1,5-dicarboxylic acid 1-tert-butyl ester 5-methyl ester. A solution of 5-bromo-2,3-dihydro-indole-1-carboxylic acid tert-butyl ester (4.0 g, 13.5 mmol), tributylamine and bis-triphenylphosphinopalladium(II) chloride (0.65 g, 0.926 mmol) in methanol was sealed in a Parr pressure apparatus and pressurized with 600 psi of carbon monoxide. The solution was heated at 100° C. for one week. The vessel was cooled to room temperature and the gas vented. The solution was filtered, and the solvent was evaporated in vacuo. The residue was purified by flash chromatography, on silica gel eluted with 10-40% ethyl acetate in hexane to give the product mixed with tributylamine, 2.5 g (67%). The product was used without further purification in the subsequent step.

2,3-Dihydro-indole-1,5-dicarboxylic acid 1-tert-butyl ester. A solution of 2,3-dihydro-indole-1,5-dicarboxylic acid 1-tert-butyl ester 5-methyl ester (2.3 g, 8.29 mmol) in methanol (30 mL) was treated with 3 N aqueous sodium hydroxide (2.77 mL, 8.29 mmol) and heated at reflux for 4 hours. An additional portion of 3N aqueous sodium hydroxide (1.38 mL, 4.14 mmol) was added and the solution was heated at reflux for an additional 28 hours. The solution was concentrated in vacuo and then diluted with water. The resultant solution was neutralized with 2N hydrochloric acid (6.3 mL). The product precipitated and was collected by filtration and washed with water, to give the product 1.5 g (69%). $^1$H NMR (DMSO-d$_6$): δ 1.51 (s, 9 H), 3.10 (t, 2 H), 3.95 (t, 2 H), 7.53-7.82 (m, 3 H) and 12.59 (s, 1 H).

5-(Quinolin-3-ylcarbamoyl)-2,3-dihydro-indole-1-carboxylic acid tert-butyl ester. A solution of 2,3-dihydro-indole-1,5-dicarboxylic acid 1-tert-butyl ester (1.5 g, 5.70 mmol), O-benzotriazol-1-yl-N,N,N',N'-tetramethyluronium hexafluorophosphate (HBTU) (2.37 g, 6.27 mmol), N,N-diisopropylethylamine (2.41 mL, 13.8 mmol) and 3-amino-quinoline (0.904 g, 6.27 mmol) in acetonitrile was heated to reflux for 20 hours. The solvent was evaporated in vacuo and the residue was partitioned between water and dichloromethane. The organic layer was separated, and the solvent was evaporated. The residue was purified by flash chromatography on silica gel eluted with ethyl acetate/hexane to give the product, 1.43 g (64%). MS: m/z 390 (MH$^+$). $^1$H NMR (DMSO-d$_6$): δ 1.54 (s, 9 H), 3.16 (t, 2 H), 4.00 (t, 2 H), 7.57-7.83 (m, 3 H), 7.88-8.00 (m, 4 H), 8.84 (d, 1 H), 9.15 (d, 1 H) and 10.53 (s, 1 H).

2,3-Dihydro-1H-indole-5-carboxylic acid quinolin-3-ylamide. A solution of 5-(Quinolin-3-ylcarbamoyl)-2,3-dihydro-indole-1-carboxylic acid tert-butyl ester (1.4 g, 3.59 mmol) in trifluoroacetic acid (9 mL), water (1 mL) and dichloromethane (20 mL) was stirred at room temperature for 18 hours. The solvents were evaporated in vacuo and the residue was triturated in aqueous sodium bicarbonate. The product was collected by filtration and washed with water, to give an off white solid 1.03 g (99%). MS: m/z 290 (MH$^+$). $^1$H NMR (DMSO-d$_6$): δ 3.02 (t, 2 H), 3.56 (t, 2 H), 6.27 (br s, 1 H), 6.54 (d, 1 H), 7.56 (t, 1 H), 7.64 (t, 1 H), 7.71-7.76 (m, 2 H), 7.94 (m, 2 H), 8.82 (d, 1 H), 9.14 (d, 1 H) and 10.23 (s, 1 H).

Example (252)

1-Acetyl-2,3-dihydro-1H-indole-5-carboxylic acid quinolin-3-ylamide

A solution of 2,3-dihydro-1H-indole-5-carboxylic acid quinolin-3-ylamide (77 mg, 0.266 mmol) and N,N-diisopropylethylamine (0.060 mL, 0.345 mmol) in 1,2-dichloroethane (2 mL) was treated with acetyl chloride (0.020 mL, 0.292 mmol). The resultant solution was stirred at room temperature overnight. The solvent was evaporated and the residue was triturated in water (1 mL) and saturated aqueous sodium bicarbonate (1 mL). The product was collected by filtration, to give the product 74 mg (84%). MS: m/z 332 (MH$^+$). $^1$H NMR (DMSO-d$_6$): δ 2.21 (s, 3H), 3.24 (t, 2 H), 4.18 (t, 2 H), 7.59 (t, 1 H), 7.67 (t, 1 H), 7.89-7.98 (m, 4 H), 8.15 (d, 1 H), 8.84 (s, 1 H), 9.14 (s, 1 H) and 10.566 (s, 1 H).

The following compounds were prepared according to the method of Examples 251 and 252:

| Example No. | Compound name | M Wt | MH$^+$ |
|---|---|---|---|
| (253) | 1-Butyryl-2,3-dihydro-1H-indole-5-carboxylic acid quinolin-3-ylamide | 359.43 | 360 |
| (254) | 1-Cyclohexanecarbonyl-2,3-dihydro-1H-indole-5-carboxylic acid quinolin-3-ylamide | 399.49 | 400 |
| (255) | 1-Benzoyl-2,3-dihydro-1H-indole-5-carboxylic acid quinolin-3-ylamide | 393.44 | 394 |

Example (256)

4-(3-Aza-bicyclo[3.2.2]non-3-yl)-N-(6-fluoro-quinolin-3-yl)-benzamide

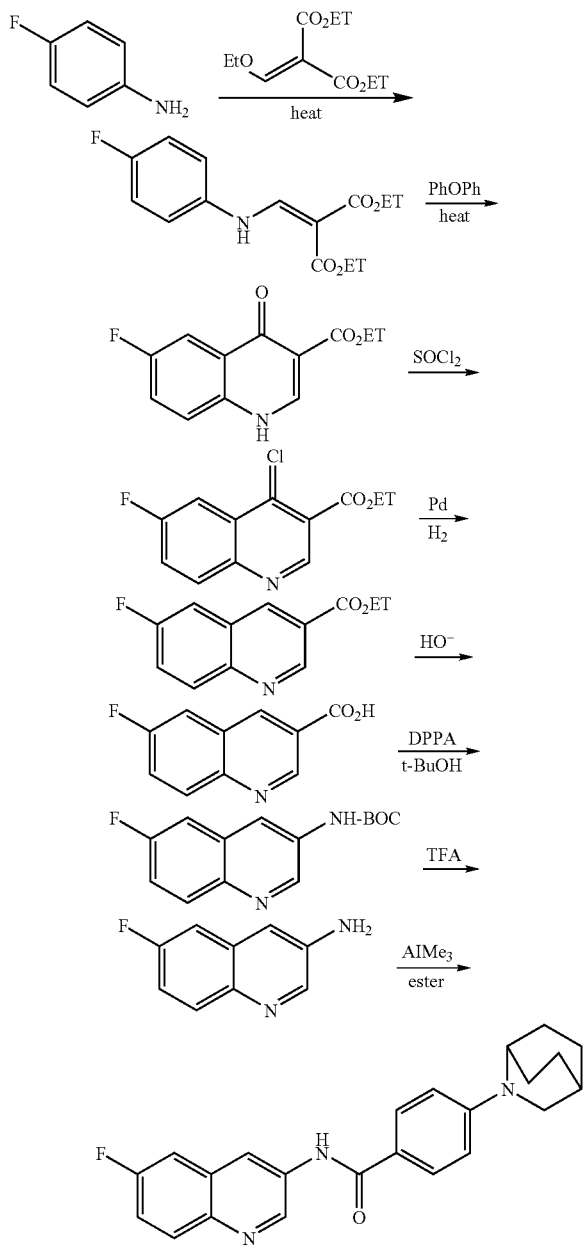

2-[(4-Fluoro-phenylamino)-methylene]-malonic acid diethyl ester. A mixture of 4-fluoro-phenylamine (5.1 mL, 54.4 mmol) and diethyl ethoxymethylenemalonate (10 mL, 49.5 mmol) was heated at 100° C. for 4 hours, an oil which solidified on cooling. The solid was triturated in heptane, collected by filtration and washed with heptane, to give the product as a colorless solid, 10.5 g (75%). MS: m/z 282.1 (MH+).

6-Fluoro-4-oxo-1,4-dihydro-quinoline-3-carboxylic acid ethyl ester. 2-[(4-Fluoro-phenylamino)-methylene]-malonic acid diethyl ester (11.5 g, 40.9 mmol)) was added in portions to hot diphenylether (80 mL), while heating at reflux. The resultant mixture was heated an additional 2 hours, then allowed to cool to room temperature. A solid white precipitate developed. The mixture was diluted with heptanes, and the product was collected by filtration, washed with heptane, to give the product as a colorless crystalline solid, 3.0 g (31%). MS: m/z 235.9 (MH+).

4-Chloro-6-fluoro-quinoline-3-carboxylic acid ethyl ester. A mixture of 6-fluoro-4-oxo-1,4-dihydro-quinoline-3-carboxylic acid ethyl ester (4.4 g, 18.7 mmol) in thionyl chloride (50 mL) was heated at reflux for 3 hours (at 30 min. mixture changed to a clear solution). The resultant solution was cooled to room temperature, and the excess thionyl chloride was evaporated in vacuo. The residue was added to ammonium hydroxide on ice (note: highly exothermic). Let resultant mixture stir for 15 minutes, and the product was collected by filtration and washed generously with water. The solid was purified by flash chromatography, on silica gel, eluted with a gradient of ethyl acetate (0% to 30%) in heptane, to give the product, 4.24 g (89%) as a colorless solid. MS: m/z 253.8 (MH+).

6-Fluoro-quinoline-3-carboxylic acid ethyl ester. A solution of 4-chloro-6-fluoro-quinoline-3-carboxylic acid ethyl ester (4.2 g, 16.6 mmol) and diisopropylethylamine (8.7 mL, 50 mmol) in ethanol (50 mL) was hydrogenated over 10% palladium on carbon (0.2 g) at 1 atmosphere of hydrogen for 1 day. Additional catalyst (0.3 g) was added and the hydrogenation was continued at 50 psi of hydrogen for 2 hours. The catalyst was removed by filtration. The solvent was evaporated in vacuo, and the residue was partitioned between water and dichloromethane. The organic layer was dried over sodium sulfate. The product was preabsorbed onto silica gel and purified by flash chromatography, using a gradient of ethyl acetate (0% to 30%) in heptanes as the eluant, to give the product as a yellow solid, 2.2 g (60%). MS: m/z 219.9 (MH+).

6-Fluoro-quinoline-3-carboxylic acid. 3 N aqueous sodium hydroxide (5 mL, 15 mmol) was added to a solution of 6-fluoro-quinoline-3-carboxylic acid ethyl ester (2.2 g, 10 mmol) in methanol (50 mL). A heavy precipitate developed, and the mixture was diluted with an additional 50 mL of methanol to facilitate stirring. The mixture was stirred for 3 hours, then neutralized with of 1N hydrochloric acid (15 mL). The methanol was evaporated in vacuo, and the slurry diluted with water. The product was collected by filtration and washed with water, to give the product, 1.76 g (92%) as a colorless solid. MS: m/z 192.1 (MH+).

(6-Fluoro-quinolin-3-yl)-carbamic acid tert-butyl ester. A solution of 6-fluoro-quinoline-3-carboxylic acid (1.7 g, 8.89 mmol), diphenylphosphoryl azide (2.3 mL, 10.7 mmol) and diisopropylethylamine (4.65 mL, 26.67 mmol) in t-butanol (40 mL) was heated at reflux for 1 hour. The solution was cooled to room temperature, and the solvent was evaporated in vacuo. The residue was partitioned between aqueous sodium bicarbonate and dichloromethane. The organic layer was dried over sodium sulfate, and the product was preabsorbed onto silica gel. Purification by flash chromatography, using a gradient of ethyl acetate (0% to 30%) in heptane as the eluant, to give the product as a colorless solid, 1.3 g (56%). MS: m/z 263.0 (MH+).

6-Fluoro-quinolin-3-ylamine. A solution of (6-fluoro-quinolin-3-yl)-carbamic acid tert-butyl ester (1.3 g, 4.95 mmol) in 1,2-dichloroethane (15 mL) was treated with trifluoroacetic acid (15 mL) and water (1 mL). The resultant solution was stirred at room temperature for 6 hours. The solvents were evaporated in vacuo, and the residue was triturated in diethyl ether. The solid was purified by flash chromatography using a gradient of 2 N ammonia in methanol (0% to 3%) in dichloromethane as the eluant, to give the product as a colorless solid, 0.47 g (59%). MS: m/z 162.9 (MH+).

4-(3-Aza-bicyclo[3.2.2]non-3-yl)-N-(6-fluoro-quinolin-3-yl)-benzamide. In a sealed tube, a solution of trimethylaluminum in toluene (3N, 0.41 mL, 1.23 mmol) was added to a solution of 6-fluoro-quinolin-3-ylamine (90 mg, 0.56 mmol) and 4-(3-aza-bicyclo[3.2.2]non-3-yl)-benzoic acid ethyl ester (180 mg, 0.65 mmol) in 1,2-dichloroethane (2 mL). The solution was allowed to stir at room temperature for 15 minutes, and then heated at 83° C. for 16 hours. The tube was cooled and carefully opened. Methanol (0.5 mL) was added and the resultant mixture was allowed to stir at room temperature for several hours. The mixture was diluted with dichloromethane and preabsorbed onto silica gel. Flash chromatography, using a gradient of methanol (0% to 3%) in dichloromethane as the eluant, gave the product, 60 mg (28%), as a colorless solid. MS: m/z 390.0 (MH+). $^1$HNMR (DMSO-$d_6$): δ 1.67 (m, 8 H), 2.14 (m, 2 H), 3.56 (d, 2 H), 6.97 (d, 2 H), 7.54 (d of t, 1 H), 7.77 (d of d, 1 H), 7.92 (d, 2 H), 8.04 (d of d, 1 H), 8.85 (d, 1 H), 9.13 (d, 1 H) and 10.3 (s, 1 H).

The following compounds were prepared according to the method of Examples 256:

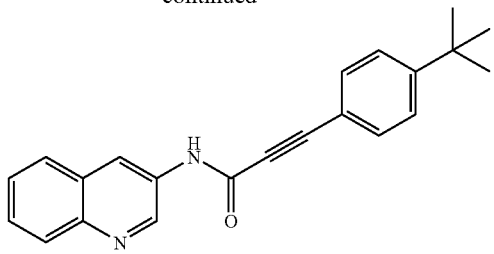

A solution of (4-tert-butyl-phenyl)-propynoic acid ethyl ester (0.23 g, 1.0 mmol) and 3-aminoquinoline (0.144 g, 1.0 mmol) in 1,2-dichloroethane (15 mL) was treated with a 2N solution of trimethylaluminum in toluene (0.75 mL, 1.5 mmol). The resultant solution was stirred at room temperature for 15 minutes, then heated at reflux for 18 h. The solution was cooled and treated with methanol (0.50 mL). The product was preabsorbed onto silica gel and purified by flash chromatography, using a gradient of methanol in dichloromethane as the eluant. The product was isolated, after trituration in

| Example No. | Compound name | M Wt | MH+ |
|---|---|---|---|
| (257) | 4-(Cyclohexyl-methyl-amino)-N-(8-fluoro-quinolin-3-yl)-benzamide | 377.47 | 378 |
| (258) | 4-Azocan-1-yl-N-(8-fluoro-quinolin-3-yl)-benzamide | 377.47 | 378 |
| (259) | 4-(3-Aza-bicyclo[3.2.2]non-3-yl)-N-(8-fluoro-quinolin-3-yl)-benzamide | 389.48 | 399 |
| (260) | 4-(3-Aza-bicyclo[3.2.2]non-3-yl)-N-(8-trifluoromethyl-quinolin-3-yl)-benzamide | 439.48 | 440 |
| (261) | 4-(Cyclohexyl-methyl-amino)-N-(8-trifluoromethyl-quinolin-3-yl)-benzamide | 427.47 | 428 |
| (262) | 4-(Cyclohexyl-methyl-amino)-N-(6-fluoro-quinolin-3-yl)-benzamide | 377.47 | 378 |
| (263) | 4-Azocan-1-yl-N-(6-fluoro-quinolin-3-yl)-benzamide | 377.47 | 378 |
| (264) | 4-(3-Aza-bicyclo[3.2.2]non-3-yl)-N-(6-fluoro-quinolin-3-yl)-benzamide | 389.48 | 390 |
| (265) | 4-(3-Aza-bicyclo[3.2.2]non-3-yl)-N-(7-trifluoromethyl-quinolin-3-yl)-benzamide | 439.48 | 440 |
| (266) | 4-Azocan-1-yl-N-(7-trifluoromethyl-quinolin-3-yl)-benzamide | 427.47 | 428 |
| (267) | 4-(Cyclohexyl-methyl-amino)-N-(7-trifluoromethyl-quinolin-3-yl)-benzamide | 427.47 | 428 |
| (268) | 4-Azocan-1-yl-N-(5-fluoro-quinolin-3-yl)-benzamide | 377.47 | 378 |
| (269) | 4-(3-Aza-bicyclo[3.2.2]non-3-yl)-N-(5-fluoro-quinolin-3-yl)-benzamide | 389.48 | 390 |

Example (270)

3-(4-tert-Butyl-phenyl)-propynoic acid quinolin-3-ylamide

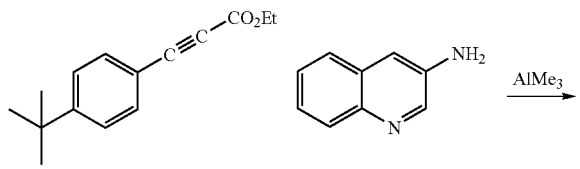

diethyl ether, as a colorless solid, 0.17 g (52%). MS: m/z 329.2 (MH+). $^1$HNMR (DMSO-$d_6$): δ 1.31 (s, 9 H), 7.54-7.72 (m, 6 H), 7.97 (d, 1 H), 8.72 (d, 1 H), 8.96 (d, 1 H) and 11.3 (s, 1 H).

The following compounds were prepared according to the method of Examples 270:

| Example No. | Compound name | M Wt | MH+ |
|---|---|---|---|
| (271) | 3-Phenyl-propynoic acid quinolin-3-ylamide | 272.31 | 273 |
| (272) | trans-2-Phenyl-cyclopropanecarboxylic acid quinolin-3-ylamide | 288.35 | 289 |
| (273) | 3-(4-tert-Butyl-phenyl)-propynoic acid quinolin-3-ylamide | 328.41 | 329 |
| (274) | 2-(4-tert-Butyl-phenyl)-cyclopropanecarboxylic acid quinolin-3-ylamide | 307.79 | 308 |

Biological Examples

Example 275

Human or Rat $VR_1$ Binding Assay

Compounds of the present invention were tested for their ability to inhibit the binding of [$^3$H] RTX to hVR1 receptors in a [$^3$H] RTX binding assay as previously described (Zhang, Sui-Po. Improved ligand binding assays for vanilloid receptors. PCT Int. Appl. (2002), 29 pp. CODEN: PIXXD2 WO 0233411 A1 20020425 AN 2002:315209; Grant, Elfrida R.; Dubin, Adrienne E.; Zhang, Sui-Po; Zivin, Robert A.; Zhong, Zhong Simultaneous intracellular calcium and sodium flux imaging in human vanilloid receptor 1 (VR1)-transfected human embryonic kidney cells: a method to resolve ionic dependence of VR1-mediated cell death. Journal of Pharmacology and Experimental Therapeutics (2002), 300(1), 9-17.)

HEK293 cells were transfected with human VR1 vanilloid receptors and washed with Hank's Balanced Salt Solution, dissociated with cell dissociation buffer (Sigma), and then centrifuged at 1000×g for 5 min. Cell pellets were homogenized in cold 20 mM HEPES buffer, pH 7.4, containing 5.8 mM NaCl, 320 mM sucrose, 2 mM $MgCl_2$, 0.75 $CaCl_2$ and 5 mM KCl and centrifuged at 1000×g for 15 min. The resultant supernate was then centrifuged at 40000×g for 15 min. The pelleted membranes were kept in an −80° C. freezer.

Approximately 120 µg protein/ml from membranes were incubated with indicated concentrations of [$^3$H] RTX in 0.5 ml of the HEPES buffer (pH 7.4) containing 0.25 mg/mL fatty acid-free bovine serum albumin at 37° C. for 60 min. The reaction mixture was then cooled to 4° C., added 0.1 mg $α_1$-acid glycoprotein to each sample and incubated at 4° C. for 15 min. The samples were centrifuged at 18500×g for 15 min. The tip of the microcentrifuge tube containing the pellet was cut off. Bound radioactivity was quantified by scintillation counting. Non-specific binding was tested in the presence of 200 nM unlabeled RTX.

Alternatively, a binding assay using rat tissue was used. Rat spinal cord was homogenized twice with a Polytron and centrifuged at 3000 rpm for 10 min in HEPES buffer containing 20 mM HEPES, pH 7.4, NaCl 5.8 mM, sucrose 320 mM, $MgCl_2$ 2 mM, $CaCl_2$ 0.75 mM and KCl 5 mM. The supernatant was then centrifuged at 18,000 rpm for 20 min. The pellet was saved in a tube and 10 ml assay buffer was added into the tube. The pellet and buffer were mixed with a Polytron. The assay contained 120 µg/ml membrane protein and 0.3-0.6 nM [$^3$H]-RTX (NEN, Boston) in a total volume of 0.5 ml HEPES buffer. Following-incubation for 60 min at 37° C., the samples were cooled down on ice, and 100 mg of α-acid glycoprotein were added into the samples. After centrifugation at 13,000 rpm for 15 min, the supernatant was aspirated and the tips of tubes were cut off and placed into 6 ml vials. Data were calculated according to the equation: % inhibition=(total binding-binding)*100/(total binding−non specific binding). Ki value values were calculated using a Prism program.

Example 276

Human $VR_1$ Functional Assay

The functional activity of the test compounds was determined by measuring changes in intracellular calcium concentration using a $Ca^{++}$-sensitive fluorescent dye and FLIPR™ technology. Increases in $Ca^{++}$ concentration were readily detected upon challenge with capsaicin.

HEK293 Cells expressing human VR1 were grown on poly-D-lysine coated 96 well black-walled plates (BD 354640) and 2 days later loaded with Fluo-3/AM for 1 hour and subsequently tested for agonist-induced increases in intracellular $Ca^{2+}$ levels using FLIPR™ technology. Cells were challenged with test compounds (at varying concentrations) and intracellular $Ca^{++}$ was measured for 3 min prior to the addition of capsaicin to all wells to achieve a final concentration of 0.015 µM eliciting ~80% maximal response. $EC_{50}$ or $IC_{50}$ values were determined from dose-response studies.

Alternatively, a rat electrophysiological assay was used. Compounds were tested for their activity on VR1 expressed endogenously on small rat dorsal root ganglion (DRG) neurons. DRG neurons from normal rats were dissociated and whole cell currents mediated by VR1 were recorded using the whole cell patch clamp technique. The estimated potency of the compounds was determined by measuring the shift in the capsaicin-induced dose response in the presence of compound under conditions of limited capsaicin-induced VR1 desensitization (i.e., using 0 $Ca^{2+}$-containing saline solutions). $pA_2$ values were determined.

TABLE 2

| | Vanilloid In vitro assay data | | | |
|---|---|---|---|---|
| | $^3$H-RTX binding assay | | FLIPR functional assay | |
| Compound Name | % Inhibition @ 1 µM | Ki hVR1 (nM) | $IC_{50}$ hVR1 (nM) | $IC_{50}$ hVR1 60 min (nM) |
| 1-Acetyl-2,3-dihydro-1H-indole-5-carboxylic acid quinolin-3-ylamide | 1 | | $3.15 \times 10^3$ | |
| 1-Benzoyl-2,3-dihydro-1H-indole-5-carboxylic acid quinolin-3-ylamide | 3 | | $1.45 \times 10^3$ | |
| 1-Butyryl-2,3-dihydro-1H-indole-5-carboxylic acid quinolin-3-ylamide | 2 | | $1.80 \times 10^3$ | |
| 1-Cyclohexanecarbonyl-2,3-dihydro-1H-indole-5-carboxylic acid quinolin-3-ylamide | 25 | | $1.50 \times 10^3$ | |

TABLE 2-continued

Vanilloid In vitro assay data

| Compound Name | ³H-RTX binding assay | | FLIPR functional assay | |
|---|---|---|---|---|
| | % Inhibition @ 1 μM | Ki hVR1 (nM) | IC$_{50}$ hVR1 (nM) | IC$_{50}$ hVR1 60 min (nM) |
| 1-Cyclohexyl-2,3-dihydro-1H-indole-5-carboxylic acid quinolin-3-ylamide | 103 | $4.87 \times 10^0$ | $4.40 \times 10^1$ | $7.40 \times 10^1$ |
| 1-Isopropyl-2-trifluoromethyl-1H-benzoimidazole-5-carboxylic acid quinolin-3-ylamide | | $3.64 \times 10^2$ | $8.00 \times 10^3$ | |
| 1-Methyl-1,2,3,4-tetrahydro-quinoline-6-carboxylic acid quinolin-3-ylamide | 79 | $3.41 \times 10^2$ | $6.90 \times 10^2$ | |
| 1-Methyl-2,3-dihydro-1H-indole-5-carboxylic acid quinolin-3-ylamide | 12 | | $9.00 \times 10^2$ | |
| 1-Pentyl-1,2,3,4-tetrahydro-quinoline-6-carboxylic acid quinolin-3-ylamide | 93 | $3.91 \times 10^1$ | $1.60 \times 10^3$ | $4.70 \times 10^2$ |
| 1-Pentyl-1H-indole-5-carboxylic acid quinolin-3-ylamide | 95 | $6.31 \times 10^1$ | | $1.50 \times 10^2$ |
| 1-Pentyl-2,3-dihydro-1H-indole-5-carboxylic acid quinolin-3-ylamide | 98 | $2.41 \times 10^1$ | $8.40 \times 10^1$ | $1.06 \times 10^2$ |
| 1-Propyl-2,3-dihydro-1H-indole-5-carboxylic acid quinolin-3-ylamide | 93 | $1.56 \times 10^1$ | $4.10 \times 10^2$ | |
| 2-(4-Dipentylamino-phenyl)-N-quinolin-3-yl-acetamide | | $5.08 \times 10^2$ | | |
| 2-(4-Pentyl-phenyl)-N-quinolin-3-yl-acetamide | | $2.20 \times 10^3$ | | |
| 2-(4-tert-Butyl-phenyl)-N-quinolin-3-yl-acetamide | | $5.76 \times 10^3$ | | |
| 2-(Heptyl-methyl-amino)-N-quinolin-3-yl-benzamide | 0 | | | |
| 2-(Methyl-pentyl-amino)-N-quinolin-3-yl-benzamide | 21 | | | |
| 2,3-Dihydro-1H-indole-5-carboxylic acid quinolin-3-ylamide | 1 | | $1.05 \times 10^4$ | |
| 2-{4-(Methyl-pentyl-amino)-phenyl}-N-quinolin-3-yl-acetamide | | $1.35 \times 10^3$ | | |
| 2-Chloro-4-(cyclohexylmethyl-amino)-N-quinolin-3-yl-benzamide | 65 | $1.13 \times 10^3$ | | |
| 2-Chloro-4-pentylamino-N-quinolin-3-yl-benzamide | 40 | | $1.00 \times 10^4$ | |
| 2-Heptylamino-N-quinolin-3-yl-benzamide | 79 | $1.12 \times 10^3$ | $1.60 \times 10^3$ | $5.00 \times 10^3$ |
| 2-Pentylamino-N-quinolin-3-yl-benzamide | 23 | | | |
| 3-(1-Cyclohexyl-2,3-dihydro-1H-indol-5-yl)-N-quinolin-3-yl-propionamide | | | | |
| 3-(1-Cyclohexylmethyl-2,3-dihydro-1H-indol-5-yl)-N-quinolin-3-yl-propionamide | 61 | $5.12 \times 10^2$ | $1.20 \times 10^3$ | |
| 3-(1-Propyl-1H-indol-5-yl)-N-quinolin-3-yl-propionamide | 59 | $2.64 \times 10^2$ | $4.80 \times 10^2$ | |
| 3-(1-Propyl-2,3-dihydro-1H-indol-5-yl)-N-quinolin-3-yl-propionamide | 51 | $1.07 \times 10^3$ | $1.06 \times 10^3$ | |
| 3-(2,2-Dimethyl-chroman-6-yl)-N-quinolin-3-yl-acrylamide | | | | |
| 3-(2,2-Dimethyl-chroman-6-yl)-N-quinolin-3-yl-propionamide | | | | |
| 3-(4-Azepan-1-yl-phenyl)-N-quinolin-3-yl-acrylamide | | | | |
| 3-(4-Azepan-1-yl-phenyl)-N-quinolin-3-yl-propionamide | | | | |
| 3-(4-Cyclohexylmethyl-phenyl)-N-quinolin-3-yl-propionamide | | $9.41 \times 10^1$ | $6.70 \times 10^2$ | $3.50 \times 10^1$ |
| 3-(4-Dipentylamino-phenyl)-N-quinolin-3-yl-propionamide | | $1.53 \times 10^2$ | | |

TABLE 2-continued

Vanilloid In vitro assay data

| Compound Name | $^3$H-RTX binding assay | | FLIPR functional assay | |
|---|---|---|---|---|
| | % Inhibition @ 1 μM | Ki hVR1 (nM) | IC$_{50}$ hVR1 (nM) | IC$_{50}$ hVR1 60 min (nM) |
| 3-(4-Pentyl-phenyl)-N-quinolin-3-yl-acrylamide | | $4.28 \times 10^2$ | | $5.20 \times 10^3$ |
| 3-(4-Pentyl-phenyl)-N-quinolin-3-yl-propionamide | | $1.81 \times 10^2$ | | $5.90 \times 10^2$ |
| 3-(4-sec-Butyl-phenyl)-N-quinolin-3-yl-propionamide | | $1.39 \times 10^1$ | $1.20 \times 10^3$ | |
| 3-(4-tert-Butyl-phenyl)-N-quinolin-3-yl-acrylamide | | $1.11 \times 10^0$ | | |
| 3-(4-tert-Butyl-phenyl)-N-quinolin-3-yl-propionamide | | $2.03 \times 10^0$ | | |
| 3-(Cyclohexyl-methyl-amino)-N-quinolin-3-yl-benzamide | 89 | $9.82 \times 10^1$ | | |
| 3-(Heptyl-methyl-amino)-N-quinolin-3-yl-benzamide | 82 | $1.42 \times 10^2$ | $8.80 \times 10^3$ | |
| 3-(Methyl-pentyl-amino)-N-quinolin-3-yl-benzamide | 72 | $2.62 \times 10^2$ | $5.00 \times 10^2$ | |
| 3,4,5,6-Tetrahydro-2H-[1,2']bipyridinyl-5'-carboxylic acid quinolin-3-ylamide | 1 | | | |
| 3,4,5,6-Tetrahydro-2H-{1,2'}bipyridinyl-5'-carboxylic acid quinolin-3-ylamide | 100 | $2.05 \times 10^1$ | $4.30 \times 10^3$ | $1.40 \times 10^2$ |
| 3-[4-(Methyl-phenethyl-amino)-phenyl]-N-quinolin-3-yl-propionamide | 90 | $1.92 \times 10^2$ | $1.80 \times 10^2$ | |
| 3-{4-(1,1-Dimethyl-3-phenyl-propyl)-phenyl}-N-quinolin-3-yl-propionamide | | $1.59 \times 10^1$ | | |
| 3-{4-(1,1-Dimethyl-pentyl)-2,6-dimethoxy-phenyl}-N-quinolin-3-yl-propionamide | 96 | $1.06 \times 10^1$ | $1.00 \times 10^3$ | |
| 3-{4-(1,1-Dimethyl-pentyl)-phenyl}-N-quinolin-3-yl | | $4.03 \times 10^1$ | $1.14 \times 10^2$ | |
| 3-{4-(1,1-Dimethyl-propyl)-2,6-dimethoxy-phenyl}-N-quinolin-3-yl-propionamide | 93 | $5.20 \times 10^1$ | $3.20 \times 10^2$ | |
| 3-{4-(1,1-Dimethyl-propyl)-phenyl}-N-quinolin-3-yl-propionamide | | $5.24 \times 10^0$ | $3.67 \times 10^1$ | $3.00 \times 10^1$ |
| 3-{4-(1-Cyclohexyl-1-methyl-ethyl)-phenyl}-N-quinolin-3-yl-propionamide | | $3.15 \times 10^1$ | $5.70 \times 10^2$ | |
| 3-{4-(1-Methyl-pentyl)-phenyl}-N-quinolin-3-yl-propionamide | | $1.32 \times 10^1$ | $1.10 \times 10^3$ | |
| 3-{4-(1-Methyl-pentyl)-phenyl}-N-quinolin-3-yl-propionamide | | $1.50 \times 10^1$ | $1.00 \times 10^4$ | |
| 3-{4-(Benzyl-methyl-amino)-phenyl}-N-quinolin-3-yl-propionamide | | $1.11 \times 10^2$ | $3.54 \times 10^2$ | |
| 3-{4-(Cyclohexyl-methyl-amino)-phenyl}-N-quinolin-3-yl-acrylamide | 91 | $1.31 \times 10^2$ | | $4.00 \times 10^2$ |
| 3-{4-(Cyclohexyl-methyl-amino)-phenyl}-N-quinolin-3-yl-propionamide | 51 | $1.17 \times 10^3$ | $3.90 \times 10^3$ | |
| 3-{4-(Cyclohexylmethyl-methyl-amino)-phenyl}-N-quinolin-3-yl-propionamide | | $8.15 \times 10^1$ | $2.60 \times 10^2$ | $3.90 \times 10^2$ |
| 3-{4-(Methyl-pentyl-amino)-phenyl}-N-quinolin-3-yl-acrylamide | 65 | $1.22 \times 10^2$ | | |
| 3-{4-(Methyl-pentyl-amino)-phenyl}-N-quinolin-3-yl-propionamide | | $1.78 \times 10^2$ | $1.10 \times 10^3$ | $1.90 \times 10^2$ |
| 3-{4-(Methyl-propyl-amino)-phenyl}-N-quinolin-3-yl-propionamide | | $1.96 \times 10^2$ | $5.00 \times 10^2$ | |
| 3-{5-(1,1-Dimethyl-propyl)-thiophen-2-yl}-N-quinolin-3-yl-propionamide | | $1.42 \times 10^1$ | | |

TABLE 2-continued

Vanilloid In vitro assay data

| Compound Name | $^3$H-RTX binding assay % Inhibition @ 1 μM | $^3$H-RTX binding assay Ki hVR1 (nM) | FLIPR functional assay IC$_{50}$ hVR1 (nM) | FLIPR functional assay IC$_{50}$ hVR1 60 min (nM) |
|---|---|---|---|---|
| 3-Cyclohexylamino-N-quinolin-3-yl-benzamide | 1 | | $3.20 \times 10^3$ | |
| 3-Dipentylamino-N-quinolin-3-yl-benzamide | 93 | $1.07 \times 10^2$ | | $2.60 \times 10^2$ |
| 3-Heptylamino-N-quinolin-3-yl-benzamide | 20 | | $1.00 \times 10^4$ | |
| 3-Indan-5-yl-N-quinolin-3-yl-propionamide | | $1.58 \times 10^2$ | $1.00 \times 10^4$ | |
| 3-Methyl-4-(methyl-pentyl-amino)-N-quinolin-3-yl-benzamide | 107 | $3.79 \times 10^1$ | $5.40 \times 10^1$ | |
| 3-Methyl-4-pentylamino-N-quinolin-3-yl-benzamide | 81 | $7.35 \times 10^1$ | $7.80 \times 10^2$ | $1.20 \times 10^1$ |
| 3-Pentylamino-N-quinolin-3-yl-benzamide | 12 | | $2.70 \times 10^3$ | |
| 4-(1,3-Dihydro-isoindol-2-yl)-N-quinolin-3-yl-benzamide | 1 | | | |
| 4-(1,4-Dioxa-8-aza-spiro[4.5]dec-8-yl)-N-quinolin-3-yl-benzamide | 9 | | | |
| 4-(2,6-Dimethyl-morpholin-4-yl)-N-quinolin-3-yl-benzamide | 18 | | $1.00 \times 10^4$ | |
| 4-(3,5-Dimethyl-piperidin-1-yl)-N-quinolin-3-yl-benzamide | 91 | $8.61 \times 10^1$ | $1.80 \times 10^3$ | |
| 4-(3-Aza-bicyclo{3.3.1}non-3-yl)-N-quinolin-3-yl-benzamide | 99 | $5.15 \times 10^0$ | $1.70 \times 10^2$ | $1.27 \times 10^2$ |
| 4-(3-Methyl-piperidin-1-yl)-N-quinolin-3-yl-benzamide | 78 | | | |
| 4-(4-Benzoyl-piperidin-1-yl)-N-quinolin-3-yl-benzamide | 61 | $2.76 \times 10^2$ | | |
| 4-(4-Benzyl-piperidin-1-yl)-N-quinolin-3-yl-benzamide | 99 | $1.76 \times 10^1$ | | $3.57 \times 10^2$ |
| 4-(4-Phenylacetyl-piperazin-1-yl)-N-quinolin-3-yl-benzamide | | $1.00 \times 10^5$ | $1.00 \times 10^4$ | |
| 4-(4-Phenyl-piperidin-1-yl)-N-quinolin-3-yl-benzamide | 34 | $2.93 \times 10^4$ | | |
| 4-(4-Propyl-piperidin-1-yl)-N-quinolin-3-yl-benzamide | 92 | $1.03 \times 10^2$ | $1.60 \times 10^4$ | $1.70 \times 10^2$ |
| 4-(Acetyl-cyclohexyl-amino)-N-quinolin-3-yl-benzamide | 1 | | $1.00 \times 10^4$ | |
| 4-(Benzyl-methyl-amino)-N-quinolin-3-yl-benzamide | 98 | $7.53 \times 10^1$ | $2.30 \times 10^3$ | $3.70 \times 10^2$ |
| 4-(Benzyl-pentyl-amino)-N-quinolin-3-yl-benzamide | 67 | $1.69 \times 10^2$ | | |
| 4-(Cycloheptyl-methyl-amino)-N-quinolin-3-yl-benzamide | 100 | $1.40 \times 10^1$ | $4.00 \times 10^2$ | |
| 4-(Cyclohexanecarbonyl-methyl-amino)-N-quinolin-3-yl-benzamide | | | | |
| 4-(Cyclohexyl-ethyl-amino)-N-quinolin-3-yl-benzamide | | $1.26 \times 10^1$ | $3.00 \times 10^2$ | |
| 4-(Cyclohexylmethyl-amino)-3-methyl-N-quinolin-3-yl-benzamide | 111 | $8.70 \times 10^1$ | | |
| 4-(Cyclohexyl-methyl-amino)-3-methyl-N-quinolin-3-yl-benzamide | | $2.20 \times 10^1$ | $5.60 \times 10^2$ | $2.30 \times 10^1$ |
| 4-(Cyclohexyl-methyl-amino)-N-methyl-N-quinolin-3-yl-benzamide | 12 | | $2.00 \times 10^3$ | |
| 4-(Cyclohexyl-methyl-amino)-N-quinolin-3-yl-benzamide | | $1.03 \times 10^1$ | $4.65 \times 10^2$ | $2.20 \times 10^1$ |
| 4-(Cyclohexylmethyl-methyl-amino)-3-methyl-N-quinolin-3-yl-benzamide | | $6.83 \times 10^1$ | $1.00 \times 10^4$ | |
| 4-(Cyclohexylmethyl-methyl-amino)-N-quinolin-3-yl-benzamide | 104 | $1.57 \times 10^1$ | $1.70 \times 10^3$ | |
| 4-(Cyclohexylmethyl-phenethyl-amino)-N-quinolin-3-yl-benzamide | 87 | $1.62 \times 10^2$ | | |

TABLE 2-continued

Vanilloid In vitro assay data

| Compound Name | $^3$H-RTX binding assay % Inhibition @ 1 μM | $^3$H-RTX binding assay Ki hVR1 (nM) | FLIPR functional assay IC$_{50}$ hVR1 (nM) | FLIPR functional assay IC$_{50}$ hVR1 60 min (nM) |
|---|---|---|---|---|
| 4-(Cyclohexyl-propyl-amino)-N-quinolin-3-yl-benzamide | | $8.46 \times 10^1$ | $1.00 \times 10^4$ | |
| 4-(Cyclopentyl-methyl-amino)-N-quinolin-3-yl-benzamide | | $2.79 \times 10^1$ | $1.85 \times 10^2$ | |
| 4-(Dec-4-enyl-methyl-amino)-N-quinolin-3-yl-benzamide | 104 | $2.31 \times 10^1$ | | $6.60 \times 10^1$ |
| 4-(Hept-4-enyl-methyl-amino)-N-quinolin-3-yl-benzamide | 104 | $2.98 \times 10^1$ | $1.90 \times 10^3$ | $4.60 \times 10^1$ |
| 4-(Heptyl-methyl-amino)-N-quinolin-3-yl-benzamide | 101 | $2.45 \times 10^1$ | $1.00 \times 10^4$ | $1.16 \times 10^2$ |
| 4-(Methyl-butyl-amino)-N-quinolin-3-yl-benzamide | 97 | $8.33 \times 10^1$ | $7.86 \times 10^2$ | $1.00 \times 10^2$ |
| 4-(Methyl-hexyl-amino)-N-quinolin-3-yl-benzamide | 98 | $7.01 \times 10^1$ | $1.30 \times 10^3$ | $8.60 \times 10^1$ |
| 4-(Methyl-non-6-enyl-amino)-N-quinolin-3-yl-benzamide | 101 | $3.65 \times 10^1$ | | $4.80 \times 10^1$ |
| 4-(Methyl-nonyl-amino)-N-quinolin-3-yl-benzamide | 101 | $2.32 \times 10^1$ | | $1.50 \times 10^2$ |
| 4-(Methyl-pentyl-amino)-N-quinolin-3-yl-benzamide | | $1.03 \times 10^2$ | $4.30 \times 10^2$ | $1.32 \times 10^2$ |
| 4-(Methyl-phenethyl-amino)-N-quinolin-3-yl-benzamide | 101.500000 | $2.73 \times 10^1$ | $1.90 \times 10^3$ | $7.20 \times 10^1$ |
| 4-(Methyl-propyl-amino)-N-quinolin-3-yl-benzamide | 91 | $2.67 \times 10^2$ | $8.80 \times 10^3$ | $3.90 \times 10^2$ |
| 4-(Methyl-tetradecyl-amino)-N-quinolin-3-yl-benzamide | 23 | $1.47 \times 10^3$ | | $1.00 \times 10^4$ |
| 4-(Octyl-methyl-amino)-N-quinolin-3-yl-benzamide | 105 | $1.47 \times 10^1$ | | $1.90 \times 10^2$ |
| 4-(Phenethyl-propyl-amino)-N-quinolin-3-yl-benzamide | 105 | $7.16 \times 10^1$ | | $3.60 \times 10^2$ |
| 4-[1,4']Bipiperidinyl-1'-yl-N-quinolin-3-yl-benzamide | 8 | | | |
| 4-{(3,3-Dimethyl-butyl)-methyl-amino}-N-quinolin-3-yl-benzamide | 99 | $2.09 \times 10^1$ | $1.00 \times 10^4$ | $1.30 \times 10^3$ |
| 4-{4-(1,1-Dimethyl-pentyl)-phenyl}-but-3-enoic acid quinolin-3-ylamide | 80 | $1.94 \times 10^2$ | | |
| 4-{4-(1,1-Dimethyl-pentyl)-phenyl}-N-quinolin-3-yl-butyramide | 82 | $2.21 \times 10^2$ | $1.00 \times 10^4$ | |
| 4-{4-(1,1-Dimethyl-propyl)-phenyl}-but-3-enoic acid quinolin-3-ylamide | 55 | $1.37 \times 10^2$ | $1.00 \times 10^4$ | |
| 4-{4-(1,1-Dimethyl-propyl)-phenyl}-N-quinolin-3-yl-butyramide | 65 | $5.27 \times 10^2$ | | |
| 4-{Methyl-(3-methyl-butyl)-amino}-N-quinolin-3-yl-benzamide | 90 | $5.54 \times 10^2$ | $2.80 \times 10^2$ | |
| 4-{Methyl-(3-phenyl-allyl)-amino}-N-quinolin-3-yl-benzamide | 79 | $1.25 \times 10^2$ | | |
| 4-{Methyl-(3-phenyl-propyl)-amino}-N-quinolin-3-yl-benzamide | 97 | $7.41 \times 10^1$ | $1.00 \times 10^4$ | $1.56 \times 10^2$ |
| 4-{Methyl-(tetrahydro-pyran-4-yl)-amino}-N-quinolin-3-yl-benzamide | 19 | | | |
| 4-{Methyl-{3-(5-methyl-furan-2-yl)-butyl}-amino}-N-quinolin-3-yl-benzamide | 102 | $3.12 \times 10^1$ | $1.50 \times 10^3$ | |
| 4-Azepan-1-yl-N-quinolin-3-yl-benzamide | 96 | $1.79 \times 10^1$ | $2.30 \times 10^3$ | $2.10 \times 10^2$ |
| 4-Azepan-1-yl-N-quinolin-3-yl-benzamide | | $5.90 \times 10^0$ | $5.31 \times 10^3$ | $1.11 \times 10^2$ |
| 4-Azocan-1-yl-N-quinolin-3-yl-benzamide | | $1.85 \times 10^1$ | $2.90 \times 10^2$ | |
| 4-Azonan-1-yl-N-quinolin-3-yl-benzamide | | $1.18 \times 10^1$ | $9.20 \times 10^1$ | |

TABLE 2-continued

Vanilloid In vitro assay data

| Compound Name | $^3$H-RTX binding assay | | FLIPR functional assay | |
|---|---|---|---|---|
| | % Inhibition @ 1 μM | Ki hVR1 (nM) | IC$_{50}$ hVR1 (nM) | IC$_{50}$ hVR1 60 min (nM) |
| 4-Benzyl-3,4,5,6-tetrahydro-2H-{1,2'}bipyridinyl-5'-carboxylic acid quinolin-3-ylamide | 100 | $2.56 \times 10^1$ | $4.40 \times 10^2$ | |
| 4-Butoxy-N-quinolin-3-yl-benzamide | | $1.55 \times 10^2$ | $1.00 \times 10^4$ | |
| 4-Butyl-cyclohexanecarboxylic acid quinolin-3-ylamide | 81 | $1.24 \times 10^2$ | $1.70 \times 10^2$ | |
| 4-Butyl-cyclohexanecarboxylic acid quinolin-3-ylamide | 81 | $1.24 \times 10^2$ | $1.70 \times 10^2$ | |
| 4-Cycloheptylamino-N-quinolin-3-yl-benzamide | | | $7.30 \times 10^2$ | |
| 4-Cyclohexylamino-N-methyl-N-quinolin-3-yl-benzamide | | $2.16 \times 10^3$ | $1.00 \times 10^4$ | |
| 4-Cyclohexylamino-N-quinolin-3-yl-benzamide | 77 | $1.56 \times 10^2$ | | |
| 4-Cyclopentylamino-N-quinolin-3-yl-benzamide | 32 | | $3.20 \times 10^3$ | |
| 4-Dibenzylamino-N-quinolin-3-yl-benzamide | 51 | $4.41 \times 10^2$ | | $4.20 \times 10^3$ |
| 4-Dibutylamino-N-quinolin-3-yl-benzamide | | $2.41 \times 10^2$ | $4.60 \times 10^3$ | $2.70 \times 10^2$ |
| 4-Dihexylamino-N-quinolin-3-yl-benzamide | 74 | $1.85 \times 10^2$ | | $2.90 \times 10^3$ |
| 4-Dipentylamino-N-quinolin-3-yl-benzamide | | $1.58 \times 10^2$ | | |
| 4-Dipropylamino-N-quinolin-3-yl-benzamide | | $2.19 \times 10^2$ | $6.10 \times 10^2$ | $1.66 \times 10^2$ |
| 4-Morpholin-4-yl-N-quinolin-3-yl-benzamide | 4 | | | |
| 4-Pentylamino-N-quinolin-3-yl-benzamide | | $8.76 \times 10^2$ | $8.10 \times 10^3$ | $3.00 \times 10^4$ |
| 4-Phenethylamino-N-quinolin-3-yl-benzamide | 31 | | $9.20 \times 10^3$ | |
| 4-Piperazin-1-yl-N-quinolin-3-yl-benzamide | 1 | | $7.40 \times 10^2$ | |
| 4-Piperidin-1-yl-N-quinolin-3-yl-benzamide | 60 | $6.12 \times 10^1$ | | |
| 4-Propyl-3,4,5,6-tetrahydro-2H-{1,2'}bipyridinyl-5'-carboxylic acid quinolin-3-ylamide | 93 | $1.17 \times 10^2$ | $4.90 \times 10^2$ | |
| 4-Pyrrolidin-1-yl-N-quinolin-3-yl-benzamide | 27 | | | |
| 4-tert-Butyl-cyclohexanecarboxylic acid quinolin-3-ylamide | 97 | $6.49 \times 10^1$ | $1.00 \times 10^4$ | |
| 4-tert-Butyl-cyclohexanecarboxylic acid quinolin-3-ylamide | 97 | $6.49 \times 10^1$ | $1.00 \times 10^4$ | |
| 5,5,8,8-Tetramethyl-5,6,7,8-tetrahydro-naphthalene-2-carboxylic acid quinolin-3-ylamide | | $3.04 \times 10^1$ | | |
| 5,6,7,8-Tetrahydro-naphthalene-2-carboxylic acid quinolin-3-ylamide | | $6.23 \times 10^1$ | $1.00 \times 10^4$ | |
| 5-Chloro-1H-indole-2-carboxylic acid quinolin-3-ylamide | 36 | | $2.80 \times 10^3$ | |
| 5-Pentyl-thiophene-2-carboxylic acid quinolin-3-ylamide | 57 | $6.47 \times 10^2$ | $9.00 \times 10^2$ | |
| 6-(3-Aza-bicyclo{3.3.1}non-3-yl)-N-quinolin-3-yl-nicotinamide | 80 | $9.86 \times 10^0$ | $3.70 \times 10^3$ | $2.79 \times 10^2$ |
| 6-(Benzyl-methyl-amino)-N-quinolin-3-yl-nicotinamide | 43 | | $3.90 \times 10^2$ | |
| 6-(Cyclohexyl-methyl-amino)-N-quinolin-3-yl-nicotinamide | 99 | $3.59 \times 10^1$ | $3.00 \times 10^2$ | |
| 6-(Cyclohexyl-methyl-amino)-N-quinolin-3-yl-nicotinamide | | $2.18 \times 10^2$ | $2.45 \times 10^2$ | |
| 6-(Heptyl-methyl-amino)-N-quinolin-3-yl-nicotinamide | 90 | $9.73 \times 10^1$ | $1.50 \times 10^3$ | |
| 6-(Methyl-pentyl-amino)-N-quinolin-3-yl-nicotinamide | 91 | $1.22 \times 10^2$ | $4.00 \times 10^2$ | |

TABLE 2-continued

Vanilloid In vitro assay data

| Compound Name | $^3$H-RTX binding assay % Inhibition @ 1 μM | $^3$H-RTX binding assay Ki hVR1 (nM) | FLIPR functional assay IC$_{50}$ hVR1 (nM) | FLIPR functional assay IC$_{50}$ hVR1 60 min (nM) |
|---|---|---|---|---|
| 6-(Methyl-phenethyl-amino)-N-quinolin-3-yl-nicotinamide | 97 | $2.43 \times 10^2$ | $1.20 \times 10^3$ | $5.40 \times 10^2$ |
| 6-Azepan-1-yl-N-quinolin-3-yl-nicotinamide | 44 | $1.24 \times 10^2$ | $2.15 \times 10^2$ | |
| 6-Azocan-1-yl-N-quinolin-3-yl-nicotinamide | 102 | $3.04 \times 10^1$ | $5.16 \times 10^3$ | $2.50 \times 10^2$ |
| 6-Cyclohexylamino-N-quinolin-3-yl-nicotinamide | 1 | | $9.90 \times 10^2$ | |
| 6-Pentylamino-N-quinolin-3-yl-nicotinamide | 57 | $2.81 \times 10^5$ | | $8.00 \times 10^3$ |
| cis-4-(Octahydro-isoquinolin-2-yl)-N-quinolin-3-yl-benzamide | 105 | $4.56 \times 10^1$ | $1.85 \times 10^2$ | $2.20 \times 10^2$ |
| cis-6-(Octahydro-isoquinolin-2-yl)-N-quinolin-3-yl-nicotinamide | 99 | $3.68 \times 10^1$ | $4.20 \times 10^2$ | |
| N-Quinolin-3-yl-3-(3-trifluoromethyl-phenyl)-acrylamide | | | | |
| N-Quinolin-3-yl-3-(4-tricyclo{5.3.1.13,9}dodec-1-yl-phenyl)-propionamide | | $1.76 \times 10^2$ | | $1.90 \times 10^3$ |
| N-Quinolin-3-yl-3-(4-trifluoromethyl-phenyl)-acrylamide | | | | |
| N-Quinolin-3-yl-3-(5,5,8,8-tetramethyl-5,6,7,8-tetrahydro-naphthalen-2-yl)-propionamide | | $1.30 \times 10^1$ | $7.00 \times 10^1$ | |
| N-Quinolin-3-yl-3-(5,6,7,8-tetrahydro-naphthalen-2-yl)-propionamide | | $2.00 \times 10^2$ | $1.00 \times 10^4$ | |
| N-Quinolin-3-yl-4-(tetrahydro-pyran-4-ylamino)-benzamide | 9 | | | |
| N-Quinolin-3-yl-4-thiomorpholin-4-yl-benzamide | 41 | | | |
| R-4-{(3,7-Dimethyl-oct-6-enyl)-methyl-amino}-N-quinolin-3-yl-benzamide | 105 | $1.11 \times 10^1$ | | |
| S-4-{(3,7-Dimethyl-oct-6-enyl)-methyl-amino}-N-quinolin-3-yl-benzamide | 105 | $1.29 \times 10^1$ | | $1.50 \times 10^2$ |
| trans-4-(Octahydro-isoquinolin-2-yl)-N-quinolin-3-yl-benzamide | 104 | $2.92 \times 10^1$ | | |
| trans-6-(Octahydro-isoquinolin-2-yl)-N-quinolin-3-yl-nicotinamide | 104 | $3.32 \times 10^1$ | $8.50 \times 10^1$ | |
| 1-Cyclohexyl-1H-indole-5-carboxylic acid (4-chloro-quinolin-3-yl)-amide | | | $1.66 \times 10^2$ | |
| N-(4-Chloro-quinolin-3-yl)-4-(cyclohexyl-methyl-amino)-benzamide | | | $1.07 \times 10^2$ | |
| N-Quinolin-3-yl-3-(5,5,8,8-tetramethyl-5,6,7,8-tetrahydro-naphthalen-2-yl)-acrylamide | | | $6.50 \times 10^1$ | |
| N-(4-Chloro-quinolin-3-yl)-3-(5,5,8,8-tetramethyl-5,6,7,8-tetrahydro-naphthalen-2-yl)-acrylamide | | | $3.00 \times 10^1$ | |
| 3-(4-tert-Butyl-phenyl)-propynoic acid quinolin-3-ylamide | | | $6.60 \times 10^1$ | |
| 1-Cyclohexyl-1H-indole-5-carboxylic acid quinolin-3-ylamide | | | $7.40 \times 10^1$ | |

Example 277

Carrageenan Paw-induced Thermal Hyperalgesia

The hot-plate test originally described by Eddy and Leimbach (*J. Pharmacol. Exp. Ther.* 107:385-393, 1953) with minor modifications (e.g., O'Callaghan and Holtzman, *J. Pharmacol. Exp. Ther.* 192: 497-505, 1975) is used to ascertain the analgesic potential of compounds. Generally this procedure is most sensitive to centrally-acting analgesics (e.g., opioids) in that other compounds are inactive in this test. Thus, any activity demonstrated by a compound in this test which is shown to be nonopioid-like (i.e., not naloxone reversible) represents a potentially novel analgesic agent.

Generally, male, Swiss-derived albino mice (CRS-CD1®; Charles River Laboratories), weighing 18-24 g at the time of testing or male Sprague Dawley rats (CD1, Charles River Laboratories) 100-300 g are used. The animals are weighed, placed in a plastic box with wood chips (typically 10 mice or 4-6 rats per box) and allowed to acclimate before testing. The hot-plate (e.g., Technilab instruments, Inc.) is maintained at some preset temperature, usually 48±0.5° C., 52.5±0.5° C. or 55±0.5° C. for mice and 51±0.5° C. for rats.

An animal is placed on the heated surface and the time interval between placement and a shaking, licking or tucking of the hindpaw is recorded as the control reaction time ($RT_C$). The reaction time of drug-treated animals is compared to the reaction time of untreated animals or to the animals own predrug latency. A 'cut-off' time is established to prevent injury to the animals tail: 90 sec for the 48° C. test (based on control reaction times generally between 25 and 40 sec) and 60 sec for the 55° C. test (based on control reaction times generally between 10 and 20 sec). A reaction time for drug-treated animals greater than 3 SD from the mean of the control reaction time for all the animals in the group is the criterion for an analgesic response (% analgesia) according to the formula:

% analgesia=100×(No. of animals at criterion)/(No. animals in group).

A percent maximum possible effect (% MPE) can also be calculated from the following formula:

% $MPE=100\times(RTdc-RTc)/(CO-RTc)$, where RTdc and RTc are drug-treated and control reaction times, respectively, and CO is cut-off time.

As a screen, the largest possible nontoxic dose of test drug is administered. If activity is detected, and if appropriate, generally 3-5 doses (usually 10 mice or 6-8 rats per dose) are used to construct a dose response curve or time course. Appropriate computer-assisted analysis (e.g., SAS Probit Analysis for quantal data or EDPLOT for graded data) is used to calculate ED50 values and 95% confidence interval (C.I.). The ED50 value is determined at the time of peak effect. Representative ED50 values for some reference compounds in mice are listed below:

| Compound | Route | Pre-treat time (min) | ED50 (95% C.I.) |
|---|---|---|---|
| Morphine | i.p. | 30 | 4.1 (2.7-6.9) |
| Codeine | i.p. | 30 | 16.5 (11.2-25.2) |
| Pentazocine | i.p. | 30 | 32.7 (10.8-91.9) |
| Zomepirac | i.p. | 30 | inactive |

Results

| Compound | dose (mg/kg) | route | % Recovery |
|---|---|---|---|
| 4-(Methyl-pentyl-amino)-N-quinolin-3-yl-benzamide | 10 | sc | 83 |
| 4-(Cyclohexyl-methyl-amino)-N-quinolin-3-yl-benzamide | 30 | po | 55 |
| 3-{4-(Methyl-pentyl-amino)-phenyl}-N-quinolin-3-yl-propionamide | 30 | po | 58 |
| 4-(Methyl-phenethyl-amino)-N-quinolin-3-yl-benzamide | 10 | po | 42 |
| 4-(4-Benzyl-piperidin-1-yl)-N-quinolin-3-yl-benzamide | 10 | po | 64 |
| 3-{4-(Cyclohexylmethyl-methyl-amino)-phenyl}-N-quinolin-3-yl-propionamide | 20 | po | 87 |
| 4-Azepan-1-yl-N-quinolin-3-yl-benzamide | 1 | po | 46 |
| 3-{4-(1,1-Dimethyl-propyl)-phenyl}-N-quinolin-3-yl-propionamide | 30 | po | 47 |
| 1-Pentyl-2,3-dihydro-1H-indole-5-carboxylic acid quinolin-3-ylamide | 10 | po | 52 |
| 3-(4-Chloro-3-trifluoromethyl-phenyl)-N-quinolin-3-yl-acrylamide | 10 | po | 58 |
| 3-(4-tert-Butyl-phenyl)-N-(4-chloro-quinolin-3-yl)-acrylamide | 10 | po | 70 |

Example (278)

Intraplantar Inflammatory Hyperalgesia Testing

Rats and mice are allowed to become familiar with the conduct of the testing protocol and the experimental equipment. This preconditioning is meant to reduce the confounding effect of stress and novelty on the behavioral assessments being undertaken. Following preconditioning, baseline behavioral responses to either thermal (radiant light or hot/cold plate) or mechanical (paw pressure or von Frey filament) stimulation are recorded. Additionally, to minimize animal number requirements non-noxious passive measures (paw volume, weight bearing, activity monitoring) may be collected where they do not interfere with the evoked sensory endpoints. The subjects then receive a unilateral intraplantar injection of inflammogen (e.g. carrageenan, zymosan, or Freund's Complete Adjuvant) or neuronal sensitizing agent (e.g., capsaicin, inflammatory cytokine, neuropeptide or neurokinin) to initiate a localized inflammatory/sensitization response in a single hind paw. Following a defined period, behavioral responses are again assessed to verify shortened thermal latencies or reduced mechanical thresholds indicative of hyperalgesia and/or increased paw volume associated with edema. Test compound or vehicle administration is followed by behavioral assessment at defined times (e.g., one or two hours). The test may also be run using prophylactic dosing to assess the ability of test compounds to prevent the development of inflammatory hyperalgesia. Note that the incubation period relating to the time of peak hyperalgesia ranges from minutes following capsaicin, to ~4 hours following carrageenan or zymosan. The hyperalgesia produced by these inflammogens is self-limiting and resolves by 6-8 hours post-injection. Freund's Complete Adjuvant (CFA), which has a more lengthily course of action, may be studied over a longer time period, especially for repeated dose studies.

Thermal sensitivities: each animal's latency to respond (by lifting or licking of foot or jumping) is assessed when placed on a heated surface (up to 55° C.) or cooled surface (down to 1 C). In experiments where comparisons between individual hind paws are required, a radiant thermal stimulus (beam of light) focused on the sole of each hind paw in turn is utilized. Mechanical sensitivities: response thresholds to mechanical pressure are determined using the Randall-Selitto method wherein a Paw Pressure Instrument applies a gradually increasing force to the subject's hind paw. A deliberate paw withdrawal or vocalization is considered a positive response, at which time the test is stopped and the gram-force is recorded. A reduced response threshold to this graded stimulus following inflammation is considered mechanical hyperalgesia. Alternatively, von Frey filaments (a set of fibers providing a graduated series of bending forces) or an electronic version thereof may be applied to the sole of the foot to detect alterations in mechanical response thresholds below the noxious level. Mechanical allodynia is defined as the perception of pain ascribed to a normally non-noxious mechanical stimulus.

Passive measures: 1) paw volume measurements are obtained using an automated volume displacement device wherein the subject is held elevated above a small fluid reservoir and each hind paw is submerged in turn providing a direct digital readout of paw volume (mL). Post-inflammation paw volumes are compared to baseline and contralateral paw volumes to determine the level of edema. 2) weight-bearing test (rats only) utilizes the "incapacitence meter" (Stoelting) to simultaneously measure the distribution of body weight on the two hind paws. Postural favoring of the inflamed paw can thusly be quantified in grams. 3) open field ambulatory activity is a measure of willingness to use an inflamed paw. Automated activity monitoring boxes count photocell beam interruptions to quantitate both horizontal and vertical (rearing) activity levels.

Test compound administration: compounds are typically administered orally, however under special circumstances other routes of administration (s.c., i.p., i.m., i.v., i.t., i.c.v, topical) or combinations of agents are utilized.

Example 279

Guinea Pig Bronchial Ring Constriction

Figure 7:
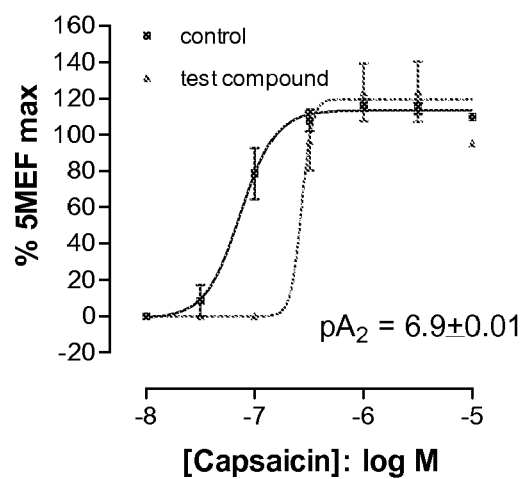
FIG. 7. Effect of a compound of the invention on guinea pig bronchial ring constriction.

Two mm rings of bronchial tissue obtained from male guinea pigs were suspended in normal Krebs solution between two wire hooks under an initial loading tension of 1 gram. The saline was maintained in a 5% $CO_2$ and 95% $O_2$ atmosphere at 37° C. in the presence of indomethacin (5 µM). A sub-maximal dose of 5-methylfurmethide (5 Mef, 1 µM) was added to each tissue to determine responsiveness using an isometric force transducer. After washout, tissues were exposed to compounds or vehicle for 30 min and treated with thiorphan (10 µM, 5% $Na_2CO_3$). A concentration-response curve was then constructed using capsaicin (10 nM-10 µM) increasing in 0.5 log unit increments. The dose response curve was calculated as % max of the 5-Mef response and estimated $pA_2$ were determined. As shown in FIG. 7, 4-(3-Aza-bicyclo[3.3.1]non-3-yl)-N-quinolin-3-yl-benzamide shifted the capsaicin dose-response curve to the right, indicative of its antagonism of the capsaicin-induced response.

Example 280

Mouse Colitis Model

Dextran Sulfate Sodium Induced Colitis.

The dextran sulfate sodium model of experimental colitis is characterized by a discontinuous pattern of mucosal epithelial damage in the distal colon, shrinkage of the colon's length, decreases in the wet weight of the colon, infiltration of inflammatory cells that include macrophages and neutrophils into the mucosa and submucosa, and diarrhea (Blumberg, R. S., Saubermann, L. J., and Strober, W., *Current Opinion in Immunology*, 11: 648-656, 1999; Okayasu, I. et al., *Gastroenterology*, 98: 694-702, 1990; Cooper, H. et al., *Lab Invest.*, 69: 238-249, 1993; Egger, B., et al., *Digestion*, 62: 240-248, 2000; Stevceva, L., et al., *BMC Clinical Pathology*, 1: 3-13, 2001). These are similar to what occurs in human colitis.

Balb/c female mice are provided with a solution of tap water containing 5% DSS (ICN chemicals) ad libitum over a 7-day period. During this same time, test animals are administered a preparation of 4-(Cyclohexyl-methyl-amino)-N-quinolin-3-yl-benzamide. This material may be administered orally or intraperitoneally, once or twice daily. At the end of this period, the animals are euthanized and their colons are collected for further analysis. Among the parameters analyzed are the length of the colon starting from 1 cm above the anus to the top of the cecum, the weight of the colon, the consistency of any stools found within the colon, and the gross macroscopic appearance of the colon. The distal colon between the 1st and the 4th centimeter are dissected into two halves. One half is placed in 10% neutral buffered formalin for later histological analysis if desired. The other half is cleaned in a bath of physiological buffer, patted dry, weighed and then placed in a solution of 0.5% hexadecyltrimethylammonium bromide (HTAB; Sigma) dissolved in 50 mM phosphate buffer, adjusted to pH 5.4. The tissue sample thus treated is then frozen at −80° C.

For the following parameters, colon length, colon weight, stool consistency and appearance and macroscopic damage a scoring system is used to describe the changes. The 4 scores for each animal are added to provide a Total Score. Thus, Stool Score:
0=normal (well-formed fecal pellets);
1=loosely-shaped moist pellets;
2=amorphous, moist, sticky pellets;
3=bloody diarrhea. Presence of blood in stool: add 1 to scores <3
Colon Damage Score:
0=no inflammation
1=reddening mild inflammation;
2=moderate inflammation or more widely distributed;
3=severe inflammation and/or extensively distributed
Colon Weight Score:
0=<5% weight loss;
1=5-14% weight loss;
2=15-24% weight loss;
3=25-35% weight loss; 4=>35% weight loss.
Colon Length Score:
0=<5% shortening;
1=5-14% shortening;
2=15-24% shortening;
3=25-35% shortening;
4=>35% shortening.

Colon weight changes and colon length changes are also directly measured and the net changes compared to DSS and untreated controls are used to calculate a % inhibition of colon weight loss or colon shrinkage induced by DSS treatment.

Myeloperoxidase Assay

The tissue sample previously frozen at −80° C. in 0.5% solution of HTAB is thawed, homogenized twice for 15 seconds using a Brinkman Polytron homogenizer fitted with a TS10 generator. The crude homogenate is next sonicated at 60 watts for two 5-second bursts and then centrifuged for 20 minutes at 15000×g. The supernatant of this homogenate is collected, aliquoted and frozen at −70° C. for future analysis for myeloperoxidase analysis (MPO). MPO is an intracellular enzyme found in neutrophils and can be considered a surrogate marker for neutrophil infiltration into tissues, including those afflicted with colitis (Diaz-Granados, et al., 2000).

Results

For FIGS. 1-6, data are from 3 experiments for animals given 5% DSS in their drinking water and dosed with 4-(Cyclohexyl-methyl-amino)-N-quinolin-3-yl-benzamide twice daily, orally at 0.05 mg/kg (n=10), 0.5 mg/kg (n=20), 5 mg/kg (n=30), 10 mg/kig (n=30), or 30 mg/kg (n=20) and are compared to animals administered only 5% DSS (n=30) and animals not administered 5% DSS (n=29).

Statistical analyses were performed by ANOVA using Multiple Comparisons Test and Tukey's test.

The data in FIG. 1 show that there was significant (p<0.05) inhibition of colon weight loss by treatment with 4-(Cyclohexyl-methyl-amino)-N-quinolin-3-yl-benzamide. The prevention or reversal of colon weight loss suggests that the tissues retained normal amounts of water and that the stools are more solid and are retained within the colon. This is thus an indirect measure of correcting increased motility that occurs during colitis.

Figure 2:
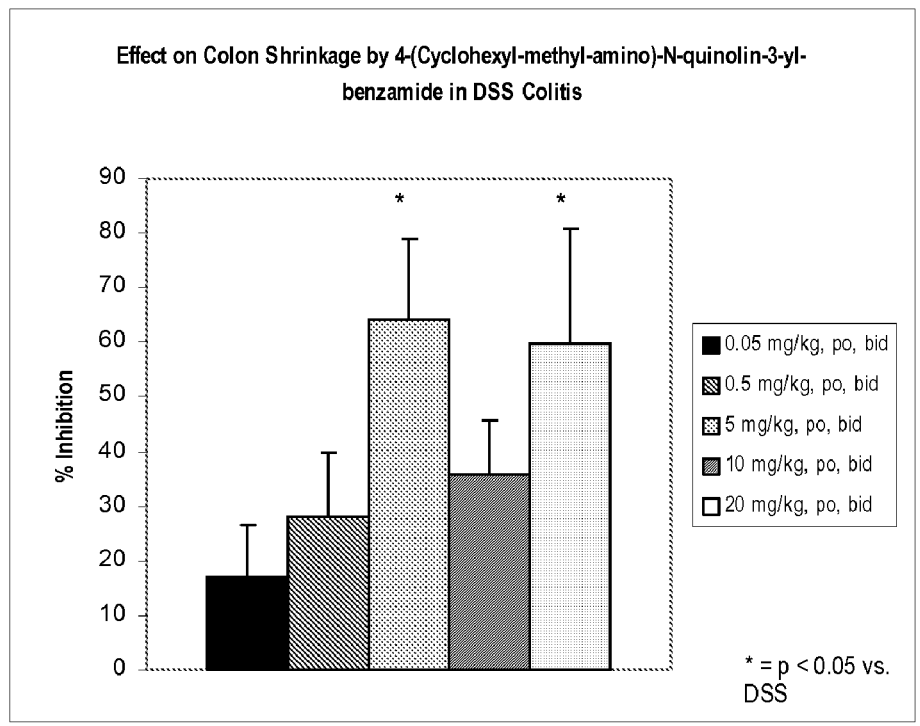
FIG. 2. Effect of a compound of the invention on Colon Length. Data presented are mean % inhibition±s.e. of colon shrinkage from 3 experiments following twice daily oral administration of the compound at the doses indicated FIG. 3. Effect of a compound of the invention on Colon Damage Score. Data presented are mean % inhibition±s.e. of macroscopic colon damage scores from 3 experiments following twice daily oral administration of the compound at the doses indicated.

FIG. 2 shows that there was significant (p<0.05) inhibition of colon shrinkage after treatment with 4-(Cyclohexyl-methyl-amino)-N-quinolin-3-yl-benzamide. Colon shrinkage induced by DSS is an indication of neuronally mediated smooth muscle contraction in the intestine that may be stimulated by inflammation.

Figure 3:
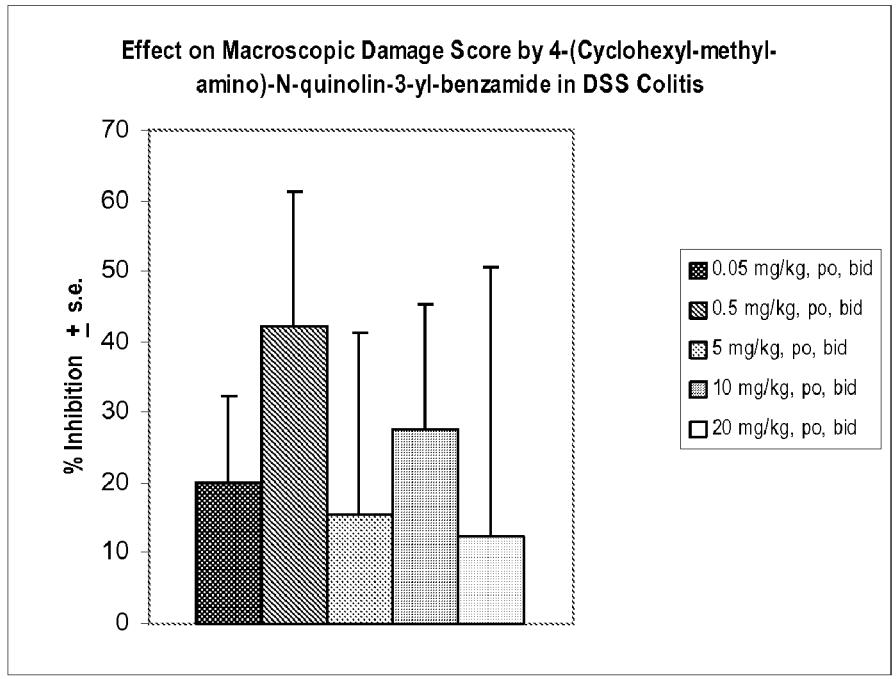

Colon Damage Score was diminished (p>0.05), but not statistically significantly, after treatment with 4-(Cyclohexyl-methyl-amino)-N-quinolin-3-yl-benzamide, as shown in FIG. 3. A decrease in a colon damage score indicates that there was decreased inflammation (reddening) of the tissues, and decreases in the extent of the tissue damage. A lower score indicates improvement compared to DSS alone.

Figure 4:
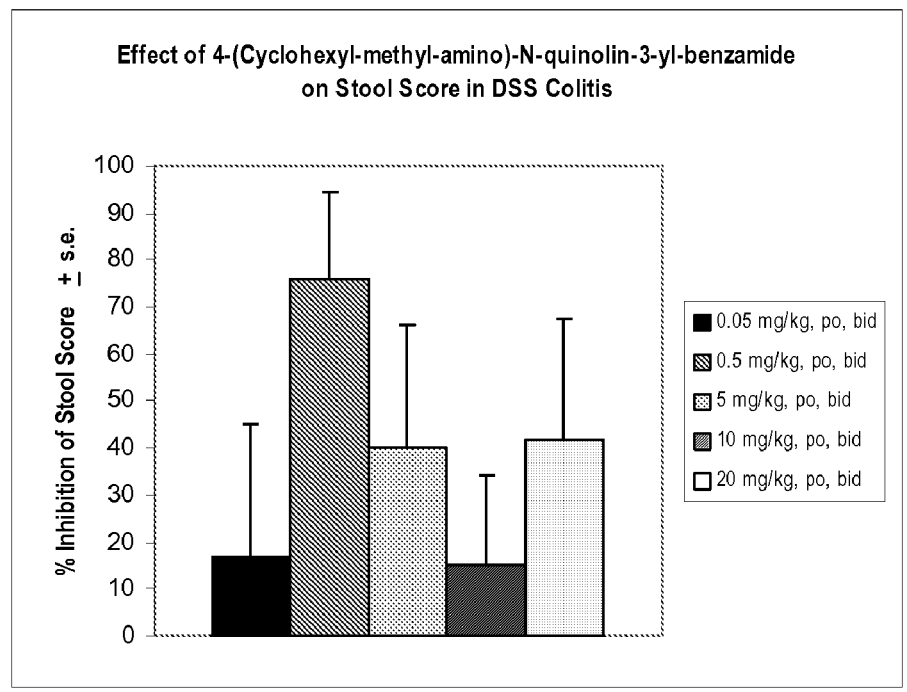
FIG. 4. Effect of a compound of the invention on Stool Score. Data presented are mean % inhibition±s.e. of stool scores from 3 experiments following twice daily oral administration of the compound at the doses indicated.

Stool Score was decreased (p>0.05), but not statistically significantly, after treatment with 4-(Cyclohexyl-methyl-amino)-N-quinolin-3-yl-benzamide, as shown in FIG. 4. A decrease in a stool score indicates that there was decreased evidence of diarrhea or softened stools contained within the colon and increases in firmness of the stool contained therein. This is also an indicator of changes in motility that occurs during colitis and the correction of those changes. A lower score indicates improvement compared to DSS alone.

Figure 5:
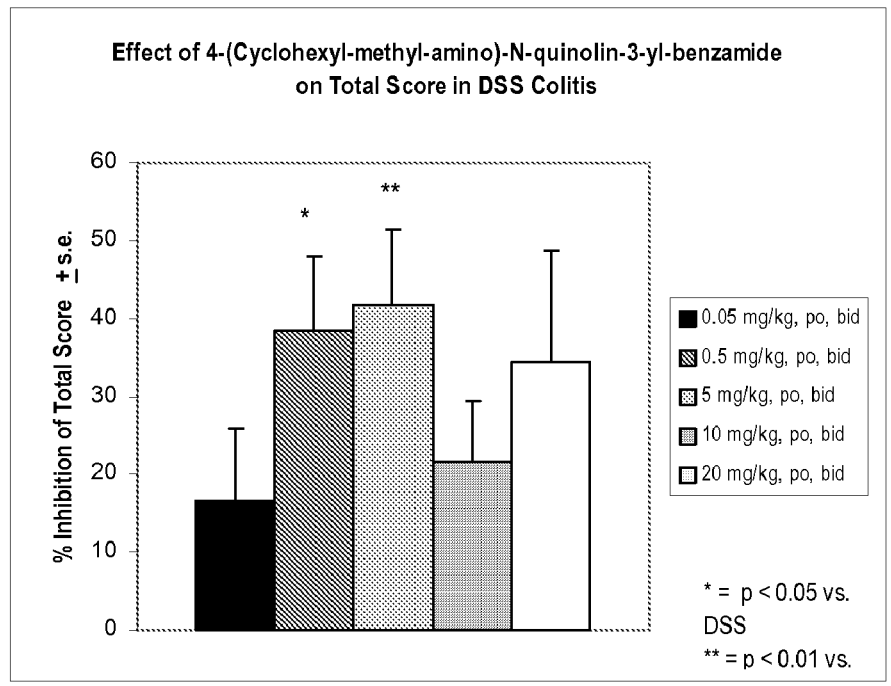
FIG. 5. Effect of a compound of the invention on Total Score. Data presented are mean % inhibition±s.e. of total scores from 3 experiments following twice daily oral administration of the compound at the doses indicated.

There was significant (p<0.05) inhibition of Total Score after treatment with 4-(Cyclohexyl-methyl-amino)-N-quinolin-3-yl-benzamide, as shown in FIG. 5. The total score is the sum of the individual scores and provides an overall assessment of the health or disease state of the subject. A lower score indicates improvement compared to DSS alone.

Figure 6:
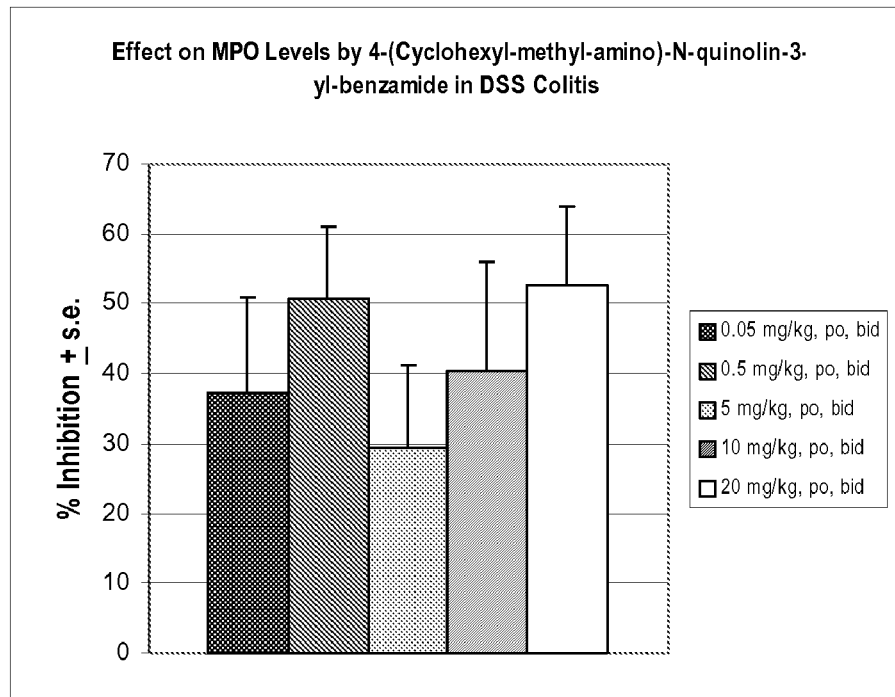
FIG. 6. Effect of a compound of the invention on MPO. Data presented are mean % inhibition±s.e. of MPO accumulation from 3 experiments following twice daily oral administration of the compound at the doses indicated.

Myleoperoxidase (MPO) inhibition (p>0.05) after treatment with 4-(Cyclohexyl-methyl-amino)-N-quinolin-3-yl-benzamide is shown in FIG. 6. MPO is an enzyme contained within neutrophils. Increases in MPO correlate with increased tissue neutrophil numbers. This represents a measure of inflammatory cell recruitment into the tissues and a decrease would indicate a reduction in inflammatory cell presence.

The invention claimed is:

1. A compound of Formula (I):

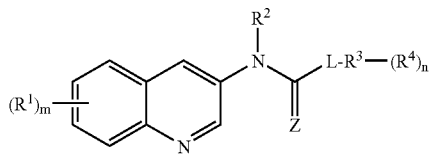

Formula (I)

wherein:
$R^1$ is a substituent independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; $diC_{1-7}$alkanylaminocarbonyl; and formyl; wherein the heteroatom contained in the quinoline ring of Formula (I) is optionally substituted with an oxo substituent;

m is 0, 1 or 2;

$R^2$ is hydrogen or $C_{1-8}$ alkanyl;

L is a direct bond or $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R^3$ is selected from the group consisting of pyrrolyl, pyridyl, furyl, thienyl, phenyl and cyclohexyl;

$R^4$ is independently selected from the group consisting of $C_{1-12}$alkanyl, $C_{4-8}$alkanyloxy, $C_{3-8}$cycloalkanyloxy, $C_{1-8}$alkanylamino, $C_{3-8}$cycloalkanylamino, $C_{3-14}$ cyclic heteroalkanyl, $C_{1-6}$fluorinated alkanyl and —N($R^5$)($R^6$); or when n is 2 or 3, optionally two $R^4$ substituents taken together form a $C_{3-14}$ cyclic heteroalkyl or $C_{3-14}$ cyclic alkanyl;

$R^5$ is hydrogen, $C_{1-16}$alkyl, alkanylcarbonyl or arylcarbonyl;

$R_6$ is $C_{4-16}$ alkyl, alkanylcarbonyl, $C_{1-3}$alkyl substituted with a substituent selected from the group consisting of pyrrolyl, furyl, thienyl, phenyl, and furyl, or arylcarbonyl; or optionally $R^6$ and one of $R^4$ taken together form a saturated or partially unsaturated cyclic heteroalkyl or a heteroaryl; or $R^5$ and $R^6$ optionally taken together form a bridged or non-bridged cyclic heteroalkanyl, wherein said heteroalkanyl is optionally substituted with $C_{1-6}$alkanylcarbonyl;

wherein the alkanyls in any of the foregoing alkanyl-containing substituents of $R^4$, $R^5$ or $R^6$ are optionally and independently substituted with pyrrolyl, furyl, thienyl, phenyl, furyl, $C_{1-4}$alkylpyrrolyl, $C_{1-4}$alkylpyridyl, $C_{1-4}$alkylthienyl, $C_{1-4}$alkylphenyl, or $C_{1-4}$alkylfuryl;

n is 1, 2 or 3;

Z is O or S; and enantiomers, diastereomers, tautomers, and pharmaceutically acceptable salts thereof.

2. The compound according to claim 1 wherein L is a direct bond.

3. The compound according to claim 1 wherein L is $C_{1-4}$alkyldiyl.

4. The compound according to claim 1 wherein $R^3$ is phenyl.

5. The compound according to claim 1 wherein $R^3$ is pyridyl.

6. The compound according to claim 1 wherein $R^3$ is thienyl.

7. The compound according to claim 1 wherein n is 1.

8. The compound according to claim 1 wherein n is 2 or 3 and $R^4$ is $C_{1-12}$alkanyl.

9. The compound according to claim 1 wherein $R^4$ is —$N(R^5)(R^6)$.

10. The compound according to claim 9 wherein $R^5$ and $R^6$ are different.

11. The compound according to claim 1 wherein L is $C_{1-4}$alkyldiyl, $R^3$ is phenyl, n is 1 and $R^4$ is $C_{1-12}$alkanyl.

12. The compound according to claim 1 wherein $R^3$ is phenyl, n is 1 and $R^4$ is —$N(R^5)(R^6)$.

13. The compound according to claim 1 wherein $R^3$ is phenyl, n is 2 or 3, and two $R^4$ substituents taken together form a $C_{3-14}$ cyclic heteroalkyl or $C_{3-14}$ cyclic alkyl.

14. The compound according to claim 1 wherein Z is O.

15. The compound according to claim 1 wherein m is 0.

16. The compound according to claim 1 wherein $R^2$ is hydrogen.

17. A compound of Formula (I):

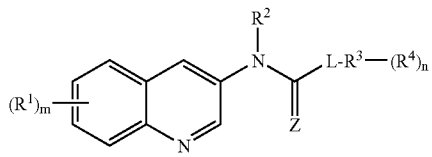

Formula (I)

wherein:

$R^1$ is a substituent independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl; wherein the heteroatom contained in the quinoline ring of Formula (I) is optionally substituted with an oxo substituent;

m is 0, 1 or 2;

$R^2$ is hydrogen or $C_{1-8}$alkanyl;

L is a $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R^3$ is selected from the group consisting of pyrrolyl, pyridyl, furyl, thienyl, phenyl and cyclohexyl;

$R^4$ is independently selected from the group consisting of $C_{1-12}$alkanyl, $C_{4-8}$alkanyloxy, $C_{3-8}$cycloalkanyloxy, $C_{1-8}$alkanylamino, $C_{3-8}$cycloalkanylamino, $C_{3-14}$ cyclic heteroalkanyl, $C_{1-6}$ fluorinated alkanyl, and —$N(R^5)$ ($R^6$); or when n is 2 or 3, optionally two $R^4$ substituents taken together form a $C_{3-14}$ cyclic heteroalkyl or $C_{3-14}$ cyclic alkanyl;

$R^5$ is hydrogen, $C_{1-16}$alkyl, alkanylcarbonyl or arylcarbonyl;

$R_6$ is $C_{4-16}$ alkyl, alkanylcarbonyl, $C_{1-3}$alkyl substituted with a substituent selected from the group consisting of pyrrolyl, pyridyl, furyl, thienyl, phenyl, and furyl, or arylcarbonyl; or optionally $R^6$ and one of $R^4$ taken together form a saturated or partially unsaturated cyclic heteroalkyl or a heteroaryl; or $R^5$ and $R^6$ optionally taken together form a bridged or non-bridged cyclic heteroalkanyl, wherein said heteroalkanyl is optionally substituted with $C_{1-6}$alkanylcarbonyl;

wherein the alkanyls in any of the foregoing alkanyl-containing substituents of $R^4$, $R^5$ or $R^6$ are optionally and independently substituted with pyrrolyl, pyridyl, furyl, thienyl, phenyl, furyl, $C_{1-4}$alkylpyrrolyl, $C_{1-4}$alkylpyridyl, $C_{1-4}$alkylthienyl, $C_{1-4}$alkylphenyl, or $C_{1-4}$alkylfuryl;

n is 1, 2 or 3;

Z is O or S; and enantiomers, diastereomers, tautomers, and pharmaceutically acceptable salts thereof 18. The compound according to claim 17 wherein $R^3$ is phenyl.

19. The compound according to claim 17 wherein $R^3$ is pyridyl.

20. The compound according to claim 17 wherein $R^3$ is thienyl.

21. The compound according to claim 17 wherein n is 1.

22. The compound according to claim 17 wherein n is 2 or 3 and $R^4$ is $C_{1-12}$alkanyl.

23. The compound according to claim 17 wherein $R^4$ is —$N(R^5)(R^6)$.

24. The compound according to claim 23 wherein $R^5$ and $R^6$ are different.

25. The compound according to claim 17 wherein L is $C_{1-4}$alkyldiyl, $R^3$ is phenyl, n is 1 and $R^4$ is $C_{1-12}$alkanyl.

26. The compound according to claim 17 wherein $R^3$ is phenyl, n is 1 and $R^4$ is —$N(R^5)(R^6)$.

27. The compound according to claim 17 wherein $R^3$ is phenyl, n is 2 or 3, and two $R^4$ substituents taken together form a $C_{3-14}$ cyclic heteroalkyl or $C_{3-14}$ cyclic alkyl.

28. The compound according to claim 17 wherein Z is O.

29. The compound according to claim 17 wherein m is 0.

30. The compound according to claim 17 wherein $R^2$ is hydrogen.

31. A compound of Formula (I):

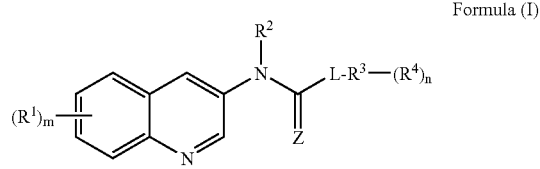

Formula (I)

wherein:

$R^1$ is a substituent independently selected from the group consisting of hydrogen; hydroxyl; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; $diC_{1-7}$alkanylaminocarbonyl; and formyl; wherein the heteroatom contained in the quinoline ring of Formula (I) is optionally substituted with an oxo substituent;

m is 0, 1 or 2;

$R^2$ is hydrogen or $C_{1-8}$alkanyl;

L is a direct bond or $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, ydroxyl, fluorinated alkanyl, fluorinated alkanyloxy, amino, di($C_{1-3}$)alkanylamino, and $C_{1-3}$alkanylamino;

$R^3$ is selected from the group consisting of pyrrolyl, pyridyl, furyl, thienyl, phenyl and cyclohexyl;

$R^4$ is independently selected from the group consisting of $C_{1-8}$alkanyl, $C_{4-8}$alkanyloxy, $C_{3-8}$cycloalkanyloxy, $C_{1-8}$alkanylamino, $C_{3-8}$cycloalkanylamino, $C_{3-14}$ cyclic heteroalkanyl, $C_{1-6}$ fluorinated alkanyl, and —N($R^5$)($R^6$); or both $R^4$ substituents taken together form a $C_{3-14}$ cyclic heteroalkyl or $C_{3-14}$ cyclic alkanyl;

$R^5$ is hydrogen, $C_{1-16}$alkyl, alkanylcarbonyl or arylcarbonyl;

$R_6$ is $C_{4-16}$ alkyl, alkanylcarbonyl, $C_{1-3}$alkyl substituted with a substituent selected from the group consisting of pyrrolyl, pyridyl, furyl, thienyl, phenyl, and furyl, or arylcarbonyl; or optionally $R^6$ and one of $R^4$ taken together form a saturated or partially unsaturated cyclic heteroalkyl or a heteroaryl; or $R^5$ and $R^6$ optionally taken together form a bridged or non-bridged cyclic heteroalkanyl, wherein said heteroalkanyl is optionally substituted with $C_{1-6}$alkanylcarbonyl;

wherein the alkanyls in any of the foregoing alkanyl-containing substituents of $R^4$, $R^5$ or $R^6$ are optionally and independently substituted with pyrrolyl, pyridyl, furyl, thienyl, phenyl, furyl, $C_{1-4}$alkylpyrrolyl, $C_{1-4}$alkylpyridyl, $C_{1-4}$alkylthienyl, $C_{1-4}$alkylphenyl, or $C_{1-4}$alkylfuryl;

n is 2 or 3;

Z is O or S; and enantiomers, diastereomers, tautomers, and pharmaceutically acceptable salts thereof 32. The compound according to claim 31 wherein L is a direct bond.

33. The compound according to claim 31 wherein L is $C_{1-4}$alkyldiyl.

34. The compound according to claim 31 wherein $R^3$ is phenyl.

35. The compound according to claim 31 wherein $R^3$ is pyridyl.

36. The compound according to claim 31 wherein $R^3$ is thienyl.

37. The compound according to claim 31 wherein $R^4$ is $C_{1-12}$alkanyl.

38. The compound according to claim 31 wherein $R^4$ is —N($R^5$)($R^6$).

39. The compound according to claim 38 wherein $R^5$ and $R^6$ are different.

40. The compound according to claim 31 wherein L is $C_{1-4}$alkyldiyl, $R^3$ is phenyl, and one $R^4$ is $C_{1-12}$alkanyl.

41. The compound according to claim 31 wherein $R^3$ is phenyl, and one $R^4$ is —N($R^5$)($R^6$).

42. The compound according to claim 31 wherein $R^3$ is phenyl and two $R^4$ substituents taken together form a $C_{3-14}$ cyclic heteroalkyl or $C_{3-14}$ cyclic alkyl.

43. The compound according to claim 31 wherein Z is O.

44. The compound according to claim 31 wherein m is 0.

45. The compound according to claim 31 wherein $R^2$ is hydrogen.

46. A compound of Formula (I):

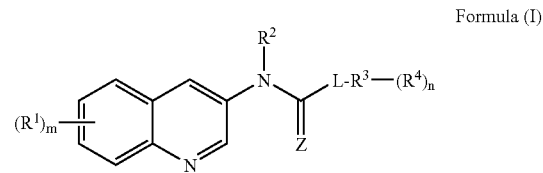

Formula (I)

wherein:

$R^1$ is a substituent independently selected from the group consisting of hydroxyl; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; $diC_{1-7}$alkanylaminocarbonyl; and formyl; wherein the heteroatom contained in the quinoline ring of Formula (I) is optionally substituted with an oxo substituent;

m is 1 or 2;

$R^2$ is hydrogen or $C_{1-8}$alkanyl;

L is a direct bond or $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, ydroxyl, fluorinated alkanyl, fluorinated alkanyloxy, amino, di($C_{1-3}$)alkanylamino, and $C_{1-3}$alkanylamino;

$R^3$ is selected from the group consisting of pyrrolyl, pyridyl, furyl, thienyl, phenyl and cyclohexyl;

$R^4$ is independently selected from the group consisting of $C_{1-8}$alkanyl, $C_{4-8}$alkanyloxy, $C_{3-8}$cycloalkanyloxy, $C_{1-8}$alkanylamino, $C_{3-8}$cycloalkanylamino, $C_{3-14}$ cyclic heteroalkanyl, $C_{1-6}$ fluorinated alkanyl, and —N($R^5$)($R^6$); or both $R^4$ substituents taken together form a $C_{3-14}$ cyclic heteroalkyl or $C_{3-14}$ cyclic alkanyl;

$R^5$ is hydrogen, $C_{1-16}$alkyl, alkanylcarbonyl or arylcarbonyl;

$R_6$ is $C_{4-16}$ alkyl, alkanylcarbonyl, $C_{1-3}$alkyl substituted with a substituent selected from the group consisting of pyrrolyl, pyridyl, furyl, thienyl, phenyl, and furyl, or arylcarbonyl; or optionally $R^6$ and one of $R^4$ taken together form a saturated or partially unsaturated cyclic heteroalkyl or a heteroaryl; or $R^5$ and $R^6$ optionally taken together form a bridged or non-bridged cyclic heteroalkanyl, wherein said heteroalkanyl is optionally substituted with $C_{1-6}$alkanylcarbonyl;

wherein the alkanyls in any of the foregoing alkanyl-containing substituents of $R^4$, $R^5$ or $R^6$ are optionally and independently substituted with pyrrolyl, pyridyl, furyl, thienyl, phenyl, furyl, $C_{1-4}$alkylpyrrolyl, $C_{1-4}$alkylpyridyl, $C_{1-4}$alkylthienyl, $C_{1-4}$alkylphenyl, or $C_{1-4}$alkylfuryl;

n is 1, 2 or 3;

Z is O or S; and enantiomers, diastereomers, tautomers, and pharmaceutically acceptable salts thereof.

47. The compound according to claim 46 wherein L is a direct bond.

48. The compound according to claim 46 wherein L is $C_{1-4}$alkyldiyl.

49. The compound according to claim 46 wherein $R^3$ is phenyl.

50. The compound according to claim 46 wherein $R^3$ is pyridyl.

51. The compound according to claim 46 wherein $R^3$ is thienyl.

52. The compound according to claim 46 wherein $R^4$ is $C_{1-12}$alkanyl.

53. The compound according to claim 46 wherein $R^4$ is —$N(R^5)(R^6)$.

54. The compound according to claim 46 wherein $R^5$ and $R^6$ are different.

55. The compound according to claim 46 wherein L is $C_{1-4}$alkyldiyl, $R^3$ is phenyl, and one $R^4$ is $C_{1-12}$alkanyl.

56. The compound according to claim 46 wherein $R^3$ is phenyl, and one $R^4$ is —$N(R^5)(R^6)$.

57. The compound according to claim 46 wherein $R^3$ is phenyl and two $R^4$ substituents taken together form a $C_{3-14}$ cyclic heteroalkyl or $C_{3-14}$ cyclic alkyl.

58. The compound according to claim 46 wherein Z is O.

59. The compound according to claim 46 wherein m is 0.

60. The compound according to claim 46 wherein $R^2$ is hydrogen.

61. A compound of Formula (I):

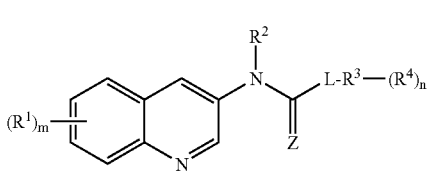

Formula (I)

wherein:

$R^1$ is a substituent independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; $diC_{1-7}$alkanylaminocarbonyl; and formyl; wherein the heteroatom contained in the quinoline ring of Formula (I) is optionally substituted with an oxo substituent;

m is 0, 1 or 2;

$R^2$ is hydrogen or $C_{1-8}$alkanyl;

L is ethen-1,2-diyl;

$R^3$ is selected from the group consisting of pyrrolyl, pyridyl, furyl, thienyl, phenyl and cyclohexyl;

$R^4$ is independently selected from the group consisting of $C_{1-12}$alkanyl, $C_{4-8}$alkanyloxy, $C_{3-8}$cycloalkanyloxy, $C_{1-8}$alkanylamino, $C_{3-8}$cycloalkanylamino, $C_{3-14}$ cyclic heteroalkanyl, $C_{1-6}$ fluorinated alkanyl, halogen, and —$N(R^5)(R^6)$; or when n is 2 or 3, optionally two $R^4$ substituents taken together form a $C_{3-14}$ cyclic heteroalkyl or $C_{3-14}$ cyclic alkanyl;

$R^5$ is hydrogen, $C_{1-16}$alkyl, alkanylcarbonyl or arylcarbonyl;

$R_6$ is $C_{4-16}$ alkyl, alkanylcarbonyl, $C_{1-3}$alkyl substituted with a substituent selected from the group consisting of pyrrolyl, pyridyl, furyl, thienyl, phenyl, and furyl, or arylcarbonyl; or optionally $R^6$ and one of $R^4$ taken together form a saturated or partially unsaturated cyclic heteroalkyl or a heteroaryl; or $R^5$ and $R^6$ optionally taken together form a bridged or non-bridged cyclic heteroalkanyl, wherein said heteroalkanyl is optionally substituted with $C_{1-6}$alkanylcarbonyl;

wherein the alkanyls in any of the foregoing alkanyl-containing substituents of $R^4$, $R^5$ or $R^6$ are optionally and independently substituted with pyrrolyl, pyridyl, furyl, thienyl, phenyl, furyl, $C_{1-4}$alkylpyrrolyl, $C_{1-4}$alkylpyridyl, $C_{1-4}$alkylthienyl, $C_{1-4}$alkylphenyl, or $C_{1-4}$alkylfuryl;

n is 1, 2 or 3;

Z is O or S; and enantiomers, diastereomers, tautomers, and pharmaceutically acceptable salts thereof.

62. The compound according to claim 61 wherein $R^3$ is phenyl.

63. The compound according to claim 61 wherein $R^3$ is pyridyl.

64. The compound according to claim 61 wherein $R^3$ is thienyl.

65. The compound according to claim 61 wherein n is 1.

66. The compound according to claim 61 wherein n is 2 or 3 and $R^4$ is $C_{1-12}$alkanyl.

67. The compound according to claim 61 wherein n is 2, one $R^4$ is halogen, and the other $R^4$ is $C_{1-6}$ fluorinated alkanyl.

68. The compound according to claim 61 wherein $R^4$ is $C_{1-6}$ fluorinated alkanyl.

69. The compound according to claim 61 $R^4$ is halogen.

70. The compound according to claim 61 wherein $R^4$ is —$N(R^5)(R^6)$.

71. The compound according to claim 70 wherein $R^5$ and $R^6$ are different.

72. The compound according to claim 61 wherein L is $C_{1-4}$alkyldiyl, $R^3$ is phenyl, n is 1 and $R^4$ is $C_{1-12}$alkanyl.

73. The compound according to claim 61 wherein $R^3$ is phenyl, n is 1 and $R^4$ is —$N(R^5)(R^6)$.

74. The compound according to claim 61 wherein $R^3$ is phenyl, n is 2 or 3, and two $R^4$ substituents taken together form a $C_{3-14}$ cyclic heteroalkyl or $C_{3-14}$ cyclic alkyl.

75. The compound according to claim 61 wherein Z is O.

76. The compound according to claim 61 wherein m is 0.

77. The compound according to claim 61 wherein $R^2$ is hydrogen.

78. A compound of Formula (I):

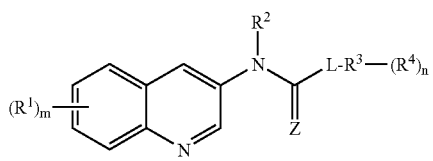

Formula (I)

wherein:
$R^1$ is a substituent independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; $diC_{1-7}$alkanylaminocarbonyl; and formyl; wherein the heteroatom contained in the quinoline ring of Formula (I) is optionally substituted with an oxo substituent;
m is 0, 1 or 2;
$R^2$ is hydrogen or $C_{1-8}$alkanyl;
L is a direct bond;
$R^3$ is selected from the group consisting of pyrrolyl, pyridyl, furyl, thienyl, and cyclohexyl;
$R^4$ is selected from the group consisting of $C_{1-12}$alkanyl, $C_{4-8}$alkanyloxy, $C_{3-8}$cycloalkanyloxy, $C_{1-8}$alkanylamino, $C_{3-8}$cycloalkanylamino, $C_{3-14}$ cyclic heteroalkanyl, $C_{1-6}$ fluorinated alkanyl, and —$N(R^5)(R^6)$, wherein the alkanyls in any of the foregoing alkanyl-containing substituents of $R^4$ is optionally substituted with thienyl or phenyl; or when n is 2 or 3, optionally two $R^4$ substituents taken together form a $C_{3-14}$ cyclic heteroalkyl or $C_{3-14}$ cyclic alkanyl;
$R^5$ is hydrogen, $C_{1-16}$alkyl, alkanylcarbonyl or arylcarbonyl;
$R_6$ is $C_{4-16}$ alkyl, alkanylcarbonyl, $C_{1-3}$alkyl substituted with a substituent selected from the group consisting of pyrrolyl, pyridyl, furyl, thienyl, phenyl, and furyl, or arylcarbonyl; or optionally $R^6$ and one of $R^4$ taken together form a saturated or partially unsaturated cyclic heteroalkyl or a heteroaryl; or $R^5$ and $R^6$ optionally taken together form a bridged or non-bridged cyclic heteroalkanyl, wherein said heteroalkanyl is optionally substituted with $C_{1-6}$alkanylcarbonyl;
wherein the alkanyls in any of the foregoing alkanyl-containing substituents of $R^4$, $R^5$ or $R^6$ are optionally and independently substituted with pyrrolyl, pyridyl, furyl, thienyl, phenyl, furyl, $C_{1-4}$alkylpyrrolyl, $C_{1-4}$alkylpyridyl, $C_{1-4}$alkylthienyl, $C_{1-4}$alkylphenyl, or $C_{1-4}$alkylfuryl;

n is 1, 2 or 3;
Z is O or S; and
enantiomers, diastereomers, tautomers, and pharmaceutically acceptable salts thereof.

79. The compound according to claim 78 wherein L is a direct bond.

80. The compound according to claim 78 wherein $R^3$ is pyridyl.

81. The compound according to claim 78 wherein $R^3$ is thienyl.

82. The compound according to claim 78 wherein $R^3$ is furyl.

83. The compound according to claim 78 wherein $R^3$ is cyclohexyl.

84. The compound according to claim 78 wherein n is 1.

85. The compound according to claim 78 wherein n is 2 or 3 and $R^4$ is $C_{1-12}$alkanyl.

86. The compound according to claim 78 wherein $R^4$ is —$N(R^5)(R^6)$.

87. The compound according to claim 86 wherein $R^5$ and $R^6$ are different.

88. The compound according to claim 78 wherein Z is O.

89. The compound according to claim 78 wherein m is 0.

90. The compound according to claim 78 wherein $R^2$ is hydrogen.

91. A compound selected from the group consisting of
1-Acetyl-2,3-dihydro-1H-indole-5-carboxylic acid quinolin-3-ylamide;
1-Benzoyl-2,3-dihydro-1H-indole-5-carboxylic acid quinolin-3-ylamide;
1-Butyryl-2,3-dihydro-1H-indole-5-carboxylic acid quinolin-3-ylamide;
1-Cyclohexanecarbonyl-2,3-dihydro-1H-indole-5-carboxylic acid quinolin-3-ylamide;
1-Cyclohexyl-2,3-dihydro-1H-indole-5-carboxylic acid quinolin-3-ylamide;
1-Isopropyl-2-trifluoromethyl-1H-benzoimidazole-5-carboxylic acid quinolin-3-ylamide;
1-Methyl-1,2,3,4-tetrahydro-quinoline-6-carboxylic acid quinolin-3-ylamide;
1-Methyl-2,3-dihydro-1H-indole-5-carboxylic acid quinolin-3-ylamide;
1-Pentyl-1,2,3,4-tetrahydro-quinoline-6-carboxylic acid quinolin-3-ylamide;
1-Pentyl-1H-indole-5-carboxylic acid quinolin-3-ylamide;
1-Pentyl-2,3-dihydro-1H-indole-5-carboxylic acid quinolin-3-ylamide;
2-(4-Dipentylamino-phenyl)-N-quinolin-3-yl-acetamide;
2-(4-Pentyl-phenyl)-N-quinolin-3-yl-acetamide;
2-(4-tert-Butyl-phenyl)-N-quinolin-3-yl-acetamide;
2-(Heptyl-methyl-amino)-N-quinolin-3-yl-benzamide;
2-(Methyl-pentyl-amino)-N-quinolin-3-yl-benzamide;
2,3-Dihydro-1H-indole-5-carboxylic acid quinolin-3-ylamide;
2-{4-(Methyl-pentyl-amino)-phenyl}-N-quinolin-3-yl-acetamide;
2-Chloro-4-(cyclohexylmethyl-amino)-N-quinolin-3-yl-benzamide;
2-Chloro-4-pentylamino-N-quinolin-3-yl-benzamide;
2-Heptylamino-N-quinolin-3-yl-benzamide;
2-Pentylamino-N-quinolin-3-yl-benzamide;
3-(1-Cyclohexyl-2,3-dihydro-1H-indol-5-yl)-N-quinolin-3-yl-propionamide;
3-(1-Cyclohexylmethyl-2,3-dihydro-1H-indol-5-yl)-N-quinolin-3-yl-propionamide;

3-(1-Propyl-1H-indol-5-yl)-N-quinolin-3-yl-propionamide;
3-(1-Propyl-2,3-dihydro-1H-indol-5-yl)-N-quinolin-3-yl-propionamide;
3-(2,2-Dimethyl-chroman-6-yl)-N-quinolin-3-yl-acrylamide;
3-(2,2-Dimethyl-chroman-6-yl)-N-quinolin-3-yl-propionamide;
3-(4-Azepan-1-yl-phenyl)-N-quinolin-3-yl-acrylamide;
3-(4-Azepan-1-yl-phenyl)-N-quinolin-3-yl-propionamide;
3-(4-Cyclohexylmethyl-phenyl)-N-quinolin-3-yl-propionamide;
3-(4-Dipentylamino-phenyl)-N-quinolin-3-yl-propionamide;
3-(4-Pentyl-phenyl)-N-quinolin-3-yl-acrylamide;
3-(4-Pentyl-phenyl)-N-quinolin-3-yl-propionamide;
3-(4-sec-Butyl-phenyl)-N-quinolin-3-yl-propionamide;
3-(4-tert-Butyl-phenyl)-N-quinolin-3-yl-acrylamide;
3-(4-tert-Butyl-phenyl)-N-quinolin-3-yl-propionamide;
3-(Cyclohexyl-methyl-amino)-N-quinolin-3-yl-benzamide;
3-(Heptyl-methyl-amino)-N-quinolin-3-yl-benzamide;
3-(Methyl-pentyl-amino)-N-quinolin-3-yl-benzamide;
3,4,5,6-Tetrahydro-2H-[1,2']bipyridinyl-5'-carboxylic acid quinolin-3-ylamide;
3[4-(Methyl-phenethyl-amino)-phenyl]-N-quinolin-3-yl-propionamide;
3-{4-(1,1-Dimethyl-3-phenyl-propyl)-phenyl}-N-quinolin-3-yl-propionamide;
3-{4-(1,1-Dimethyl-pentyl)-2,6-dimethoxy-phenyl}-N-quinolin-3-yl-propionamide;
3-{4-(1,1-Dimethyl-pentyl)-phenyl}-N-quinolin-3-yl;
3-{4-(1,1-Dimethyl-propyl)-2,6-dimethoxy-phenyl}-N-quinolin-3-yl-propionamide;
3-{4-(1,1-Dimethyl-propyl)-phenyl}-N-quinolin-3-yl-propionamide;
3-{4-(1-Cyclohexyl-1-methyl-ethyl)-phenyl}-N-quinolin-3-yl-propionamide;
3-{4-(1-Methyl-pentyl)-phenyl}-N-quinolin-3-yl-propionamide;
3-{4-(Benzyl-methyl-amino)-phenyl}-N-quinolin-3-yl-propionamide;
3-{4-(Cyclohexyl-methyl-amino)-phenyl}-N-quinolin-3-yl-acrylamide;
3-{4-(Cyclohexyl-methyl-amino)-phenyl}-N-quinolin-3-yl-propionamide;
3-{4-(Cyclohexylmethyl-methyl-amino)-phenyl}-N-quinolin-3-yl-propionamide;
3-{4-(Methyl-pentyl-amino)-phenyl}-N-quinolin-3-yl-acrylamide;
3-{4-(Methyl-pentyl-amino)-phenyl}-N-quinolin-3-yl-propionamide;
3-{4-(Methyl-propyl-amino)-phenyl}-N-quinolin-3-yl-propionamide;
3-{5-(1,1-Dimethyl-propyl)-thiophen-2-yl}-N-quinolin-3-yl-propionamide;
3-Cyclohexylamino-N-quinolin-3-yl-benzamide;
3-Dipentylamino-N-quinolin-3-yl-benzamide;
3-Heptylamino-N-quinolin-3-yl-benzamide;
3-Indan-5-yl-N-quinolin-3-yl-propionamide;
3-Methyl-4-(methyl-pentyl-amino)-N-quinolin-3-yl-benzamide;
3-Methyl-4-pentylamino-N-quinolin-3-yl-benzamide;
3-Pentylamino-N-quinolin-3-yl-benzamide;
4-(1,3-Dihydro-isoindol-2-yl)-N-quinolin-3-yl-benzamide;
4-(1,4-Dioxa-8-aza-spiro[4.5]dec-8-yl)-N-quinolin-3-yl-benzamide;
4-(2,6-Dimethyl-morpholin-4-yl)-N-quinolin-3-yl-benzamide;
4-(3,5-Dimethyl-piperidin-1-yl)-N-quinolin-3-yl-benzamide;
4-(3-Aza-bicyclo{3.3.}non-3-yl)-N-quinolin-3-yl-benzamide;
4-(3-Methyl-piperidin-1-yl)-N-quinolin-3-yl-benzamide;
4-(4-Benzoyl-piperidin-1-yl)-N-quinolin-3-yl-benzamide;
4-(4-Benzyl-piperidin-1-yl)-N-quinolin-3-yl-benzamide;
4-(4-Phenylacetyl-piperazin-1-yl)-N-quinolin-3-yl-benzamide;
4-(4-Phenyl-piperidin-1-yl)-N-quinolin-3-yl-benzamide;
4-(4-Propyl-piperidin-1-yl)-N-quinolin-3-yl-benzamide;
4-(Acetyl-cyclohexyl-amino)-N-quinolin-3-yl-benzamide;
4-(Benzyl-methyl-amino)-N-quinolin-3-yl-benzamide;
4-(Benzyl-pentyl-amino)-N-quinolin-3-yl-benzamide;
4-(Cycloheptyl-methyl-amino)-N-quinolin-3-yl-benzamide;
4-(Cyclohexanecarbonyl-methyl-amino)-N-quinolin-3-yl-benzamide;
4-(Cyclohexyl-ethyl-amino)-N-quinolin-3-yl-benzamide;
4-(Cyclohexylmethyl-amino)-3-methyl-N-quinolin-3-yl-benzamide;
4-(Cyclohexyl-methyl-amino)-3-methyl-N-quinolin-3-yl-benzamide;
4-(Cyclohexyl-methyl-amino)-N-methyl-N-quinolin-3-yl-benzamide;
4-(Cyclohexyl-methyl-amino)-N-quinolin-3-yl-benzamide;
4-(Cyclohexylmethyl-methyl-amino)-3-methyl-N-quinolin-3-yl-benzamide;
4-(Cyclohexylmethyl-methyl-amino)-N-quinolin-3-yl-benzamide;
4-(Cyclohexylmethyl-phenethyl-amino)-N-quinolin-3-yl-benzamide;
4-(Cyclohexyl-propyl-amino)-N-quinolin-3-yl-benzamide;
4-(Cyclopentyl-methyl-amino)-N-quinolin-3-yl-benzamide;
4-(Dec-4-enyl-methyl-amino)-N-quinolin-3-yl-benzamide;
4-(Hept-4-enyl-methyl-amino)-N-quinolin-3-yl-benzamide;
4-(Heptyl-methyl-amino)-N-quinolin-3-yl-benzamide;
4-(Methyl-butyl-amino)-N-quinolin-3-yl-benzamide;
4-(Methyl-hexyl-amino)-N-quinolin-3-yl-benzamide;
4-(Methyl-non-6-enyl-amino)-N-quinolin-3-yl-benzamide;
4-(Methyl-nonyl-amino)-N-quinolin-3-yl-benzamide;
4-(Methyl-pentyl-amino)-N-quinolin-3-yl-benzamide;
4-(Methyl-phenethyl-amino)-N-quinolin-3-yl-benzamide;
4-(Methyl-propyl-amino)-N-quinolin-3-yl-benzamide;
4-(Methyl-tetradecyl-amino)-N-quinolin-3-yl-benzamide;
4-(Octyl-methyl-amino)-N-quinolin-3-yl-benzamide;
4-(Phenethyl-propyl-amino)-N-quinolin-3-yl-benzamide;
4[1,4']Bipiperidinyl-1'-yl-N-quinolin-3-yl-benzamide;
4-{(3,3-Dimethyl-butyl)-methyl-amino}-N-quinolin-3-yl-benzamide;
4-{4-(1,1-Dimethyl-pentyl)-phenyl}-but-3-enoic acid quinolin-3-ylamide;

4-{4-(1,1-Dimethyl-pentyl)-phenyl}-N-quinolin-3-yl-butyramide;
4-{4-(1,1-Dimethyl-propyl)-phenyl}-but-3-enoic acid quinolin-3-ylamide;
4-{4-(1,1-Dimethyl-propyl)-phenyl}-N-quinolin-3-yl-butyramide;
4-{Methyl-(3-methyl-butyl)-amino}-N-quinolin-3-yl-benzamide;
4-{Methyl-(3-phenyl-allyl)-amino}-N-quinolin-3-yl-benzamide;
4-{Methyl-(3-phenyl-propyl)-amino}-N-quinolin-3-yl-benzamide;
4-{Methyl-(tetrahydro-pyran-4-yl)-amino}-N-quinolin-3-yl-benzamide;
4-{Methyl-{3-(5-methyl-furan-2-yl)-butyl}-amino}-N-quinolin-3-yl-benzamide;
4-Azepan-1-yl-N-quinolin-3-yl-benzamide;
4-Azocan-1-yl-N-quinolin-3-yl-benzamide;
4-Azonan-1-yl-N-quinolin-3-yl-benzamide;
4-Benzyl-3,4,5,6-tetrahydro-2H-{1,2'}bipyridinyl-5'-carboxylic acid quinolin-3-ylamide;
4-Butoxy-N-quinolin-3-yl-benzamide;
4-Butyl-cyclohexanecarboxylic acid quinolin-3-ylamide;
4-Cycloheptylamino-N-quinolin-3-yl-benzamide;
4-Cyclohexylamino-N-methyl-N-quinolin-3-yl-benzamide;
4-Cyclohexylamino-N-quinolin-3-yl-benzamide;
4-Cyclopentylamino-N-quinolin-3-yl-benzamide;
4-Dibenzylamino-N-quinolin-3-yl-benzamide;
4-Dibutylamino-N-quinolin-3-yl-benzamide;
4-Dihexylamino-N-quinolin-3-yl-benzamide;
4-Dipentylamino-N-quinolin-3-yl-benzamide;
4-Dipropylamino-N-quinolin-3-yl-benzamide;
4-Morpholin-4-yl-N-quinolin-3-yl-benzamide;
4-Pentylamino-N-quinolin-3-yl-benzamide;
4-Phenethylamino-N-quinolin-3-yl-benzamide;
4-Piperazin-1-yl-N-quinolin-3-yl-benzamide;
4-Piperidin-1-yl-N-quinolin-3-yl-benzamide;
4-Propyl-3,4,5,6-tetrahydro-2H-{1,2'}bipyridinyl-5'-carboxylic acid quinolin-3-ylamide;
4-Pyrrolidin-1-yl-N-quinolin-3-yl-benzamide;
4-tert-Butyl-cyclohexanecarboxylic acid quinolin-3-ylamide;
5,5,8,8-Tetramethyl-5,6,7,8-tetrahydro-naphthalene-2-carboxylic acid quinolin-3-ylamide;
5,6,7,8-Tetrahydro-naphthalene-2-carboxylic acid quinolin-3-ylamide;
5-Chloro-1H-indole-2-carboxylic acid quinolin-3-ylamide;
5-Pentyl-thiophene-2-carboxylic acid quinolin-3-ylamide;
6-(3-Aza-bicyclo{3.3.1}non-3-yl)-N-quinolin-3-yl-nicotinamide;
6-(Benzyl-methyl-amino)-N-quinolin-3-yl-nicotinamide;
6-(Cyclohexyl-methyl-amino)-N-quinolin-3-yl-nicotinamide;
6-(Heptyl-methyl-amino)-N-quinolin-3-yl-nicotinamide;
6-(Methyl-pentyl-amino)-N-quinolin-3-yl-nicotinamide;
6-(Methyl-phenethyl-amino)-N-quinolin-3-yl-nicotinamide;
6-Azepan-1-yl-N-quinolin-3-yl-nicotinamide;
6-Azocan-1-yl-N-quinolin-3-yl-nicotinamide;
6-Cyclohexylamino-N-quinolin-3-yl-nicotinamide;
6-Pentylamino-N-quinolin-3-yl-nicotinamide;
cis-4-(Octahydro-isoquinolin-2-yl)-N-quinolin-3-yl-benzamide;
cis-6-(Octahydro-isoquinolin-2-yl)-N-quinolin-3-yl-nicotinamide;
N-Quinolin-3-yl-3-(3-trifluoromethyl-phenyl)-acrylamide;
N-Quinolin-3-yl-3-(4-tricyclo{5.3.1.13,9}dodec-1-yl-phenyl)-propionamide;
N-Quinolin-3-yl-3-(4-trifluoromethyl-phenyl)-acrylamide;
N-Quinolin-3-yl-3-(5,5,8,8-tetramethyl-5,6,7,8-tetrahydro-naphthalen-2-yl)-propionamide;
N-Quinolin-3-yl-3-(5,6,7,8-tetrahydro-naphthalen-2-yl)-propionamide;
N-Quinolin-3-yl-4-(tetrahydro-pyran-4-ylamino)-benzamide;
N-Quinolin-3-yl-4-thiomorpholin-4-yl-benzamide;
R-4-{(3,7-Dimethyl-oct-6-enyl)-methyl-amino}-N-quinolin-3-yl-benzamide;
S-4-{(3,7-Dimethyl-oct-6-enyl)-methyl-amino}-N-quinolin-3-yl-benzamide;
trans-4-(Octahydro-isoquinolin-2-yl)-N-quinolin-3-yl-benzamide;
trans-6-(Octahydro-isoquinolin-2-yl)-N-quinolin-3-yl-nicotinamide;
4-tert-Butyl-N-(4-hydroxy-quinolin-3-yl)-benzamide;
3-(4-tert-Butyl-phenyl)-N-(4-hydroxy-quinolin-3-yl)-acrylamide;
N-Quinolin-3-yl-3-(5,5,8,8-tetramethyl-5,6,7,8-tetrahydro-naphthalen-2-yl)-acrylamide;
N-(4-Chloro-quinolin-3-yl)-3-(5,5,8,8-tetramethyl-5,6,7,8-tetrahydro-naphthalen-2-yl)-acrylamide;
N-(4-Chloro-quinolin-3-yl)-4-(cyclohexyl-methyl-amino)-benzamide;
N-(2-Chloro-quinolin-3-yl)-4-(cyclohexyl-methyl-amino)-benzamide;
4-tert-Butyl-N-(2-methoxy-quinolin-3-yl)-benzamide;
4-Azepan-1-yl-N-(4-chloro-quinolin-3-yl)-benzamide;
4-(3-Aza-bicyclo[3.2.2]non-3-yl)-N-(2-chloro-quinolin-3-yl)-benzamide;
4-Azepan-1-yl-N-(2-chloro-quinolin-3-yl)-benzamide;
4-(3-Aza-bicyclo[3.2.2]non-3-yl)-N-(4-chloro-quinolin-3-yl)-benzamide;
3-(1-Cyclohexyl-2,3-dihydro-1H-indol-5-yl)-N-quinolin-3-yl-acrylamide;
1-Cyclohexyl-2,3-dihydro-1H-indole-5-carboxylic acid (2-chloro-quinolin-3-yl)-amide;
N-(2-Chloro-quinolin-3-yl)-3-(1-cyclohexyl-2,3-dihydro-1H-indol-5-yl)-acrylamide;
3-(1-Cyclohexyl-1H-indol-5-yl)-N-quinolin-3-yl-acrylamide;
N-(4-Chloro-quinolin-3-yl)-3-(1-cyclohexyl-1H-indol-5-yl)-acrylamide;
1-Cyclohexyl-1H-indole-5-carboxylic acid (4-chloro-quinolin-3-yl)-amide;
1-Cyclohexyl-1H-indole-5-carboxylic acid quinolin-3-ylamide;
1-Cyclohexyl-1H-indole-5-carboxylic acid (2-chloro-quinolin-3-yl)-amide;
N-(2-Chloro-quinolin-3-yl)-3-(1-cyclohexyl-1H-indol-5-yl)-acrylamide;
4-(Cyclohexyl-methyl-amino)-N-(8-fluoro-quinolin-3-yl)-benzamide;
4-Azocan-1-yl-N-(8-fluoro-quinolin-3-yl)-benzamide;
4-(3-Aza-bicyclo[3.2.2]non-3-yl)-N-(8-fluoro-quinolin-3-yl)-benzamide;
4-(3-Aza-bicyclo[3.2.2]non-3-yl)-N-(8-trifluoromethyl-quinolin-3-yl)-benzamide;

4-(Cyclohexyl-methyl-amino)-N-(8-trifluoromethyl-quinolin-3-yl)-benzamide;
4-(Cyclohexyl-methyl-amino)-N-(6-fluoro-quinolin-3-yl)-benzamide;
4-Azocan-1-yl-N-(6-fluoro-quinolin-3-yl)-benzamide;
4-(3-Aza-bicyclo[3.2.2]non-3-yl)-N-(6-fluoro-quinolin-3-yl)-benzamide;
4-(3-Aza-bicyclo[3.2.2]non-3-yl)-N-(7-trifluoromethyl-quinolin-3-yl)-benzamide;
4-Azocan-1-yl-N-(7-trifluoromethyl-quinolin-3-yl)-benzamide;
4-(Cyclohexyl-methyl-amino)-N-(7-trifluoromethyl-quinolin-3-yl)-benzamide;
4-Azocan-1-yl-N-(5-fluoro-quinolin-3-yl)-benzamide;
4-(3-Aza-bicyclo[3.2.2]non-3-yl)-N-(5-fluoro-quinolin-3-yl)-benzamide;
3-Phenyl-propynoic acid quinolin-3-ylamide;
trans-2-Phenyl-cyclopropanecarboxylic acid quinolin-3-ylamide;
3-(4-tert-Butyl-phenyl)-propynoic acid quinolin-3-ylamide; and
2-(4-tert-Butyl-phenyl)-cyclopropanecarboxylic acid quinolin-3-ylamide.

92. A compound selected from the group consisting of
1-Cyclohexyl-2,3-dihydro-1H-indole-5-carboxylic acid quinolin-3-ylamide;
1-Pentyl-1,2,3,4-tetrahydro-quinoline-6-carboxylic acid quinolin-3-ylamide;
1-Pentyl-2,3-dihydro-1H-indole-5-carboxylic acid quinolin-3-ylamide;
1-Propyl-2,3-dihydro-1H-indole-5-carboxylic acid quinolin-3-ylamide;
3-(4-sec-Butyl-phenyl)-N-quinolin-3-yl-propionamide;
3-(4-tert-Butyl-phenyl)-N-quinolin-3-yl-acrylamide;
3-(4-tert-Butyl-phenyl)-N-quinolin-3-yl-propionamide;
3,4,5,6-Tetrahydro-2H-{1,2'} bipyridinyl-5'-carboxylic acid quinolin-3-ylamide;
3-{4-(1,1-Dimethyl-3-phenyl-propyl)-phenyl}-N-quinolin-3-yl-propionamide;
3-{4-(1,1-Dimethyl-pentyl)-2,6-dimethoxy-phenyl}-N-quinolin-3-yl-propionamide;
3-{4-(1,1-Dimethyl-pentyl)-phenyl}-N-quinolin-3-yl;
3-{4-(1,1-Dimethyl-propyl)-2,6-dimethoxy-phenyl}-N-quinolin-3-yl-propionamide;
3-{4-(1,1-Dimethyl-propyl)-phenyl}-N-quinolin-3-yl-propionamide;
3-{4-(1-Cyclohexyl-1-methyl-ethyl)-phenyl}-N-quinolin-3-yl-propionamide;
3-{4-(1-Methyl-pentyl)-phenyl}-N-quinolin-3-yl-propionamide;
3-{5-(1,1-Dimethyl-propyl)-thiophen-2-yl}-N-quinolin-3-yl-propionamide;
4-(3-Aza-bicyclo{3.3.1}non-3-yl)-N-quinolin-3-yl-benzamide;
4-(4-Benzyl-piperidin-1-yl)-N-quinolin-3-yl-benzamide;
4-(Cycloheptyl-methyl-amino)-N-quinolin-3-yl-benzamide;
4-(Cyclohexyl-ethyl-amino)-N-quinolin-3-yl-benzamide;
4-(Cyclohexyl-methyl-amino)-3-methyl-N-quinolin-3-yl-benzamide;
4-(Cyclohexyl-methyl-amino)-N-quinolin-3-yl-benzamide;
4-(Cyclohexylmethyl-methyl-amino)-N-quinolin-3-yl-benzamide;
4-(Cyclopentyl-methyl-amino)-N-quinolin-3-yl-benzamide;
4-(Dec-4-enyl-methyl-amino)-N-quinolin-3-yl-benzamide;
4-(Hept-4-enyl-methyl-amino)-N-quinolin-3-yl-benzamide;
4-(Heptyl-methyl-amino)-N-quinolin-3-yl-benzamide;
4-(Methyl-non-6-enyl-amino)-N-quinolin-3-yl-benzamide;
4-(Methyl-nonyl-amino)-N-quinolin-3-yl-benzamide;
4-(Methyl-phenethyl-amino)-N-quinolin-3-yl-benzamide;
4-(Octyl-methyl-amino)-N-quinolin-3-yl-benzamide;
4-{(3,3-Dimethyl-butyl)-methyl-amino}-N-quinolin-3-yl-benzamide;
4-{Methyl-{3-(5-methyl-furan-2-yl)-butyl}-amino}-N-quinolin-3-yl-benzamide;
4-Azepan-1-yl-N-quinolin-3-yl-benzamide;
4-Azocan-1-yl-N-quinolin-3-yl-benzamide;
4-Azonan-1-yl-N-quinolin-3-yl-benzamide;
4-Benzyl-3,4,5,6-tetrahydro-2H-{1,2'}bipyridinyl-5'-carboxylic acid quinolin-3-ylamide;
5,5,8,8-Tetramethyl-5,6,7,8-tetrahydro-naphthalene-2-carboxylic acid quinolin-3-ylamide;
6-(3-Aza-bicyclo{3.3.1} non-3-yl)-N-quinolin-3-yl-nicotinamide;
6-Azocan-1-yl-N-quinolin-3-yl-nicotinamide;
cis-4-(Octahydro-isoquinolin-2-yl)-N-quinolin-3-yl-benzamide;
cis-6-(Octahydro-isoquinolin-2-yl)-N-quinolin-3-yl-nicotinamide;
N-Quinolin-3-yl-3-(5,5,8,8-tetramethyl-5,6,7,8-tetrahydro-naphthalen-2-yl)-propionamide;
R-4-{(3,7-Dimethyl-oct-6-enyl)-methyl-amino}-N-quinolin-3-yl-benzamide;
S-4-{(3,7-Dimethyl-oct-6-enyl)-methyl-amino}-N-quinolin-3-yl-benzamide;
trans-4-(Octahydro-isoquinolin-2-yl)-N-quinolin-3-yl-benzamide;
trans-6-(Octahydro-isoquinolin-2-yl)-N-quinolin-3-yl-nicotinamide;
4-tert-Butyl-N-(4-hydroxy-quinolin-3-yl)-benzamide;
3-(4-tert-Butyl-phenyl)-N-(4-hydroxy-quinolin-3-yl)-acrylamide;
N-Quinolin-3-yl-3-(5,5,8,8-tetramethyl-5,6,7,8-tetrahydro-naphthalen-2-yl)-acrylamide;
N-(4-Chloro-quinolin-3-yl)-3-(5,5,8,8-tetramethyl-5,6,7,8-tetrahydro-naphthalen-2-yl)-acrylamide;
N-(4-Chloro-quinolin-3-yl)-4-(cyclohexyl-methyl-amino)-benzamide;
N-(2-Chloro-quinolin-3-yl)-4-(cyclohexyl-methyl-amino)-benzamide;
4-tert-Butyl-N-(2-methoxy-quinolin-3-yl)-benzamide;
4-Azepan-1-yl-N-(4-chloro-quinolin-3-yl)-benzamide;
4-(3-Aza-bicyclo[3.2.2]non-3-yl)-N-(2-chloro-quinolin-3-yl)-benzamide;
4-Azepan-1-yl-N-(2-chloro-quinolin-3-yl)-benzamide;
4-(3-Aza-bicyclo[3.2.2]non-3-yl)-N-(4-chloro-quinolin-3-yl)-benzamide;
3-(1-Cyclohexyl-2,3-dihydro-1H-indol-5-yl)-N-quinolin-3-yl-acrylamide;
1-Cyclohexyl-2,3-dihydro-1H-indole-5-carboxylic acid (2-chloro-quinolin-3-yl)-amide;
N-(2-Chloro-quinolin-3-yl)-3-(1-cyclohexyl-2,3-dihydro-1H-indol-5-yl)-acrylamide;
3-(1-Cyclohexyl-1H-indol-5-yl)-N-quinolin-3-yl-acrylamide;
N-(4-Chloro-quinolin-3-yl)-3-(1-cyclohexyl-1H-indol-5-yl)-acrylamide;

1-Cyclohexyl-1H-indole-5-carboxylic acid (4-chloro-quinolin-3-yl)-amide;
1-Cyclohexyl-1H-indole-5-carboxylic acid quinolin-3-ylamide;
1-Cyclohexyl-1H-indole-5-carboxylic acid (2-chloro-quinolin-3-yl)-amide;
N-(2-Chloro-quinolin-3-yl)-3-(1-cyclohexyl-1H-indol-5-yl)-acrylamide;
4-(Cyclohexyl-methyl-amino)-N-(8-fluoro-quinolin-3-yl)-benzamide;
4-Azocan-1-yl-N-(8-fluoro-quinolin-3-yl)-benzamide;
4-(3-Aza-bicyclo[3.2.2]non-3-yl)-N-(8-fluoro-quinolin-3-yl)-benzamide;
4-(3-Aza-bicyclo[3.2.2]non-3-yl)-N-(8-trifluoromethyl-quinolin-3-yl)-benzamide;
4-(Cyclohexyl-methyl-amino)-N-(8-trifluoromethyl-quinolin-3-yl)-benzamide;
4-(Cyclohexyl-methyl-amino)-N-(6-fluoro-quinolin-3-yl)-benzamide;
4-Azocan-1-yl-N-(6-fluoro-quinolin-3-yl)-benzamide;
4-(3-Aza-bicyclo[3.2.2]non-3-yl)-N-(6-fluoro-quinolin-3-yl)-benzamide;
4-(3-Aza-bicyclo[3.2.2]non-3-yl)-N-(7-trifluoromethyl-quinolin-3-yl)-benzamide;
4-Azocan-1-yl-N-(7-trifluoromethyl-quinolin-3-yl)-benzamide;
4-(Cyclohexyl-methyl-amino)-N-(7-trifluoromethyl-quinolin-3-yl)-benzamide;
4-Azocan-1-yl-N-(5-fluoro-quinolin-3-yl)-benzamide;
4-(3-Aza-bicyclo[3.2.2]non-3-yl)-N-(5-fluoro-quinolin-3-yl)-benzamide;
3-Phenyl-propynoic acid quinolin-3-ylamide;
trans-2-Phenyl-cyclopropanecarboxylic acid quinolin-3-ylamide;
3-(4-tert-Butyl-phenyl)-propynoic acid quinolin-3-ylamide; and
2-(4-tert-Butyl-phenyl)-cyclopropanecarboxylic acid quinolin-3-ylamide.

93. A compound selected from the group consisting of
1-Cyclohexyl-2,3-dihydro-1H-indole-5-carboxylic acid quinolin-3-ylamide;
1-Pentyl-2,3-dihydro-1H-indole-5-carboxylic acid quinolin-3-ylamide;
1-Propyl-2,3-dihydro-1H-indole-5-carboxylic acid quinolin-3-ylamide;
3-(4-sec-Butyl-phenyl)-N-quinolin-3-yl-propionamide;
3-(4-tert-Butyl-phenyl)-N-quinolin-3-yl-acrylamide;
3-(4-tert-Butyl-phenyl)-N-quinolin-3-yl-propionamide;
3,4,5,6-Tetrahydro-2H-{1,2'}bipyridinyl-5'-carboxylic acid quinolin-3-ylamide;
3-{4-(1,1-Dimethyl-3-phenyl-propyl)-phenyl}-N-quinolin-3-yl-propionamide;
3-{4-(1,1-Dimethyl-pentyl)-2,6-dimethoxy-phenyl}-N-quinolin-3-yl-propionamide;
3-{4-(1,1-Dimethyl-propyl)-phenyl}-N-quinolin-3-yl-propionamide;
3-{4-(1-Methyl-pentyl)-phenyl}-N-quinolin-3-yl-propionamide;
3-{5-(1,1-Dimethyl-propyl)-thiophen-2-yl}-N-quinolin-3-yl-propionamide;
4-(3-Aza-bicyclo{3.3.1}non-3-yl)-N-quinolin-3-yl-benzamide;
4-(4-Benzyl-piperidin-1-yl)-N-quinolin-3-yl-benzamide;
4-(Cycloheptyl-methyl-amino)-N-quinolin-3-yl-benzamide;;
4-(Cyclohexyl-ethyl-amino)-N-quinolin-3-yl-benzamide;
4-(Cyclohexyl-methyl-amino)-3-methyl-N-quinolin-3-yl-benzamide;
4-(Cyclohexyl-methyl-amino)-N-quinolin-3-yl-benzamide;
4-(Cyclohexylmethyl-methyl-amino)-N-quinolin-3-yl-benzamide;
4-(Cyclopentyl-methyl-amino)-N-quinolin-3-yl-benzamide;
4-(Dec-4-enyl-methyl-amino)-N-quinolin-3-yl-benzamide;
4-(Heptyl-methyl-amino)-N-quinolin-3-yl-benzamide;
4-(Methyl-nonyl-amino)-N-quinolin-3-yl-benzamide;
4-(Methyl-phenethyl-amino)-N-quinolin-3-yl-benzamide;
4-(Octyl-methyl-amino)-N-quinolin-3-yl-benzamide;
4-{(3,3-Dimethyl-butyl)-methyl-amino}-N-quinolin-3-yl-benzamide;
4-Azepan-1-yl-N-quinolin-3-yl-benzamide;
4-Azocan-1-yl-N-quinolin-3-yl-benzamide;
4-Azonan-1-yl-N-quinolin-3-yl-benzamide;
4-Benzyl-3,4,5,6-tetrahydro-2H-{1,2'}bipyridinyl-5'-carboxylic acid quinolin-3-ylamide;
6-(3-Aza-bicyclo{3.3.1}non-3-yl)-N-quinolin-3-yl-nicotinamide;
N-Quinolin-3-yl-3-(5,5,8,8-tetramethyl-5,6,7,8-tetrahydro-naphthalen-2-yl)-propionamide;
R-4-{(3,7-Dimethyl-oct-6-enyl)-methyl-amino}-N-quinolin-3-yl-benzamide;
S-4-{(3,7-Dimethyl-oct-6-enyl)-methyl-amino}-N-quinolin-3-yl-benzamide;
4-tert-Butyl-N-(4-hydroxy-quinolin-3-yl)-benzamide;
3-(4-tert-Butyl-phenyl)-N-(4-hydroxy-quinolin-3-yl)-acrylamide;
N-Quinolin-3-yl-3-(5,5,8,8-tetramethyl-5,6,7,8-tetrahydro-naphthalen-2-yl)-acrylamide;
N-(4-Chloro-quinolin-3-yl)-3-(5,5,8,8-tetramethyl-5,6,7,8-tetrahydro-naphthalen-2-yl)-acrylamide;
N-(4-Chloro-quinolin-3-yl)-4-(cyclohexyl-methyl-amino)-benzamide;
N-(2-Chloro-quinolin-3-yl)-4-(cyclohexyl-methyl-amino)-benzamide;
4-tert-Butyl-N-(2-methoxy-quinolin-3-yl)-benzamide;
4-Azepan-1-yl-N-(4-chloro-quinolin-3-yl)-benzamide;
4-(3-Aza-bicyclo[3.2.2]non-3-yl)-N-(2-chloro-quinolin-3-yl)-benzamide;
4-Azepan-1-yl-N-(2-chloro-quinolin-3-yl)-benzamide;
4-(3-Aza-bicyclo[3.2.2]non-3-yl)-N-(4-chloro-quinolin-3-yl)-benzamide;
3-(1-Cyclohexyl-2,3-dihydro-1H-indol-5-yl)-N-quinolin-3-yl-acrylamide;
1-Cyclohexyl-2,3-dihydro-1H-indole-5-carboxylic acid (2-chloro-quinolin-3-yl)-amide;
N-(2-Chloro-quinolin-3-yl)-3-(1-cyclohexyl-2,3-dihydro-1H-indol-5-yl)-acrylamide;
3-(1-Cyclohexyl-1H-indol-5-yl)-N-quinolin-3-yl-acrylamide;
N-(4-Chloro-quinolin-3-yl)-3-(1-cyclohexyl-1H-indol-5-yl)-acrylamide;
1-Cyclohexyl-1H-indole-5-carboxylic acid (4-chloro-quinolin-3-yl)-amide;
1-Cyclohexyl-1H-indole-5-carboxylic acid quinolin-3-ylamide;
1-Cyclohexyl-1H-indole-5-carboxylic acid (2-chloro-quinolin-3-yl)-amide;
N-(2-Chloro-quinolin-3-yl)-3-(1-cyclohexyl-1H-indol-5-yl)-acrylamide;

4-(Cyclohexyl-methyl-amino)-N-(8-fluoro-quinolin-3-yl)-benzamide;
4-Azocan-1-yl-N-(8-fluoro-quinolin-3-yl)-benzamide;
4-(3-Aza-bicyclo[3.2.2]non-3-yl)-N-(8-fluoro-quinolin-3-yl)-benzamide;
4-(3-Aza-bicyclo[3.2.2]non-3-yl)-N-(8-trifluoromethyl-quinolin-3-yl)-benzamide;
4-(Cyclohexyl-methyl-amino)-N-(8-trifluoromethyl-quinolin-3-yl)-benzamide;
4-(Cyclohexyl-methyl-amino)-N-(6-fluoro-quinolin-3-yl)-benzamide;
4-Azocan-1-yl-N-(6-fluoro-quinolin-3-yl)-benzamide;
4-(3-Aza-bicyclo[3.2.2]non-3-yl)-N-(6-fluoro-quinolin-3-yl)-benzamide;
4-(3-Aza-bicyclo[3.2.2]non-3-yl)-N-(7-trifluoromethyl-quinolin-3-yl)-benzamide;
4-Azocan-1-yl-N-(7-trifluoromethyl-quinolin-3-yl)-benzamide;
4-(Cyclohexyl-methyl-amino)-N-(7-trifluoromethyl-quinolin-3-yl)-benzamide;
4-Azocan-1-yl-N-(5-fluoro-quinolin-3-yl)-benzamide;
4-(3-Aza-bicyclo[3.2.2]non-3-yl)-N-(5-fluoro-quinolin-3-yl)-benzamide;
3-Phenyl-propynoic acid quinolin-3-ylamide;
trans-2-Phenyl-cyclopropanecarboxylic acid quinolin-3-ylamide;
3-(4-tert-Butyl-phenyl)-propynoic acid quinolin-3-ylamide; and
2-(4-tert-Butyl-phenyl)-cyclopropanecarboxylic acid quinolin-3-ylamide.

94. A compound selected from the group consisting of 1-Cyclohexyl-2,3-dihydro-1H-indole-5-carboxylic acid quinolin-3-ylamide;
1-Propyl-2,3-dihydro-1H-indole-5-carboxylic acid quinolin-3-ylamide;
3-(4-sec-Butyl-phenyl)-N-quinolin-3-yl-propionamide;
3-(4-tert-Butyl-phenyl)-N-quinolin-3-yl-acrylamide;
3-(4-tert-Butyl-phenyl)-N-quinolin-3-yl-propionamide;
3-{4-(1,1-Dimethyl-3-phenyl-propyl)-phenyl}-N-quinolin-3-yl-propionamide;
3-{4-(1,1-Dimethyl-pentyl)-2,6-dimethoxy-phenyl}-N-quinolin-3-yl-propionamide;
3-{4-(1,1-Dimethyl-propyl)-phenyl}-N-quinolin-3-yl-propionamide;
3-{4-(1-Methyl-pentyl)-phenyl}-N-quinolin-3-yl-propionamide;
3-{5-(1,1-Dimethyl-propyl)-thiophen-2-yl}-N-quinolin-3-yl-propionamide;
4-(3-Aza-bicyclo{3.3.1}non-3-yl)-N-quinolin-3-yl-benzamide;
4-(4-Benzyl-piperidin-1-yl)-N-quinolin-3-yl-benzamide;
4-(Cycloheptyl-methyl-amino)-N-quinolin-3-yl-benzamide;;
4-(Cyclohexyl-ethyl-amino)-N-quinolin-3-yl-benzamide;
4-(Cyclohexyl-methyl-amino)-N-quinolin-3-yl-benzamide;
4-(Cyclohexylmethyl-methyl-amino)-N-quinolin-3-yl-benzamide;
4-(Octyl-methyl-amino)-N-quinolin-3-yl-benzamide;
4-Azepan-1-yl-N-quinolin-3-yl-benzamide;
4-Azocan-1-yl-N-quinolin-3-yl-benzamide;
4-Azonan-1-yl-N-quinolin-3-yl-benzamide;
6-(3-Aza-bicyclo{3.3.1}non-3-yl)-N-quinolin-3-yl-nicotinamide;
N-Quinolin-3-yl-3-(5,5,8,8-tetramethyl-5,6,7,8-tetrahydro-naphthalen-2-yl)-propionamide;
R-4-{(3,7-Dimethyl-oct-6-enyl)-methyl-amino}-N-quinolin-3-yl-benzamide;
S-4-{(3,7-Dimethyl-oct-6-enyl)-methyl-amino}-N-quinolin-3-yl-benzamide;
4-tert-Butyl-N-(4-hydroxy-quinolin-3-yl)-benzamide;
3-(4-tert-Butyl-phenyl)-N-(4-hydroxy-quinolin-3-yl)-acrylamide;
N-Quinolin-3-yl-3-(5,5,8,8-tetramethyl-5,6,7,8-tetrahydro-naphthalen-2-yl)-acrylamide;
N-(4-Chloro-quinolin-3-yl)-3-(5,5,8,8-tetramethyl-5,6,7,8-tetrahydro-naphthalen-2-yl)-acrylamide;
N-(4-Chloro-quinolin-3-yl)-4-(cyclohexyl-methyl-amino)-benzamide;
N-(2-Chloro-quinolin-3-yl)-4-(cyclohexyl-methyl-amino)-benzamide;
4-tert-Butyl-N-(2-methoxy-quinolin-3-yl)-benzamide;
4-Azepan-1-yl-N-(4-chloro-quinolin-3-yl)-benzamide;
4-(3-Aza-bicyclo[3.2.2]non-3-yl)-N-(2-chloro-quinolin-3-yl)-benzamide;
4-Azepan-1-yl-N-(2-chloro-quinolin-3-yl)-benzamide;
4-(3-Aza-bicyclo[3.2.2]non-3-yl)-N-(4-chloro-quinolin-3-yl)-benzamide;
3-(1-Cyclohexyl-2,3-dihydro-1H-indol-5-yl)-N-quinolin-3-yl-acrylamide;
1-Cyclohexyl-2,3-dihydro-1H-indole-5-carboxylic acid (2-chloro-quinolin-3-yl)-amide;
N-(2-Chloro-quinolin-3-yl)-3-(1-cyclohexyl-2,3-dihydro-1H-indol-5-yl)-acrylamide;
3-(1-Cyclohexyl-1H-indol-5-yl)-N-quinolin-3-yl-acrylamide;
N-(4-Chloro-quinolin-3-yl)-3-(1-cyclohexyl-1H-indol-5-yl)-acrylamide;
1-Cyclohexyl-1H-indole-5-carboxylic acid (4-chloro-quinolin-3-yl)-amide;
1-Cyclohexyl-1H-indole-5-carboxylic acid quinolin-3-ylamide;
1-Cyclohexyl-1H-indole-5-carboxylic acid (2-chloro-quinolin-3-yl)-amide;
N-(2-Chloro-quinolin-3-yl)-3-(1-cyclohexyl-1H-indol-5-yl)-acrylamide;
4-(Cyclohexyl-methyl-amino)-N-(8-fluoro-quinolin-3-yl)-benzamide;
4-Azocan-1-yl-N-(8-fluoro-quinolin-3-yl)-benzamide;
4-(3-Aza-bicyclo[3.2.2]non-3-yl)-N-(8-fluoro-quinolin-3-yl)-benzamide;
4-(3-Aza-bicyclo[3.2.2]non-3-yl)-N-(8-trifluoromethyl-quinolin-3-yl)-benzamide;
4-(Cyclohexyl-methyl-amino)-N-(8-trifluoromethyl-quinolin-3-yl)-benzamide;
4-(Cyclohexyl-methyl-amino)-N-(6-fluoro-quinolin-3-yl)-benzamide;
4-Azocan-1-yl-N-(6-fluoro-quinolin-3-yl)-benzamide;
4-(3-Aza-bicyclo[3.2.2]non-3-yl)-N-(6-fluoro-quinolin-3-yl)-benzamide;
4-(3-Aza-bicyclo[3.2.2]non-3-yl)-N-(7-trifluoromethyl-quinolin-3-yl)-benzamide;
4-Azocan-1-yl-N-(7-trifluoromethyl-quinolin-3-yl)-benzamide;
4-(Cyclohexyl-methyl-amino)-N-(7-trifluoromethyl-quinolin-3-yl)-benzamide;
4-Azocan-1-yl-N-(5-fluoro-quinolin-3-yl)-benzamide;
4-(3-Aza-bicyclo[3.2.2]non-3-yl)-N-(5-fluoro-quinolin-3-yl)-benzamide;
3-Phenyl-propynoic acid quinolin-3-ylamide;
trans-2-Phenyl-cyclopropanecarboxylic acid quinolin-3-ylamide;

3-(4-tert-Butyl-phenyl)-propynoic acid quinolin-3-ylamide; and 2-(4-tert-Butyl-phenyl)-cyclopropanecarboxylic acid quinolin-3-ylamide.

95. A compound selected from the group consisting of 1-Cyclohexyl-2,3-dihydro-1H-indole-5-carboxylic acid quinolin-3-ylamide;

3-(4-tert-Butyl-phenyl)-N-quinolin-3-yl-acrylamide;
3-(4-tert-Butyl-phenyl)-N-quinolin-3-yl-propionamide;
3-{4-(1,1-Dimethyl-propyl)-phenyl}-N-quinolin-3-yl-propionamide;
4-(3-Aza-bicyclo{3.3.1}non-3-yl)-N-quinolin-3-yl-benzamide;
4-Azepan-1-yl-N-quinolin-3-yl-benzamide;
6-(3-Aza-bicyclo{3.3.1}non-3-yl)-N-quinolin-3-yl-nicotinamide;
4-tert-Butyl-N-(4-hydroxy-quinolin-3-yl)-benzamide;
3-(4-tert-Butyl-phenyl)-N-(4-hydroxy-quinolin-3-yl)-acrylamide;
N-Quinolin-3-yl-3-(5,5,8,8-tetramethyl-5,6,7,8-tetrahydro-naphthalen-2-yl)-acrylamide;
N-(4-Chloro-quinolin-3-yl)-3-(5,5,8,8-tetramethyl-5,6,7,8-tetrahydro-naphthalen-2-yl)-acrylamide;
N-(4-Chloro-quinolin-3-yl)-4-(cyclohexyl-methyl-amino)-benzamide;
N-(2-Chloro-quinolin-3-yl)-4-(cyclohexyl-methyl-amino)-benzamide;
4-tert-Butyl-N-(2-methoxy-quinolin-3-yl)-benzamide;
4-Azepan-1-yl-N-(4-chloro-quinolin-3-yl)-benzamide;
4-(3-Aza-bicyclo[3.2.2]non-3-yl)-N-(2-chloro-quinolin-3-yl)-benzamide;
4-Azepan-1-yl-N-(2-chloro-quinolin-3-yl)-benzamide;
4-(3-Aza-bicyclo[3.2.2]non-3-yl)-N-(4-chloro-quinolin-3-yl)-benzamide;
3-(1-Cyclohexyl-2,3-dihydro-1H-indol-5-yl)-N-quinolin-3-yl-acrylamide;
1-Cyclohexyl-2,3-dihydro-1H-indole-5-carboxylic acid (2-chloro-quinolin-3-yl)-amide;
N-(2-Chloro-quinolin-3-yl)-3-(1-cyclohexyl-2,3-dihydro-1H-indol-5-yl)-acrylamide;
3-(1-Cyclohexyl-1H-indol-5-yl)-N-quinolin-3-yl-acrylamide;
N-(4-Chloro-quinolin-3-yl)-3-(1-cyclohexyl-1H-indol-5-yl)-acrylamide;
1-Cyclohexyl-1H-indole-5-carboxylic acid (4-chloro-quinolin-3-yl)-amide;
1-Cyclohexyl-1H-indole-5-carboxylic acid quinolin-3-ylamide;
1-Cyclohexyl-1H-indole-5-carboxylic acid (2-chloro-quinolin-3-yl)-amide;
N-(2-Chloro-quinolin-3-yl)-3-(1-cyclohexyl-1H-indol-5-yl)-acrylamide;
4-(Cyclohexyl-methyl-amino)-N-(8-fluoro-quinolin-3-yl)-benzamide;
4-Azocan-1-yl-N-(8-fluoro-quinolin-3-yl)-benzamide;
4-(3-Aza-bicyclo[3.2.2]non-3-yl)-N-(8-fluoro-quinolin-3-yl)-benzamide;
4-(3-Aza-bicyclo[3.2.2]non-3-yl)-N-(8-trifluoromethyl-quinolin-3-yl)-benzamide;
4-(Cyclohexyl-methyl-amino)-N-(8-trifluoromethyl-quinolin-3-yl)-benzamide;
4-(Cyclohexyl-methyl-amino)-N-(6-fluoro-quinolin-3-yl)-benzamide;
4-Azocan-1-yl-N-(6-fluoro-quinolin-3-yl)-benzamide;
4-(3-Aza-bicyclo[3.2.2]non-3-yl)-N-(6-fluoro-quinolin-3-yl)-benzamide;
4-(3-Aza-bicyclo[3.2.2]non-3-yl)-N-(7-trifluoromethyl-quinolin-3-yl)-benzamide;
4-Azocan-1-yl-N-(7-trifluoromethyl-quinolin-3-yl)-benzamide;
4-(Cyclohexyl-methyl-amino)-N-(7-trifluoromethyl-quinolin-3-yl)-benzamide;
4-Azocan-1-yl-N-(5-fluoro-quinolin-3-yl)-benzamide;
4-(3-Aza-bicyclo[3.2.2]non-3-yl)-N-(5-fluoro-quinolin-3-yl)-benzamide;
3-Phenyl-propynoic acid quinolin-3-ylamide;
trans-2-Phenyl-cyclopropanecarboxylic acid quinolin-3-ylamide;
3-(4-tert-Butyl-phenyl)-propynoic acid quinolin-3-ylamide; and
2-(4-tert-Butyl-phenyl)-cyclopropanecarboxylic acid quinolin-3-ylamide.

96. A pharmaceutical composition comprising a compound or a salt according to claim 1 admixed with a pharmaceutically acceptable carrier, excipient or diluent.

97. A veterinary composition comprising a compound or a salt according to claim 1 admixed with a veterinarily acceptable carrier, excipient or dilluent.

98. A method for treating a chronic-pain causing disease or condition, an acute-pain causing disease or condition, or a pulmonary dysfunction comprising the step of administering to a mammal in need of such treatment a therapeutically effective amount of a compound or a salt of claim 1.

99. A method for treating a disease or condition, wherein said disease or condition causes inflammatory pain, burning pain, itch urinary incontinence, or chronic obstructive pulmonary disease, said method comprising the step of administering to a mammal in need of such treatment a therapeutically effective amount of a compound or a salt of claim 1.

100. A method for treating a disease or condition selected from the group consisting of Irritable Bowel Syndrome, Crohn's Disease, and ulcerative colitis, said method comprising the step of administering to a mammal in need of such treatment a therapeutically effective amount of a compound or a salt of claim 1.

101. The method of claim 100 wherein the disease or condition is ulcerative colitis.

102. The method of claim 100 wherein said therapeutically effective amount comprises a dose range of from about 0.001 mg to about 1,000 mg.

103. The method of claim 100 wherein said therapeutically effective amount comprises a dose range of from about 0.1 mg to about 500 mg.

104. The method of claim 100 wherein said therapeutically effective amount comprises a dose range of from about 1 mg to about 250 mg.

105. A pharmaceutical composition comprising a compound or salt according to claim 17 admixed with a pharmaceutically acceptable carrier, excipient or diluent.

106. A veterinary composition comprising a compound or salt according to claim 17 admixed with a veterinarily acceptable carrier, excipient or dilluent.

107. A method for treating a disease or condition selected from the group consisting of Irritable Bowel Syndrome, Crohn's Disease, and ulcerative colitis, said method comprising the step of administering to a mammal in need of such treatment a therapeutically effective amount of a compound or a salt of claim 17.

108. The method of claim 107 wherein the disease or condition is ulcerative colitis.

109. The method of claim 107 wherein said therapeutically effective amount comprises a dose range of from about 0.001 mg to about 1,000 mg.

110. The method of claim 107 wherein said therapeutically effective amount comprises a dose range of from about 0.1 mg to about 500 mg.

111. The method of claim 107 wherein said therapeutically effective amount comprises a dose range of from about 1 mg to about 250 mg.

112. A pharmaceutical composition comprising a compound or a salt according to claim 31 admixed with a pharmaceutically acceptable carrier, excipient or diluent.

113. A veterinary composition comprising a compound or a salt according to claim 31 admixed with a veterinarily acceptable carrier, excipient or dilluent.

114. A method for treating a disease or condition selected from the group consisting of Irritable Bowel Syndrome, Crohn's Disease, ulcerative colitis, said method comprising the step of administering to a mammal in need of such treatment a therapeutically effective amount of a compound a salt of claim 31.

115. The method of claim 114 wherein the disease or condition is ulcerative colitis.

116. The method of claim 114 wherein said therapeutically effective amount comprises a dose range of from about 0.001 mg to about 1,000 mg.

117. The method of claim 114 wherein said therapeutically effective amount comprises a dose range of from about 0.1 mg to about 500 mg.

118. The method of claim 114 wherein said therapeutically effective amount comprises a dose range of from about 1 mg to about 250 mg.

119. A pharmaceutical composition comprising a compound or a salt according to claim 61 admixed with a pharmaceutically acceptable carrier, excipient or diluent.

120. A veterinary composition comprising a compound or salt according to claim 61 admixed with a veterinarily acceptable carrier, excipient or dilluent.

121. A method for treating a disease or condition selected from the group consisting of Irritable Bowel Syndrome, Crohn's Disease, ulcerative colitis, said method comprising the step of administering to a mammal in need of such treatment a therapeutically effective amount of a compound or a salt of claim 61.

122. The method of claim 121 wherein the disease or condition is ulcerative colitis.

123. The method of claim 121 wherein said therapeutically effective amount comprises a dose range of from about 0.001 mg to about 1,000 mg.

124. The method of claim 121 wherein said therapeutically effective amount comprises a dose range of from about 0.1 mg to about 500 mg.

125. The method of claim 121 wherein said therapeutically effective amount comprises a dose range of from about 1 mg to about 250 mg.

126. A pharmaceutical composition comprising a compound or salt according to claim 78 admixed with a pharmaceutically acceptable carrier, excipient or diluent.

127. A veterinary composition comprising a compound or a salt according to claim 78 admixed with a veterinarily acceptable carrier, excipient or dilluent.

128. A method for treating a disease or condition selected from the group consisting of Irritable Bowel Syndrome, Crohn's Disease, ulcerative colitis, said method comprising the step of administering to a mammal in need of such treatment a therapeutically effective amount of a compound or a salt of claim 78.

129. The method of claim 128 wherein the disease or condition is ulcerative colitis.

130. The method of claim 128 wherein said therapeutically effective amount comprises a dose range of from about 0.001 mg to about 1,000 mg.

131. The method of claim 128 wherein said therapeutically effective amount comprises a dose range of from about 0.1 mg to about 500 mg.

132. The method of claim 128 wherein said therapeutically effective amount comprises a dose range of from about 1 mg to about 250 mg.

133. A method for treating a chronic-pain causing disease or condition, an acute-pain causing disease or condition, or a pulmonary dysfunction comprising the step of administering to a mammal in need of such treatment a therapeutically effective amount of a compound or a salt of claim 17.

134. A method for treating a disease or condition, wherein said disease or condition causes inflammatory pain, burning pain, itch urinary incontinence, or chronic obstructive pulmonary disease, said method comprising the step of administering to a mammal in need of such treatment a therapeutically effective amount of a compound or a salt of claim 17.

135. A method for treating a chronic-pain causing disease or condition, an acute-pain causing disease or condition, or a pulmonary dysfunction comprising the step of administering to a mammal in need of such treatment a therapeutically effective amount of a compound or a salt of claim 31.

136. A method for treating a disease or condition, wherein said disease or condition causes inflammatory pain, burning pain, itch urinary incontinence, or chronic obstructive pulmonary disease, said method comprising the step of administering to a mammal in need of such treatment a therapeutically effective amount of a compound or salt of claim 31.

137. A method for treating a chronic-pain causing disease or condition, an acute-pain causing disease or condition, or a pulmonary dysfunction comprising the step of administering to a mammal in need of such treatment a therapeutically effective amount of a compound or a salt of claim 46.

138. A method for treating a disease or condition, wherein said disease or condition causes inflammatory pain, burning pain, itch urinary incontinence, or chronic obstructive pulmonary disease, said method comprising the step of administering to a mammal in need of such treatment a therapeutically effective amount of a compound or a salt of claim 46.

139. A method for treating a chronic-pain causing disease or condition, an acute-pain causing disease or condition, or a pulmonary dysfunction comprising the step of administering to a mammal in need of such treatment a therapeutically effective amount of a compound or a salt of claim 61.

140. A method for treating a disease or condition, wherein said disease or condition causes inflammatory pain, burning pain, itch urinary incontinence, or chronic obstructive pulmonary disease, said method comprising the step of administering to a mammal in need of such treatment a therapeutically effective amount of a compound or a salt of claim 61.

141. A method for treating a chronic-pain causing disease or condition, an acute-pain causing disease or condition, or a pulmonary dysfunction comprising the step of administering to a mammal in need of such treatment a therapeutically effective amount of a compound or a salt of claim 78.

142. A method for treating a disease or condition, wherein said disease or condition causes inflammatory pain, burning pain, itch urinary incontinence, or chronic obstructive pulmonary disease, said method comprising the step of administering to a mammal in need of such treatment a therapeutically effective amount of a compound or a salt of claim 78.

* * * * *